US011547616B2

(12) United States Patent
Gerstner et al.

(10) Patent No.: US 11,547,616 B2
(45) Date of Patent: Jan. 10, 2023

(54) PORTABLE MEDICAL TRIAGE KIT

(71) Applicant: ZOLL Medical Corporation, Chelmsford, MA (US)

(72) Inventors: Jeffrey Gerstner, Pittsford, NY (US); Jason Gotham, Victor, NY (US); Joseph A. Bart, Elma, NY (US); Christopher Strattner, Pearl River, NY (US); Seth Goldstein, Hyde Park, NY (US); Guy Gioeli, Niskayuna, NY (US); Matthew Pelak, Washington, DC (US); Joshua Ray, Pittsford, NY (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 15/499,880

(22) Filed: Apr. 27, 2017

(65) Prior Publication Data

US 2020/0375825 A1 Dec. 3, 2020

Related U.S. Application Data

(60) Provisional application No. 62/328,569, filed on Apr. 27, 2016.

(51) Int. Cl.
*A61F 17/00* (2006.01)
*A61H 31/00* (2006.01)
*A61B 42/40* (2016.01)
*G16H 50/20* (2018.01)
(Continued)

(52) U.S. Cl.
CPC ............ *A61F 17/00* (2013.01); *A61H 31/005* (2013.01); *A45C 2011/007* (2013.01); *A61B 42/40* (2016.02); *A61M 16/0051* (2013.01); *G16H 50/20* (2018.01)

(58) Field of Classification Search
CPC ....... A61F 17/00; A61H 31/005; A61B 42/40; G16H 50/20; A45C 2011/007; A61M 16/0051
See application file for complete search history.

(56) References Cited

U.S. PATENT DOCUMENTS 4,275,384 A * 6/1981 Hicks ........................ A61J 7/04
340/309.7
4,448,750 A 5/1984 Fuesting
4,643,303 A 2/1987 Arp
(Continued)

FOREIGN PATENT DOCUMENTS

EP 3200109 A1 * 8/2017 ......... A61B 1/00039
WO WO-2016079552 A1 * 5/2016 ........... G06F 19/327

OTHER PUBLICATIONS

STAT KIT by Banyan, STAT KIT 750 from Banyan, Oct. 28, 2015, url: https://www.youtube.com/watch?v=rLJNIGqHWA0, pp. 1-6 (Year: 2015).*

(Continued)

*Primary Examiner* — Devin C Hein
*Assistant Examiner* — Steven G. S. Sanghera
(74) *Attorney, Agent, or Firm* — Mintz Levin Cohn Ferris Glovsky and Popeo, P.C.

(57) ABSTRACT

A portable medical triage kit and interactive application that leads a user through a medically acceptable triage protocol for treating medical emergencies. The interactive application leads the user to treat major life threats of all nearby victims before treating minor threats of anyone.

33 Claims, 90 Drawing Sheets

(51) Int. Cl.
*A45C 11/00* (2006.01)
*A61M 16/00* (2006.01)

(56) References Cited

U.S. PATENT DOCUMENTS

| | | | |
|---|---|---|---|
| 4,839,822 A | 6/1989 | Dormond et al. | |
| 5,088,037 A | 2/1992 | Battaglia | |
| 5,394,892 A | 3/1995 | Kenny et al. | |
| 5,515,974 A | 5/1996 | Higson | |
| 5,521,812 A | 5/1996 | Feder et al. | |
| 5,552,957 A * | 9/1996 | Brown | G06F 1/1628 |
| | | | 361/679.41 |
| 5,583,758 A * | 12/1996 | McIlroy | G16H 70/20 |
| | | | 705/2 |
| 5,644,294 A | 7/1997 | Ness | |
| 5,668,954 A | 9/1997 | Feder et al. | |
| 5,848,700 A | 12/1998 | Horn | |
| 5,850,630 A * | 12/1998 | Wilson | G06F 19/3481 |
| | | | 704/270 |
| 5,868,669 A | 2/1999 | Iliff | |
| 5,913,685 A | 6/1999 | Hutchins | |
| 5,944,018 A | 8/1999 | Allgood et al. | |
| 6,024,699 A * | 2/2000 | Surwit | G06F 19/3418 |
| | | | 600/300 |
| 6,334,070 B1 | 12/2001 | Nova et al. | |
| 6,383,135 B1 | 5/2002 | Chikovani et al. | |
| 6,482,156 B2 | 11/2002 | Iliff | |
| 6,569,093 B2 | 5/2003 | Iliff | |
| 6,697,671 B1 | 2/2004 | Nova et al. | |
| 6,758,811 B1 | 7/2004 | Feder | |
| 6,800,059 B2 | 10/2004 | Muraki et al. | |
| 6,954,148 B2 * | 10/2005 | Pulkkinen | A61B 5/1113 |
| | | | 340/572.1 |
| 6,990,373 B2 | 1/2006 | Jayne et al. | |
| 7,164,945 B2 | 1/2007 | Hamilton et al. | |
| 7,259,667 B2 | 8/2007 | Sergio et al. | |
| 7,277,752 B2 | 10/2007 | Matos | |
| 7,288,072 B2 * | 10/2007 | Stott | A61B 5/12 |
| | | | 600/559 |
| 7,289,029 B2 | 10/2007 | Medema et al. | |
| 7,383,088 B2 | 6/2008 | Spinelli et al. | |
| 7,395,214 B2 * | 7/2008 | Shillingburg | G06Q 50/24 |
| | | | 705/2 |
| 7,567,180 B2 | 7/2009 | Blevins et al. | |
| 7,623,915 B2 | 11/2009 | Sullivan et al. | |
| 7,628,275 B2 | 12/2009 | Smith | |
| 7,706,878 B2 | 4/2010 | Freeman | |
| 7,747,319 B2 | 6/2010 | Freeman | |
| 7,769,465 B2 | 8/2010 | Matos | |
| 7,774,060 B2 | 8/2010 | Westenskow et al. | |
| 7,792,577 B2 | 9/2010 | Hamilton et al. | |
| 7,899,545 B2 * | 3/2011 | John | G16H 40/63 |
| | | | 607/60 |
| 8,160,901 B2 * | 4/2012 | Heywood | G16H 10/60 |
| | | | 705/3 |
| 8,167,130 B2 | 5/2012 | Holstein | |
| 8,180,457 B2 | 5/2012 | Matos | |
| 8,285,525 B2 | 10/2012 | Soto et al. | |
| 8,302,775 B2 | 11/2012 | Holstein | |
| 8,317,519 B1 | 11/2012 | Orlando | |
| 8,321,011 B2 | 11/2012 | Parascandola et al. | |
| 8,346,573 B2 * | 1/2013 | Glimp | G16H 40/67 |
| | | | 600/300 |
| 8,481,970 B2 | 7/2013 | Cooper et al. | |
| 8,548,768 B2 | 10/2013 | Greenwald et al. | |
| 8,548,937 B2 | 10/2013 | Saigal et al. | |
| 8,647,123 B1 | 2/2014 | Carter et al. | |
| 8,679,528 B2 | 3/2014 | Macphee | |
| 8,725,254 B2 | 5/2014 | Freeman | |
| 8,738,130 B2 | 5/2014 | Freeman et al. | |
| 8,978,980 B2 | 3/2015 | Santiago Fontaina | |
| 9,101,527 B2 | 8/2015 | Madanat | |
| 9,286,440 B1 | 3/2016 | Carter et al. | |
| 9,339,427 B2 | 5/2016 | Martin et al. | |
| 9,387,147 B2 | 7/2016 | Elghazzawi et al. | |
| 9,536,407 B2 | 1/2017 | Todasco | |
| 9,666,062 B1 | 5/2017 | Rachal | |
| 9,844,417 B2 | 12/2017 | Gerstner et al. | |
| 9,878,171 B2 * | 1/2018 | Kaib | A61N 1/3931 |
| 10,085,900 B2 | 10/2018 | Johnson | |
| 2002/0007288 A1 | 1/2002 | Endou | |
| 2002/0076679 A1 | 6/2002 | Aman | |
| 2002/0078966 A1 | 6/2002 | Lewis | |
| 2003/0004788 A1 * | 1/2003 | Edmundson | G16H 10/20 |
| | | | 705/2 |
| 2003/0092976 A1 * | 5/2003 | Murase | A61B 5/0002 |
| | | | 600/300 |
| 2003/0208357 A1 | 11/2003 | Hammond | |
| 2004/0143298 A1 | 7/2004 | Nova et al. | |
| 2004/0143594 A1 * | 7/2004 | Kalies | G06Q 50/22 |
| 2005/0177393 A1 * | 8/2005 | Sacco | G16H 50/80 |
| | | | 705/2 |
| 2005/0261742 A1 | 11/2005 | Nova et al. | |
| 2006/0137694 A1 | 6/2006 | Probert et al. | |
| 2008/0202978 A1 | 8/2008 | Salomon et al. | |
| 2009/0177493 A1 * | 7/2009 | Narayan | G16H 70/20 |
| | | | 705/3 |
| 2010/0087883 A1 | 4/2010 | Sullivan et al. | |
| 2010/0125186 A1 | 5/2010 | Abuachi | |
| 2010/0160990 A1 | 6/2010 | Gótzy | |
| 2010/0169111 A1 | 7/2010 | Brue et al. | |
| 2010/0297594 A1 | 11/2010 | Sullivan et al. | |
| 2011/0011886 A1 | 1/2011 | Zaima | |
| 2011/0130636 A1 * | 6/2011 | Daniel | B64C 39/024 |
| | | | 709/201 |
| 2012/0191476 A1 * | 7/2012 | Reid | G06Q 50/24 |
| | | | 705/3 |
| 2014/0155827 A1 | 6/2014 | Ostrander et al. | |
| 2014/0243914 A1 | 8/2014 | Freeman et al. | |
| 2014/0243915 A1 | 8/2014 | Freeman et al. | |
| 2014/0243916 A1 | 8/2014 | Freeman et al. | |
| 2014/0263633 A1 * | 9/2014 | Schmucker | G16H 40/20 |
| | | | 235/385 |
| 2015/0073816 A1 * | 3/2015 | Ha | G16H 50/70 |
| | | | 705/2 |
| 2015/0134350 A1 * | 5/2015 | Lacy | G16H 40/63 |
| | | | 705/2 |
| 2015/0213232 A1 * | 7/2015 | Walker, II | G16H 50/30 |
| | | | 702/19 |
| 2015/0250956 A1 | 9/2015 | Ostrander et al. | |
| 2016/0119753 A1 | 4/2016 | Ostrander et al. | |
| 2016/0140299 A1 | 5/2016 | Al Harbi | |
| 2016/0140320 A1 | 5/2016 | Moturu et al. | |

OTHER PUBLICATIONS

In Ho Kwon, "Application of Telemedicine System to Prehospital Medical Control", Jul. 2015, pp. 196-200 (Year: 2015).*
Andrew Liszewski, "A Better First Aid Kit That Makes Suggestions and Knows What's Missing" web article, 2014, 2 pages (Year: 2014).*
"Cupboard never bare with hi-tech kit" web article, 2014, 2 pages (Year: 2014).*
Steve Levenstein, "Intelligent First Aid Kit Talks You Through Any Emergency" web article, captured Mar. 25, 2016, 3 pages (Year: 2016).*

* cited by examiner

Marche 1

Marche 2

FIG. 5  Marche 4

FIG.6 Bad Bleeding Arm

FIG.7 Bad Bleeding Leg

FIG. 9  Bad Bleeding Stomach

FIG.10  Bad Bleeding Junctional Arm

FIG. 11  Bad Bleeding Junctional Pelvis

FIG.12 Bad Bleeding Face Location Choose

FIG.13 Bad Bleeding Face SCALP

FIG.15 Bad Bleeding Face EARS

FIG. 16  Bad Bleeding Face CHIN

FIG. 17 Bad Bleeding Face NOSE

FIG. 18 Bad Bleeding Face MOUTH

FIG.20 Bad Bleeding Face CHEEK

FIG.24 Chest Pain

FIG.25 Injured/Hurt (Non-Immediate Life Threats)

FIG. 26 Pain/Fracture (Body Chooser)

FIG.27 Generic Pain

FIG.28  Fracture ARM

FIG.29 Fracture ANKLE/FOOT

FIG.30 Fracture UPPER LEG

FIG.31 Fracture LOWER LEG

FIG. 32  Fracture HIP

FIG. 33  Fracture NECK/BACK

FIG.34 Fracture RIBS

FIG. 35 Burns

FIG.36 Severed Limb/Amputation

FIG. 37  Trapped Limb

FIG.38 Impaled Object

FIG.40 Bleeding Arm

FIG. 42 Bleeding Chest

FIG.43 Bleeding Stomach

FIG.44 Bleeding Junctional Arm

FIG. 45 Bleeding Junctional Pelvis

FIG.46 Bleeding Chin

FIG. 49  Bleeding Cheek

FIG. 50 Bleeding Nose

FIG. 52 Bleeding Scalp

FIG. 53 Bleeding Ears

FIG. 54   Seizures

FIG.56 Confusion/Disorientation

FIG. 58 Narcan/Overdose Second Dose

FIG.59   Final Protocol (Patient Protocol Complete)

FIG.60  Something Happens After Victim Treated

FIG.61 Victim Woke up from being Unconscious

FIG.62 Chest Seal Recheck

FIG.63    Chest Pain Recheck

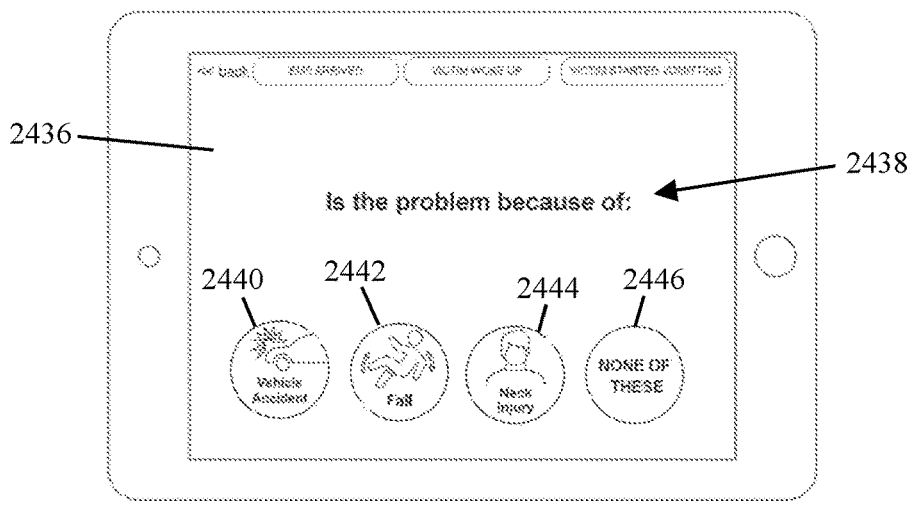
Fig. 88
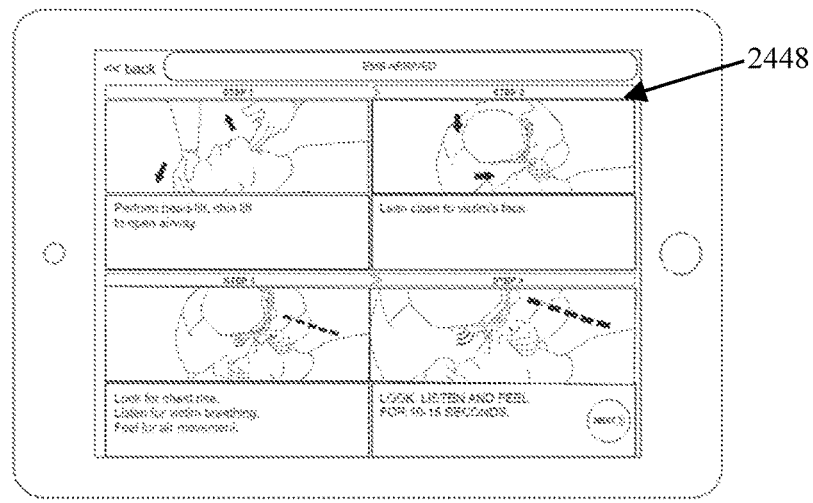
Fig. 89
Fig. 90

PORTABLE MEDICAL TRIAGE KIT

CROSS-REFERENCES TO RELATED APPLICATIONS

The present application is a non-provisional patent application claiming benefit under 35 U.S.C. § 119(e) from U.S. Provisional Application Ser. No. 62/328,569, filed on Apr. 27, 2016, the entire contents of which are hereby expressly incorporated by reference into this disclosure as if set forth fully herein.

FIELD

The present disclosure relates generally to a medical supply kit containing treatments for life threatening injuries. More specifically the disclosure provides guidance for a person with insufficient knowledge or skill to not only identify the correct injury but also provide the correct treatment correlating to a specific injury.

BACKGROUND

Numerous traditional hard kits, tackle boxes, backpacks and duffle bag medical first aid kits exist that supply general first aid to an injured person. Several known devices also provide written and/or audible application instructions for the contained medical supplies. Some known devices also contain individual compartments or zippered bags that organize the medical supplies by type of medical emergency. The problem with these devices is that they do not provide any guidance or instruction that tell the user where the priority of treatment lies let alone how to apply the correct treatment. In the event of an emergency situation when there is not a professionally trained responder on the scene of a medical emergency, chances are that the survival of a victim lies in the hands and action of an untrained civilian or lay person that is nearby the scene.

Therefore, there is a need for a portable medical triage kit where a user does not have to be aware of the medical emergency type and the severity of that medical emergency, but can still define, locate and apply the correct treatment as if they were professionally trained. Additionally there is a need for a portable medical triage kit that leads a layperson to determine the correct priority treatment order of multiple victims (i.e. treating the person with the most dire injuries first, and so on) in a multiple victim emergency situation.

SUMMARY

One problem that Emergency Medical Technicians face on the job is that they are not able to arrive to the scene of a medical emergency quickly enough, and as a result some medical emergency victims suffer extensive injuries or death that may have been prevented if treatment was applied immediately after the medical emergency occurred. The portable medical triage kit disclosed by way of example herein empowers an untrained lay person with the knowledge and ability to address a number of medical emergency situations in order to preserve the victim(s) as well as possible until professional medical help arrives.

By way of example, the portable medical triage kit described herein includes a medical tool kit and an interactive instructional device. The medical tool kit may be may be similar in structure and function to the medical tool kits described in commonly owned U.S. Pat. No. 8,911,677, issued Dec. 16, 2014 (incorporated by reference) and commonly owned and co-pending U.S. patent application Ser. No. 14/539,376, filed Nov. 12, 2014 (incorporated by reference). Generally, the medical tool kit comprises a portable case containing a variety of triage-related medical instruments and supplies that one may find useful and/or necessary to assist a medical emergency victim until professionally trained emergency medical personnel arrive on the scene. For example, the medical tool kit may include (but is not limited to) a tourniquet, hemostatic gauze, CPR face shields, pressure dressings, and the like.

The interactive instructional device may be a customized touch screen tablet device, for example a tablet similar to an Apple iPad, Microsoft Surface, Samsung Galaxy, and the like. The tablet device may contain but is not limited to a two way communication assembly with a microphone and speaker, GPS locator, battery, touch screen LCD, programmable memory, a central processing unit (CPU), and wireless connectivity. The tablet device further includes an interactive instructional application (also referred to herein as "app" or "MOBILIZE app") that is configured to guide any user (e.g. trained professional rescuer, untrained lay person, etc.) through a triage process regardless of the number of victims present and severity of injuries, to empower the user to preserve the victim(s) until professional medical help arrives on the scene.

The MOBILIZE app follows the MARCHE triage protocol (Massive hemorrhage control, Airway management, Respiratory management, Circulation, Head injury/Hypothermia, Everything else). By way of example, the MOBILIZE app provides an objective system of questions that leads a user to a correct course of action based on the user's responses to the system of questions. The app includes several different interactive body choice images (e.g. "select where the pain/injury is located) that define and then display the best treatment protocol based on the chosen body location. Specific choices appear based on where a user is in the query flow and based upon the user's answers to previous questions. For example, if during the query flow a user indicates that an injured party is currently awake, after that time a button choice will appear on later screens to enable the user to tell the system if the injured party becomes unconscious during the course of treatment.

The MOBILIZE app directs the user to identify and treat first the worst injury or the injury that will cause death the fastest. The app also allows for the treatment of multiple victims and/or multiple injuries at the same time without having to exit and/or restart the query flow. In such a situation, the query flow directs the user to locate and treat the injured party with the worst injury first, and then continues to dynamically direct the user to locate and treat the remaining injured parties in descending order of injury severity.

The MOBILIZE app interacts with the provided medical tool kit by providing visual guidance to the physical location of the correct treatment device within the medical tool kit. The app also provides visual instruction on how to properly administer the treatment device to the injured party. The app may provide audible instructions/guidelines and may accept voice-supplied responses.

Many other features may be incorporated into the MOBILIZE app. For example, the app may include built-in timers and audio indicators for correct treatment times when a treatment protocol requires (e.g. applying direct pressure for a predetermined amount of time in a bleeding case before moving on to a different injury or victim). Built-in timers also may remind the user to recheck applied treatments periodically until trained professionals arrive. The app may provide audible cadences for CPR (metronome) and other treatments. The app may integrate with AED (automated external defibrillator) devices. The app may integrate with 911 and/or professional health care providers. The app may allow for $3^{rd}$ party offsite viewing/interaction to allow for extra real time support from medical professionals. The app may automatically alert first responders and provide GPS location when the user performs a task (e.g. upon opening of the kit or upon the user proactively confirming the need for EMT services once the system has been activated). The app may include the ability to gather and record data about the incident, including date/time, responses to questions, actions recommended, etc, for hand off to professional responders upon arrival. This information may be displayed on the device (in full or summary form), transmitted to a secondary device carried by the professional responder, and/or transmitted to an offsite location for storage and/or analysis. The app may include the ability to "push out" updates via a wireless network so that the treatment protocols may be changed if the medical community proposed changes to the recommended protocols.

BRIEF DESCRIPTIONS OF THE DRAWINGS

Many advantages of the present disclosure will be apparent to those skilled in the art with a reading of this specification in conjunction with the attached drawings, wherein like reference numerals are applied to like elements and wherein.

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The portable medical triage kit disclosed herein boasts a variety of inventive features and components that warrant patent protection, both individually and in combination.

Figure 1:
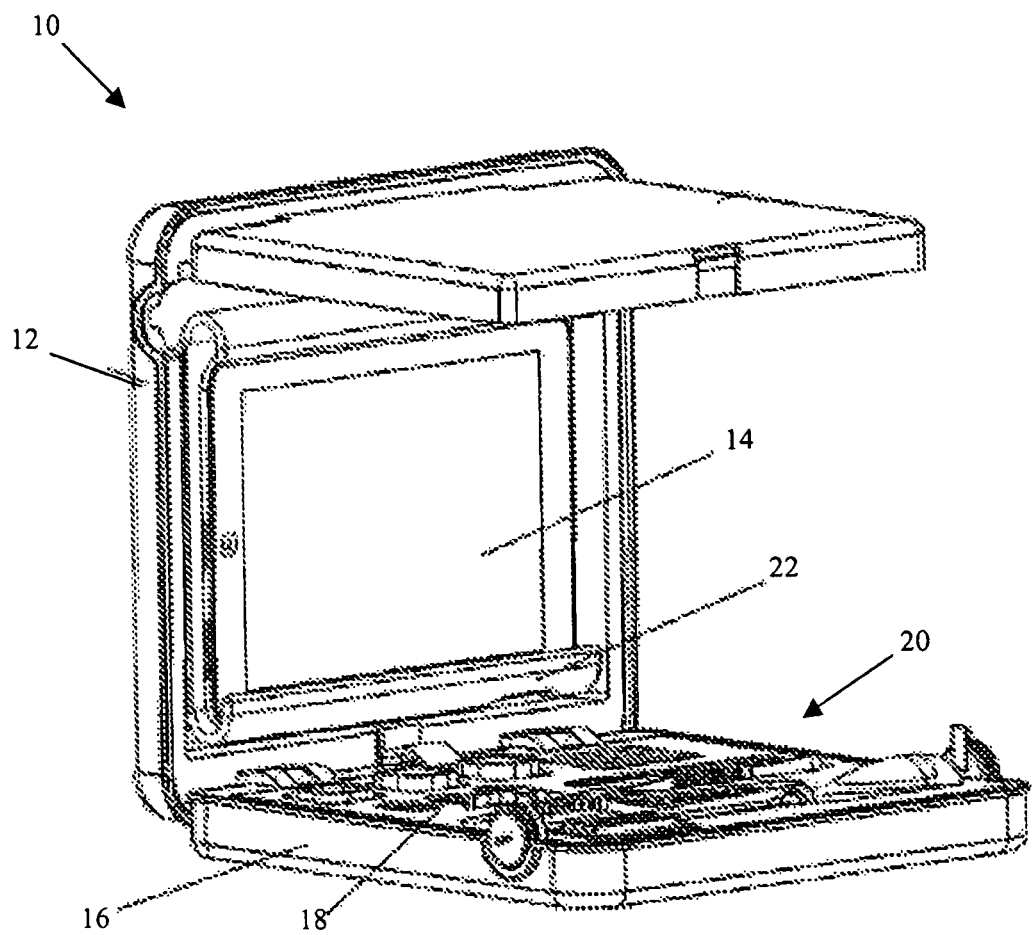
FIG. 1 is a perspective view of an example of a portable medical tool kit according to the disclosure.

FIG. 1 illustrates an example of a portable medical triage kit 10 according to one embodiment of the disclosure. By way of example, the portable medical triage kit 10 described herein includes a medical tool kit 12 and an interactive instructional device 14. The medical tool kit 12 may be may be similar in structure and function to one or more of the medical tool kits described in commonly owned U.S. Pat. No. 8,911,677, issued Dec. 16, 2014 (incorporated by reference) and commonly owned and co-pending U.S. patent application Ser. No. 14/539,376, filed Nov. 12, 2014 (incorporated by reference). Generally, the medical tool kit 10 comprises a case 16 having a tool support insert 18 that houses a variety of triage-related medical instruments and supplies 20 that one may find useful and/or necessary to assist a trauma victim until professionally trained emergency medical personnel arrive on the scene. For example, the medical tool kit 10 may include (but is not limited to) a tourniquet, hemostatic gauze, CPR face shields, pressure dressings, and the like.

The interactive instructional device 14 may be secured to the case via a mounting device 22. The interactive instructional device 14 may be a customized touch screen tablet computer, for example a tablet computer similar to an Apple iPad, Microsoft Surface, Samsung Galaxy, and the like. The interactive instructional device 14 may include but is not limited to a two way communication assembly with a microphone and speaker, GPS locator, battery, touch screen LCD, programmable memory, a central processing unit (CPU), and wireless connectivity. The interactive instructional device 14 further includes an interactive instructional application 15 (also referred to herein as "app" and "MOBILIZE app") and graphic user interface (GUI) configured to visually, audibly, and interactively guide a user through a triage process regardless of the number of victims present and severity of injuries, to enable preservation of the victim(s) until professional medical help arrives on the scene.

Generally, the interactive instructional application 15 comprises a set of algorithms that when executed by the CPU, provides via the graphic user interface an interactive presentation of an objective system of questions (query flow) that leads any user (e.g. professional emergency responder, untrained lay person, etc.) to a correct course of action based on the user's responses to the system of questions. Through the MOBILIZE app 15, the computer directs the user to first identify and treat the worst injury or the injury that will cause death the fastest, using the MARCHE triage protocol (Massive hemorrhage control, Airway management, Respiratory management, Circulation, Head injury/Hypothermia, Everything else). It is important to note that the query flow is non-linear in that a user's answer to one question will necessarily determine the next question that is presented. This has several benefits. Not only does this save time and keep the user engaged (by not making them answer irrelevant questions), but it also enables the treatment of multiple victims and/or multiple injuries concurrently without having to exit and/or restart the query flow. In such a situation, the query flow directs the user to first locate and treat the injured party with the worst injury, and then continues to dynamically direct the user to locate and treat the remaining injured parties in descending order of injury severity.

Figure 2:
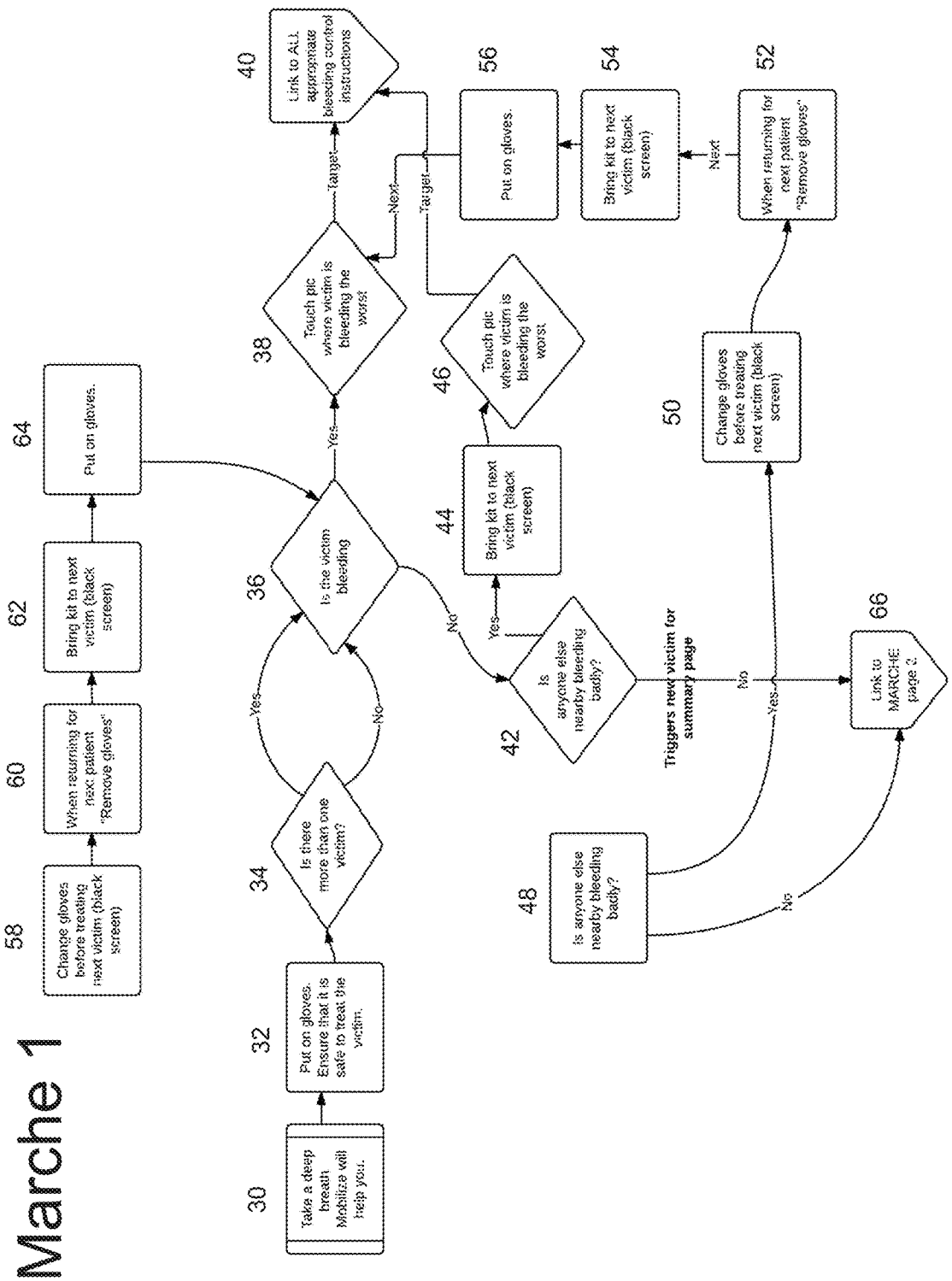
FIGS. 2-5 illustrate different portions of a flowchart depicting an example triage protocol forming part of the portable medical tool kit of FIG. 1.
Figure 63:
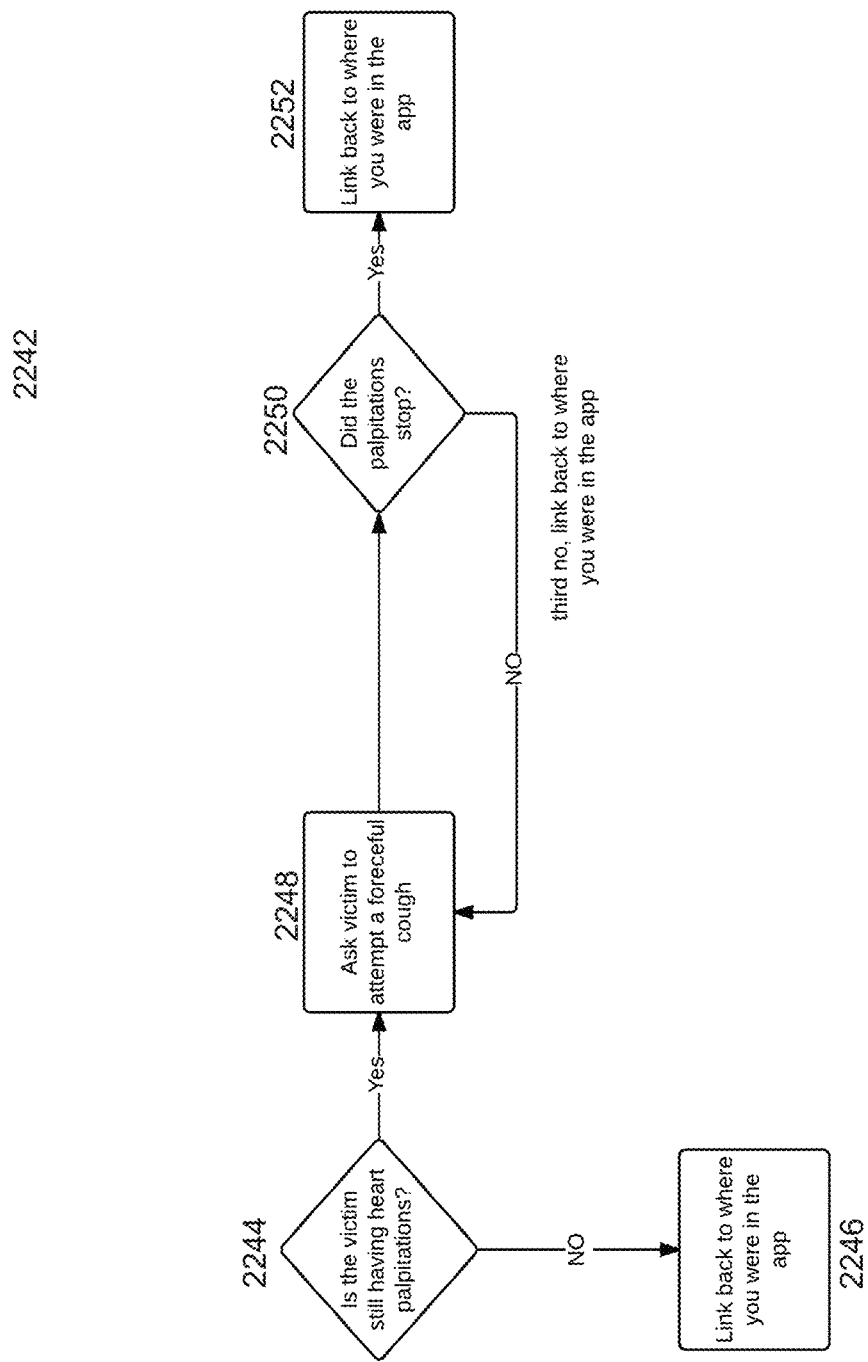
FIG. 63 is a flowchart illustrating an example query flow for a chest pain recheck, which is initiated automatically after a timer runs out, forming part of the triage protocol of FIGS. 2-5.

FIGS. 2-63 are flowchart diagrams that illustrate the interactive instructional application's query flow in greater detail. More specifically, FIGS. 2-5 illustrate the query flow for the initial MARCHE triage protocol. FIGS. 6-63 illustrate query flows for specific injuries, which are presented based upon the user's selections during the MARCHE triage process. In all of the flowchart diagrams, each box presented (with the exception of the isosceles right pentagon shaped boxes) corresponds to and represents a different GUI screen that the computer may present to the user on a display device in response to user input (e.g. tapping icons on a touch screen display and/or using voice commands) on previous GUI screens while guiding the user through the triage protocol of the MOBILIZE app 15. For example, the rectangular shaped boxes represent instructional GUI screens, the diamond shaped boxes represent interactive query GUI screens, and the banner shaped boxes represent alert GUI screens. The isosceles right pentagon shaped boxes represent link spots where the query flow will proceed to a flow on a different flowchart diagram. Unless specified otherwise herein, it should be understood that any advancement through the query flow, and corresponding change in GUI screen, is performed by the computer in response to an input by the user, for example, by tapping a "Next" icon, tapping a selection from a list of choices, tapping on a specific spot on an image displayed by the computer, tapping on an alert icon (e.g. "Victim has fallen unconscious" or "EMT has arrived") and/or through voice commands.

It should be noted as an initial matter that reference herein to "computer" refers to the interactive instructional device 14 operating the MOBILIZE application software 15. Discussion herein of users pressing/tapping buttons (or icons) and being directed by the computer to different GUI screens includes the computer determining that user input was received at a location that corresponds to a display of a particular user interface element (e.g., a "button" or an "icon") and in response, and sometimes without receipt of further user input, transitioning the display of the computer from a first user interface screen to a second user interface screen. Furthermore, although the pressing/tapping of buttons (or icons) indicates the presence of a touchscreen interface, it is to be understood that certain computers that may operate the application software of the present disclosure may not be equipped with a touchscreen interface and therefore the pressing of buttons may be achieved by another suitable way, such as using a mouse to direct a pointer to the correct spot on the screen and then "clicking" the mouse button. In response to the user input, the computer then performs additional actions, for example switching GUI screens, communicating with a host server, etc.

FIGS. 2-5 illustrate the MARCHE triage protocol query flow in detail. Generally, Part 1 of the MARCHE triage protocol (e.g. FIG. 2) presents the query flow for massive hemorrhage control (e.g. severe bleeding). Part 2 of the MARCHE triage protocol (e.g. FIG. 3) presents the query flow for an unconscious victim who may be having trouble breathing, and includes links to specific protocols regarding seizure, CPR, and chest wound. Part 3 of the MARCHE triage protocol (e.g. FIG. 4) presents the query flow for an awake victim who may be having trouble breathing, and includes determining whether the victim is choking, having an allergic reaction, or are otherwise sick or injured. Part 4 of the MARCHE triage protocol (e.g. FIG. 5) presents the query flow for everything else, including determining whether there are other victims in need of emergency assistance, or whether the victim(s) are complaining of anything else beyond what was initially treated.

Figure 113:
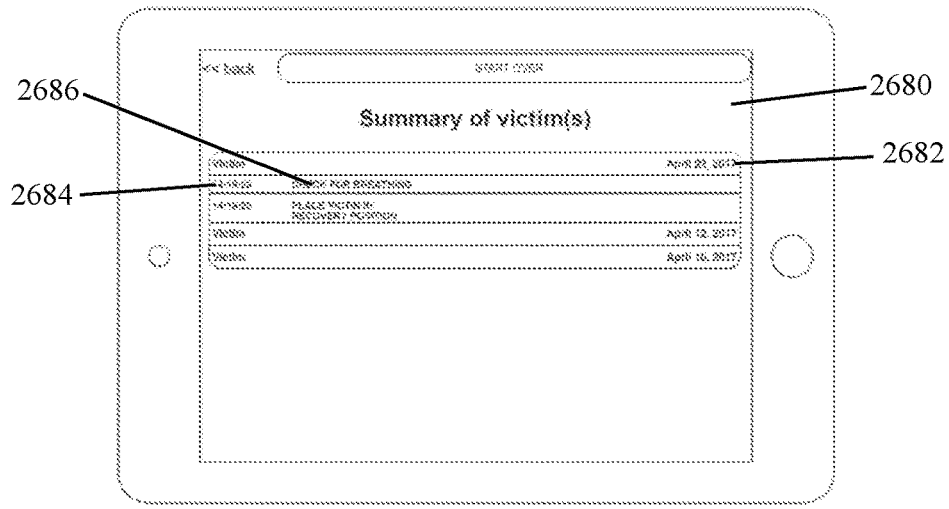

Referring to FIG. 2, part 1 of the MARCHE triage protocol will now be discussed in detail. By way of example, the first box 30 represents the initial GUI screen that the computer presents in response to the user opening the portable medical triage kit 10 (and optionally pressing a power button). As an initial step, the computer creates a victim persona to track data for the Summary page (see, e.g. FIG. 113), which may then be made available to arriving professional rescuers, etc. The next box 32 represents an instructional GUI screen that for example instructs the user to put on gloves. The next box 34 represents a query GUI screen that asks the user if there is more than one victim present. Answering "Yes" to this question may cause the computer to display certain GUI screens to the user involving multiple victims without further asking the user if there are multiple victims. The next box 36 represents another query GUI screen, that seeks to determine whether the victim (or any of multiple victims) are bleeding severely, as blood loss before help arrives is a major cause of concern in an emergency situation. If the user indicates a "Yes" answer to this question, the user is then presented with another query GUI screen (box 38) in the form of graphic representation of a human body on the touch screen display (e.g. FIG. 68), and then is directed to touch the area where the victim is bleeding the most. This action will then cause the query flow to link (box 40) to the severe bleeding flow for the selected body part (FIGS. 6-20).

If the user indicates a "No" answer to the question in query box 36, then the next box 42 represents another query GUI screen that seeks to determine whether anyone else nearby is bleeding badly. If the user indicates a "Yes" answer to this question, the computer creates a new victim persona to track data for the Summary page (see, e.g. FIG. 113), and the user is presented with an instructional GUI screen (box 44) that instructs the user to bring the medial triage kit 10 to the next victim. The user is then presented with another query GUI screen (box 46) in the form of graphic representation of a human body on the touch screen display (e.g. FIG. 68), and then is directed to touch the area where the victim is bleeding the most. This action will then cause the query flow to link (box 40) to the severe bleeding flow for the selected body part (see, e.g. FIGS. 6-20).

Each of the flowchart diagrams for specific severely bleeding body parts (e.g. FIGS. 6-20) links back to MARCHE part 1, and more specifically to box 48 of FIG. 2, which represents a GUI screen that again asks the user if there is anyone else bleeding nearby. If the user indicates a "Yes" answer to this question, then the next box 50 is an instructional box representing a GUI screen telling the user to change gloves before treating the next victim. The next box 52 in the flow represents a GUI screen that reminds the user to remove gloves before returning to patient. Box 54 represents a GUI screen that instructs the user to bring the medial triage kit 10 to the next victim. Box 56 represents a GUI screen that instructs the user to put on gloves. The user is then presented with another query GUI screen (box 38) in the form of graphic representation of a human body on the touch screen display (e.g. FIG. 68), and then is directed to touch the area where the victim is bleeding the most. This action will then cause the query flow to link (box 40) to the severe bleeding flow for the selected body part (FIGS. 6-20).

Figure 5:
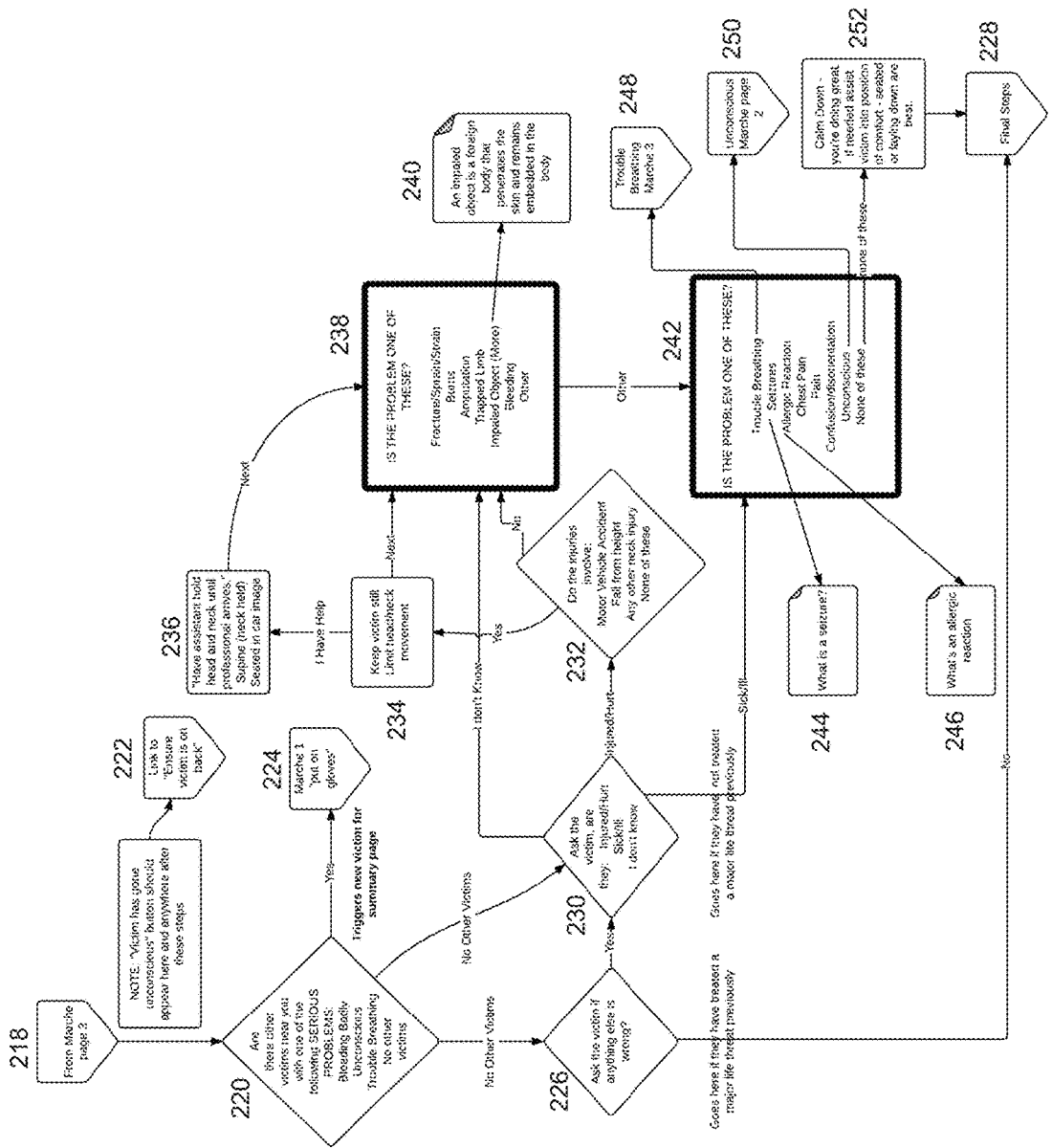
Figure 6:
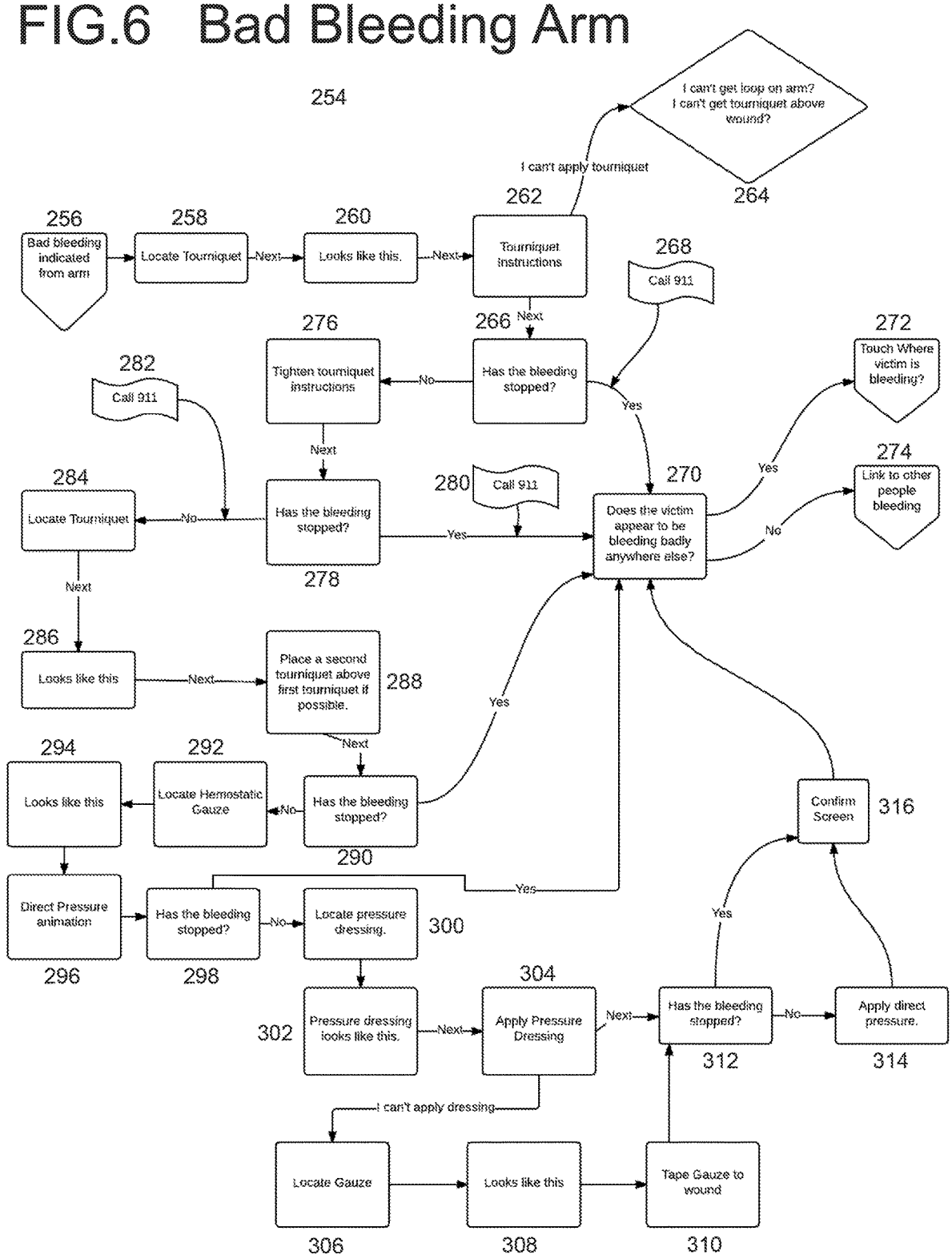
FIG. 6 is a flowchart illustrating an example query flow for a severely bleeding arm, forming part of the triage protocol of FIGS. 2-5.

If the answer to query box 220 of FIG. 5 (e.g. MARCHE part 4) is "yes", then the query flow links (via link box 224) to box 58 of FIG. 2, which is an instructional box representing a GUI screen telling the user to change gloves before treating the next victim. The next box 60 in the flow represents a GUI screen that reminds the user to remove gloves before returning to patient. Box 62 represents a GUI screen that instructs the user to bring the medial triage kit 10 to the next victim. Box 64 represents a GUI screen that instructs the user to put on gloves. The flow then returns to query box 38 and proceeds in a similar manner until all instances of severe bleeding have been addressed.

Figure 3:
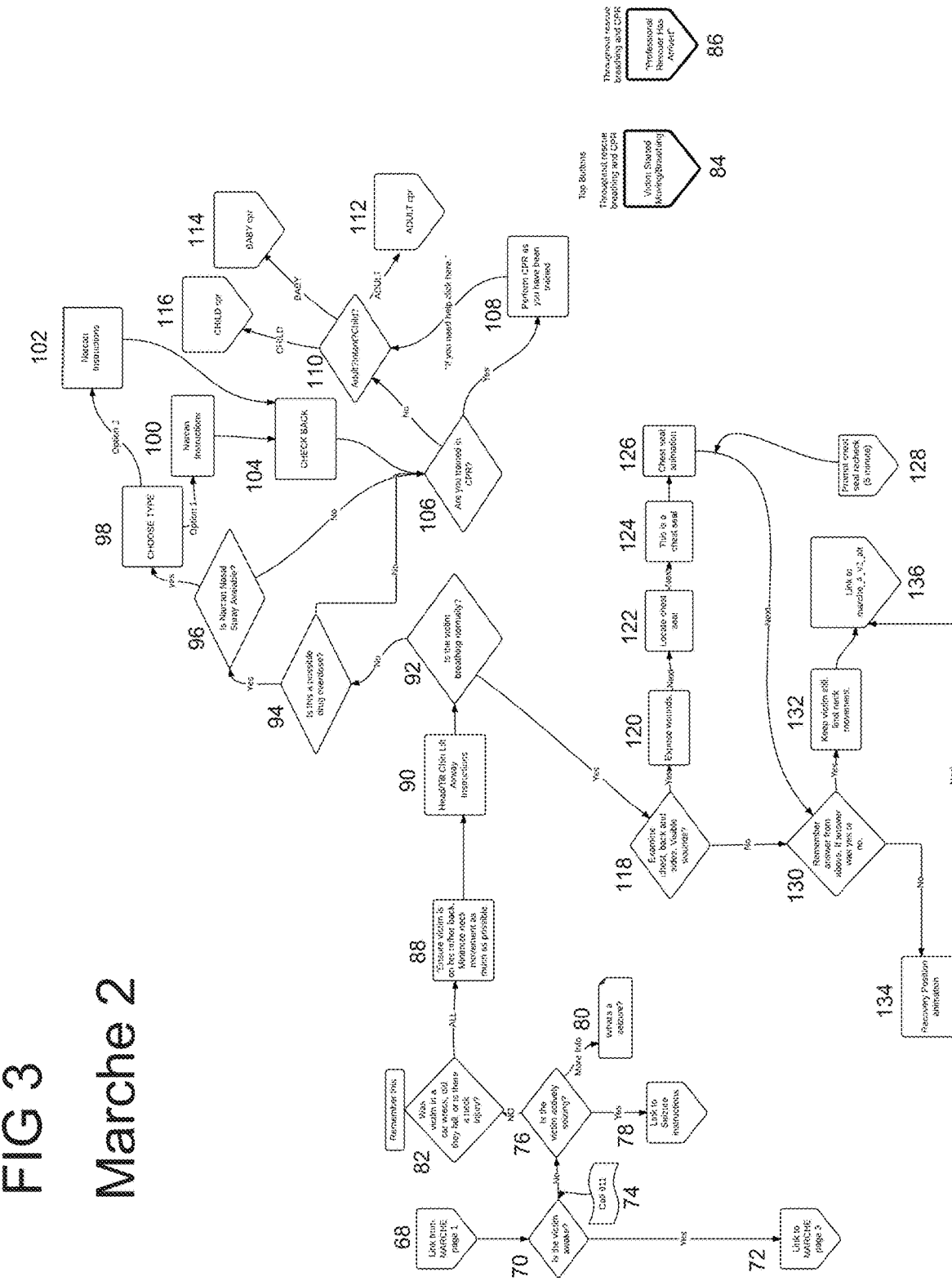

If the victim is not (or no longer) bleeding severely, and no other victims nearby are bleeding severely (e.g. the answers to query box 42 and query box 48 are both "no"), then the query flow proceeds (via link box 66) to part 2 of the MARCHE protocol (via link box 68), illustrated by way of example in FIG. 3. The initial query box 70 in this part of the protocol represents a GUI screen that asks the user whether the victim is awake. If the answer is "yes", then the query flow proceeds (via link box 72) to part 3 of the MARCHE protocol, described in detail below with reference to FIG. 3. If the answer is "No", the user is then first alerted to call 9-1-1 (box 74), and then presented with a series of queries to determine whether the victim is having a seizure, whether they are safe to move, whether they need CPR, and whether they have a chest wound. Affirmative answers to any of these questions will immediately cause the application to link to the appropriate treatment protocol.

By way of example, query box 76 represents a GUI screen that asks the user if the victim is actively seizing. If the user indicates a "Yes" answer to this question, then the query flow proceeds to link box 78, and the MOBILIZE app jumps the user to instruction box 1954 of the Seizure query flow (described in detail below with reference to FIG. 54), which represents a GUI screen that informs the user on what to do if the victim is actively seizing. Box 80 represents a popup information window accessible by the user by pressing an appropriate icon (or speaking a command) on the GUI screen represented by box 76 for example if the user is unsure of what constitutes a "seizure." If the user indicates a "No" answer to the question in box 76, then the query flow proceeds to box 82, which is the starting point of the "Rescue Breathing/CPR" protocol. By way of example, box 82 represents a query GUI screen that asks the user whether the victim was in a car wreck, whether the victim fell, and whether the victim suffered a neck injury. This information is important because these types of injuries require special care to keep the head and neck as stable as possible. At this point, the GUI screen of box 82 as well as each subsequent GUI screen in the "Rescue Breathing/CPR" query flow includes a "Victim Started Moving/Breathing" icon (represented in the flow by link box 84) and a "Professional Rescuer Has Arrived" icon (represented in the flow by link box 86). Tapping on the "Victim Started Moving/Breathing" icon (or vocally indicating as such) prompts the computer to link to box 92 of the query flow (discussed below), and tapping on the "Professional Rescuer Has Arrived" icon (or vocally indicating as such) prompts the computer to link to box 2182 (e.g. produce summary report for professional rescuer review) of the Final Protocol 2184, described below with reference to FIG. 59. For all answers to the question of box 82, the query flow advances to box 88, which represents a GUI screen instructing the user how to position the victim (e.g. "Ensure victim is on his/her back. Minimize neck movement as much as possible."). The next box 90 in the query flow represents a GUI screen that instructs the user on how to tilt the victim's head and lift the victim's chin to clear the victim's airway.

The next box in the flow is a query box 102 representing a GUI screen that asks the user if the victim is breathing. If the user indicates a "No" answer to this question, then the query flow proceeds to box 94, which represents a GUI screen that asks if the victim could be the result of a drug overdose. If the user indicates a "Yes" answer to this question, then the computer advances the query flow to query box 96, which represents a GUI screen that asks if naloxone is available. If the user indicates a "Yes" answer to this question, the flow advances to box 98, which represents a GUI screen prompting the user to choose the type of naloxone between two options (e.g. nasal spray and injection). If the user chooses option 1 (e.g. nasal spray), the query flow advances to box 100, which represents a GUI screen providing instructions for administering the naloxone spray. If the user chooses option 2 (e.g. injection), the query flow advances to box 102, which represents a GUI screen providing instructions for administering the naloxone injection. From either box 100 or box 102, the query flow will advance to box 104, which represents a GUI screen instructing the user to check back to make sure the naloxone was effective.

Continuing from box 104, or if the user answered "no" to the question of box 94 (e.g. not drug overdose) or the question of box 96 (e.g. no naloxone available), the next box in the flow is query box 106, which represents a GUI screen that asks if the user is trained in Cardiopulmonary Resuscitation ("CPR") technique. If the user indicates a "Yes" answer to this question, the query flow advances to box 108, which represents a GUI screen instructing the user to perform CPR as trained, until the victim starts breathing or until a professional rescuer arrives. When the victim resumes breathing, the user may tap (or vocally indicate) on the "Victim Started Moving/Breathing" icon discussed above (e.g. link box 84).

The GUI screen represented by box 108 includes an option for the CPR-trained user to seek further help from the app (e.g. "If you need help click here"). If the CPR-trained user exercises that option, or if the user indicates a "No" answer to the question of box 106, the computer directs the query flow to box 110, which represents a GUI screen asking the user if the victim is an adult, an infant, or a child. If the user selects the indicator for an adult victim, the query flow proceeds to box 900 of the CPR—Adult query flow 892 (discussed in detail below with reference to FIG. 21) via link box 112. If the user selects the indicator for an infant victim, the query flow proceeds to box 1012 of the CPR—Infant query flow 1004 (discussed in detail below with reference to FIG. 23) via link box 114. If the user selects the indicator for a child victim, the query flow proceeds to box 940 of the CPR—Child query flow 932 (discussed in detail below with reference to FIG. 22) via link box 116.

Once the user taps the "Victim Started Moving/Breathing" icon (link box 84) or if the user indicates a "Yes" answer to the question of box 92 (e.g. the victim is breathing), the computer directs the query flow to box 118, which represents a GUI screen asking if the victim has any visible wounds on his/her chest, back and/or sides. If the user indicates a "Yes" answer to this question, then the query flow proceeds to information box 120, which represents a GUI presented by the computer instructing the user to expose the victim's wounds. Once the user has alerted the computer that these instructions have been followed (e.g. by tapping an icon on the screen or through voice command), the flow proceeds to box 122, which represents a GUI screen instructing the user to locate a chest seal device in the medical tool kit 12. Upon receiving input from the user to proceed (e.g. by tapping an icon or through voice command), the computer advances the flow to box 124, which represents a GUI screen showing the user what a chest seal device looks like, to make it easier for the user to recognize the device when looking in the medical too kit 12. Upon receiving input from the user to proceed (e.g. by tapping an icon or through voice command), the computer advances the flow to box 126, which represents a GUI screen showing the user how to apply the chest seal to the victim (e.g. through animated video). Once the user indicates to the app that the chest seal has been applied to the victim, the computer starts a recheck timer to remind/require the user to complete the chest seal reset protocol at a regular specified interval. In the instant example the chest seal recheck interval is set at every five minutes (5:00), however the app may be programmed to include a different medically reasonable time interval (not determined or adjusted by the user in the field). At the expiration of the specified time interval, regardless of the GUI screen the user may be currently viewing, the computer directs the query flow automatically via link box 128 to the Chest Seal Recheck flow, discussed below with reference to FIG. 62.

Once the chest seal has been applied, or if the user indicates a "No" answer to the question of box 118 (e.g. no visible wounds), then the query flow proceeds to box 130, which represents a GUI screen in which the app recalls the answer to the question of box 82 (e.g. was victim in car wreck, fall from height, or suffer neck injury). If the user chose any of the options as an answer to this question (other than "none of these"), then the query flow proceeds to box 132, which represents a GUI screen instructing the user to keep the victim still and limit neck movement. If the user indicated a "None of These" answer to the question of box 82, then the query flow proceeds to box 134, which represents a GUI screen that instructs the user on recovery position, including for example displaying an animation showing the user proper recovery position. From either box 132 or box 134, the flow proceeds to link box 136, which links the flow to box 226 of Part 4 of the MARCHE protocol, discussed below with reference to FIG. 5.

Figure 4:
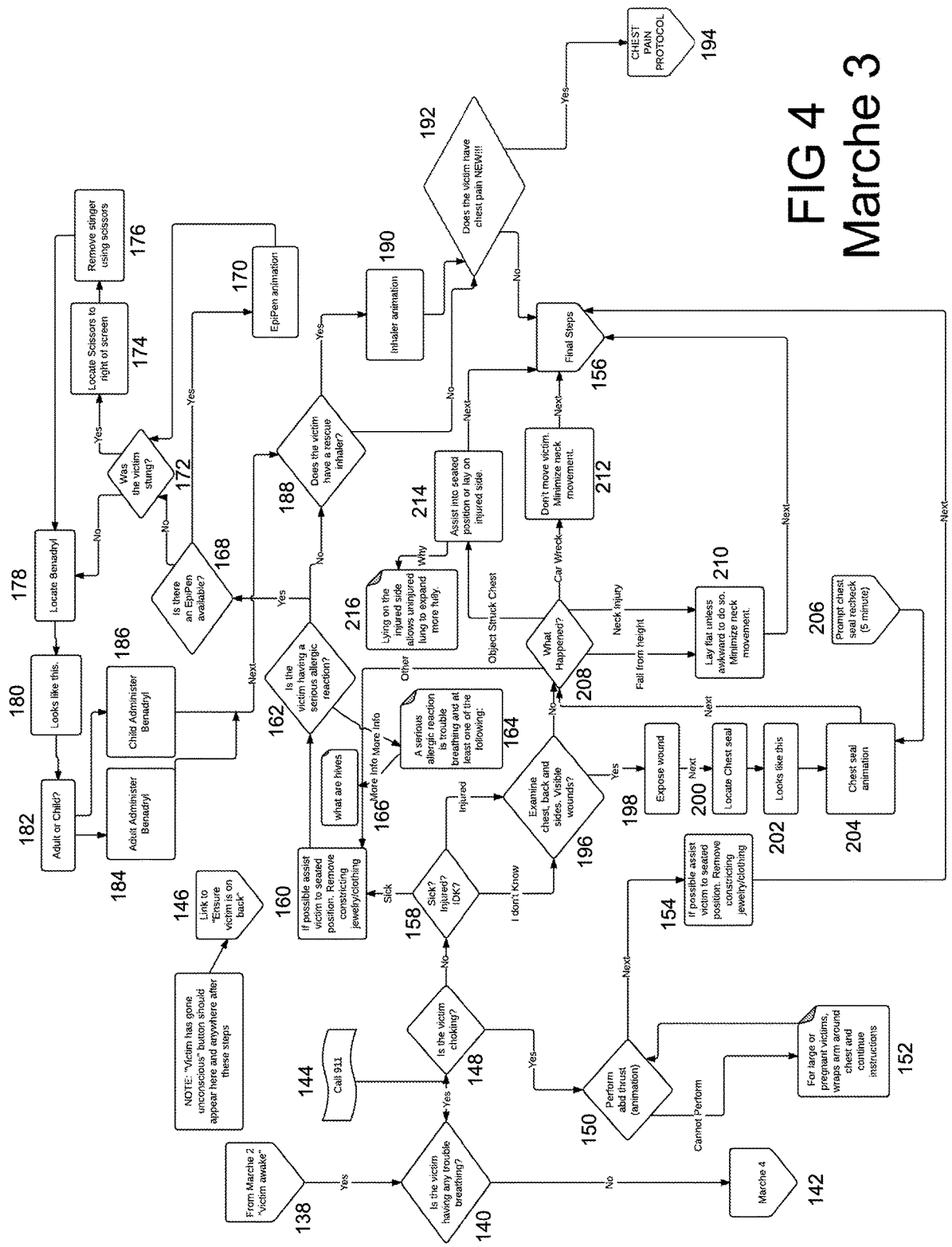

If the victim is awake, for example if the user indicates a "Yes" answer to the question of box 70 of FIG. 3 (e.g. "is the victim awake") or if an unconscious victim wakes up, then the query flow proceeds (via link box 72) to part 3 of the MARCHE protocol (via link box 138), illustrated by way of example in FIG. 4. The initial query box 140 in this part of the protocol represents a GUI screen that asks the user if the victim is having any trouble breathing. If the user indicates a "No" answer to this question, then the query flow proceeds (via link box 142) to part 4 of the MARCHE protocol, discussed below with reference to FIG. 5. If the user indicates a "Yes" answer to the question of box 140, the user is then first alerted to call 9-1-1 (alert box 144), and then presented with a series of queries to determine whether the victim is choking, suffering an allergic reaction, has visible wounds, or is otherwise sick or injured. Affirmative answers to any of these questions will immediately cause the application to link to the appropriate treatment protocol. It should be noted that the GUI screen associated with box 140 and each subsequent GUI screen associated with part 3 of the MARCHE protocol includes a "Victim has gone unconscious" icon, the activation of which (physically or vocally) alerts the computer that the victim has gone unconscious. In response, the computer will redirect the query flow (via link box 146) to box 88 of FIG. 3 (e.g. Ensure the victim is on back), and the flow will continue from there.

By way of example, query box 148 represents a GUI screen that asks the user if the victim is choking. If the user indicates a "Yes" answer to this question, the flow proceeds to box 150, which represents a GUI screen that instructs the user to perform choking first aid in the form of abdominal thrusts (e.g. Heimlich maneuver) and displays an animation depicting abdominal thrusts being performed. In the event the user is unable to perform the abdominal thrusts on the victim (e.g. for an obese or pregnant victim), the user may tap a "cannot perform" button on the GUI screen (or express vocally), which prompts the computer to display information box 152, which instructs the user to wrap their arm around the victim's chest and continue following the instructions provided in box 150. Once the user has stopped the victim from choking, the flow advances to box 154, which represents a GUI screen instructing the user to assist the victim to a seated position and remove constricting jewelry and/or clothing, if possible. From this point the query flow proceeds to link box 156, which links to the Final Protocol of FIG. 59.

If the user indicates a "No" answer to the question in box 148 (e.g. the victim is not choking), then the query flow proceeds to query box 158, which represents a GUI screen asking the user whether the victim is sick or injured, or if they don't know (e.g. cannot determine why the victim is having trouble breathing). If the user answers "sick", then the flow proceeds to box 160, which represents a GUI screen that instructs the user to (if possible) assist the victim to a seated position and remove any constricting jewelry and/or clothing. The next box in the flow is query box 162, which represents a GUI screen that asks the user if the victim is having a serious allergic reaction. If the user needs more information about what constitutes an allergic reaction, the GUI screen represented by box 162 includes a "more info" button that, when tapped by the user, prompts the computer to display an information box 164 that gives further guidance on what constitutes an allergic reaction. Another information box 166, accessible by pressing a "more info" button on the information box 164, may give further define "hives" for the user.

If the user indicates a "Yes" answer to the question of box 162 (e.g. the victim is having a serious allergic reaction), the computer advances the query flow to box 168, which represents a GUI screen that asks the user if the victim has a properly prescribed epinephrine autoinjector (e.g. EpiPen). If the user indicates a "Yes" answer (e.g. epinephrine autoinjector available), then the query flow advances to box 170, which represents a GUI screen with animated instructions on how to administer the epinephrine autoinjector to the victim. After administering the epinephrine autoinjector, or alternatively if the user indicates a "No" answer to the question of box 168 (e.g. no epinephrine autoinjector available), the computer advances the query flow to box 172, which represents a GUI screen that asks the user if the victim was stung. If the user indicates a "Yes" answer to this question, the computer directs the query flow to box 174, which instructs the user to locate the scissors within the medical tool kit 12. When the user successfully locates the scissors and alerts the computer to that fact, the computer advances the query flow to box 176, which represents an instructional GUI screen instructing the user to remove the stinger using the scissors. Upon removal of the stinger, or alternatively if the user indicates a "No" answer to the question of box 172 (e.g. the victim was not stung), the query flow proceeds to box 178, which represents a GUI screen instructing the user to locate the Benadryl within the medical tool kit 12. Box 180 represents a GUI screen that shows the user what Benadryl looks like. Box 182 of the flow represents a GUI Screen that asks the user whether the victim is an adult or a child. If the user answers "adult", then the computer advances the query flow to box 184, which represents a GUI screen providing instruction on how to administer Benadryl to an adult. If the user answers "child" to the question of box 182, then the computer advances the query flow to box 186, which represents a GUI screen providing instruction on how to administer Benadryl to a child.

After Benadryl has been administered (to either and adult or a child), or alternatively if the user indicates a "No" answer to the question of box 162 the query flow advances to box 188, which represents a GUI screen asking the user if the victim has a rescue inhaler. If the user indicates a "Yes" answer, then the flow advances to box 190, which represents a GUI screen that instructs the user how to use the inhaler, for example using animation. After the inhaler is administered, or conversely if the user indicated a "no" answer to the question of box 188 (e.g. no rescue inhaler), the query flow advances to box 192, which represents a GUI screen asking the user if the victim has chest pain. If the user indicates a "Yes" answer, the query flow is redirected to box 1076 of the Chest Pain Protocol via link box 194, which is described below with reference to FIG. 24. If the user indicates a "No" answer to the question of box 192 (e.g. no chest pain), the computer directs the query flow to the Final Protocol of FIG. 59.

Returning to box 158, if the user answers the question on the GUI represented by box 158 (e.g. is the victim is sick or injured) as either "injured" or "I don't know," the computer directs the query flow to box 196, which represents a GUI screen asking if the victim has any visible wounds on his/her chest, back and/or sides. If the user indicates a "Yes" answer to this question, then the query flow proceeds to information box 198, which represents a GUI presented by the computer instructing the user to expose the victim's wounds. Once the user has alerted the computer that these instructions have been followed (e.g. by tapping an icon on the screen or through voice command), the flow proceeds to box 200, which represents a GUI screen instructing the user to locate a chest seal device in the medical tool kit 12. Upon receiving input from the user to proceed (e.g. by tapping an icon or through voice command), the computer advances the flow to box 202, which represents a GUI screen showing the user what a chest seal device looks like, to make it easier for the user to recognize the device when looking in the medical too kit 12. Upon receiving input from the user to proceed (e.g. by tapping an icon or through voice command), the computer advances the flow to box 204, which represents a GUI screen showing the user how to apply the chest seal to the victim (e.g. through animated video). Once the user indicates to the app that the chest seal has been applied to the victim, the computer starts a recheck timer to remind/require the user to complete the chest seal reset protocol at a regular specified interval. In the instant example the chest seal recheck interval is set at every five minutes (5:00), however the app may be programmed to include a different medically reasonable time interval (not determined or adjusted by the user in the field). At the expiration of the specified time interval, regardless of the GUI screen the user may be currently viewing, the computer directs the query flow automatically via link box 206 to the Chest Seal Recheck flow, discussed below with reference to FIG. 62.

Once the chest seal has been applied, or if the user indicates a "No" answer to the question of box 196 (e.g. no visible wounds), then the query flow proceeds to query box 208, which represents a GUI screen that asks the user what happened, giving possible choices of "Fall from height," "Neck injury," "Car wreck", "Object struck chest," and "Other." If the user selects "Fall from height" or "Neck injury" (for example by tapping on a "Fall from height" or "Neck injury" button on the GUI screen or by speaking the words aloud), the query flow proceeds to instruction box 210, which represents a GUI screen that instructs the user to lay the victim flat unless it is awkward to do so, as well as to minimize neck movement. From this point the query flow proceeds to link box 156, which links to the Final Protocol of FIG. 59.

If, in response to the question of box 208, the user selects "Car wreck" (for example by tapping on a "Car wreck" button on the GUI screen or by speaking the words aloud), the query flow proceeds to instruction box 212, which represents a GUI screen that instructs the user to not move the victim, as well as to minimize neck movement. From this point the query flow proceeds to link box 156, which links to the Final Protocol of FIG. 59.

If, in response to the question of box 208, the user selects "Object struck chest" (for example by tapping on a "Object struck chest" button on the GUI screen or by speaking the words aloud), the query flow proceeds to instruction box 214, which represents a GUI screen that instructs the user to assist the victim to a seated position, or alternatively to lay the victim on the injured side. A "Why?" icon may be present on the represented GUI that, if activated by the user (e.g. by touch or voice) prompts the computer to display a popup information box 216 that explains to the user that laying a victim on his/her injured side allows the uninjured lung to expand more fully. From this point the query flow proceeds to link box 156, the Final Protocol of FIG. 59.

If, in response to the question of box 208, the user selects "Other" (for example by tapping on an "Other" button on the GUI screen or by speaking the word aloud), the query flow proceeds to instruction box 160 and the computer directs the user through the "sick" flow described above.

If the victim is not (or no longer) bleeding severely, if the victim is awake, and breathing normally, then the query flow proceeds (via link box 142) to part 4 of the MARCHE protocol (via link box 218), illustrated by way of example in FIG. 5. Part 4 of the protocol helps direct the user to determine whether there are other victims in need of emergency assistance, or whether the victim(s) are complaining of anything else beyond what was initially treated. The initial query box 220 in this part of the protocol represents a GUI screen that asks the user if there are any other victims nearby with one of the problems addressed by parts 1-3 of the MARCHE protocol, namely "bleeding badly," "unconscious," and/or "trouble breathing." It should be noted that the GUI screen associated with box 220 and each subsequent GUI screen associated with part 4 of the MARCHE protocol includes a "Victim has gone unconscious" icon, the activation of which (physically or vocally) alerts the computer that the victim has gone unconscious. In response, the computer will redirect the query flow (via link box 222) to box 88 of FIG. 3 (e.g. Ensure the victim is on back), and the flow will continue from there.

If the user indicates a "Yes" answer to the question of box 220 (e.g. there is at least one more victim nearby with a serious problem), then the computer creates a new victim persona to track data for the Summary page (see, e.g. FIG. 113), and the query flow links (via link box 224) to box 58 of FIG. 2, which is an instructional box representing a GUI screen telling the user to change gloves before treating the next victim. The query flow will continue from there to ensure the user treats the potential life-threatening issue(s) (e.g. serious bleeding, unconscious, and/or trouble breathing) of the new victim before addressing less serious problems with the first (or any other) victim.

If the user answers "No other victims" to the question of box 220 (e.g. no other victims with serious life-threatening injuries), and the user has already treated a major life threat of this particular victim in this event (e.g. serious bleeding, unconscious, and/or trouble breathing as described above), the computer directs the query flow to box 226, which represents a GUI screen instructing the user to ask the victim if anything else is wrong. If the user indicates that the victim answered "No", then the query flow proceeds to link box 228, which links to the Final Protocol of FIG. 59.

If the user indicates that the victim answered "Yes" to the question of box 226, or alternatively if the user answers "No other victims" to the question of box 220 (e.g. no other victims with serious life-threatening injuries), and the user has not already treated a major life threat of this particular victim in this event (e.g. serious bleeding, unconscious, and/or trouble breathing as described above), the computer directs the query flow to box 230, which represents a GUI screen directing the user to ask the victim if he/she is injured/hurt or sick/ill.

If the user indicates that the victim's answer was "Injured/hurt", the computer directs the query flow to query box 232, which represents a GUI screen that asks the user if the injuries involve a car wreck, fall from height, or any other neck injury. If the user indicates a "Yes" answer, then the computer directs the query flow to instructional box 234, which represents a GUI screen that instructs the user to keep the victim still and limit head and next movement. The GUI screen associated with instructional box 234 may include a button that, when tapped (or via spoken command) alerts the computer that the user has help present. If the user so indicates, the computer directs the query flow to box 236, which represents a GUI screen that by way of example instructs the user to instruct the assistant to hold the victim's head and neck until professional help arrives, and may include a image demonstrating a supine victim seated in car with neck being held.

From either box 234 (if the user does not have help) or box 236, or if the user indicates an answer of "I don't know" in response to the question of box 230, the query flow proceeds to box 238, which represents a GUI screen that asks the user if the problem is one of: Fracture/Sprain/Strain, Burns, Amputation, Trapped Limb, Impaled Object, Bleeding, or Other. For the "Impaled Object" choice, the represented GUI screen includes a "More Info" icon that, if activated by the user (e.g. by touch or voice) prompts the computer to display a popup information box 240 that explains to the user that an impaled object is a foreign body that penetrates the skin and remains embedded in the body. By way of example, if the user indicates "Fracture/Sprain/Strain," the computer will direct the query flow to the Pain/Fracture (Body Chooser) flow, described below with reference to FIG. 26. If the user indicates "Burns," the computer will direct the query flow to the Burns query flow, described below with reference to FIG. 35. If the user indicates "Amputation," the computer will direct the query flow to the Amputation query flow, described below with reference to FIG. 36. If the user indicates "Trapped Limb," the computer will direct the query flow to the Trapped Limb query flow, described below with reference to FIG. 37. If the user indicates "Impaled Object," the computer will direct the query flow to the Impaled Object query flow, described below with reference to FIG. 38. If the user indicates "Bleeding (mild)," the computer will direct the query flow to the Bleeding (Body Chooser) flow, described below with reference to FIG. 39.

If the user indicates "Other" in response to the question displayed by the GUI represented by box 238, or alternatively if the user indicates an answer of "Sick/Ill" to the question displayed by the GUI represented by box 230, the computer advances the query flow to box 242, which represents a GUI screen that asks the user if the problem is one of: Trouble Breathing, Seizures, Allergic Reaction, Chest Pain, General Pain, Confusion/Disorientation, Unconsciousness, or None of These. For the "Seizure" choice, the represented GUI screen includes a "More Info" icon that, if activated by the user (e.g. by touch or voice) prompts the computer to display a popup information box 244 that explains a seizure to the user. For the "Allergic Reaction" choice, the represented GUI screen includes a "More Info" icon that, if activated by the user (e.g. by touch or voice) prompts the computer to display a popup information box 246 that explains an allergic reaction to the user. By way of example, if the user indicates "Trouble Breathing," the computer will direct the query flow to box 140 of the part 3 of the MARCHE protocol (via link box 250), described above with reference to FIG. 4. If the user indicates "Seizures," the computer will direct the query flow to the Seizures query flow, described below with reference to FIG. 54. If the user indicates "Allergic Reaction," the computer will direct the query flow to the Allergic Reaction query flow, described below with reference to FIG. 55. If the user indicates "Chest Pain," the computer will direct the query flow to the Chest Pain query flow, described below with reference to FIG. 24. If the user indicates "General Pain," the computer will direct the query flow to the General Pain query flow, described below with reference to FIG. 27. If the user indicates "Confusion/Disorientation," the computer will direct the query flow to the Confusion/Disorientation query flow, described below with reference to FIG. 56. If the user indicates "Unconsciousness," the computer will direct the query flow to box 70 of Part 2 of the MARCHE protocol (via link box 250), described above with reference to FIG. 3. If the user indicates "None of These", the computer will advance the query flow to instruction box 252, which (by way of example) reassures the user that they are doing great, and instructs the user to if needed "assist the victim into a position of comfort—seated or laying down are best." From this point the query flow proceeds to link box 228, which links to the Final Protocol of FIG. 59.

The query flows for specific triage protocols are illustrated in FIGS. 6-63. As mentioned previously, these are primarily accessed through the MARCHE triage query flow discussed above. However, the way that the user indicates answers to certain questions within each specific injury treatment protocol may cause the application to shift the query flow to a different specific injury treatment. For example, if the computer displays a question to the user such as "Is the victim bleeding anywhere else?" and the user indicates an affirmative answer, the computer will display a GUI screen prompting the user to select a new location of bleeding. Once the user selects the new location there is no need to reset the query flow again. The computer merely "jumps" to the appropriate query flow for the newly indicated location.

FIG. 6 illustrates the query flow for a severely bleeding arm 254, which is accessed via link box 40 of FIG. 2 (e.g. in response to the user touching the arm on the graphic representation of a human body on the touch screen display (e.g. FIG. 68)) and begins at link box 256. When a user arrives in this query flow, the goal is to stop the bleeding arm as quickly and effectively as possible. The first instructional box 258 of the query flow 254 is an instructional box representing a GUI screen that instructs the user to locate a tourniquet within the accompanying medical tool kit 12. By way of example, the represented GUI screen may also display a layout image of the tool kit and highlight with specificity the location of the tourniquet. The next box 260 represents a GUI screen that displays a zoomed in image of a tourniquet so the user knows what to look for. The next box in the query flow is an instruction box 262 that represents a GUI screen that provides specific instruction on how to apply a tourniquet to a victim's arm, for example with text instructions, visual aid (e.g. pictures and/or video) and/or audio instructions. If the user is unable to apply the tourniquet properly, he/she alerts the computer by activating (e.g. physically or vocally) an "I can't apply tourniquet" button, which prompts the computer to direct the query flow to box 264, which represents a GUI screen that asks the user to choose between "I can't get loop on arm" and "I can't get tourniquet above wound." If the user indicates a selection of "I can't get loop on arm", then the computer will link the query flow to the Trapped Limb query flow 1412, discussed below with reference to FIG. 37. If the user indications a selection of "I can't get tourniquet above wound," then the computer will link to box 292 of the current flow (e.g. Hemostatic gauze placement).

If the user can successfully apply the tourniquet as instructed by box 262, the computer advances the query flow to box 266, which represents a GUI screen asking the user if the bleeding has stopped. If the user indicates an answer of "Yes" to this question, the computer directs the query flow to box 268, which is a GUI screen prompting the user to call 9-1-1 if they have not already done so. The query flow then proceeds to box 270, which represents a GUI screen that asks the user if the victim appears to be bleeding badly anywhere else. If the user indicates a "Yes" answer (e.g. the victim is badly bleeding elsewhere), then the computer redirects the query flow (via link box 272) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 274) to box 48 of FIG. 2 (e.g. query box asking if anyone else is bleeding badly), and the flow proceeds from there.

If the user indicates an answer of "No" to the question of box 266 (e.g. bleeding has not stopped), the computer advances the query flow to box 276, which represents a GUI screen presenting instructions to the user on how to tighten the tourniquet. The next box 278 in the flow represents a GUI screen asking the user if the bleeding has stopped. If the user indicates an answer of "Yes" to this question, the computer directs the query flow to box 280, which represents a GUI screen prompting the user to call 9-1-1 if they have not already done so. The query flow then proceeds to box 270 and proceeds as discussed above.

If the user indicates an answer of "No" to the question of box 278 (e.g. bleeding has not stopped yet), the computer directs the query flow to box 282, which represents a GUI screen prompting the user to call 9-1-1 if they have not already done so. The query flow then proceeds to box 284, which represents a GUI screen that instructs the user to locate another tourniquet within the accompanying medical tool kit 12. By way of example, the represented GUI screen may also display a layout image of the tool kit and highlight with specificity the location of the tourniquet. The next box 286 represents a GUI screen that displays a zoomed in image of a tourniquet in case the user needs to be reminded of what to look for. The query flow then proceeds to instruction box 288, which represents a GUI screen instructing the user to apply a second tourniquet above the first tourniquet if possible. The next box in the query flow is query box 290, which represents a GUI screen asking the user if the bleeding has stopped. If the user indicates an answer of "Yes" to this question, the computer directs the query flow to box 270 and proceeds as discussed above.

If the user indicates an answer of "No" to the question of box 290 (e.g. bleeding has not stopped yet), the computer directs the query flow to box 292, which represents a GUI screen prompting the user to locate the hemostatic gauze within the accompanying medical tool kit 12. By way of example, the represented GUI screen may also display a layout image of the tool kit and highlight with specificity the location of the hemostatic gauze. The next box 294 represents a GUI screen that displays a zoomed in image of hemostatic gauze so the user knows what to look for. The next box in the query flow is an instruction box 296 that represents a GUI screen that provides specific instruction on how to apply direct pressure to a victim's arm using hemostatic gauze, for example with text instructions, visual aid (e.g. pictures and/or video) and/or audio instructions. The next box in the query flow is query box 298, which represents a GUI screen asking the user if the bleeding has stopped. If the user indicates an answer of "Yes" to this question, the computer directs the query flow to box 270 and proceeds as discussed above.

If the user indicates an answer of "No" to the question of box 298 (e.g. bleeding has not stopped yet), the computer directs the query flow to box 300, which represents a GUI screen prompting the user to locate the pressure dressing within the accompanying medical tool kit 12. By way of example, the represented GUI screen may also display a layout image of the tool kit and highlight with specificity the location of the pressure dressing. The next box 302 represents a GUI screen that displays a zoomed in image of pressure dressing so the user knows what to look for. The next box in the query flow is an instruction box 304 that represents a GUI screen that provides specific instruction on how to apply the pressure dressing to a victim's arm, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 306, which represents a GUI screen that prompts the user to locate the gauze within the accompanying medical tool kit 12. By way of example, the represented GUI screen may also display a layout image of the tool kit and highlight with specificity the location of the gauze. The next box 308 represents a GUI screen that displays a zoomed in image of gauze so the user knows what to look for. The next box in the query flow is an instruction box 310 that represents a GUI screen that instructs the user to tape the gauze to the wound. Once the gauze has been taped to the wound, or alternatively if the user was able to apply the pressure dressing to the wound, the next box in the query flow is query box 312, which represents a GUI screen asking the user if the bleeding has stopped. If the user indicates an answer of "No" to this question (e.g. bleeding has not stopped yet), then the query flow is directed to box 314, which instructs the user how to apply direct pressure to the arm. At this point, after direct pressure has been applied to the badly bleeding arm, or alternatively if the user indicates a "Yes" answer to the question of box 312 (e.g. the bleeding has stopped), the computer directs the query flow to box 316, which asks the user to confirm that bleeding has stopped. The query flow then proceeds to box 270 and proceeds as discussed above.

Figure 7:
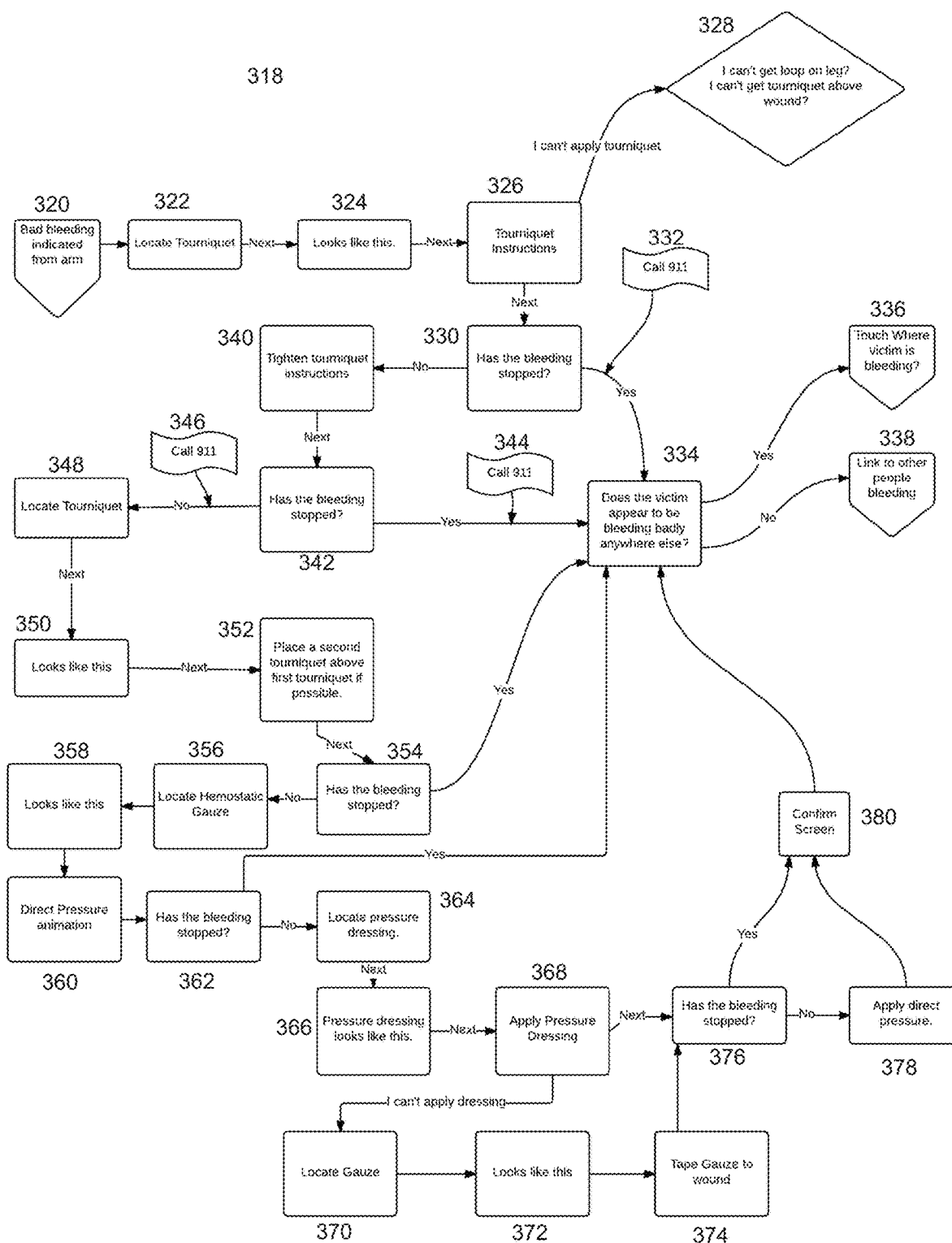
FIG. 7 is a flowchart illustrating an example query flow for a severely bleeding leg, forming part of the triage protocol of FIGS. 2-5.

FIG. 7 illustrates the query flow for a severely bleeding leg 318, which is accessed via link box 40 of FIG. 2 (e.g. in response to the user touching the leg on the graphic representation of a human body on the touch screen display (e.g. FIG. 68)) and begins at link box 320. When a user arrives in this query flow, the goal is to stop the bleeding leg as quickly and effectively as possible. The first box 322 of the query flow 318 is an instructional box representing a GUI screen that instructs the user to locate a tourniquet within the accompanying medical tool kit 12. By way of example, the represented GUI screen may also display a layout image of the tool kit and highlight with specificity the location of the tourniquet. The next box 324 represents a GUI screen that displays a zoomed in image of a tourniquet so the user knows what to look for. The next box in the query flow is an instruction box 326 that represents a GUI screen that provides specific instruction on how to apply a tourniquet to a victim's leg, for example with text instructions, visual aid (e.g. pictures and/or video) and/or audio instructions. If the user is unable to apply the tourniquet properly, he/she alerts the computer by activating (e.g. physically or vocally) an "I can't apply tourniquet" button, which prompts the computer to direct the query flow to box 328, which represents a GUI screen that asks the user to choose between "I can't get loop on leg" and "I can't get tourniquet above wound." If the user indicates a selection of "I can't get loop on leg", then the computer will link the query flow to the Trapped Limb query flow 1412, discussed below with reference to FIG. 37. If the user indications a selection of "I can't get tourniquet above wound," then the computer will link to box 356 of the current flow (e.g. Hemostatic gauze placement).

If the user can successfully apply the tourniquet as instructed by box 326, the computer advances the query flow to box 330, which represents a GUI screen asking the user if the bleeding has stopped. If the user indicates an answer of "Yes" to this question, the computer directs the query flow to box 332, which is a GUI screen prompting the user to call 9-1-1 if they have not already done so. The query flow then proceeds to box 334, which represents a GUI screen that asks the user if the victim appears to be bleeding badly anywhere else. If the user indicates a "Yes" answer (e.g. the victim is badly bleeding elsewhere), then the computer redirects the query flow (via link box 336) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 338) to box 48 of FIG. 2 (e.g. query box asking if anyone else is bleeding badly), and the flow proceeds from there.

If the user indicates an answer of "No" to the question of box 330 (e.g. bleeding has not stopped), the computer advances the query flow to box 340, which represents a GUI screen presenting instructions to the user on how to tighten the tourniquet. The next box 342 in the flow represents a GUI screen asking the user if the bleeding has stopped. If the user indicates an answer of "Yes" to this question, the computer directs the query flow to box 344, which represents a GUI screen prompting the user to call 9-1-1 if they have not already done so. The query flow then proceeds to box 334 and proceeds as discussed above.

If the user indicates an answer of "No" to the question of box 342 (e.g. bleeding has not stopped yet), the computer directs the query flow to box 346, which represents a GUI screen prompting the user to call 9-1-1 if they have not already done so. The query flow then proceeds to box 348, which represents a GUI screen that instructs the user to locate another tourniquet within the accompanying medical tool kit 12. By way of example, the represented GUI screen may also display a layout image of the tool kit and highlight with specificity the location of the tourniquet. The next box 350 represents a GUI screen that displays a zoomed in image of a tourniquet in case the user needs to be reminded of what to look for. The query flow then proceeds to instruction box 352, which represents a GUI screen instructing the user to apply a second tourniquet above the first tourniquet if possible. The next box in the query flow is query box 354, which represents a GUI screen asking the user if the bleeding has stopped. If the user indicates an answer of "Yes" to this question, the computer directs the query flow to box 334 and proceeds as discussed above.

If the user indicates an answer of "No" to the question of box 354 (e.g. bleeding has not stopped yet), the computer directs the query flow to box 356, which represents a GUI screen prompting the user to locate the hemostatic gauze within the accompanying medical tool kit 12. By way of example, the represented GUI screen may also display a layout image of the tool kit and highlight with specificity the location of the hemostatic gauze. The next box 358 represents a GUI screen that displays a zoomed in image of hemostatic gauze so the user knows what to look for. The next box in the query flow is an instruction box 360 that represents a GUI screen that provides specific instruction on how to apply direct pressure to a victim's arm using hemostatic gauze, for example with text instructions, visual aid (e.g. pictures and/or video) and/or audio instructions. The next box in the query flow is query box 362, which represents a GUI screen asking the user if the bleeding has stopped. If the user indicates an answer of "Yes" to this question, the computer directs the query flow to box 334 and proceeds as discussed above.

If the user indicates an answer of "No" to the question of box 362 (e.g. bleeding has not stopped yet), the computer directs the query flow to box 364, which represents a GUI screen prompting the user to locate the pressure dressing within the accompanying medical tool kit 12. By way of example, the represented GUI screen may also display a layout image of the tool kit and highlight with specificity the location of the pressure dressing. The next box 366 represents a GUI screen that displays a zoomed in image of pressure dressing so the user knows what to look for. The next box in the query flow is an instruction box 368 that represents a GUI screen that provides specific instruction on how to apply the pressure dressing to a victim's leg, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 370, which represents a GUI screen that prompts the user to locate the gauze within the accompanying medical tool kit 12. By way of example, the represented GUI screen may also display a layout image of the tool kit and highlight with specificity the location of the gauze. The next box 372 represents a GUI screen that displays a zoomed in image of gauze so the user knows what to look for. The next box in the query flow is an instruction box 374 that represents a GUI screen that instructs the user to tape the gauze to the wound. Once the gauze has been taped to the wound, or alternatively if the user was able to apply the pressure dressing to the wound, the next box in the query flow is query box 376, which represents a GUI screen asking the user if the bleeding has stopped. If the user indicates an answer of "No" to this question (e.g. bleeding has not stopped yet), then the query flow is directed to box 378, which instructs the user how to apply direct pressure to the leg. At this point, after direct pressure has been applied to the badly bleeding leg, or alternatively if the user indicates a "Yes" answer to the question of box 376 (e.g. the bleeding has stopped), the computer directs the query flow to box 380, which asks the user to confirm that bleeding has stopped. The query flow then proceeds to box 334 and proceeds as discussed above.

Figure 8:
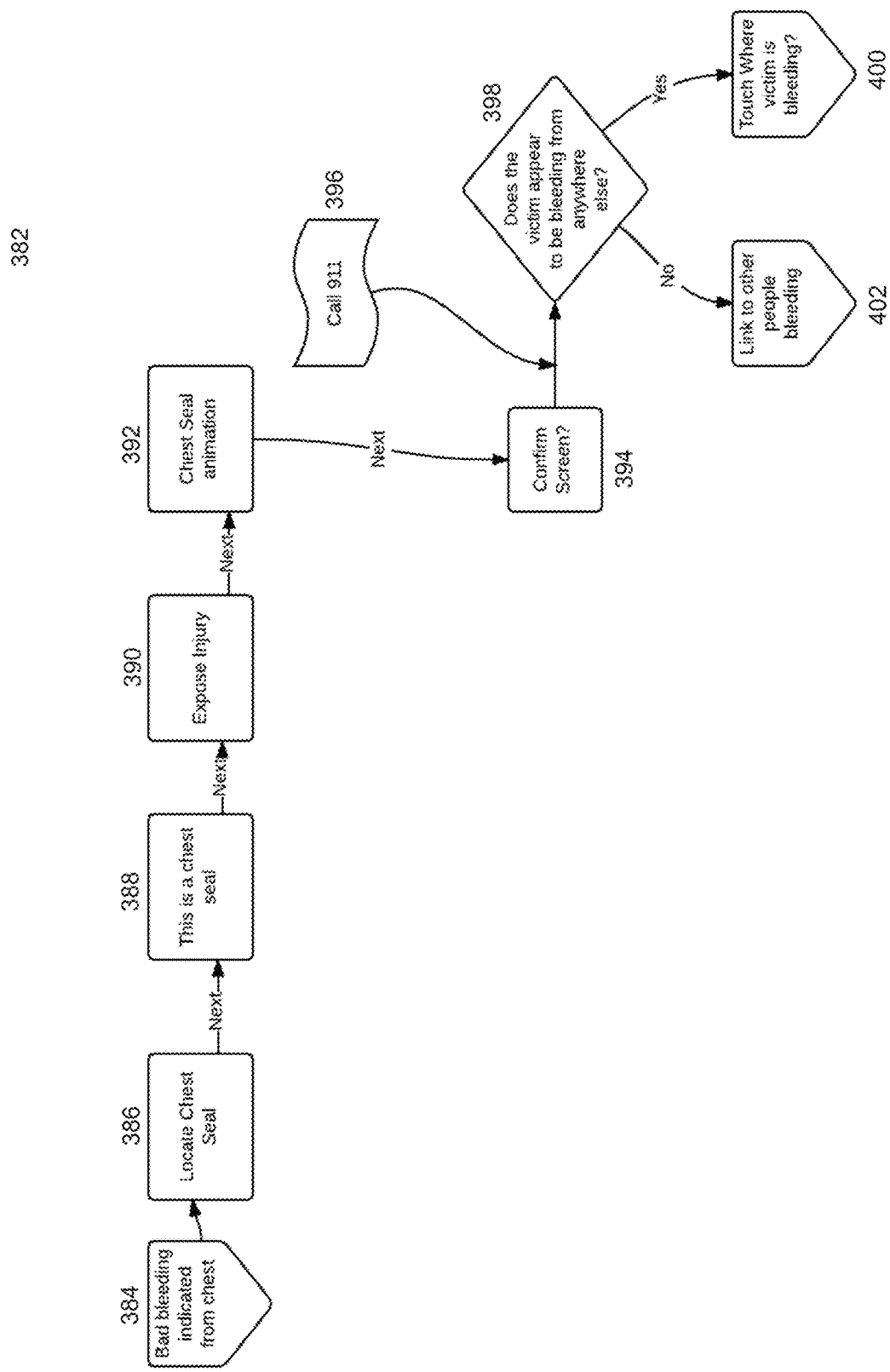
FIG. 8 is a flowchart illustrating an example query flow for a severely bleeding chest, forming part of the triage protocol of FIGS. 2-5.

FIG. 8 illustrates the query flow for a severely bleeding chest 382, which is accessed via link box 40 of FIG. 2 (e.g. in response to the user touching the chest on the graphic representation of a human body on the touch screen display (e.g. FIG. 68)) and begins at link box 384. The first box 386 of the query flow 382 is an instructional box representing a GUI screen that instructs the user to locate a chest seal within the accompanying medical tool kit 12. By way of example, the represented GUI screen may also display a layout image of the tool kit and highlight with specificity the location of the chest seal. The next box 388 represents a GUI screen that displays a zoomed in image of a chest seal so the user knows what to look for. The query flow proceeds to information box 390, which represents a GUI screen presented by the computer instructing the user to expose the victim's injury. Upon receiving input from the user to proceed (e.g. by tapping an icon or through voice command), the computer advances the flow to box 392, which represents a GUI screen showing the user how to apply the chest seal to the victim (e.g. through animated video). The next box 394 in the flow represents a GUI screen presented to the user to confirm that the chest seal is in place. After the user positively indicates that the chest seal is in place, the computer alerts the user (via alert box 396) to dial 9-1-1 to call for help if they have not already done so. The query flow then proceeds to box 398, which represents a GUI screen that asks the user if the victim appears to be bleeding badly anywhere else. If the user indicates a "Yes" answer (e.g. the victim is badly bleeding elsewhere), then the computer redirects the query flow (via link box 400) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 402) to box 48 of FIG. 2 (e.g. query box asking if anyone else is bleeding badly), and the flow proceeds from there.

Once the user indicates to the app that the chest seal has been applied to the victim, the computer starts a recheck timer to remind/require the user to complete the chest seal reset protocol at a regular specified interval. In the instant example the chest seal recheck interval is set at every five minutes (5:00), however the app may be programmed to include a different medically reasonable time interval (not determined or adjusted by the user in the field). At the expiration of the specified time interval, regardless of the GUI screen the user may be currently viewing, the computer directs the query flow automatically to the Chest Seal Recheck flow of FIG. 62.

Figure 9:
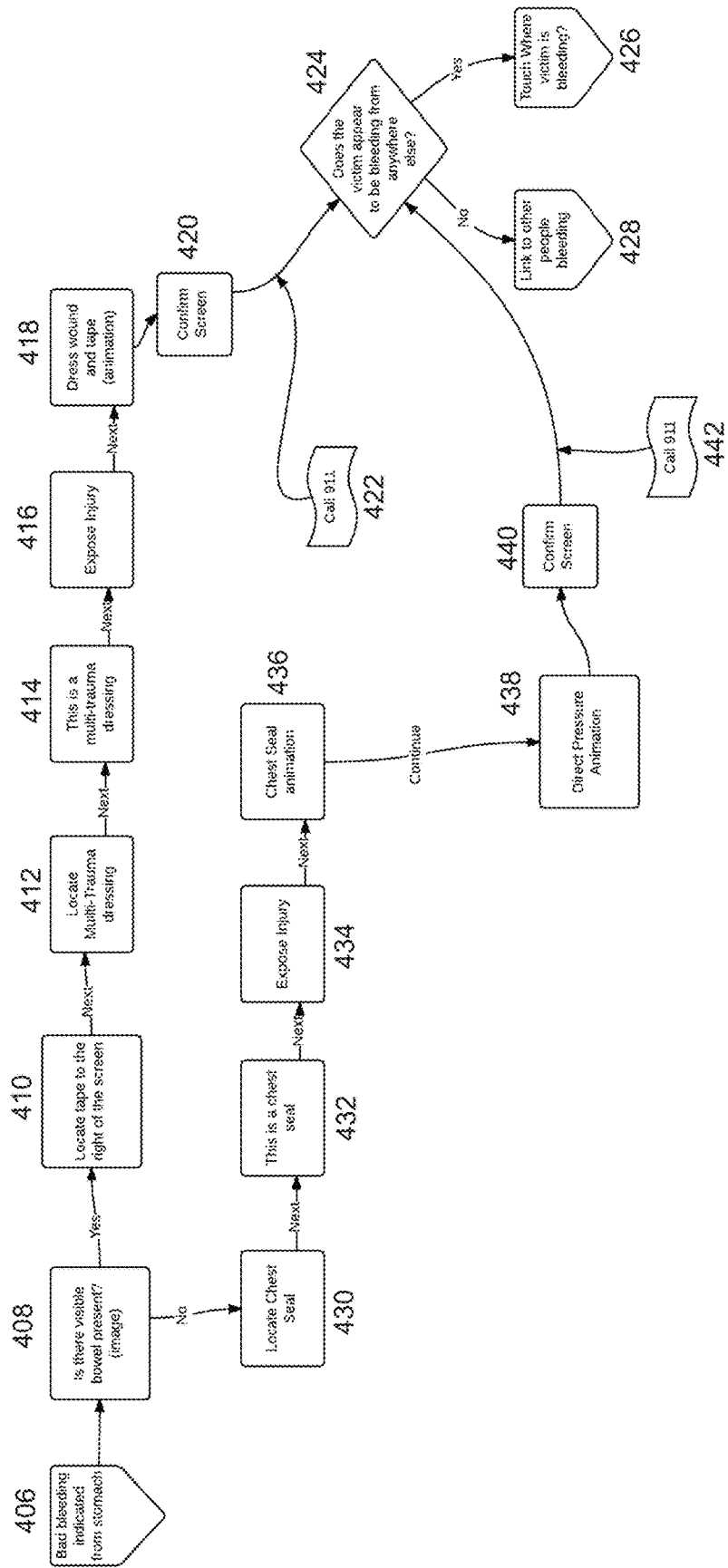
FIG. 9 is a flowchart illustrating an example query flow for a severely bleeding stomach, forming part of the triage protocol of FIGS. 2-5.

FIG. 9 illustrates the query flow for a severely bleeding stomach 404, which is accessed via link box 40 of FIG. 2 (e.g. in response to the user touching the stomach on the graphic representation of a human body on the touch screen display (e.g. FIG. 68)) and begins at link box 406. The first box 408 of the query flow represents a GUI screen that asks the user if there is visible bowel present, and may include a visual image of what this might look like. If the user indicates a "Yes" answer to the computer (e.g. there is visible bowel present), the query flow proceeds to box 410, which represents a GUI screen that instructs the user to locate tape in the medical tool kit 12, which by way of example may be located to the right of the display screen. The next box 412 of the query flow 404 is an instructional box representing a GUI screen that instructs the user to locate a multi-trauma dressing within the accompanying medical tool kit 12. By way of example, the represented GUI screen may also display a layout image of the tool kit and highlight with specificity the location of the multi-trauma dressing. The next box 414 represents a GUI screen that displays a zoomed in image of a multi-trauma dressing so the user knows what to look for. The query flow proceeds to information box 416, which represents a GUI screen presented by the computer instructing the user to expose the victim's injury. Upon receiving input from the user to proceed (e.g. by tapping an icon or through voice command), the computer advances the flow to box 418, which represents a GUI screen showing the user how to apply the multi-trauma dressing and tape to the victim (e.g. through animated video). The next box 420 in the flow 404 represents a GUI screen presented to the user to confirm that the multi-trauma dressing and tape are in place. After the user positively indicates that the multi-trauma dressing and tape are in place, the computer alerts the user (via alert box 422) to dial 9-1-1 to call for help if they have not already done so. The query flow 404 then proceeds to box 424, which represents a GUI screen that asks the user if the victim appears to be bleeding badly anywhere else. If the user indicates a "Yes" answer (e.g. the victim is badly bleeding elsewhere), then the computer redirects the query flow (via link box 426) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 428) to box 48 of FIG. 2 (e.g. query box asking if anyone else is bleeding badly), and the flow proceeds from there.

If the user indicates a "No" answer to the question of box 408 (e.g. there is no visible bowel present), the query flow 404 proceeds to box 430, which represents a GUI screen that instructs the user to locate a chest seal within the accompanying medical tool kit 12. By way of example, the represented GUI screen may also display a layout image of the tool kit and highlight with specificity the location of the chest seal. The next box 432 represents a GUI screen that displays a zoomed in image of a chest seal so the user knows what to look for. The query flow proceeds to information box 434, which represents a GUI screen presented by the computer instructing the user to expose the victim's injury. Upon receiving input from the user to proceed (e.g. by tapping an icon or through voice command), the computer advances the flow to box 436, which represents a GUI screen showing the user how to apply the chest seal to the victim (e.g. through animated video). In a case of a badly bleeding stomach, a chest seal alone may not be sufficient to stop the bleeding. Thus the next box 438 of the flow represents a GUI screen showing the user how to also apply direct pressure to the wound (e.g. through animated video). The next box 440 in the flow represents a GUI screen presented to the user to confirm that the chest seal is in place. After the user positively indicates that the chest seal is in place, the computer starts the chest seal recheck timer as discussed above and alerts the user (via alert box 442) to dial 9-1-1 to call for help if they have not already done so. The computer then advances query flow to box 424, which proceeds as discussed above.

Figure 10:
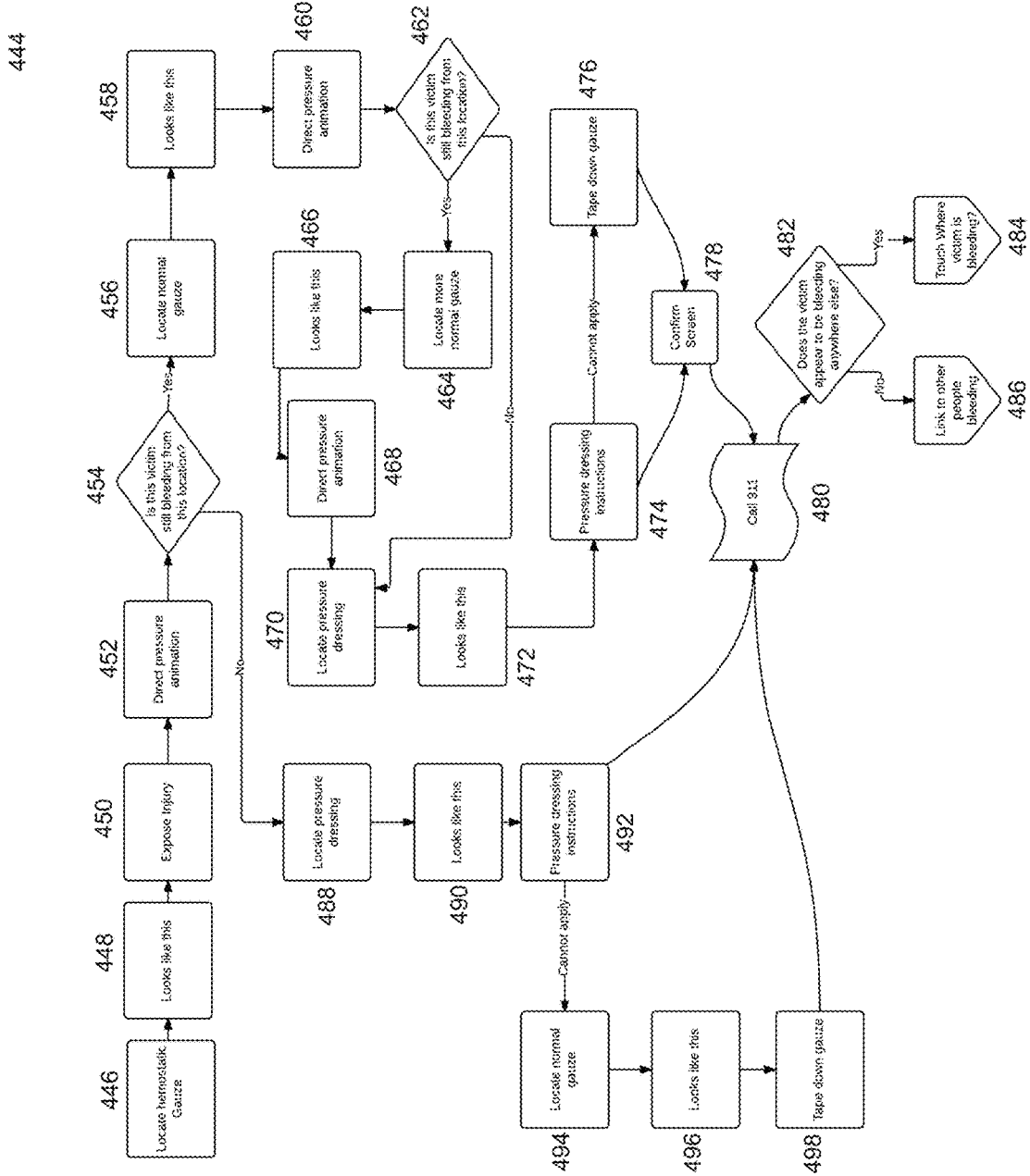
FIG. 10 is a flowchart illustrating an example query flow for a severely bleeding junctional arm, forming part of the triage protocol of FIGS. 2-5.

FIG. 10 illustrates the query flow for a severely bleeding junctional arm 444, which is accessed via link box 40 of FIG. 2 (e.g. in response to the user touching a shoulder on the graphic representation of a human body on the touch screen display (e.g. FIG. 68)) and begins with instruction box 446, which represents a GUI screen instructing the user to locate hemostatic gauze within the accompanying medical tool kit 12. By way of example, the represented GUI screen may also display a layout image of the tool kit and highlight with specificity the location of the hemostatic gauze. The next box 448 represents a GUI screen that displays a zoomed in image of hemostatic gauze so the user knows what to look for. The next box in the query flow 444 represents a GUI screen that instructs the user to expose the victim's injury.

The next box 452 represents a GUI screen that provides specific instruction on how to apply direct pressure to a victim's arm joint using hemostatic gauze, for example with text instructions, visual aid (e.g. pictures and/or video) and/or audio instructions. The next box in the query flow is query box 454, which represents a GUI screen asking the user if the victim is still bleeding in this location.

If the user indicates a "Yes" answer (e.g. the victim is still bleeding in this location), the query flow advances to box 456, which represents a GUI screen instructing the user to locate normal gauze within the accompanying medical tool kit 12. By way of example, the represented GUI screen may also display a layout image of the tool kit and highlight with specificity the location of the normal gauze. The next box 458 represents a GUI screen that displays a zoomed in image of normal gauze so the user knows what to look for. The next box in the query flow 460 represents a GUI screen that provides specific instruction on how to apply direct pressure to a victim's arm joint using normal gauze, for example with text instructions, visual aid (e.g. pictures and/or video) and/or audio instructions. The next box in the query flow is query box 462, which represents a GUI screen asking the user if the victim is still bleeding in this location.

If the user indicates a "Yes" answer (e.g. the victim is still bleeding in this location), the query flow advances to box 464, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 466 represents a GUI screen that displays a zoomed in image of normal gauze to remind the user what to look for. The next box in the query flow 468 represents a GUI screen that provides specific instruction on how to apply direct pressure to a victim's arm joint using normal gauze, for example with text instructions, visual aid (e.g. pictures and/or video) and/or audio instructions. When the user indicates that this step has been completed, or alternatively if the user indicates a "No" answer to the question of box 462 (e.g. bleeding has stopped in this location), the query flow proceeds to box 470, which represents a GUI screen prompting the user to locate the pressure dressing within the accompanying medical tool kit 12. By way of example, the represented GUI screen may also display a layout image of the tool kit and highlight with specificity the location of the pressure dressing. The next box 472 represents a GUI screen that displays a zoomed in image of pressure dressing so the user knows what to look for. The next box in the query flow is an instruction box 474 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 476, which represents a GUI screen that instructs the user to tape the normal gauze to the wound. Once the normal gauze has been taped to the wound, or alternatively if the user was able to apply the pressure dressing to the wound (e.g. box 474), the next box in the query flow is query box 478, which represents a GUI screen asking the user to confirm that the victim is no longer bleeding badly in this location.

After the user positively indicates that the pressure dressing and/or taped gauze are in place, the computer alerts the user (via alert box 480) to dial 9-1-1 to call for help if they have not already done so. The query flow 444 then proceeds to box 482, which represents a GUI screen that asks the user if the victim appears to be bleeding badly anywhere else. If the user indicates a "Yes" answer (e.g. the victim is badly bleeding elsewhere), then the computer redirects the query flow (via link box 484) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 486) to box 48 of FIG. 2 (e.g. query box asking if anyone else is bleeding badly), and the flow proceeds from there.

If the user indicates a "No" answer to the question of box 454 (e.g. the victim no longer bleeding badly at this location), the computer directs the query flow to box 488, which represents a GUI screen prompting the user to locate the pressure dressing within the accompanying medical tool kit 12. By way of example, the represented GUI screen may also display a layout image of the tool kit and highlight with specificity the location of the pressure dressing. The next box 490 represents a GUI screen that displays a zoomed in image of pressure dressing so the user knows what to look for. The next box in the query flow is an instruction box 492 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 494, which represents a GUI screen that prompts the user to locate the normal gauze within the accompanying medical tool kit 12. By way of example, the represented GUI screen may also display a layout image of the tool kit and highlight with specificity the location of the normal gauze. The next box 496 represents a GUI screen that displays a zoomed in image of normal gauze so the user knows what to look for. The next box in the query flow is an instruction box 498 that represents a GUI screen that instructs the user to tape the gauze to the wound. Once the gauze has been taped to the wound, or alternatively if the user was able to apply the pressure dressing to the wound, the query flow directs to box 480 (e.g. call 9-1-1), and proceeds as described above.

Figure 11:
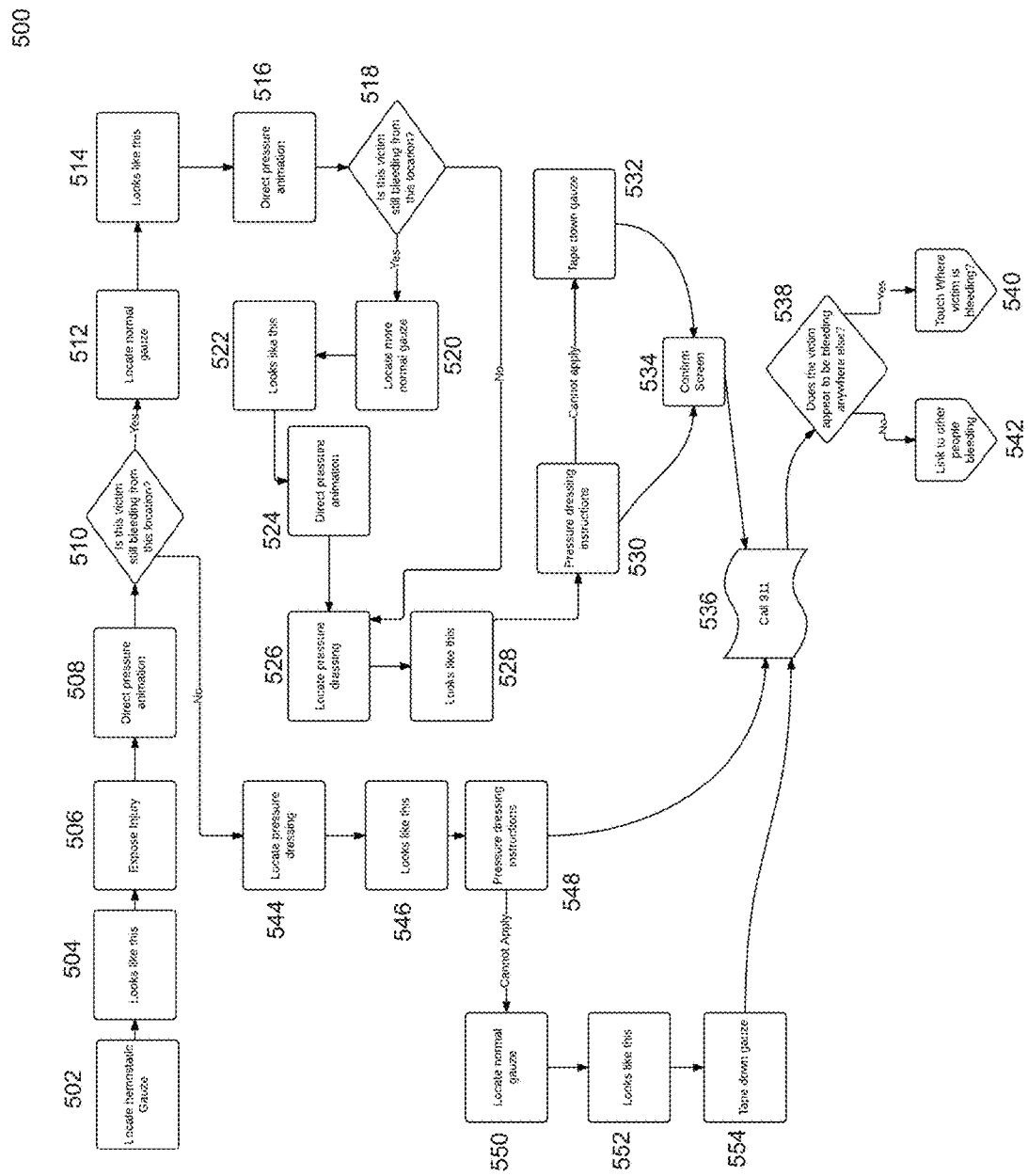
FIG. 11 is a flowchart illustrating an example query flow for a severely bleeding junctional pelvis, forming part of the triage protocol of FIGS. 2-5.

FIG. 11 illustrates the query flow for a severely bleeding junctional pelvis 500, which is accessed via link box 40 of FIG. 2 (e.g. in response to the user touching the pelvis region on the graphic representation of a human body on the touch screen display (e.g. FIG. 68)) and begins with instruction box 502, which represents a GUI screen instructing the user to locate hemostatic gauze within the accompanying medical tool kit 12. By way of example, the represented GUI screen may also display a layout image of the tool kit and highlight with specificity the location of the hemostatic gauze. The next box 504 represents a GUI screen that displays a zoomed in image of hemostatic gauze so the user knows what to look for. The next box in the query flow 506 represents a GUI screen that instructs the user to expose the victim's injury. The next box 508 represents a GUI screen that provides specific instruction on how to apply direct pressure to a victim's pelvis joint using hemostatic gauze, for example with text instructions, visual aid (e.g. pictures and/or video) and/or audio instructions. The next box in the query flow is query box 510, which represents a GUI screen asking the user if the victim is still bleeding in this location.

If the user indicates a "Yes" answer (e.g. the victim is still bleeding in this location), the query flow advances to box 512, which represents a GUI screen instructing the user to locate normal gauze within the accompanying medical tool kit 12. By way of example, the represented GUI screen may also display a layout image of the tool kit and highlight with specificity the location of the normal gauze. The next box 514 represents a GUI screen that displays a zoomed in image of normal gauze so the user knows what to look for. The next box in the query flow 516 represents a GUI screen that provides specific instruction on how to apply direct pressure to a victim's pelvis joint using normal gauze, for example with text instructions, visual aid (e.g. pictures and/or video) and/or audio instructions. The next box in the query flow is query box 518, which represents a GUI screen asking the user if the victim is still bleeding in this location.

If the user indicates a "Yes" answer (e.g. the victim is still bleeding in this location), the query flow advances to box 520, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 522 represents a GUI screen that displays a zoomed in image of normal gauze to remind the user what to look for. The next box in the query flow 524 represents a GUI screen that provides specific instruction on how to apply direct pressure to a victim's pelvis joint using normal gauze, for example with text instructions, visual aid (e.g. pictures and/or video) and/or audio instructions. When the user indicates that this step has been completed, or alternatively if the user indicates a "No" answer to the question of box 518 (e.g. bleeding has stopped in this location), the query flow proceeds to box 526, which represents a GUI screen prompting the user to locate the pressure dressing within the accompanying medical tool kit 12. By way of example, the represented GUI screen may also display a layout image of the tool kit and highlight with specificity the location of the pressure dressing. The next box 528 represents a GUI screen that displays a zoomed in image of pressure dressing so the user knows what to look for. The next box in the query flow is an instruction box 530 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 532, which represents a GUI screen that instructs the user to tape the normal gauze to the wound. Once the normal gauze has been taped to the wound, or alternatively if the user was able to apply the pressure dressing to the wound (e.g. box 530), the next box in the query flow is query box 534, which represents a GUI screen asking the user to confirm that the victim is no longer bleeding badly in this location.

After the user positively indicates that the pressure dressing and/or taped gauze are in place, the computer alerts the user (via alert box 536) to dial 9-1-1 to call for help if they have not already done so. The query flow 500 then proceeds to box 538, which represents a GUI screen that asks the user if the victim appears to be bleeding badly anywhere else. If the user indicates a "Yes" answer (e.g. the victim is badly bleeding elsewhere), then the computer redirects the query flow (via link box 540) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 542) to box 48 of FIG. 2 (e.g. query box asking if anyone else is bleeding badly), and the flow proceeds from there.

If the user indicates a "No" answer to the question of box 510 (e.g. the victim no longer bleeding badly at this location), the computer directs the query flow to box 544, which represents a GUI screen prompting the user to locate the pressure dressing within the accompanying medical tool kit 12. By way of example, the represented GUI screen may also display a layout image of the tool kit and highlight with specificity the location of the pressure dressing. The next box 546 represents a GUI screen that displays a zoomed in image of pressure dressing so the user knows what to look for. The next box in the query flow is an instruction box 548 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 550, which represents a GUI screen that prompts the user to locate the normal gauze within the accompanying medical tool kit 12. By way of example, the represented GUI screen may also display a layout image of the tool kit and highlight with specificity the location of the normal gauze. The next box 552 represents a GUI screen that displays a zoomed in image of normal gauze so the user knows what to look for. The next box in the query flow is an instruction box 554 that represents a GUI screen that instructs the user to tape the gauze to the wound. Once the gauze has been taped to the wound, or alternatively if the user was able to apply the pressure dressing to the wound, the query flow directs to box 536 (e.g. call 9-1-1), and proceeds as described above.

Figure 12:
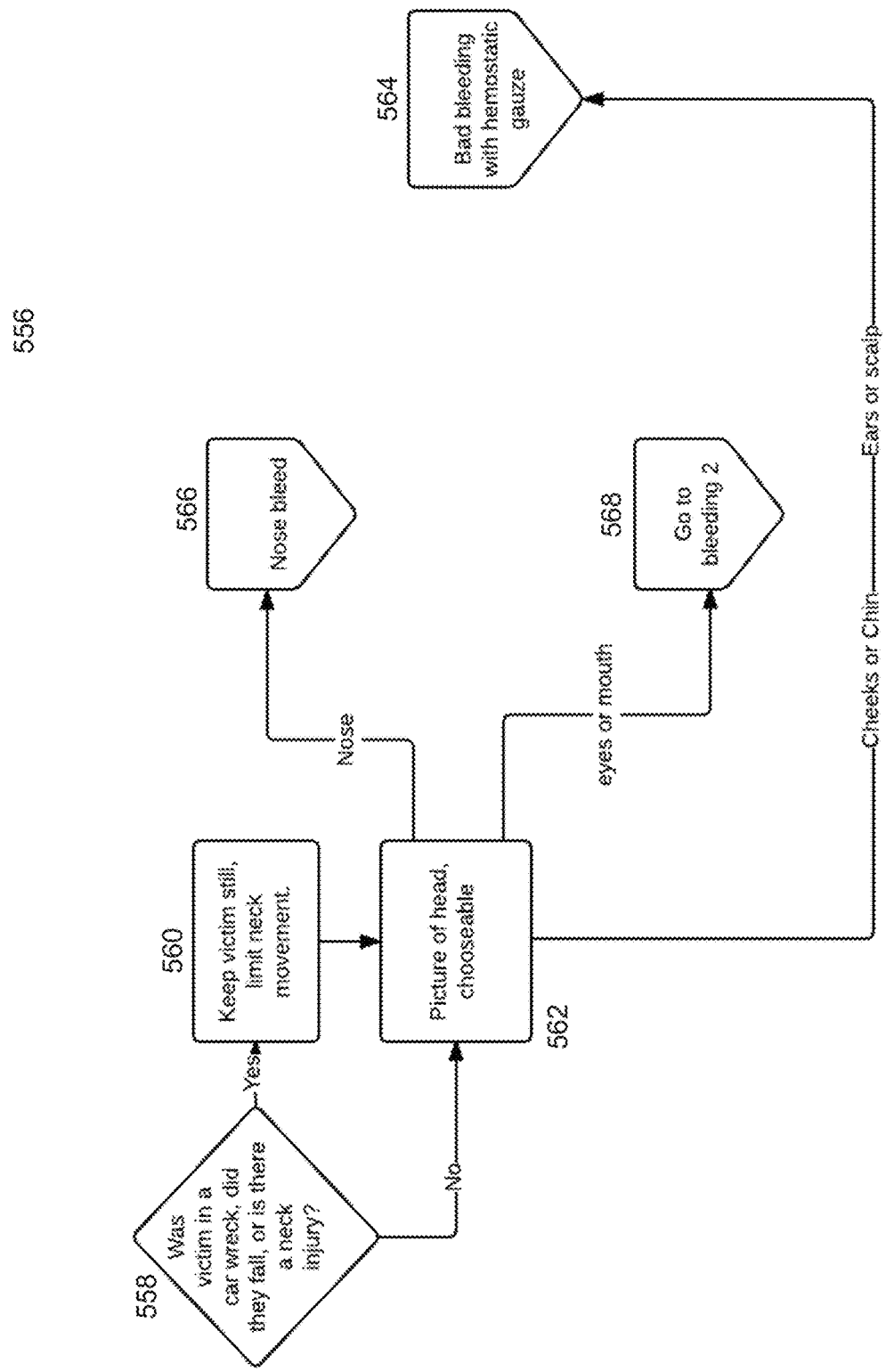
FIG. 12 is a flowchart illustrating an example query flow for determining the specific location of severe facial bleeding, forming part of the triage protocol of FIGS. 2-5.

FIG. 12 illustrates the query flow 556 for determining the specific location of severe facial bleeding, which is accessed via link box 40 of FIG. 2 (e.g. in response to the user touching the head on the graphic representation of a human body on the touch screen display (e.g. FIG. 68)) and begins with query box 558, which represents a GUI screen asking the user if the victim was in a car wreck, fell from height, or suffered a neck injury. If the user indicates a "Yes" response, the query flow advances to box 560, which represents a GUI screen instructing the user to keep the victim still and limit neck movement. From this point, or alternatively if the user indicates a "No" response to the question in box 558, the query flow advances to box 562, which represents a GUI screen that displays an interactive graphic representation of a human face/head and directs the user to touch the location of the bleeding on the human facial diagram. This will cause the computer to link to the appropriate query flow corresponding to the facial part that the user indicated. For example, the query flows for bad bleeding scalp, neck, ears, chin, and cheek may be accessed through link box 564. The query flow for bad bleeding nose may be accessed via link box 566. The query flows for bad bleeding eyes or mouth may be accessed via link box 568.

Figure 13:
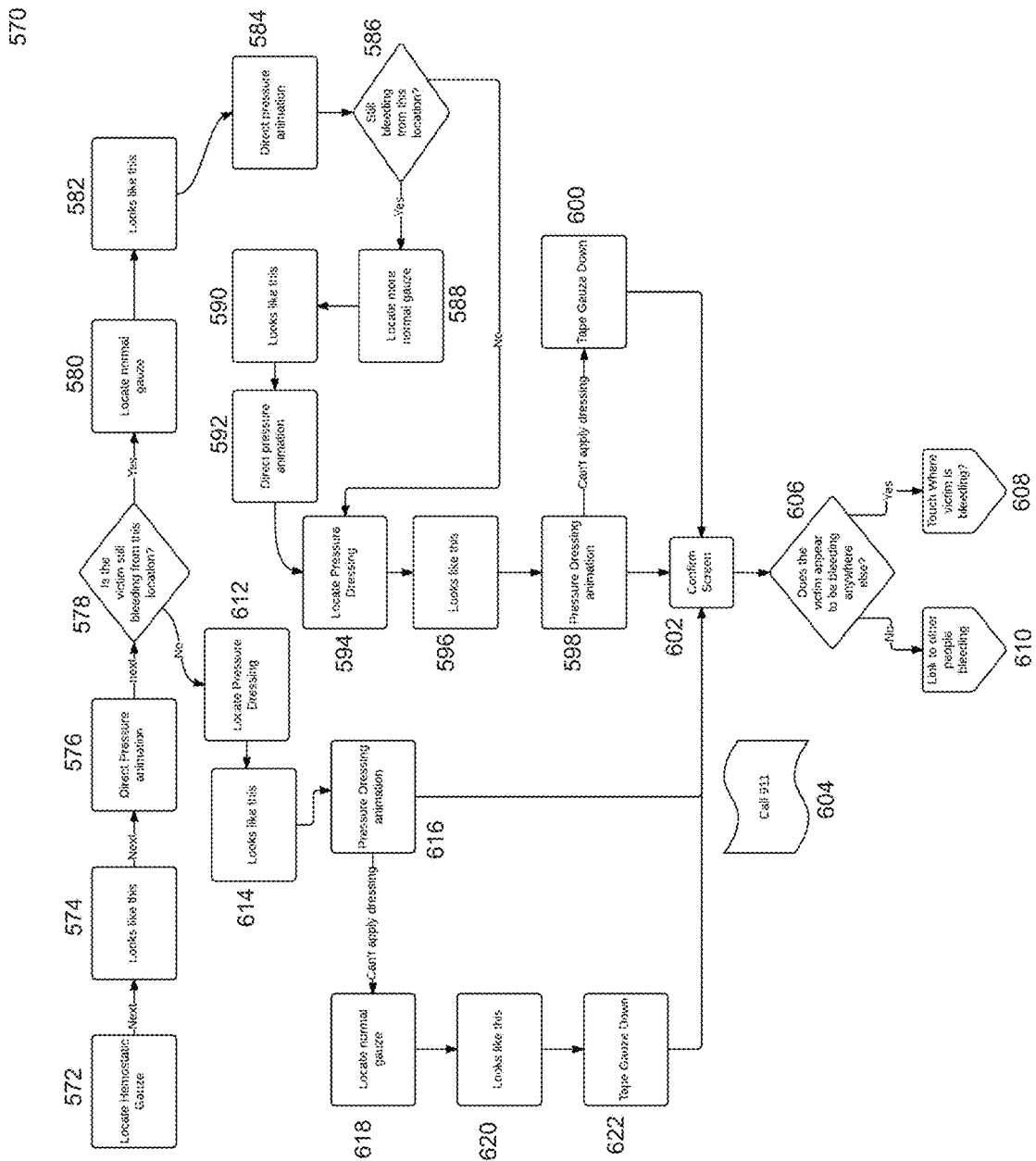
FIG. 13 is a flowchart illustrating an example query flow for a severely bleeding scalp, forming part of the triage protocol of FIGS. 2-5.

FIG. 13 illustrates the query flow for a severely bleeding scalp 570, which is accessed via link box 564 of FIG. 12 (e.g. in response to the user touching the scalp on the graphic representation of a human face/head on the touch screen display) and begins with instruction box 572, which represents a GUI screen instructing the user to locate hemostatic gauze within the accompanying medical tool kit 12. By way of example, the represented GUI screen may also display a layout image of the tool kit and highlight with specificity the location of the hemostatic gauze. The next box 574 represents a GUI screen that displays a zoomed in image of hemostatic gauze so the user knows what to look for. The next box 576 represents a GUI screen that provides specific instruction on how to apply direct pressure to a victim's wound using hemostatic gauze, for example with text instructions, visual aid (e.g. pictures and/or video) and/or audio instructions. The next box in the query flow is query box 578, which represents a GUI screen asking the user if the victim is still bleeding in this location.

If the user indicates a "Yes" answer (e.g. the victim is still bleeding in this location), the query flow advances to box 580, which represents a GUI screen instructing the user to locate normal gauze within the accompanying medical tool kit 12. By way of example, the represented GUI screen may also display a layout image of the tool kit and highlight with specificity the location of the normal gauze. The next box 582 represents a GUI screen that displays a zoomed in image of normal gauze so the user knows what to look for. The next box in the query flow 584 represents a GUI screen that provides specific instruction on how to apply direct pressure to a victim's wound using normal gauze, for example with text instructions, visual aid (e.g. pictures and/or video) and/or audio instructions. The next box in the query flow is query box 586, which represents a GUI screen asking the user if the victim is still bleeding in this location.

If the user indicates a "Yes" answer (e.g. the victim is still bleeding in this location), the query flow advances to box 588, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 590 represents a GUI screen that displays a zoomed in image of normal gauze to remind the user what to look for. The next box in the query flow 592 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 586 (e.g. bleeding has stopped in this location), the query flow proceeds to box 594, which represents a GUI screen prompting the user to locate the pressure dressing within the accompanying medical tool kit 12. By way of example, the represented GUI screen may also display a layout image of the tool kit and highlight with specificity the location of the pressure dressing. The next box 596 represents a GUI screen that displays a zoomed in image of pressure dressing so the user knows what to look for. The next box in the query flow is an instruction box 598 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 600, which represents a GUI screen that instructs the user to tape the normal gauze to the wound. Once the normal gauze has been taped to the wound, or alternatively if the user was able to apply the pressure dressing to the wound (e.g. box 598), the next box in the query flow is query box 602, which represents a GUI screen asking the user to confirm that the victim is no longer bleeding badly in this location.

After the user positively indicates that the pressure dressing and/or taped gauze are in place, the computer alerts the user (via alert box 604) to dial 9-1-1 to call for help if they have not already done so. The query flow 570 then proceeds to box 606, which represents a GUI screen that asks the user if the victim appears to be bleeding badly anywhere else. If the user indicates a "Yes" answer (e.g. the victim is badly bleeding elsewhere), then the computer redirects the query flow (via link box 608) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 610) to box 48 of FIG. 2 (e.g. query box asking if anyone else is bleeding badly), and the flow proceeds from there.

If the user indicates a "No" answer to the question of box 578 (e.g. the victim no longer bleeding badly at this location), the computer directs the query flow to box 612, which represents a GUI screen prompting the user to locate the pressure dressing within the accompanying medical tool kit 12. By way of example, the represented GUI screen may also display a layout image of the tool kit and highlight with specificity the location of the pressure dressing. The next box 614 represents a GUI screen that displays a zoomed in image of pressure dressing so the user knows what to look for. The next box in the query flow is an instruction box 616 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 618, which represents a GUI screen that prompts the user to locate the normal gauze within the accompanying medical tool kit 12. By way of example, the represented GUI screen may also display a layout image of the tool kit and highlight with specificity the location of the normal gauze. The next box 620 represents a GUI screen that displays a zoomed in image of normal gauze so the user knows what to look for. The next box in the query flow is an instruction box 622 that represents a GUI screen that instructs the user to tape the gauze to the wound. Once the gauze has been taped to the wound, or alternatively if the user was able to apply the pressure dressing to the wound, the query flow directs to box 602 (e.g. confirm no longer bleeding badly), and proceeds as described above.

Figure 14:
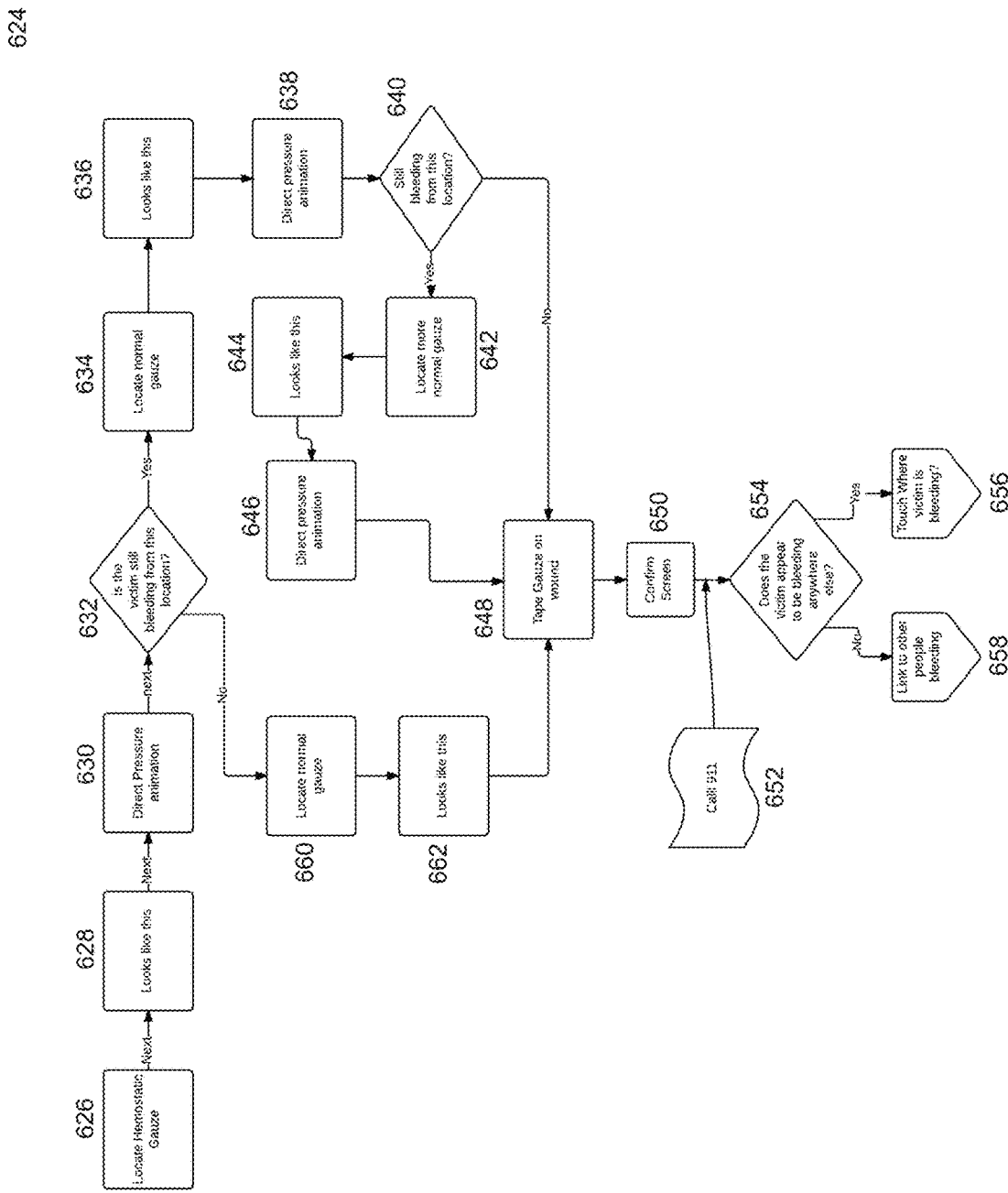
FIG. 14 is a flowchart illustrating an example query flow for a severely bleeding neck, forming part of the triage protocol of FIGS. 2-5.

FIG. 14 illustrates the query flow for a severely bleeding neck 624, which is accessed via link box 564 of FIG. 12 (e.g. in response to the user touching the neck on the graphic representation of a human face/head on the touch screen display) and begins with instruction box 626, which represents a GUI screen instructing the user to locate hemostatic gauze within the accompanying medical tool kit 12. By way of example, the represented GUI screen may also display a layout image of the tool kit and highlight with specificity the location of the hemostatic gauze. The next box 628 represents a GUI screen that displays a zoomed in image of hemostatic gauze so the user knows what to look for. The next box 630 represents a GUI screen that provides specific instruction on how to apply direct pressure to a victim's wound using hemostatic gauze, for example with text instructions, visual aid (e.g. pictures and/or video) and/or audio instructions. The next box in the query flow is query box 632, which represents a GUI screen asking the user if the victim is still bleeding in this location.

If the user indicates a "Yes" answer (e.g. the victim is still bleeding in this location), the query flow advances to box 634, which represents a GUI screen instructing the user to locate normal gauze within the accompanying medical tool kit 12. By way of example, the represented GUI screen may also display a layout image of the tool kit and highlight with specificity the location of the normal gauze. The next box 636 represents a GUI screen that displays a zoomed in image of normal gauze so the user knows what to look for. The next box in the query flow 638 represents a GUI screen that provides specific instruction on how to apply direct pressure to a victim's wound using normal gauze, for example with text instructions, visual aid (e.g. pictures and/or video) and/or audio instructions. The next box in the query flow is query box 640, which represents a GUI screen asking the user if the victim is still bleeding in this location.

If the user indicates a "Yes" answer (e.g. the victim is still bleeding in this location), the query flow advances to box 642, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 644 represents a GUI screen that displays a zoomed in image of normal gauze to remind the user what to look for. The next box in the query flow 646 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 640 (e.g. bleeding has stopped in this location), the query flow proceeds to box 648, which represents a GUI screen instructing the user to tape the normal gauze to the wound. Once the normal gauze has been taped to the wound, the next box in the query flow is query box 650, which represents a GUI screen asking the user to confirm that the victim is no longer bleeding badly in this location.

After the user positively indicates that the taped gauze is in place, the computer alerts the user (via alert box 652) to dial 9-1-1 to call for help if they have not already done so. The query flow 624 then proceeds to box 654, which represents a GUI screen that asks the user if the victim appears to be bleeding badly anywhere else. If the user indicates a "Yes" answer (e.g. the victim is badly bleeding elsewhere), then the computer redirects the query flow (via link box 656) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 658) to box 48 of FIG. 2 (e.g. query box asking if anyone else is bleeding badly), and the flow proceeds from there.

If the user indicates a "No" answer to the question of box 632 (e.g. the victim no longer bleeding badly at this location), the computer directs the query flow to box 660, which represents a GUI screen that prompts the user to locate the normal gauze within the accompanying medical tool kit 12.

By way of example, the represented GUI screen may also display a layout image of the tool kit and highlight with specificity the location of the normal gauze. The next box 662 represents a GUI screen that displays a zoomed in image of normal gauze so the user knows what to look for. The query flow then directs to box 648 (e.g. tape gauze to wound), and proceeds as described above.

Figure 15:
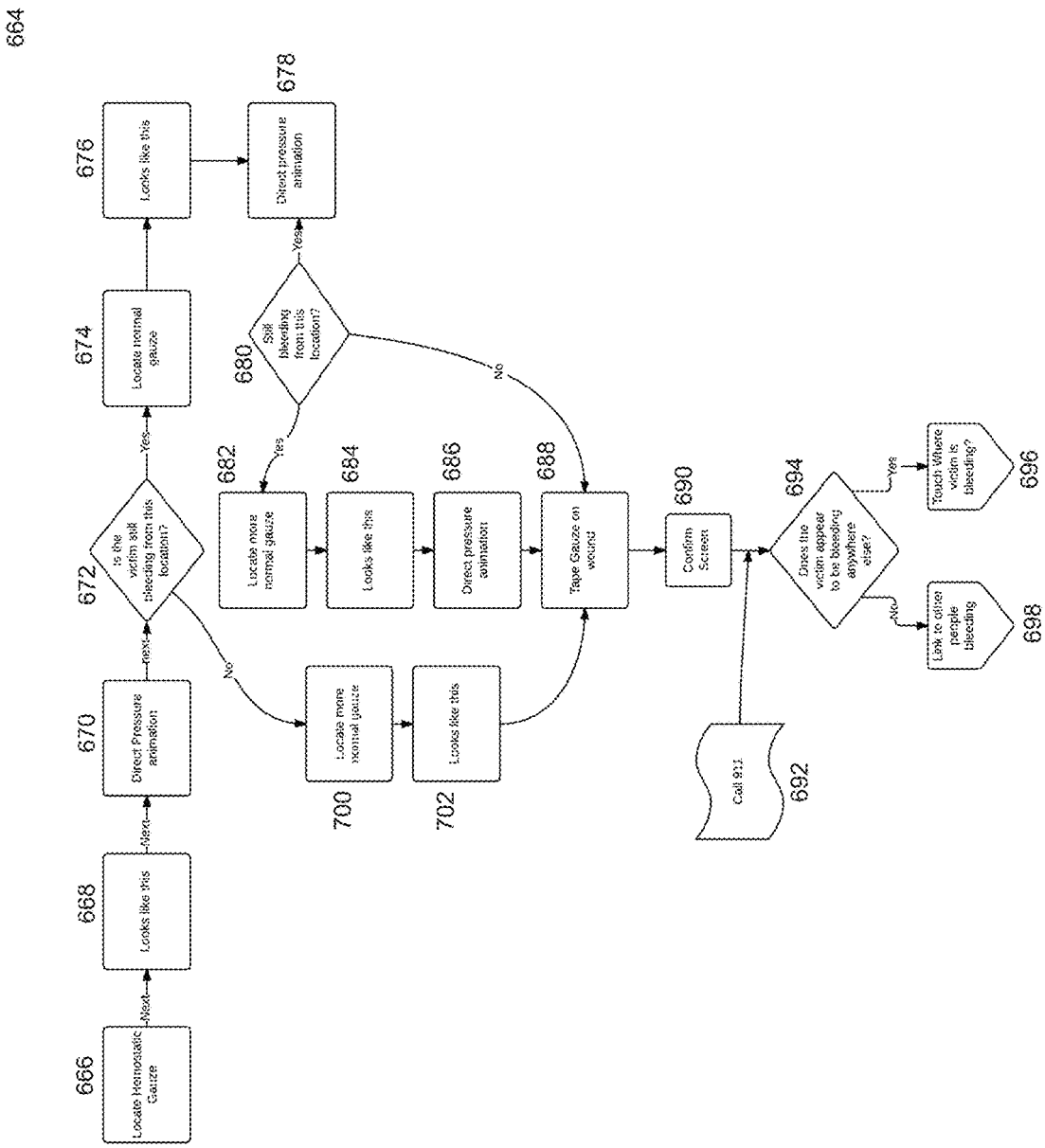
FIG. 15 is a flowchart illustrating an example query flow for one or more severely bleeding ears, forming part of the triage protocol of FIGS. 2-5.

FIG. 15 illustrates the query flow for one or more severely bleeding ears 664, which is accessed via link box 564 of FIG. 12 (e.g. in response to the user touching the ears on the graphic representation of a human face/head on the touch screen display) and begins with instruction box 666, which represents a GUI screen instructing the user to locate hemostatic gauze within the accompanying medical tool kit 12. By way of example, the represented GUI screen may also display a layout image of the tool kit and highlight with specificity the location of the hemostatic gauze. The next box 668 represents a GUI screen that displays a zoomed in image of hemostatic gauze so the user knows what to look for. The next box 670 represents a GUI screen that provides specific instruction on how to apply direct pressure to a victim's wound using hemostatic gauze, for example with text instructions, visual aid (e.g. pictures and/or video) and/or audio instructions. The next box in the query flow is query box 672, which represents a GUI screen asking the user if the victim is still bleeding in this location.

If the user indicates a "Yes" answer (e.g. the victim is still bleeding in this location), the query flow advances to box 674, which represents a GUI screen instructing the user to locate normal gauze within the accompanying medical tool kit 12. By way of example, the represented GUI screen may also display a layout image of the tool kit and highlight with specificity the location of the normal gauze. The next box 676 represents a GUI screen that displays a zoomed in image of normal gauze so the user knows what to look for. The next box in the query flow 678 represents a GUI screen that provides specific instruction on how to apply direct pressure to a victim's wound using normal gauze, for example with text instructions, visual aid (e.g. pictures and/or video) and/or audio instructions. The next box in the query flow is query box 680, which represents a GUI screen asking the user if the victim is still bleeding in this location.

If the user indicates a "Yes" answer (e.g. the victim is still bleeding in this location), the query flow advances to box 682, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 684 represents a GUI screen that displays a zoomed in image of normal gauze to remind the user what to look for. The next box in the query flow 686 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 680 (e.g. bleeding has stopped in this location), the query flow proceeds to box 688, which represents a GUI screen instructing the user to tape the normal gauze to the wound. Once the normal gauze has been taped to the wound, the next box in the query flow is query box 690, which represents a GUI screen asking the user to confirm that the victim is no longer bleeding badly in this location.

After the user positively indicates that the taped gauze is in place, the computer alerts the user (via alert box 692) to dial 9-1-1 to call for help if they have not already done so. The query flow 664 then proceeds to box 694, which represents a GUI screen that asks the user if the victim appears to be bleeding badly anywhere else. If the user indicates a "Yes" answer (e.g. the victim is badly bleeding elsewhere), then the computer redirects the query flow (via link box 696) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 698) to box 48 of FIG. 2 (e.g. query box asking if anyone else is bleeding badly), and the flow proceeds from there.

If the user indicates a "No" answer to the question of box 672 (e.g. the victim no longer bleeding badly at this location), the computer directs the query flow to box 700, which represents a GUI screen that prompts the user to locate the normal gauze within the accompanying medical tool kit 12. By way of example, the represented GUI screen may also display a layout image of the tool kit and highlight with specificity the location of the normal gauze. The next box 702 represents a GUI screen that displays a zoomed in image of normal gauze so the user knows what to look for. The query flow then directs to box 688 (e.g. tape gauze to wound), and proceeds as described above.

Figure 16:
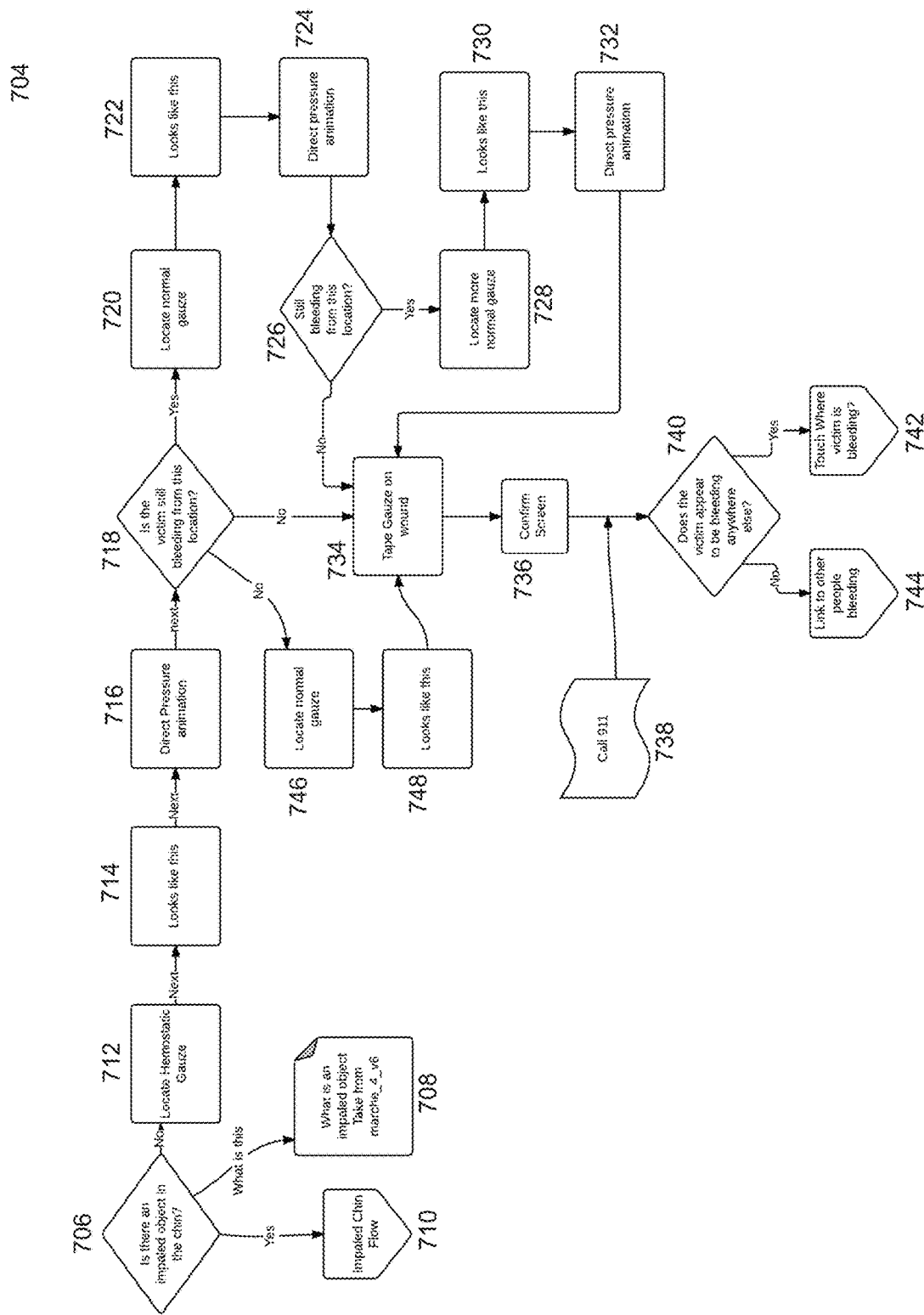
FIG. 16 is a flowchart illustrating an example query flow for a severely bleeding chin, forming part of the triage protocol of FIGS. 2-5.

FIG. 16 illustrates the query flow for a severely bleeding chin 704, which is accessed via link box 564 of FIG. 12 (e.g. in response to the user touching the chin on the graphic representation of a human face/head on the touch screen display) and begins with a query box 706, which represents a GUI screen asking the user if there is an impaled object in the chin. An information box 708 is available via an interactive icon present on the represented GUI screen if the user needs more information about what an "impaled object" is (e.g. "an impaled object is a foreign body that penetrates the skin and remains embedded in the body"). If the user indicates a "Yes" answer to the question of box 706, then the computer directs the query flow through link box 710 to box 1484 of the Impaled Object query flow 1430 (e.g. impaled chin/jaw), described below with reference to FIG. 38, and the flow continues from there.

If the user indicates a "No" answer to the question of box 706 (e.g. no impaled object), then the computer directs the query flow to instruction box 712, which represents a GUI screen instructing the user to locate hemostatic gauze within the accompanying medical tool kit 12. By way of example, the represented GUI screen may also display a layout image of the tool kit and highlight with specificity the location of the hemostatic gauze. The next box 714 represents a GUI screen that displays a zoomed in image of hemostatic gauze so the user knows what to look for. The next box 716 represents a GUI screen that provides specific instruction on how to apply direct pressure to a victim's wound using hemostatic gauze, for example with text instructions, visual aid (e.g. pictures and/or video) and/or audio instructions. The next box in the query flow is query box 718, which represents a GUI screen asking the user if the victim is still bleeding in this location.

If the user indicates a "Yes" answer (e.g. the victim is still bleeding in this location), the query flow advances to box 720, which represents a GUI screen instructing the user to locate normal gauze within the accompanying medical tool kit 12. By way of example, the represented GUI screen may also display a layout image of the tool kit and highlight with specificity the location of the normal gauze. The next box 722 represents a GUI screen that displays a zoomed in image of normal gauze so the user knows what to look for. The next box in the query flow 724 represents a GUI screen that provides specific instruction on how to apply direct pressure to a victim's wound using normal gauze, for example with text instructions, visual aid (e.g. pictures and/or video) and/or audio instructions. The next box in the query flow is query box 726, which represents a GUI screen asking the user if the victim is still bleeding in this location.

If the user indicates a "Yes" answer (e.g. the victim is still bleeding in this location), the query flow advances to box 728, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 730 represents a GUI screen that displays a zoomed in image of normal gauze to remind the user what to look for. The next box in the query flow 732 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 726 (e.g. bleeding has stopped in this location), the query flow proceeds to box 734, which represents a GUI screen instructing the user to tape the normal gauze to the wound. Once the normal gauze has been taped to the wound, the next box in the query flow is query box 736, which represents a GUI screen asking the user to confirm that the victim is no longer bleeding badly in this location.

After the user positively indicates that the taped gauze is in place, the computer alerts the user (via alert box 738) to dial 9-1-1 to call for help if they have not already done so. The query flow 704 then proceeds to box 740, which represents a GUI screen that asks the user if the victim appears to be bleeding badly anywhere else. If the user indicates a "Yes" answer (e.g. the victim is badly bleeding elsewhere), then the computer redirects the query flow (via link box 742) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 744) to box 48 of FIG. 2 (e.g. query box asking if anyone else is bleeding badly), and the flow proceeds from there.

If the user indicates a "No" answer to the question of box 718 (e.g. the victim no longer bleeding badly at this location), the computer directs the query flow to box 746, which represents a GUI screen that prompts the user to locate the normal gauze within the accompanying medical tool kit 12. By way of example, the represented GUI screen may also display a layout image of the tool kit and highlight with specificity the location of the normal gauze. The next box 748 represents a GUI screen that displays a zoomed in image of normal gauze so the user knows what to look for. The query flow then directs to box 734 (e.g. tape gauze to wound), and proceeds as described above.

Figure 17:
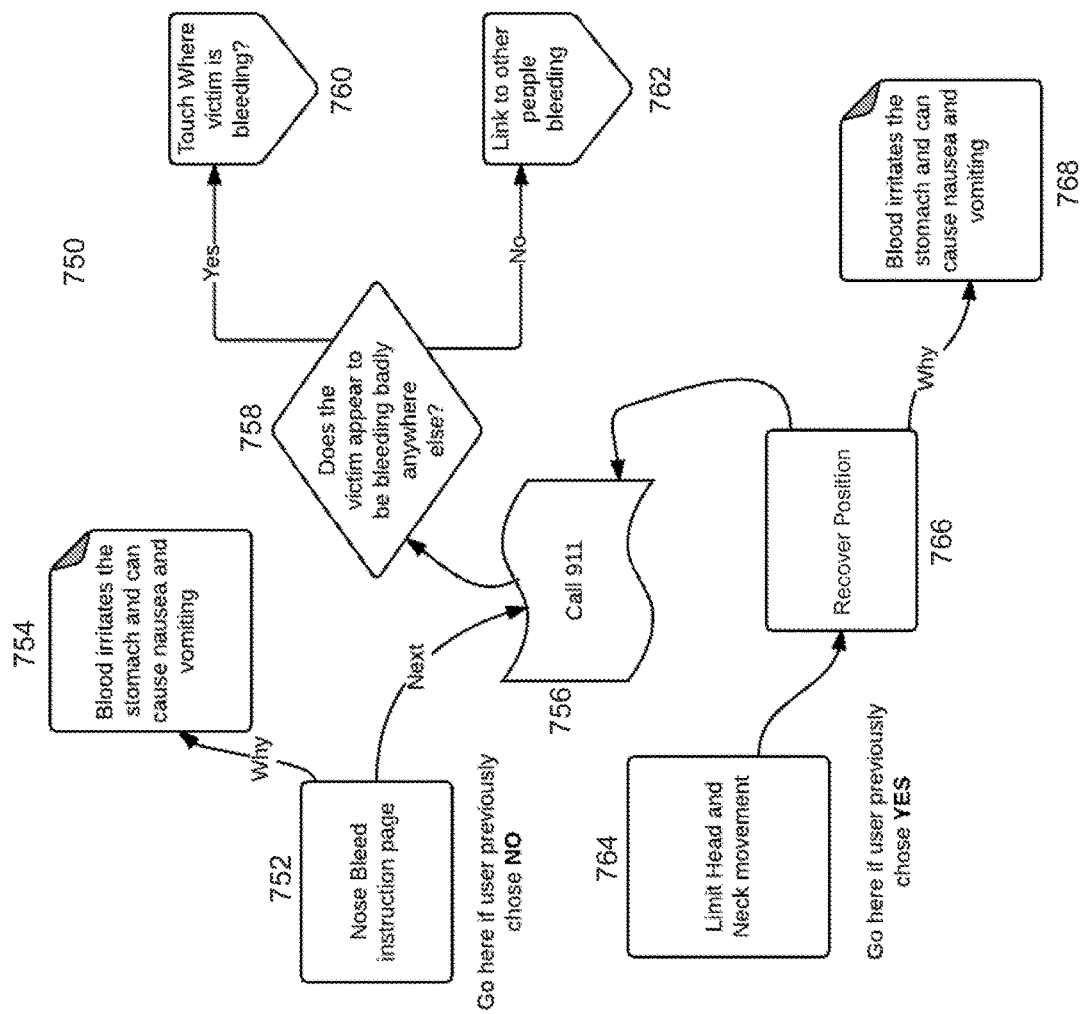
FIG. 17 is a flowchart illustrating an example query flow for a severely bleeding nose, forming part of the triage protocol of FIGS. 2-5.

FIG. 17 illustrates the query flow for a severely bleeding nose 750, which is accessed via link box 566 of FIG. 12 (e.g. in response to the user touching the nose on the graphic representation of a human face/head on the touch screen display). If the user indicated a "No" answer to the question of box 558 of FIG. 12 (e.g. victim was not in car wreck, did not fall from height, and did not suffer a neck injury), then the query flow 750 begins with instruction box 752, which represents a GUI screen providing instruction on how to treat a severely bleeding nose. An information box 754 is available via an interactive icon present on the represented GUI screen if the user needs more information about why the nosebleed needs to be abated (e.g. "blood irritates the stomach and can cause nausea and vomiting"). After the user positively indicates that the nosebleed has been treated, the computer alerts the user (via alert box 756) to dial 9-1-1 to call for help if they have not already done so. The query flow 750 then proceeds to box 758, which represents a GUI screen that asks the user if the victim appears to be bleeding badly anywhere else. If the user indicates a "Yes" answer (e.g. the victim is badly bleeding elsewhere), then the computer redirects the query flow (via link box 760) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 762) to box 48 of FIG. 2 (e.g. query box asking if anyone else is bleeding badly), and the flow proceeds from there.

If the user indicated a "Yes" answer to the question of box 558 of FIG. 12 (e.g. victim was in car wreck, fell from height, or suffered a neck injury), then the query flow 750 begins with instruction box 764, which represents a GUI screen providing instruction on how to place the victim in a proper recovery position. An information box 768 is available via an interactive icon present on the represented GUI screen if the user needs more information about why the nosebleed needs to be abated (e.g. "blood irritates the stomach and can cause nausea and vomiting"). After the user positively indicates that the nosebleed has been treated, the query flow proceeds to alert box 756 (e.g. Call 9-1-1) and the flow proceeds as described above.

Figure 18:
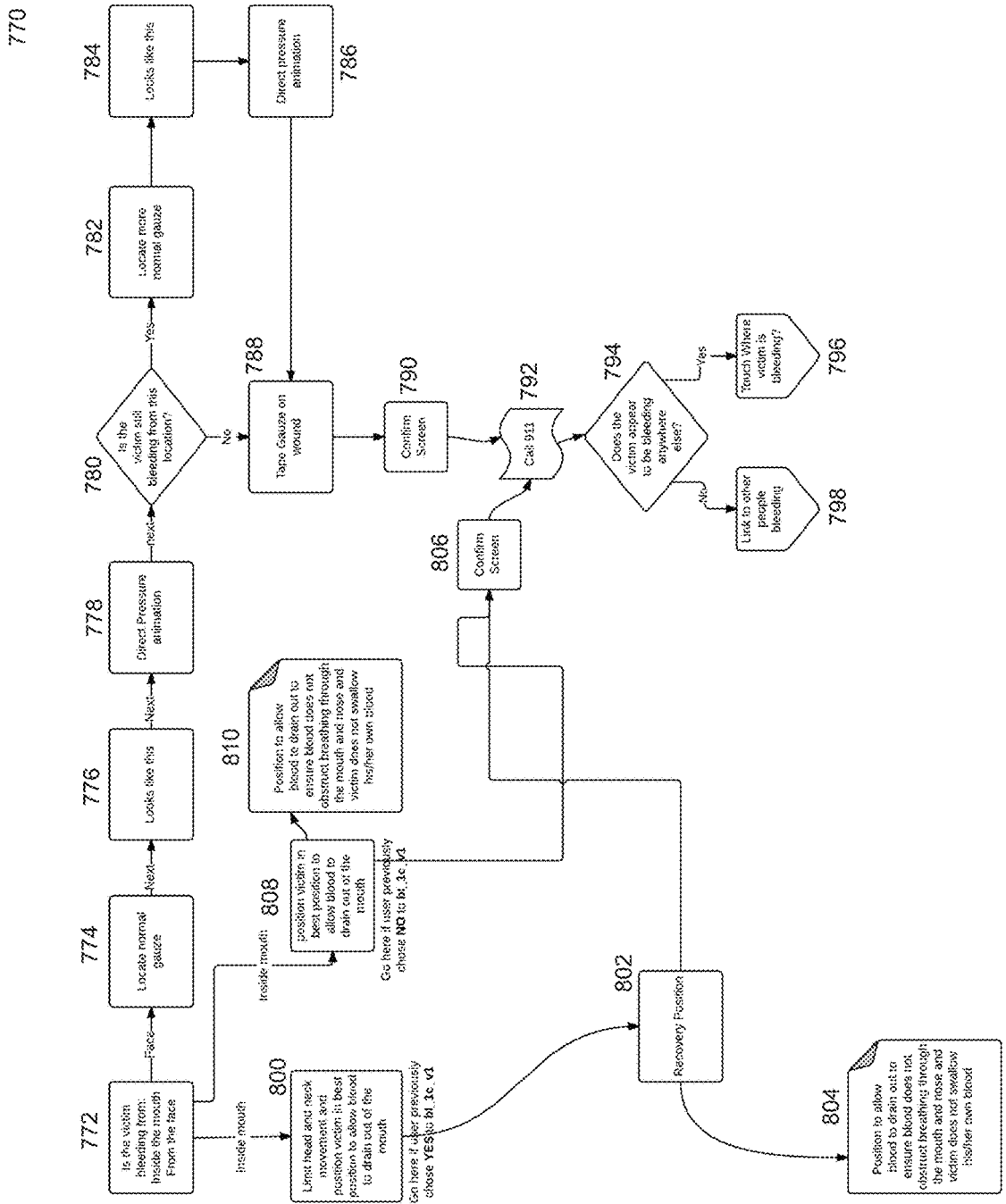
FIG. 18 is a flowchart illustrating an example query flow for a severely bleeding mouth, forming part of the triage protocol of FIGS. 2-5.

FIG. 18 illustrates the query flow for a severely bleeding mouth 770, which is accessed via link box 568 of FIG. 12 (e.g. in response to the user touching the mouth on the graphic representation of a human face/head on the touch screen display). The query flow 770 begins with query box 772 that represents a GUI screen that asks the user if the victim is bleeding from the face or from inside the mouth. If the user indicates an answer of "Face," the computer directs the query flow to information box 774, which represents a GUI screen instructing the user to locate normal gauze within the accompanying medical tool kit 12. By way of example, the represented GUI screen may also display a layout image of the tool kit and highlight with specificity the location of the normal gauze. The next box 776 represents a GUI screen that displays a zoomed in image of normal gauze so the user knows what to look for. The next box in the query flow 778 represents a GUI screen that provides specific instruction on how to apply direct pressure to a victim's wound using normal gauze, for example with text instructions, visual aid (e.g. pictures and/or video) and/or audio instructions. The next box in the query flow is query box 780, which represents a GUI screen asking the user if the victim is still bleeding in this location.

If the user indicates a "Yes" answer (e.g. the victim is still bleeding in this location), the query flow advances to box 782, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 784 represents a GUI screen that displays a zoomed in image of normal gauze to remind the user what to look for. The next box in the query flow 786 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 780 (e.g. bleeding has stopped in this location), the query flow proceeds to box 788, which represents a GUI screen instructing the user to tape the normal gauze to the wound. Once the normal gauze has been taped to the wound, the next box in the query flow is query box 790, which represents a GUI screen asking the user to confirm that the victim is no longer bleeding badly in this location.

After the user positively indicates that the taped gauze is in place, the computer alerts the user (via alert box 792) to dial 9-1-1 to call for help if they have not already done so. The query flow 770 then proceeds to box 794, which represents a GUI screen that asks the user if the victim appears to be bleeding badly anywhere else. If the user indicates a "Yes" answer (e.g. the victim is badly bleeding elsewhere), then the computer redirects the query flow (via link box 796) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 798) to box 48 of FIG. 2 (e.g. query box asking if anyone else is bleeding badly), and the flow proceeds from there.

If the user answers "Inside the Mouth" to the question of box 772 (e.g. victim is bleeding from inside the mouth) and the user answered "Yes" to the question of box 558 of FIG. 12 (e.g. victim was in car wreck, fell from height, or suffered a neck injury), then the query flow proceeds to instruction box 800, which represents a GUI screen instructing the user to limit head and neck movement and position the victim in the best position to allow blood to drain out of the mouth. The query flow then proceeds to box 802, which represents a GUI screen providing instruction on how to place the victim in a proper recovery position. An information box 804 is available via an interactive icon present on the represented GUI screen if the user needs more information about why the victim needs to be positioned so that the blood drains from his/her mouth (e.g. "Position to allow blood to drain out to ensure blood does not obstruct breathing through the mouth and nose and victim does not swallow blood"). The query flow then proceeds to box 806, which represents a GUI screen asking the user to confirm the victim is properly positioned. After the user positively indicates that the victim has been properly positioned, the query flow proceeds to alert box 792 (e.g. Call 9-1-1) and the flow proceeds as described above.

If the user answers "Inside the Mouth" to the question of box 772 (e.g. victim is bleeding from inside the mouth) and the user answered "No" to the question of box 558 of FIG. 12 (e.g. victim was not in car wreck, did not fell from height, and did not suffer a neck injury), then the query flow proceeds to instruction box 808, which represents a GUI screen instructing the user to position the victim in the best position to allow blood to drain out of the mouth. An information box 810 is available via an interactive icon present on the represented GUI screen if the user needs more information about why the victim needs to be positioned so that the blood drains from his/her mouth (e.g. "Position to allow blood to drain out to ensure blood does not obstruct breathing through the mouth and nose and victim does not swallow blood"). The query flow then proceeds to box 806, and the flow proceeds as described above.

Figure 19:
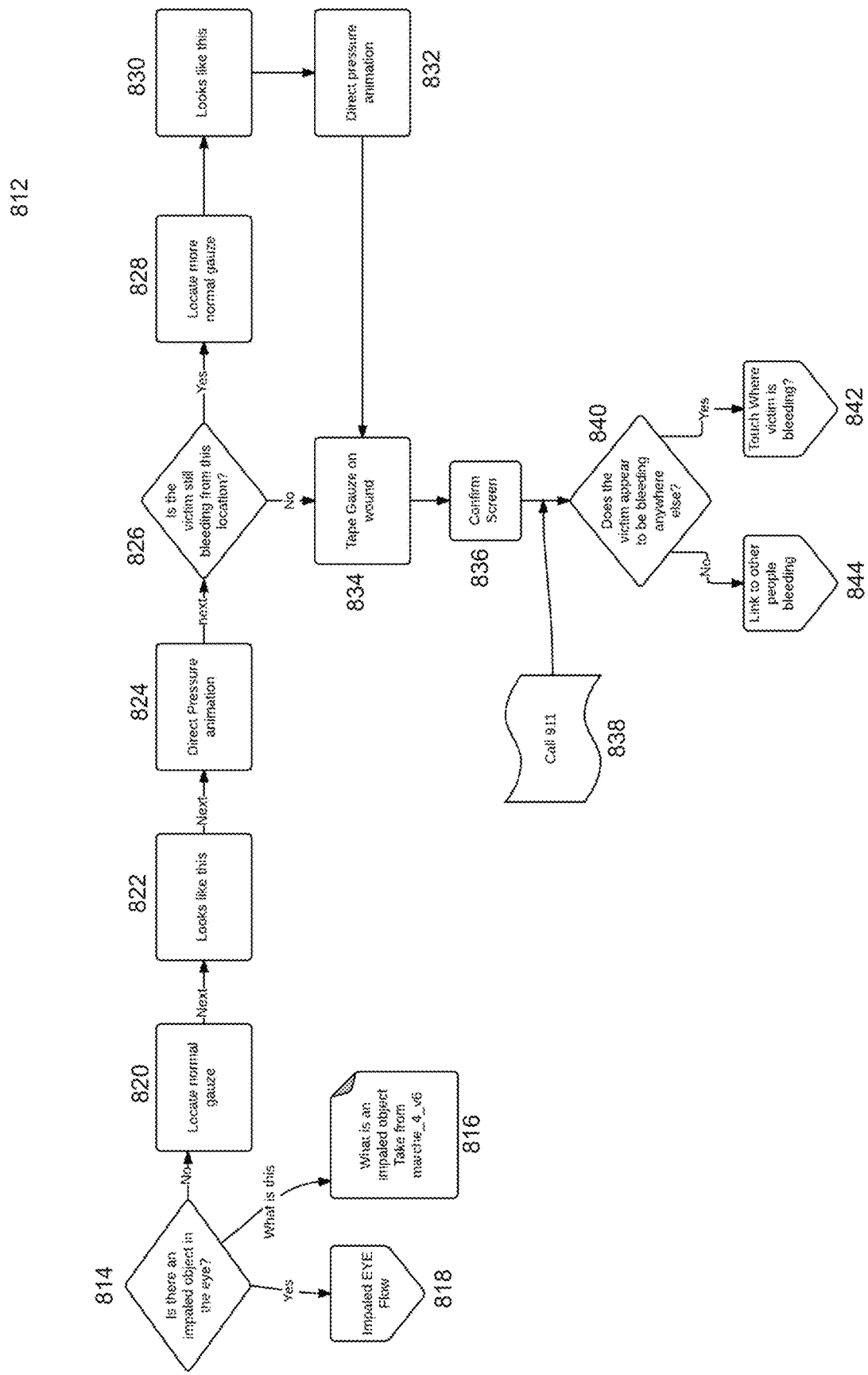
FIG. 19 is a flowchart illustrating an example query flow for one or more severely bleeding eyes, forming part of the triage protocol of FIGS. 2-5.

FIG. 19 illustrates the query flow for one or more severely bleeding eyes 812, which is accessed via link box 568 of FIG. 12 (e.g. in response to the user touching the eyes on the graphic representation of a human face/head on the touch screen display) and begins with a query box 814, which represents a GUI screen asking the user if there is an impaled object in the eyes. An information box 816 is available via an interactive icon present on the represented GUI screen if the user needs more information about what an "impaled object" is (e.g. "an impaled object is a foreign body that penetrates the skin and remains embedded in the body"). If the user indicates a "Yes" answer to the question of box 814, then the computer directs the query flow through link box 818 to box 1498 of the Impaled Object query flow 1430 (e.g. impaled eye), described below with reference to FIG. 38, and the flow continues from there.

If the user indicates a "No" answer to the question of box 814 (e.g. no impaled object), then the computer directs the query flow to instruction box 820, which represents a GUI screen instructing the user to locate normal gauze within the accompanying medical tool kit 12. By way of example, the represented GUI screen may also display a layout image of the tool kit and highlight with specificity the location of the normal gauze. The next box 822 represents a GUI screen that displays a zoomed in image of normal gauze so the user knows what to look for. The next box in the query flow 824 represents a GUI screen that provides specific instruction on how to apply direct pressure to a victim's wound using normal gauze, for example with text instructions, visual aid (e.g. pictures and/or video) and/or audio instructions. The next box in the query flow is query box 826, which represents a GUI screen asking the user if the victim is still bleeding in this location.

If the user indicates a "Yes" answer (e.g. the victim is still bleeding in this location), the query flow advances to box 828, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 830 represents a GUI screen that displays a zoomed in image of normal gauze to remind the user what to look for. The next box in the query flow 832 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 826 (e.g. bleeding has stopped in this location), the query flow proceeds to box 834, which represents a GUI screen instructing the user to tape the normal gauze to the wound. Once the normal gauze has been taped to the wound, the next box in the query flow is query box 836, which represents a GUI screen asking the user to confirm that the victim is no longer bleeding badly in this location.

After the user positively indicates that the taped gauze is in place, the computer alerts the user (via alert box 838) to dial 9-1-1 to call for help if they have not already done so. The query flow 812 then proceeds to box 840, which represents a GUI screen that asks the user if the victim appears to be bleeding badly anywhere else. If the user indicates a "Yes" answer (e.g. the victim is badly bleeding elsewhere), then the computer redirects the query flow (via link box 842) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 844) to box 48 of FIG. 2 (e.g. query box asking if anyone else is bleeding badly), and the flow proceeds from there.

Figure 20:
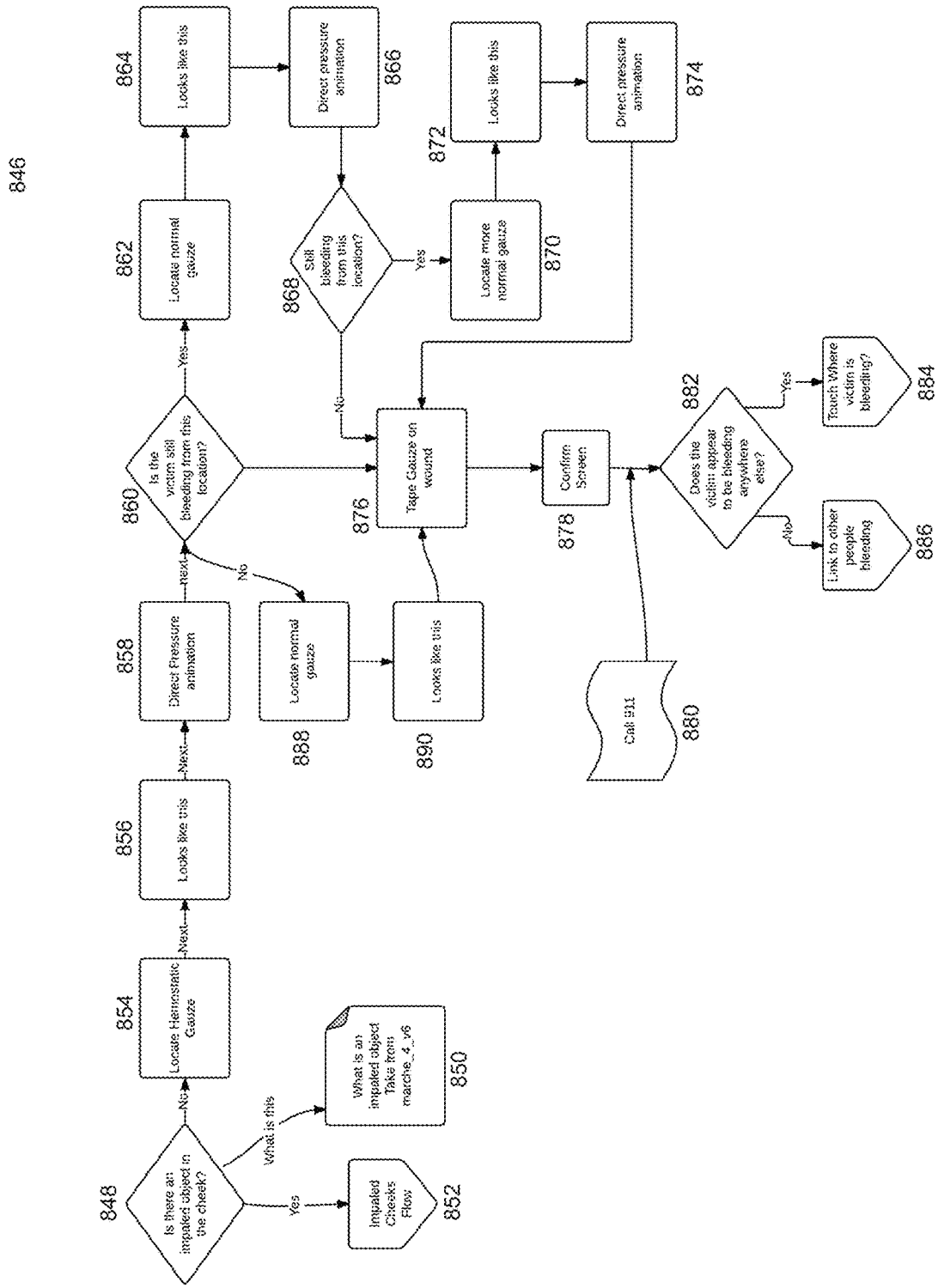
FIG. 20 is a flowchart illustrating an example query flow for a severely bleeding cheek, forming part of the triage protocol of FIGS. 2-5.

FIG. 20 illustrates the query flow for a severely bleeding cheek 846, which is accessed via link box 564 of FIG. 12 (e.g. in response to the user touching the cheek on the graphic representation of a human face/head on the touch screen display) and begins with a query box 848, which represents a GUI screen asking the user if there is an impaled object in the cheek. An information box 850 is available via an interactive icon present on the represented GUI screen if the user needs more information about what an "impaled object" is (e.g. "an impaled object is a foreign body that penetrates the skin and remains embedded in the body"). If the user indicates a "Yes" answer to the question of box 848, then the computer directs the query flow through link box 852 to box 1457 of the Impaled Object query flow 1430 (e.g. impaled cheek), described below with reference to FIG. 38, and the flow continues from there.

If the user indicates a "No" answer to the question of box 848 (e.g. no impaled object), then the computer directs the query flow to instruction box 854, which represents a GUI screen instructing the user to locate hemostatic gauze within the accompanying medical tool kit 12. By way of example, the represented GUI screen may also display a layout image of the tool kit and highlight with specificity the location of the hemostatic gauze. The next box 856 represents a GUI screen that displays a zoomed in image of hemostatic gauze so the user knows what to look for. The next box 858 represents a GUI screen that provides specific instruction on how to apply direct pressure to a victim's wound using hemostatic gauze, for example with text instructions, visual aid (e.g. pictures and/or video) and/or audio instructions. The next box in the query flow is query box 860, which represents a GUI screen asking the user if the victim is still bleeding in this location.

If the user indicates a "Yes" answer (e.g. the victim is still bleeding in this location), the query flow advances to box 862, which represents a GUI screen instructing the user to locate normal gauze within the accompanying medical tool kit 12. By way of example, the represented GUI screen may also display a layout image of the tool kit and highlight with specificity the location of the normal gauze. The next box 864 represents a GUI screen that displays a zoomed in image of normal gauze so the user knows what to look for. The next box in the query flow 866 represents a GUI screen that provides specific instruction on how to apply direct pressure to a victim's wound using normal gauze, for example with text instructions, visual aid (e.g. pictures and/or video) and/or audio instructions. The next box in the query flow is query box 868, which represents a GUI screen asking the user if the victim is still bleeding in this location.

If the user indicates a "Yes" answer (e.g. the victim is still bleeding in this location), the query flow advances to box 870, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 872 represents a GUI screen that displays a zoomed in image of normal gauze to remind the user what to look for. The next box in the query flow 874 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 868 (e.g. bleeding has stopped in this location), the query flow proceeds to box 876, which represents a GUI screen instructing the user to tape the normal gauze to the wound. Once the normal gauze has been taped to the wound, the next box in the query flow is query box 878, which represents a GUI screen asking the user to confirm that the victim is no longer bleeding badly in this location.

After the user positively indicates that the taped gauze is in place, the computer alerts the user (via alert box 880) to dial 9-1-1 to call for help if they have not already done so. The query flow 846 then proceeds to box 882, which represents a GUI screen that asks the user if the victim appears to be bleeding badly anywhere else. If the user indicates a "Yes" answer (e.g. the victim is badly bleeding elsewhere), then the computer redirects the query flow (via link box 884) to box 38 of FIG. 2 (e.g. graphic representation of a human body on the touch screen display that the user touches to indicate the area where the victim is bleeding the most), and the flow proceeds from there. If the user indicates a "No" answer (e.g. the victim is not badly bleeding elsewhere), then the computer redirects the query flow (via link box 886) to box 48 of FIG. 2 (e.g. query box asking if anyone else is bleeding badly), and the flow proceeds from there.

If the user indicates a "No" answer to the question of box 860 (e.g. the victim no longer bleeding badly at this location), the computer directs the query flow to box 888, which represents a GUI screen that prompts the user to locate the normal gauze within the accompanying medical tool kit 12. By way of example, the represented GUI screen may also display a layout image of the tool kit and highlight with specificity the location of the normal gauze. The next box 890 represents a GUI screen that displays a zoomed in image of normal gauze so the user knows what to look for. The query flow then directs to box 876 (e.g. tape gauze to wound), and proceeds as described above.

Figure 21:
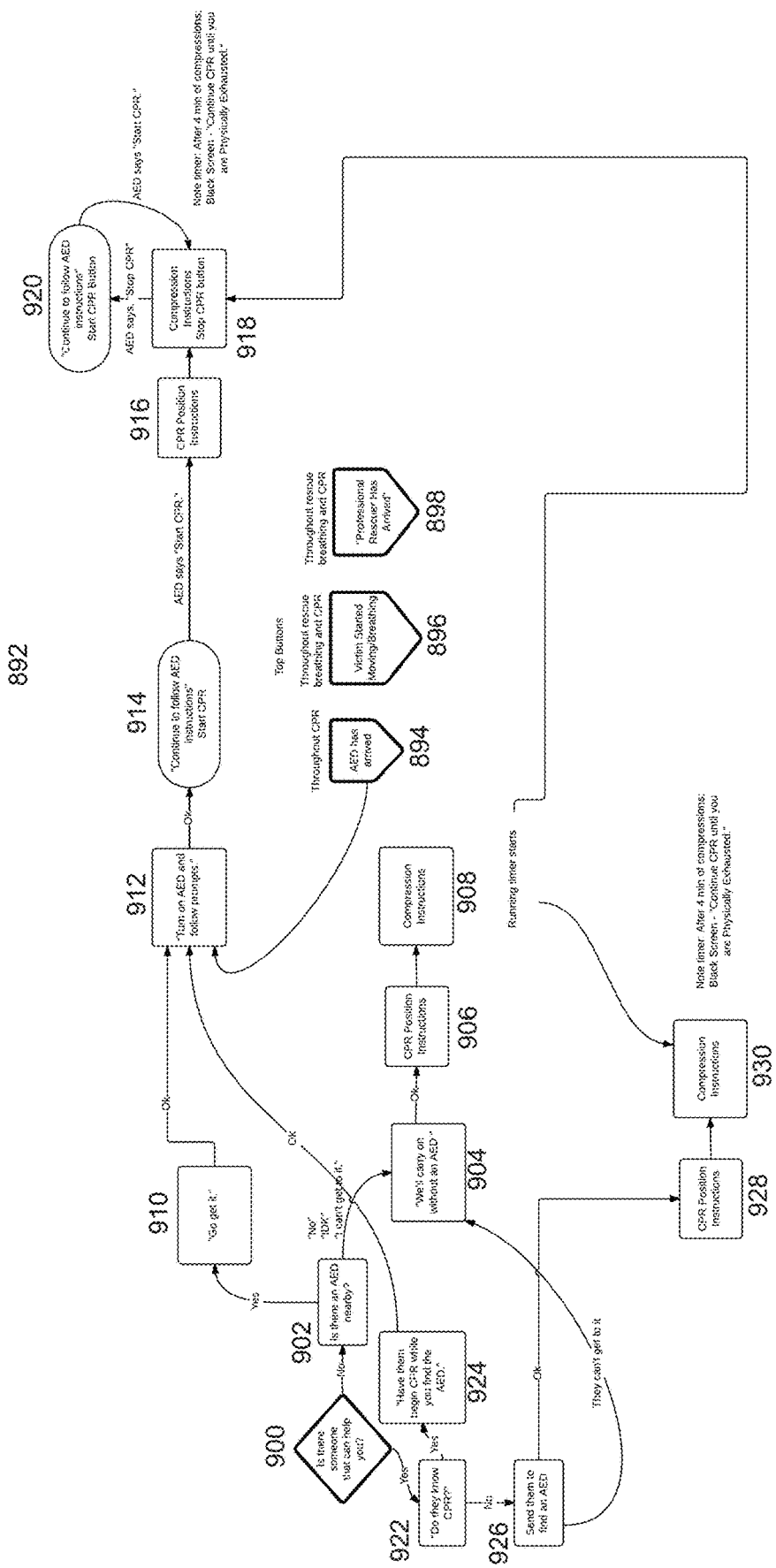
FIG. 21 is a flowchart illustrating an example query flow for administering adult compression only CPR (with AED assist), forming part of the triage protocol of FIGS. 2-5.

FIG. 21 illustrates the query flow 892 for adult compression only CPR (with AED assist). As an initial note, every represented GUI screen in this flow will include three interactive icons represented by query boxes 894, 896, 898. Box 894 represents an "AED has arrived" GUI icon that when activated by the user alerts the computer to the presence of an AED and in turn the computer jumps to box 912 of the flow, described below. Box 896 represents a "Victim started moving/breathing" GUI icon that when activated by the user causes the computer to jump the query flow to box 92 of FIG. 3 (e.g. "is victim breathing normally"). Box 898 represents a "Professional Rescuer has arrived" GUI icon that when activated by the user jumps the query flow to box 2182 (e.g. produce summary report for professional rescuer review) of the Final Protocol, described below with reference to FIG. 59.

By way of example, the flow 892 begins with a query box 900 that represents a GUI screen that asks the user if anyone is there to assist (See, e.g. FIG. 94 below). If the user indicates a "No" answer, computer directs the flow to box 902, which represents a GUI screen that asks the user if there is an automated external defibrillator (AED) nearby (See, e.g. FIG. 95 below). If the user indicates a choice of "No," "I don't know," or "I can't get to it", the query flow advances to box 904, which represents a GUI screen that reassures the user that he/she can carry on without an AED (See, e.g. FIG. 96 below). The next box 906 in the flow represents a GUI screen that instructs the user on the proper CPR positions. After the user has positioned the victim according to instructions, the computer advances the flow to box 908, which represents a GUI screen that instructs the user on performing CPR compressions. By way of example, the GUI screen represented by box 908 may contain a looping CPR animation video, including audio using a metronome beep to keep the user on track (in rhythm) while giving compressions. The animation proceeds at the pace of the metronome beep so the user may strive to match what they see on the screen. There may be an elapsed time timer on the screen that starts when the user begins CPR so that the user (and professional responder, when arrived) can know how long CPR has been performed on the victim (See, e.g. FIG. 97 below).

If the user indicates a "Yes" answer to the question in box 902 (e.g. an AED is nearby), then the computer directs the query flow to instruction box 910, which represents a GUI screen instructing the user to go retrieve the AED Once the user indicates to the computer that they have retrieved the AED (e.g. through physical or vocal command), the query flow is advanced to box 912, which represents a GUI screen instructing the user to turn on the AED and follow the prompts. The next box 914 represents a GUI screen that instructs the user to continue to follow the AED instructions, and includes an interactive "Start CPR" button that the user activates when the AED instructs the user to start CPR (See, e.g. FIG. 98 below). Once that occurs, the query flow advances to the next box 916, which represents a GUI screen that instructs the user on how to position the victim for CPR. When the user indicates that the victim is properly positioned for CPR, the query flow advances to box 918, which represents a GUI screen that instructs the user on performing CPR compressions. By way of example, the GUI screen represented by box 918 may contain a looping CPR animation video, including audio using a metronome beep to keep the user on track (in rhythm) while giving compressions, as well as an "AED says STOP CPR" icon. The animation proceeds at the pace of the metronome beep so the user may strive to match what they see on the screen. There may be an elapsed time timer on the screen that starts when the user begins CPR so that the user (and professional responder, when arrived) can know how long CPR has been performed on the victim. (See, e.g. FIG. 99 below). When the AED instructs the user to stop CPR, the user taps on the "AED says STOP CPR" icon, which instructs the computer to advance the query flow to the next box 920, which represents a GUI screen that instructs the user to continue following the AED instructions, and includes an "START CPR" icon (See, e.g. FIG. 100 below). When the AED indicates that it is time to resume CPR, the user taps the "AED says START CPR" icon and the computer displays the GUI screen represented by box 918. This cycle may continue until the victim wakes up or a professional rescuer arrives.

If the user indicates a "Yes" answer to the question of box 900 (e.g. there is somebody there who can assist), the computer advances the flow to box 922, which represents a GUI screen that asks the user if the assistant knows CPR. If the user indicates a "Yes" answer, then the computer advances the query flow to box 924, which represents a GUI screen that instructs the user to have the CPR-trained assistant begin performing CPR on the victim while the user looks for an AED At this point the computer may display the CPR compression GUI screen and start the count up timer. When the user returns with the AED the query flow is advanced to box 912, and the flow continues from there.

If the user indicates a "No" answer to the question of box 922 (e.g. the assistant does not know CPR), then the computer advances the query flow to box 926, which represents a GUI screen that instructs the user to send the assistant to find an AED. The next box 928 in the flow represents a GUI screen that instructs the user on the proper CPR positions. After the user has positioned the victim according to instructions, the computer advances the flow to box 930, which represents a GUI screen that instructs the user on performing CPR compressions. By way of example, the GUI screen represented by box 930 may contain a looping CPR animation video, including audio using a metronome beep to keep the user on track (in rhythm) while giving compressions. The animation proceeds at the pace of the metronome beep so the user may strive to match what they see on the screen. There may be an elapsed time timer on the screen that starts when the user begins CPR so that the user (and professional responder, when arrived) can know how long CPR has been performed on the victim (See, e.g. FIG. 97 below). If the assistant returns with an AED, the user can inform the computer that the AED has arrived by tapping the "AED has arrived" icon (e.g. box 894) and the computer will advance the query flow to box 912 where it continues as described above.

Figure 22:
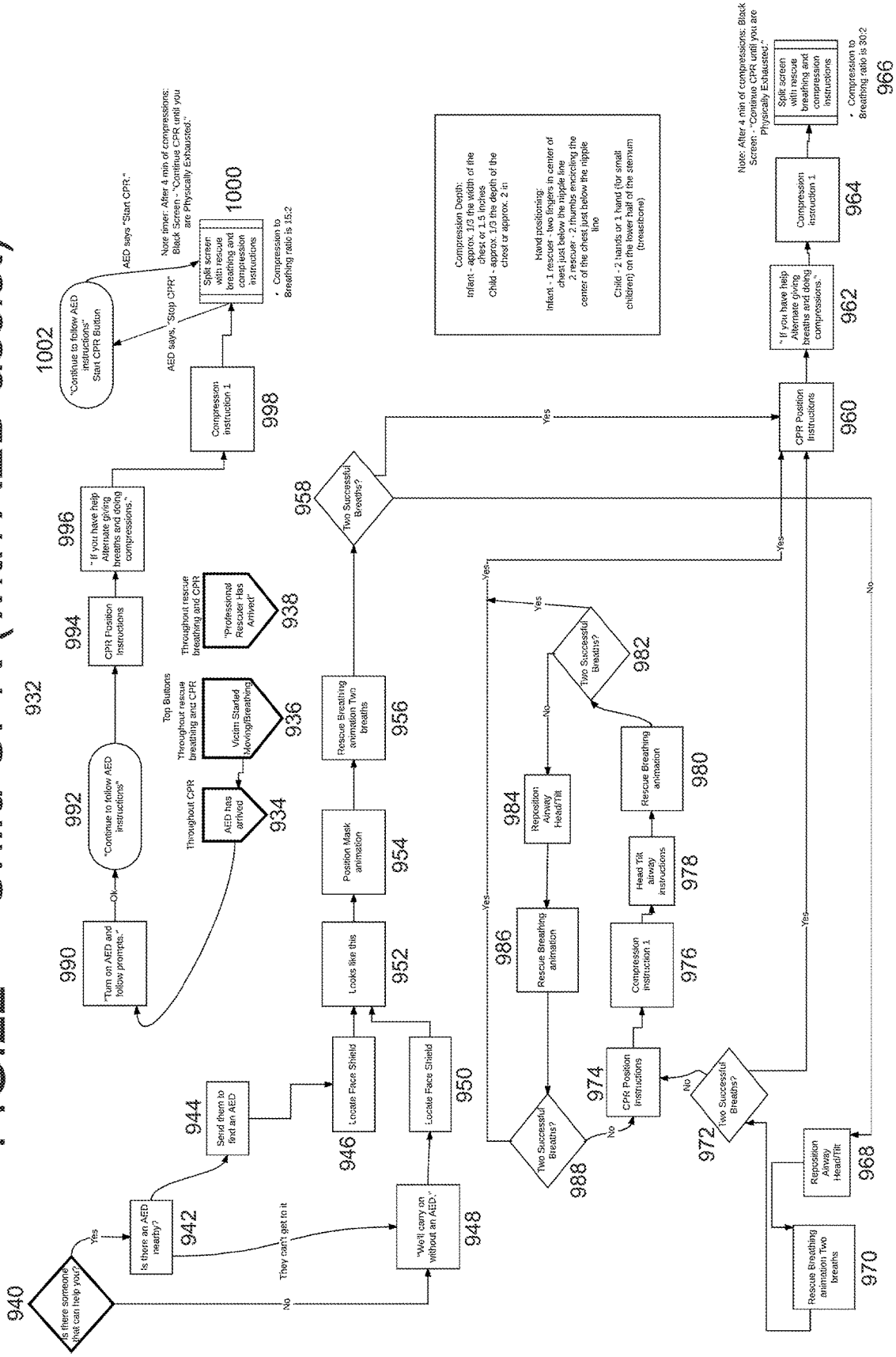
FIG. 22 is a flowchart illustrating an example query flow for administering child CPR (with AED assist), forming part of the triage protocol of FIGS. 2-5.

FIG. 22 illustrates the query flow 932 for child CPR (with AED assist). As an initial note, every represented GUI screen in this flow will include three interactive icons represented by query boxes 934, 936, 938. Box 934 represents an "AED has arrived" GUI icon that when activated by the user alerts the computer to the presence of an AED and in turn the computer jumps to box 912 of the flow, described below. Box 896 represents a "Victim started moving/breathing" GUI icon that when activated by the user causes the computer to jump the query flow to box 92 of FIG. 3 (e.g. "is victim breathing normally"). Box 898 represents a "Professional Rescuer has arrived" GUI icon that when activated by the user jumps the query flow to box 2182 (e.g. produce summary report for professional rescuer review) of the Final Protocol, described below with reference to FIG. 59.

By way of example, the flow 932 begins with a query box 940 that represents a GUI screen that asks the user if anyone is there to assist. If the user indicates a "Yes" answer, the query flow proceeds to box 942, which represents a GUI screen that asks the user if there is an AED present. If the user indicates a "Yes" response to this question, the flow proceeds to box 944, which represents a GUI screen that instructs the user to tell the assistant to go find the AED The next box 946 instructs the user to locate the face shield within the medical tool kit 12. By way of example, the represented GUI screen may also display a layout image of the tool kit and highlight with specificity the location of the face shield. If the user indicated an answer of "No" to either the question of box 940 (e.g. no assistant available) or box 942 (e.g. no AED nearby), then the computer directs the query flow to box 948, which represents a GUI screen that reassures the user to continue without an AED, and then box 950, which represents a GUI screen that instructs the user to find the face shield in the medical tool kit 12. From either box 946 or box 950, the query flow continues with box 952, which represents a GUI screen that displays a zoomed in image of a face shield so the user knows what to look for. The next box in the query flow is an instruction box 954 that represents a GUI screen that provides specific instruction on how to position the face shield, for example with text instructions, visual aid (e.g. pictures and/or video) and/or audio instructions. Once the user indicates that the face shield is properly placed, the query flow continues to box 956, which represents a GUI screen that provides specific instruction on how to perform rescue breathing, for example with text instructions, visual aid (e.g. pictures and/or video) and/or audio instructions. Query box 958 represents a GUI screen that asks the user if they were able to perform two successful rescue breaths (e.g. meaning the victim's chest rose and fell with each breath).

If the user indicates a "Yes" answer to this question, the computer advances the query flow to box 960, which represents a GUI screen that provides specific instruction on how to position the victim to perform CPR, for example with text instructions, visual aid (e.g. pictures and/or video) and/or audio instructions. Once the user indicates that the victim is properly positioned, the query flow advances to box 962, which represents a GUI screen that instructs the user if there is an assistant available, then the user and assistant should alternate giving breaths and doing compressions. Box 964 of the query flow represents a GUI screen providing instruction on performing CPR compressions. By way of example, the GUI screen represented by box 964 may contain a CPR animation video, including audio using a metronome beep to keep the user on track (in rhythm) while giving compressions. The animation proceeds at the pace of the metronome beep so the user may strive to match what they see on the screen. There may be an elapsed time timer on the screen that starts when the user begins CPR so that the user (and professional responder, when arrived) can know how long CPR has been performed on the victim (See, e.g. FIG. 101 below). After a set number of compressions (thirty, for example), the computer will automatically shift the screen to the GUI screen represented by box 966, which provides instruction on rescue breathing component of child CPR (See, e.g. FIG. 102 below). After 2 breaths, the computer will shift back to the compression GUI screen represented by box 964. This interaction will continue until the victim wakes up, the AES arrives, or the professional rescuer arrives.

If the user indicates a "No" answer to box 958 (e.g. rescue breathing not immediately successful), then the query flow advances to box 968, which represents a GUI screen that instructs the user to reposition the airway and demonstrates proper head tilt, since the user's rescue breaths were not getting to the victim's lungs. The next box 970 represents a GUI screen that again provides specific instruction on how to perform rescue breathing, for example with text instructions, visual aid (e.g. pictures and/or video) and/or audio instructions. The next step in the query flow is box 972, which represents a GUI screen that asks the user if he/she was able to deliver 2 successful breaths. If the user indicates an answer of "Yes", the flow continues to box 960 to instruct the user perform child CPR as discussed above. If the user indicates a "No" answer, then the flow continues to box 974, which represents a GUI screen that gives instruction on positioning a victim for CPR. When the user indicates that the victim is properly placed, the computer advances the flow to box 976, which represents a GUI screen providing instruction on performing CPR compressions. By way of example, the GUI screen represented by box 976 may contain a CPR animation video, including audio using a metronome beep to keep the user on track (in rhythm) while giving compressions. After a certain number of compressions (e.g. thirty), the flow advances to box 978, which represents a GUI screen that provides instructions to the user on how to properly tilt the victim's head to open the airway. Box 980 represents a GUI screen providing instruction in the form of rescue breathing animation while the user performs rescue breathing again on the victim. Box 982 represents a GUI screen that asks the user if their rescue breathing produced two successful breaths. If the user indicates an answer of "Yes" to this question, then the query flow will proceed to box 960 to instruct the user perform child CPR as discussed above.

If the user indicates a "No" answer to the question of box 982, then the query flow will continue to box 984, which represents a GUI screen instructing the user to reposition the victim's head/tilt to try to open the airway. Box 986 represents a GUI screen, which again demonstrates the rescue breathing animation for the user to emulate while attempting rescue breathing on the child again. Box 988 represents a GUI screen that again asks if rescue breathing was successful in achieving two breaths. If the user indicates a "Yes" answer, then the query flow will proceed to box 960 to instruct the user perform child CPR as discussed above. If the user indicates a "No" answer, then the query flow will proceed back to box 974 (e.g. CPR position instructions) and the compression-head tilt-rescue breath-head tilt-rescue breath cycle will continue until the user delivers two successful rescue breaths, the victim wakes up, or a professional rescuer arrives.

If at any time an AED arrives at the scene, the user may so indicate by tapping on the "AED has arrived" icon at the top of any GUI screen in the query flow 932, and the computer will shift the flow to box 990, which represents a GUI screen instructing the user to turn on the AED and follow the prompts. The next box 992 represents a GUI screen that instructs the user to continue to follow the AED instructions. Box 994 represents a GUI screen that instructs the user on proper CPR positioning. The next box 996 represents a GUI screen that instructs the user if they have help to alternate between giving breaths and compressions. The next box 998 of the query flow represents a GUI screen providing instruction on performing CPR compressions. By way of example, the GUI screen represented by box 998 may contain a CPR animation video, including audio using a metronome beep to keep the user on track (in rhythm) while giving compressions. The animation proceeds at the pace of the metronome beep so the user may strive to match what they see on the screen. There may be an elapsed time timer on the screen that starts when the user begins CPR so that the user (and professional responder, when arrived) can know how long CPR has been performed on the victim (See, e.g. FIG. 101 below). After a set number of compressions (thirty, for example), the computer will automatically shift the screen to the GUI screen represented by box 1000, which provides instruction on rescue breathing component of child CPR (See, e.g. FIG. 102 below). After 2 breaths, the computer will shift back to the compression GUI screen represented by box 964. This interaction will continue until the victim wakes up, the AES arrives, or the professional rescuer arrives. Box 1002 represents a GUI screen that reminds the user to continue following the AED instructions.

Figure 23:
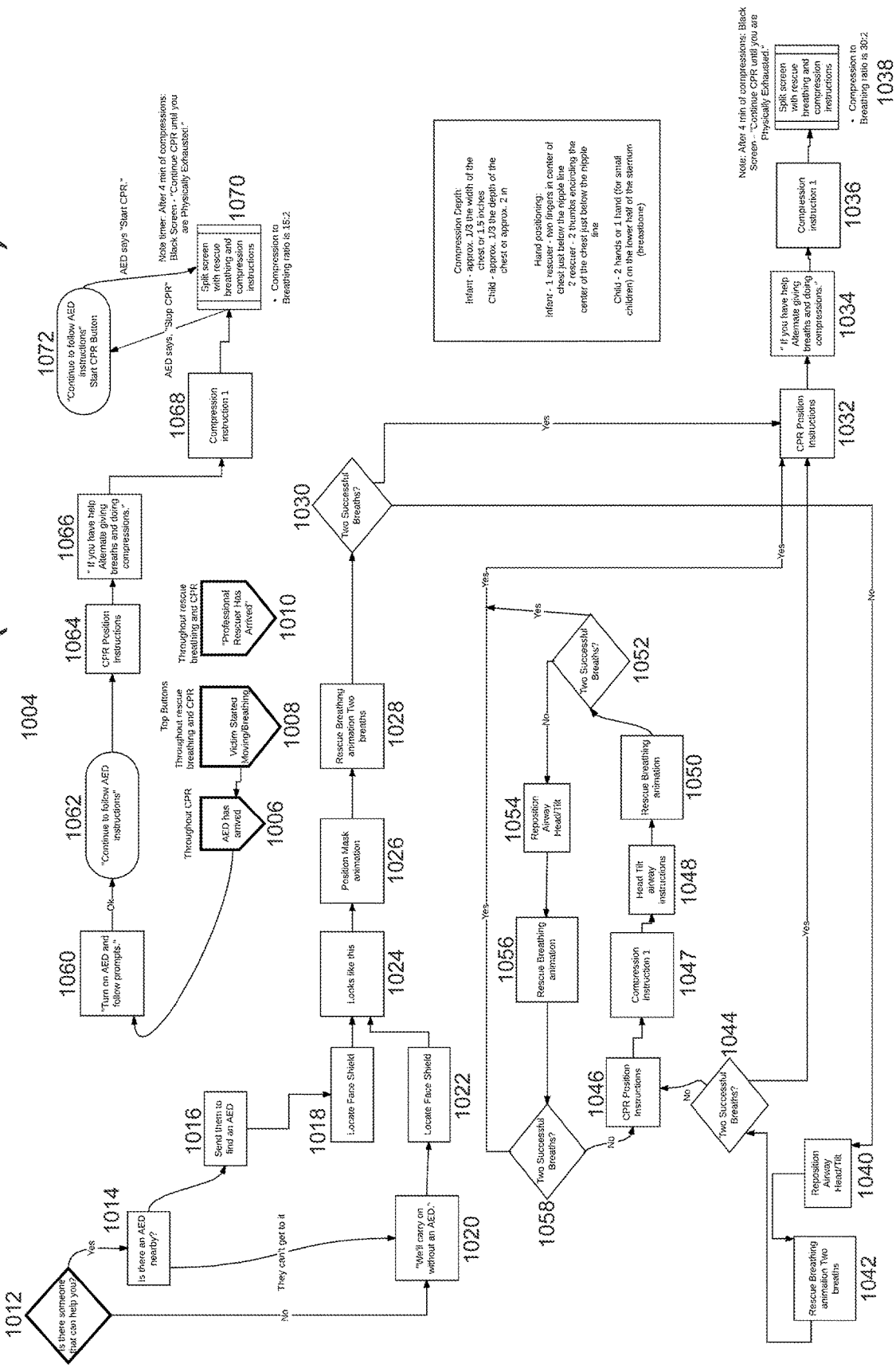
FIG. 23 is a flowchart illustrating an example query flow for administering infant CPR (with AED assist), forming part of the triage protocol of FIGS. 2-5.

FIG. 23 illustrates the query flow for infant CPR (with AED assist) 1004. As an initial note, every represented GUI screen in this flow will include three interactive icons represented by query boxes 1006, 1008, 1010. Box 1006 represents an "AED has arrived" GUI icon that when activated by the user alerts the computer to the presence of an AED and in turn the computer jumps to box 1060 of the flow, described below. Box 1008 represents a "Victim started moving/breathing" GUI icon that when activated by the user causes the computer to jump the query flow to box 92 of FIG. 3 (e.g. "is victim breathing normally"). Box 1010 represents a "Professional Rescuer has arrived" GUI icon that when activated by the user jumps the query flow to box 2182 (e.g. produce summary report for professional rescuer review) of the Final Protocol, described below with reference to FIG. 59.

By way of example, the flow 1004 begins with a query box 1012 that represents a GUI screen that asks the user if anyone is there to assist. If the user indicates a "Yes" answer, the query flow proceeds to box 1014, which represents a GUI screen that asks the user if there is an AED present. If the user indicates a "Yes" response to this question, the flow proceeds to box 1016, which represents a GUI screen that instructs the user to tell the assistant to go find the AED. The next box 1018 instructs the user to locate the face shield within the medical tool kit 12. By way of example, the represented GUI screen may also display a layout image of the tool kit and highlight with specificity the location of the face shield. If the user indicated an answer of "No" to either the question of box 1012 (e.g. no assistant available) or box 1014 (e.g. no AED nearby), then the computer directs the query flow to box 1020, which represents a GUI screen that reassures the user to continue without an AED, and then box 1022, which represents a GUI screen that instructs the user to find the face shield in the medical tool kit 12. From either box 1018 or box 1022, the query flow continues with box 1024, which represents a GUI screen that displays a zoomed in image of a face shield so the user knows what to look for. The next box in the query flow is an instruction box 1026 that represents a GUI screen that provides specific instruction on how to position the face shield, for example with text instructions, visual aid (e.g. pictures and/or video) and/or audio instructions. Once the user indicates that the face shield is properly placed, the query flow continues to box 1028, which represents a GUI screen that provides specific instruction on how to perform rescue breathing, for example with text instructions, visual aid (e.g. pictures and/or video) and/or audio instructions. Query box 1030 represents a GUI screen that asks the user if they were able to perform two successful rescue breaths (e.g. meaning the victim's chest rose and fell with each breath).

If the user indicates a "Yes" answer to this question, the computer advances the query flow to box 1032, which represents a GUI screen that provides specific instruction on how to position the victim to perform CPR, for example with text instructions, visual aid (e.g. pictures and/or video) and/or audio instructions. Once the user indicates that the victim is properly positioned, the query flow advances to box 1034, which represents a GUI screen that instructs the user if there is an assistant available, then the user and assistant should alternate giving breaths and doing compressions. Box 1036 of the query flow represents a GUI screen providing instruction on performing CPR compressions. By way of example, the GUI screen represented by box 1036 may contain a CPR animation video, including audio using a metronome beep to keep the user on track (in rhythm) while giving compressions. The animation proceeds at the pace of the metronome beep so the user may strive to match what they see on the screen. There may be an elapsed time timer on the screen that starts when the user begins CPR so that the user (and professional responder, when arrived) can know how long CPR has been performed on the victim (See, e.g. FIG. 101 below). After a set number of compressions (thirty, for example), the computer will automatically shift the screen to the GUI screen represented by box 1038, which provides instruction on rescue breathing component of infant CPR (See, e.g. FIG. 102 below). After 2 breaths, the computer will shift back to the compression GUI screen represented by box 964. This interaction will continue until the victim wakes up, the AES arrives, or the professional rescuer arrives.

If the user indicates a "No" answer to box 1030 (e.g. rescue breathing not immediately successful), then the query flow advances to box 1040, which represents a GUI screen that instructs the user to reposition the airway and demonstrates proper head tilt, since the user's rescue breaths were not getting to the victim's lungs. The next box 1042 represents a GUI screen that again provides specific instruction on how to perform rescue breathing, for example with text instructions, visual aid (e.g. pictures and/or video) and/or audio instructions. The next step in the query flow is box 1044, which represents a GUI screen that asks the user if he/she was able to deliver 2 successful breaths. If the user indicates an answer of "Yes", the flow continues to box 1032 to instruct the user perform child CPR as discussed above. If the user indicates a "No" answer, then the flow continues to box 1046, which represents a GUI screen that gives instruction on positioning a victim for CPR. When the user indicates that the victim is properly placed, the computer advances the flow to box 1078, which represents a GUI screen providing instruction on performing CPR compressions. By way of example, the GUI screen represented by box 1047 may contain a CPR animation video, including audio using a metronome beep to keep the user on track (in rhythm) while giving compressions. After a certain number of compressions (e.g. thirty), the flow advances to box 1048, which represents a GUI screen that provides instructions to the user on how to properly tilt the victim's head to open the airway. Box 1050 represents a GUI screen providing instruction in the form of rescue breathing animation while the user performs rescue breathing again on the victim. Box 1052 represents a GUI screen that asks the user if their rescue breathing produced two successful breaths. If the user indicates an answer of "Yes" to this question, then the query flow will proceed to box 1032 to instruct the user perform child CPR as discussed above.

If the user indicates a "No" answer to the question of box 1052, then the query flow will continue to box 1054, which represents a GUI screen instructing the user to reposition the victim's head/tilt to try to open the airway. Box 1056 represents a GUI screen, which again demonstrates the rescue breathing animation for the user to emulate while attempting rescue breathing on the child again. Box 1058 represents a GUI screen that again asks if rescue breathing was successful in achieving two breaths. If the user indicates a "Yes" answer, then the query flow will proceed to box 1032 to instruct the user perform child CPR as discussed above. If the user indicates a "No" answer, then the query flow will proceed back to box 1046 (e.g. CPR position instructions) and the head tilt-rescue breath-head tilt-rescue breath cycle will continue until the user gets two successful rescue breaths, the victim wakes up, or a professional rescuer arrives.

If at any time an AED arrives at the scene, the user may so indicate by tapping on the "AED has arrived" icon at the top of any GUI screen in the query flow 1004, and the computer will shift the flow to box 1060, which represents a GUI screen instructing the user to turn on the AED and follow the prompts. The next box 1062 represents a GUI screen that instructs the user to continue to follow the AED instructions. Box 1064 represents a GUI screen that instructs the user on proper CPR positioning. The next box 1066 represents a GUI screen that instructs the user if they have help to alternate between giving breaths and compressions. The next box 1068 of the query flow represents a GUI screen providing instruction on performing CPR compressions. By way of example, the GUI screen represented by box 1068 may contain a CPR animation video, including audio using a metronome beep to keep the user on track (in rhythm) while giving compressions. The animation proceeds at the pace of the metronome beep so the user may strive to match what they see on the screen. There may be an elapsed time timer on the screen that starts when the user begins CPR so that the user (and professional responder, when arrived) can know how long CPR has been performed on the victim (See, e.g. FIG. 101 below). After a set number of compressions (thirty, for example), the computer will automatically shift the screen to the GUI screen represented by box 1070, which provides instruction on rescue breathing component of infant CPR (See, e.g. FIG. 102 below). After 2 breaths, the computer will shift back to the compression GUI screen represented by box 1068. This interaction will continue until the victim wakes up, the AES arrives, or the professional rescuer arrives. Box 1072 represents a GUI screen that reminds the user to continue following the AED instructions.

By way of example in each of the CPR flows described above, after the user has been performing compression for four minutes, the computer will display a black screen with the message "Continue CPR until you are physically exhausted."

Figure 24:
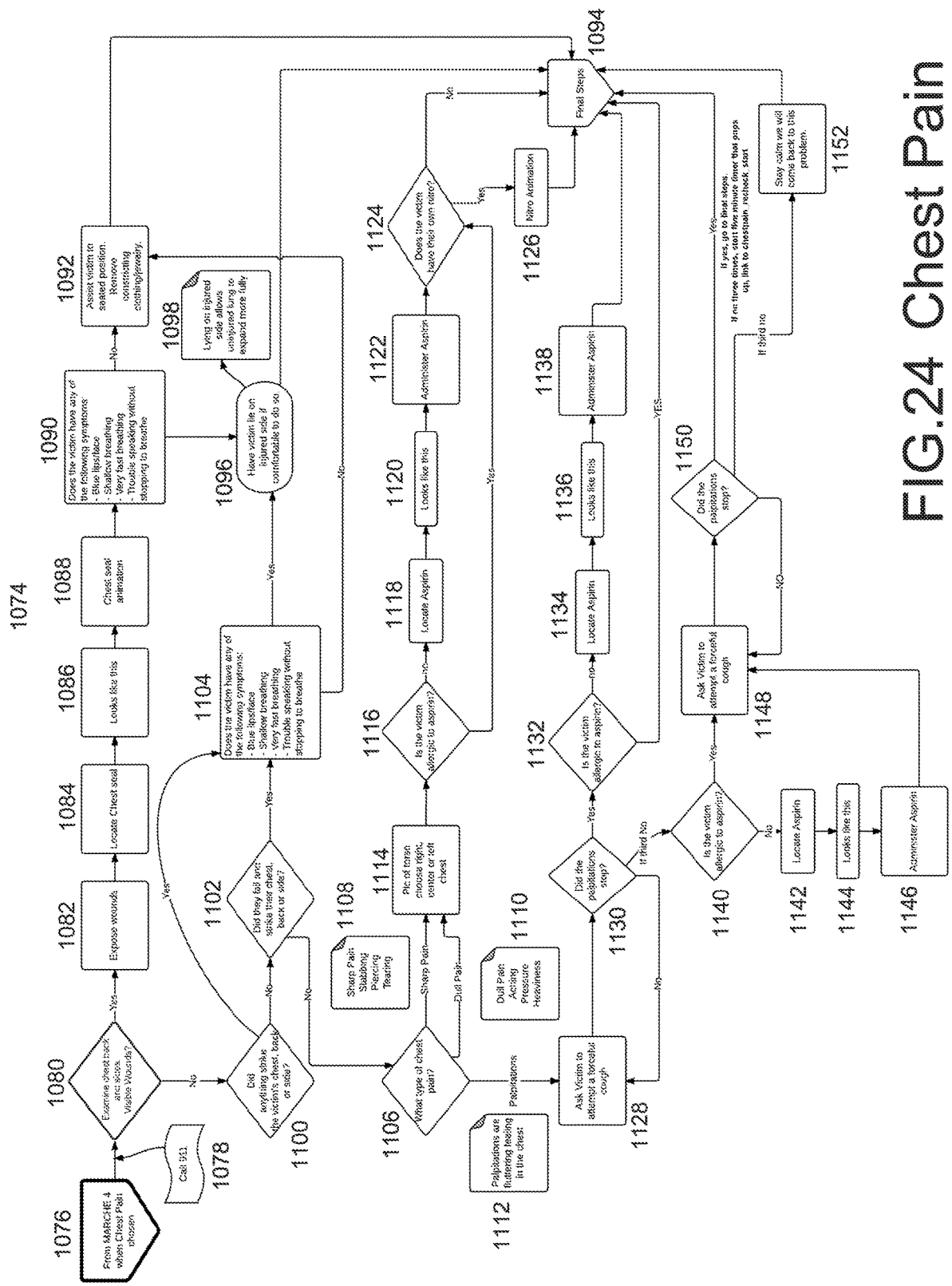
FIG. 24 is a flowchart illustrating an example query flow for chest pain, forming part of the triage protocol of FIGS. 2-5.

FIG. 24 illustrates the query flow for chest pain 1074, to which the computer directs the flow when the user selects "Chest Pain" from among the list of options on the GUI screen represented by box 242 of FIG. 5 (MARCHE part 4). By way of example, the Chest Pain query flow 1074 begins with the computer directing the query flow to box 1078, which represents a GUI screen prompting the user to call 9-1-1 if they have not already done so. The query flow then proceeds to box 1080, which represents a GUI screen asking if the victim has any visible wounds on his/her chest, back and/or sides. If the user indicates a "Yes" answer to this question, then the query flow proceeds to information box 1082, which represents a GUI presented by the computer instructing the user to expose the victim's wounds. Once the user has alerted the computer that these instructions have been followed (e.g. by tapping an icon on the screen or through voice command), the flow proceeds to box 1083, which represents a GUI screen instructing the user to locate a chest seal device in the medical tool kit 12. Upon receiving input from the user to proceed (e.g. by tapping an icon or through voice command), the computer advances the flow to box 1086, which represents a GUI screen showing the user what a chest seal device looks like, to make it easier for the user to recognize the device when looking in the medical too kit 12. Upon receiving input from the user to proceed (e.g. by tapping an icon or through voice command), the computer advances the flow to box 1088, which represents a GUI screen showing the user how to apply the chest seal to the victim (e.g. through animated video). Once the user indicates to the app that the chest seal has been applied to the victim, the computer starts a recheck timer to remind/require the user to complete the chest seal reset protocol at a regular specified interval. In the instant example the chest seal recheck interval is set at every five minutes (5:00), however the app may be programmed to include a different medically reasonable time interval (not determined or adjusted by the user in the field). At the expiration of the specified time interval, regardless of the GUI screen the user may be currently viewing, the computer directs the query flow automatically to the Chest Seal Recheck flow of FIG. 62.

After the chest seal is applied, the computer advances the query flow to box 1090, which represents a GUI screen that asks the user if the victim has any of the following symptoms: blue lips/face, shallow breathing, very fast breathing, and trouble speaking without stopping to breathe. If the user indicates an answer of "No", the query flow proceeds to box 1092, which represents a GUI screen instructing the user to assist the victim to a seated position, and remove constricting jewelry or clothing (if possible). Once the user indicates that this has occurred, the computer advances the query flow to link box 1094, which links to the Final Protocol of FIG. 59.

If the user indicates an answer of "Yes" to the question of box 1092 (e.g. the victim does display signs of at least one of blue lips/face, shallow breathing, very fast breathing, and trouble speaking without stopping to breathe), the computer directs the query flow to box 1096, which represents a GUI screen instructing the user to have the victim lie on the injured side if it is comfortable to do so. A "Why?" icon may be present on the represented GUI that, if activated by the user (e.g. by touch or voice) prompts the computer to display a popup information box 1098 that explains to the user that laying a victim on his/her injured side allows the uninjured lung to expand more fully. From this point the query flow proceeds to link box 1094, and proceeds as described above.

If the user indicates an answer of "No" to the question of box 1080 (e.g. no visible wounds), the computer directs the query flow to box 1100, which represents a GUI screen asking the user if anything struck the victim's chest, back, or side. If the user indicates an answer of "No", then the query flow advances to box 1102, which represents a GUI screen asking the user if the victim fell and struck their chest, back, or side. If the user indicates a "Yes" answer to the question in either box 1100 or box 1102, then the query flow advances to box 1104, which represents a GUI screen that asks the user if the victim has any of the following symptoms: blue lips/face, shallow breathing, very fast breathing, and trouble speaking without stopping to breathe. If the user indicates a "Yes" answer, the query flow is directed to box 1096 and proceeds as described above. If the user indicates a "No" answer, the query flow is directed to box 1092 and proceeds as described above.

If the user indicates an answer of "No" to the question of box 1102 (e.g. victim didn't fall), then the computer directs the query flow to box 1106, which represents a GUI screen that asks the user what type of chest pain the victim is experiencing, and gives three selectable choices of sharp, dull, or palpitations. The represented GUI screen may include "More Info" icons for each of the options. By way of example, a "More Info?" icon may be present on the represented GUI for each of the options that, if activated by the user (e.g. by touch or voice) prompts the computer to display a popup information box that explains information to the user. For example, information box 1108 displays that sharp pain includes stabbing, piercing, and/or tearing. Information box 1110 displays information that dull pain includes aching, pressure, and/or heaviness. Information box 112 displays information that palpitations are a fluttering feeling in the chest.

If the user indicates a selection of either "sharp pain" or "dull pain" to the question of box 1106, then the computer directs the query flow to box 1114, which represents a GUI screen with an interactive display of a human torso that asks the user to choose where the victim's pain is located, for example on the right side, left side, or center (See, e.g. FIG. 118 below). This information is stored by the computer for later user in the app, including but not limited to reporting this information in the Summary. After the user makes a selection, the computer advances the query flow to box 1116, which represents a GUI screen asking the user if the victim is allergic to aspirin. If the user indicates an answer of "No", the query flow advances to box 1118, which represents a GUI screen that instructs the user to locate the aspirin within the accompanying medical tool kit 12. By way of example, the represented GUI screen may also display a layout image of the aspirin and highlight with specificity the location of the aspirin. The next box 1120 represents a GUI screen that displays a zoomed in image of aspirin so the user knows what to look for. The next box in the query flow is an instruction box 1122 that represents a GUI screen that provides specific instruction on how to administer aspirin to a victim, for example with text instructions, visual aid (e.g. pictures and/or video) and/or audio instructions. Once the aspirin has been administered, or alternatively if the user indicated a "Yes" answer to the question of box 1116 (e.g. the victim is allergic to aspirin), the query flow proceed to box 1124, which represents a GUI screen that asks the user if the victim has his/her own nitroglycerin. If the user indicates an answer of "Yes", the flow proceeds to box 1126, which represents a GUI screen providing instruction on administering the nitroglycerin to the victim, including but not limited to text, video, and/or audio instruction. At this point, or alternatively if the user indicated an answer of "No" to the question of box 1124, the query flow directs to link box 1094 and proceeds as described above.

If the user indicates an answer of "Palpitations" to the question of box 1106, the computer directs the query flow to box 1128, which represents a GUI screen instructing the user to ask the victim to attempt a forceful cough. After the victim attempts a forceful cough, the computer advances the query flow to box 1130, which represents a GUI screen that asks the user if the palpitations have stopped. If the user indicates a "Yes" answer, then the query flow advances to box 1132, which represents a GUI screen asking the user if the victim is allergic to aspirin. If the user indicates an answer of "No", the query flow advances to box 1134, which represents a GUI screen that instructs the user to locate the aspirin within the accompanying medical tool kit 12. By way of example, the represented GUI screen may also display a layout image of the aspirin and highlight with specificity the location of the aspirin. The next box 1136 represents a GUI screen that displays a zoomed in image of aspirin so the user knows what to look for. The next box in the query flow is an instruction box 1138 that represents a GUI screen that provides specific instruction on how to administer aspirin to a victim, for example with text instructions, visual aid (e.g. pictures and/or video) and/or audio instructions. Once the aspirin has been administered, or alternatively if the user indicated a "Yes" answer to the question of box 1132 (e.g. the victim is allergic to aspirin), the query flow proceeds to link box 1094 and proceeds as described above.

If the user indicates an answer of "No" to the question of box 1130 (e.g. palpitations did not stop), then the query is redirected to box 1128, and the victim is asked to repeat the attempt at a forceful cough. If the user indicates an answer of "No" for a second time to this very question, then the query is redirected to box 1128, and the victim is again asked to repeat the attempt at a forceful cough. If the user indicates an answer of "No" to this question for a third time, the computer directs the query flow to box 1140, which represents a GUI screen asking the user if the victim is allergic to aspirin. If the user indicates an answer of "No", the query flow advances to box 1142, which represents a GUI screen that instructs the user to locate the aspirin within the accompanying medical tool kit 12. By way of example, the represented GUI screen may also display a layout image of the aspirin and highlight with specificity the location of the aspirin. The next box 1144 represents a GUI screen that displays a zoomed in image of aspirin so the user knows what to look for. The next box in the query flow is an instruction box 1146 that represents a GUI screen that provides specific instruction on how to administer aspirin to a victim, for example with text instructions, visual aid (e.g. pictures and/or video) and/or audio instructions. Once the aspirin has been administered, or alternatively if the user indicated a "Yes" answer to the question of box 1140 (e.g. the victim is allergic to aspirin), the query flow proceeds to box 1148, which represents a GUI screen instructing the user to ask the victim to attempt a forceful cough. After the victim attempts a forceful cough, the computer advances the query flow to box 1150, which represents a GUI screen that asks the user if the palpitations have stopped. If the user indicates a "Yes" answer, then the query flow advances to link box 1094 and proceeds as described above.

If the user indicates an answer of "No" to the question of box 1150 (e.g. palpitations did not stop), then the query is redirected to box 1148, and the victim is asked to repeat the attempt at a forceful cough. If the user indicates an answer of "No" for a second time to the question of box 1150 (e.g. palpitations did not stop), then the query is redirected to box 1148, and the victim is again asked to repeat the attempt at a forceful cough. If the user indicates an answer of "No" to the question of box 1150 (e.g. palpitations did not stop) for a third time, the computer starts a five minute (5:00) timer and directs the query flow to box 1152, which represents a GUI screen that informs the user to "Stay calm, we will come back to this problem." At the expiration of the five-minute timer, the computer directs the query flow the Chest Pain Recheck flow of FIG. 63.

Figure 25:
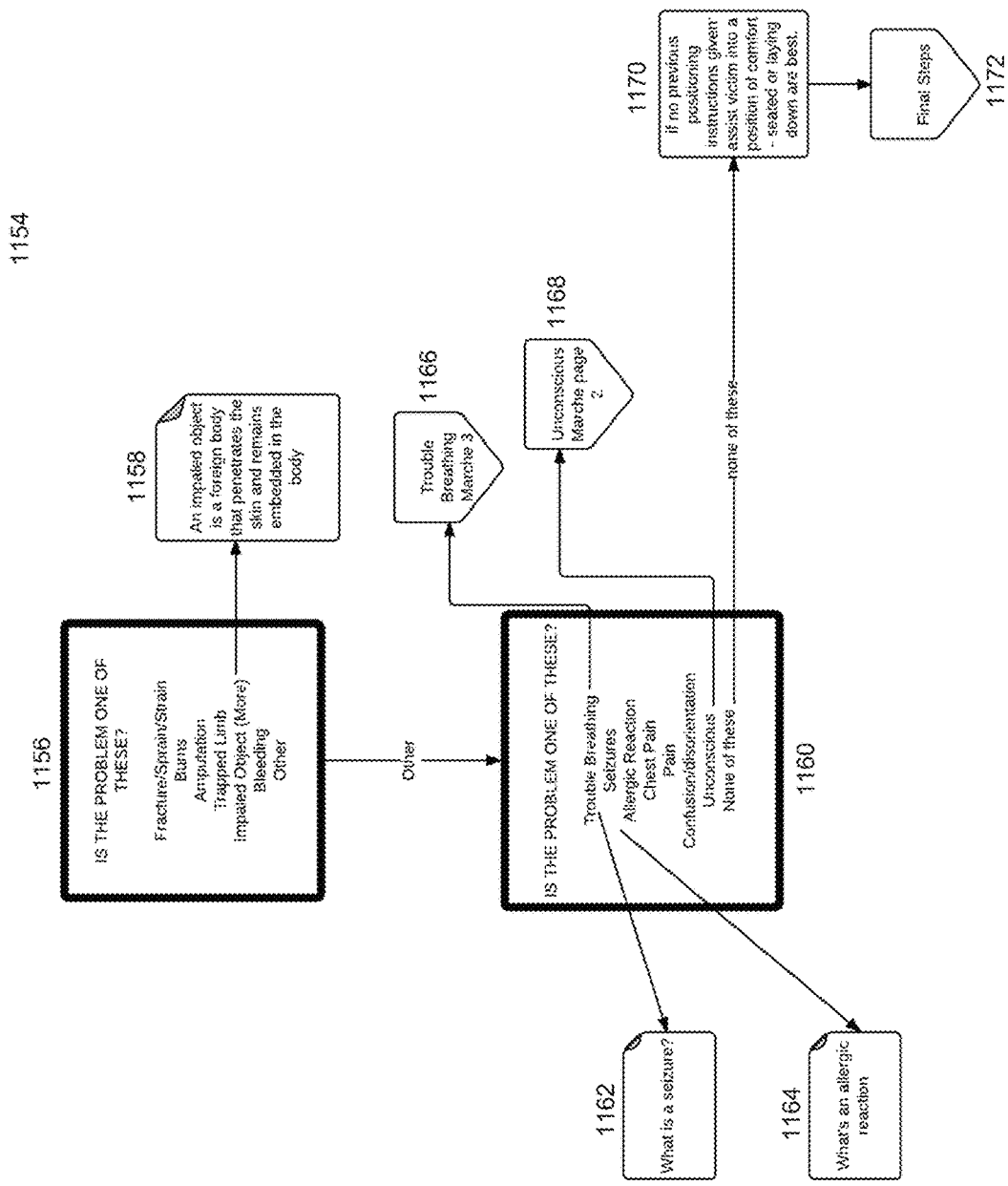
FIG. 25 is a flowchart illustrating an example query flow for determining whether the victim is suffering from a non life-threatening injury or illness, forming part of the triage protocol of FIGS. 2-5.
Figure 59:
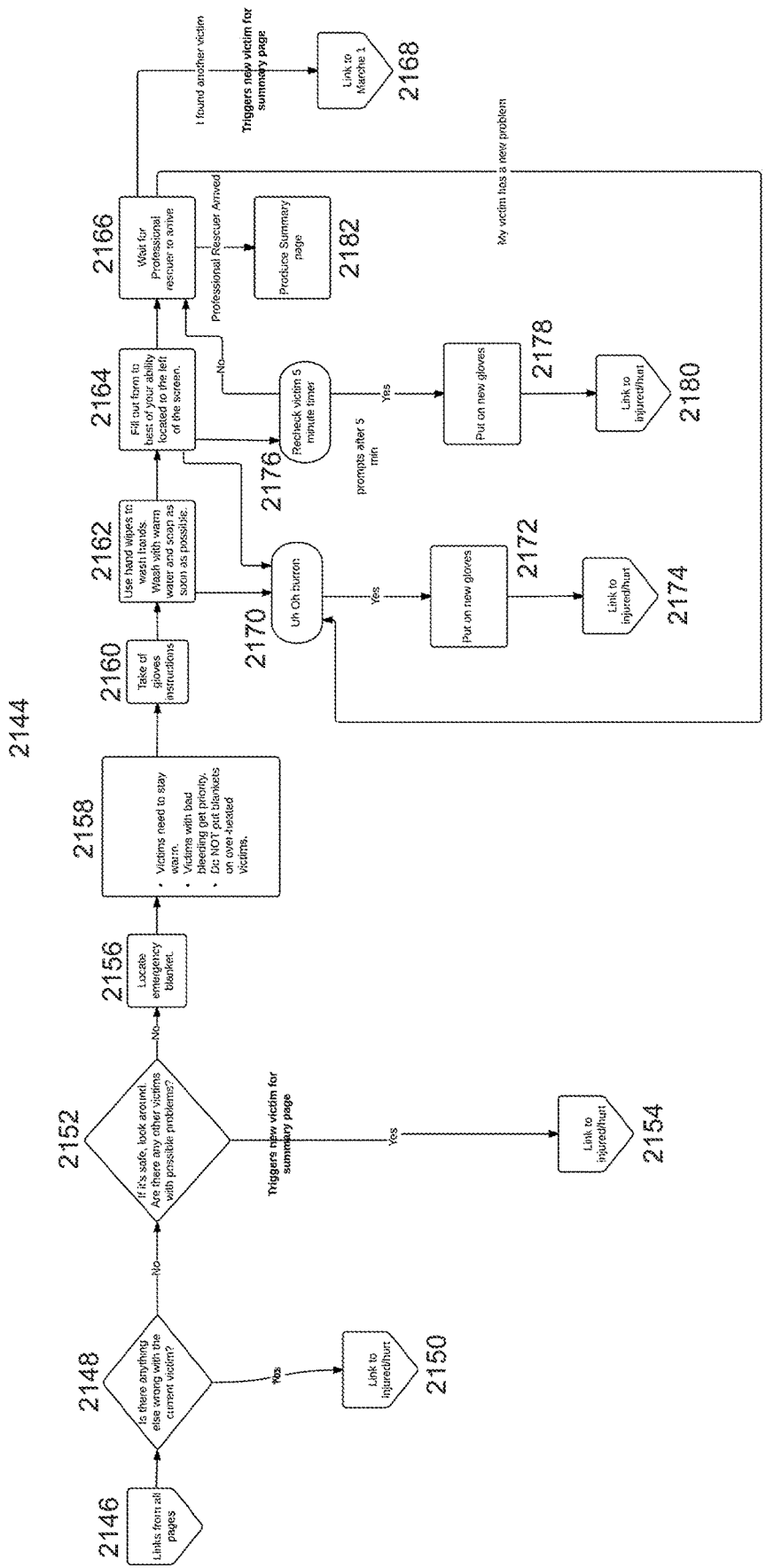
FIG. 59 is a flowchart illustrating an example query flow for the final patient protocol, forming part of the triage protocol of FIGS. 2-5.

FIG. 25 illustrates the query flow 1154 for determining whether the victim is suffering from a non life-threatening injury or illness, which is accessed from link box 2150 of the Final Patient Protocol query flow 2144 of FIG. 59. By way of example, Link box 2150 links the query flow to box 1156, which represents a GUI screen that asks the user if the problem is one of: Fracture/Sprain/Strain, Burns, Amputation, Trapped Limb, Impaled Object, Bleeding, or Other (See, e.g., FIG. 109 below). For the "Impaled Object" choice, the represented GUI screen includes a "More Info" icon that, if activated by the user (e.g. by touch or voice) prompts the computer to display a popup information box 1158 that explains to the user that an impaled object is a foreign body that penetrates the skin and remains embedded in the body. By way of example, if the user indicates "Fracture/Sprain/Strain," the computer will direct the query flow to the Pain/Fracture (Body Chooser) flow, described below with reference to FIG. 26. If the user indicates "Burns," the computer will direct the query flow to the Burns query flow, described below with reference to FIG. 35. If the user indicates "Amputation," the computer will direct the query flow to the Amputation query flow, described below with reference to FIG. 36. If the user indicates "Trapped Limb," the computer will direct the query flow to the Trapped Limb query flow, described below with reference to FIG. 37. If the user indicates "Impaled Object," the computer will direct the query flow to the Impaled Object query flow, described below with reference to FIG. 38. If the user indicates "Bleeding (mild)," the computer will direct the query flow to the Bleeding (Body Chooser) flow, described below with reference to FIG. 39.

If the user indicates "Other" in response to the question displayed by the GUI represented by box 1156, the computer advances the query flow to box 1160, which represents a GUI screen that asks the user if the problem is one of: Trouble Breathing, Seizures, Allergic Reaction, Chest Pain, General Pain, Confusion/Disorientation, Unconscious, or None of These (See, e.g. FIG. 108). For the "Seizure" choice, the represented GUI screen includes a "More Info" icon that, if activated by the user (e.g. by touch or voice) prompts the computer to display a popup information box 1162 that explains a seizure to the user. For the "Allergic Reaction" choice, the represented GUI screen includes a "More Info" icon that, if activated by the user (e.g. by touch or voice) prompts the computer to display a popup information box 1164 that explains an allergic reaction to the user. By way of example, if the user indicates "Trouble Breathing," the computer will direct the query flow to box 140 of the part 3 of the MARCHE protocol (via link box 1166), described above with reference to FIG. 4. If the user indicates "Seizures," the computer will direct the query flow to the Seizures query flow, described below with reference to FIG. 54. If the user indicates "Allergic Reaction," the computer will direct the query flow to the Allergic Reaction query flow, described below with reference to FIG. 55. If the user indicates "Chest Pain," the computer will direct the query flow to the Chest Pain query flow, described above with reference to FIG. 24. If the user indicates "General Pain," the computer will direct the query flow to the General Pain query flow, described below with reference to FIG. 27. If the user indicates "Confusion/Disorientation," the computer will direct the query flow to the Confusion/Disorientation query flow, described below with reference to FIG. 56. If the user indicates "Unconscious," the computer will direct the query flow to box 70 of Part 2 of the MARCHE protocol (via link box 1168), described above with reference to FIG. 3. If the user indicates "None of These", the computer will advance the query flow to instruction box 1170, which instructs the user to if needed "assist the victim into a position of comfort—seated or laying down are best." From this point the query flow proceeds to link box 1172, which links to the Final Protocol of FIG. 59.

Figure 26:
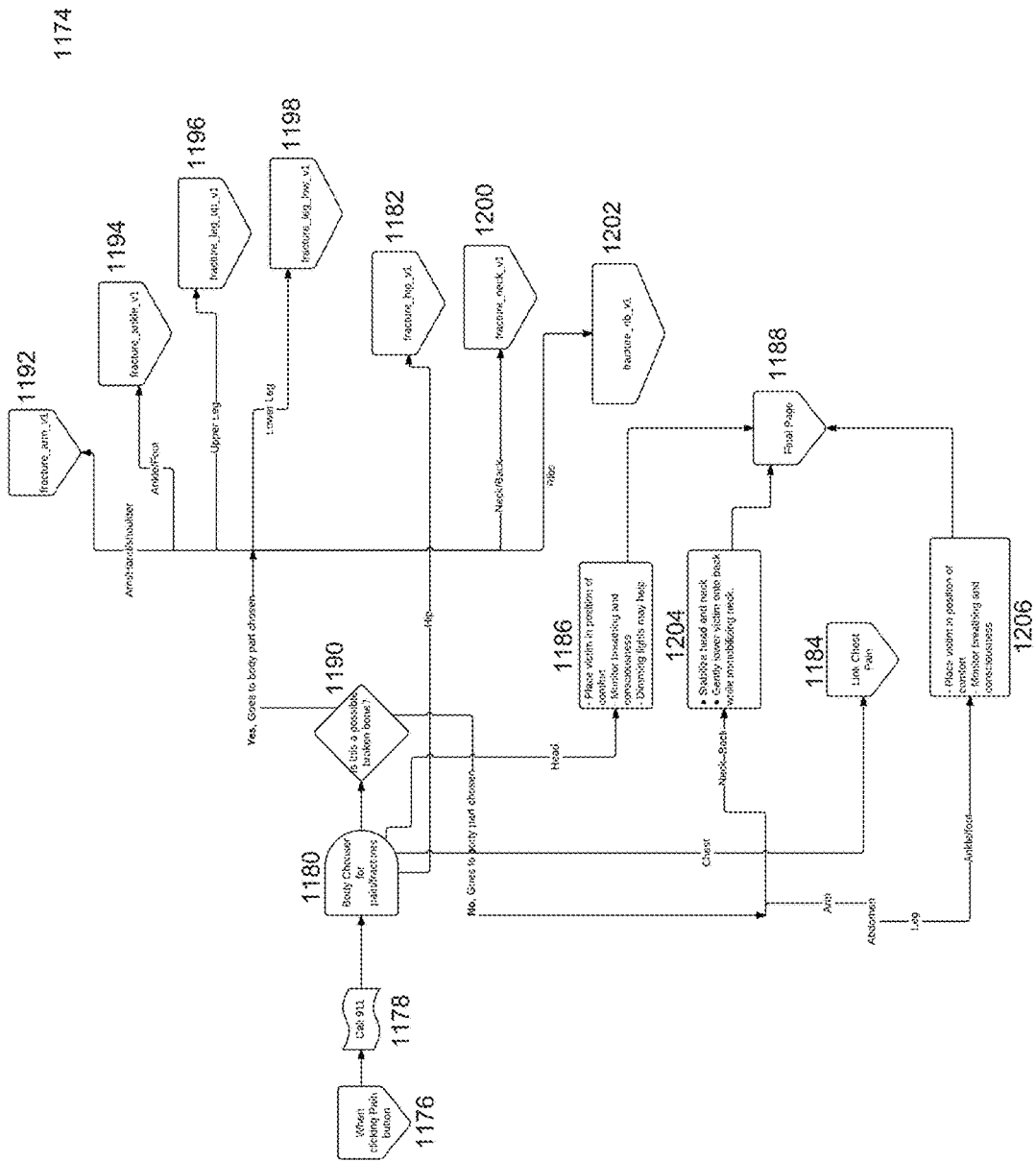
FIG. 26 is a flowchart illustrating an example query flow for determining the specific location on the body of a fracture, forming part of the triage protocol of FIGS. 2-5.

FIG. 26 illustrates the query flow 1174 for determining the specific location on the body of pain or a fracture, and is accessed when the user selects "Fracture/Sprain/Strain" in box 238 of FIG. 5 and/or box 1156 of FIG. 25. By way of example, the query flow links via link box 1176 and the computer immediately directs the flow to alert box 1178, which represents a GUI screen that instructs the user to call 9-1-1 if this has not already been done. The flow then proceeds to box 1180, which represents a GUI screen that displays an interactive diagram of the human body and directs the user to touch the location of the pain/fracture on the human body diagram. If the user selects the hip area on the interactive diagram of the human body, the computer directs the query flow to link box 1182, which links the flow to the Fracture-Hip query flow 1302, described below with reference to FIG. 32. If the user selects the chest area on the interactive diagram of the human body, the computer directs the query flow to link box 1184, which links the flow to box 1076 of the Chest Pain query flow 1074, described above with reference to FIG. 24. If the user selects the head area on the interactive diagram, the computer directs the query flow to box 1186, which represents a GUI screen that instructs the user to place the victim in position of comfort, monitor breathing and consciousness, and dim lights. The flow then proceeds to link box 1188, which links to the Final Protocol of FIG. 59.

If the user touches any other body part, the computer first directs the flow to query box 1190, which asks the user if the pain is a possible broken bone. If the answer is yes, then the query flow is directed to the appropriate flows for specific fractured bones. For example, if the user selects an arm (including hand and shoulder), the computer directs the query flow to link box 1192, which links the flow to box 1224 of the Fracture—Arm query flow 1222, described below with reference to FIG. 28. If the user selects an ankle or foot, the computer directs the query flow to link box 1194, which links the flow to box 1260 of the Fracture—Ankle/Foot query flow 1258, described below with reference to FIG. 29. If the user selects an upper leg, the computer directs the query flow to link box 1196, which links the flow to box 1292 of the Fracture—Upper Leg query flow 1290, described below with reference to FIG. 30. If the user selects a lower leg, the computer directs the query flow to link box 1198, which links the flow to box 1298 of the Fracture—Lower Leg query flow 1296, described below with reference to FIG. 31. If the user selects a neck or back, the computer directs the query flow to link box 1200, which links the flow to box 1310 of the Fracture—Neck/Back query flow 1308, described below with reference to FIG. 33. If the user selects ribs, the computer directs the query flow to link box 1202, which links the flow to box 1320 of the Fracture—Ribs query flow 1318, described below with reference to FIG. 34.

If the user answers "No" to the question of box 1190 (e.g. the selected pain is not a broken bone), then the query flow is directed to the appropriate flows for specified non-fracture injuries. For example, if the user selects neck or back, the computer directs the query flow to box 1204, which represents a GUI screen instructing the user to stabilize head and neck of victim, and to gently lower victim onto back while immobilizing the neck. If the user selects arm, abdomen, or leg (including ankle/foot), the computer directs the query flow to box 1206, which instructs the user to place the victim in a position of comfort, and to monitor breathing and consciousness. From either box 1204 or box 1206, the query flow continues to link box 1188, which links to the Final Protocol of FIG. 59.

Figure 27:
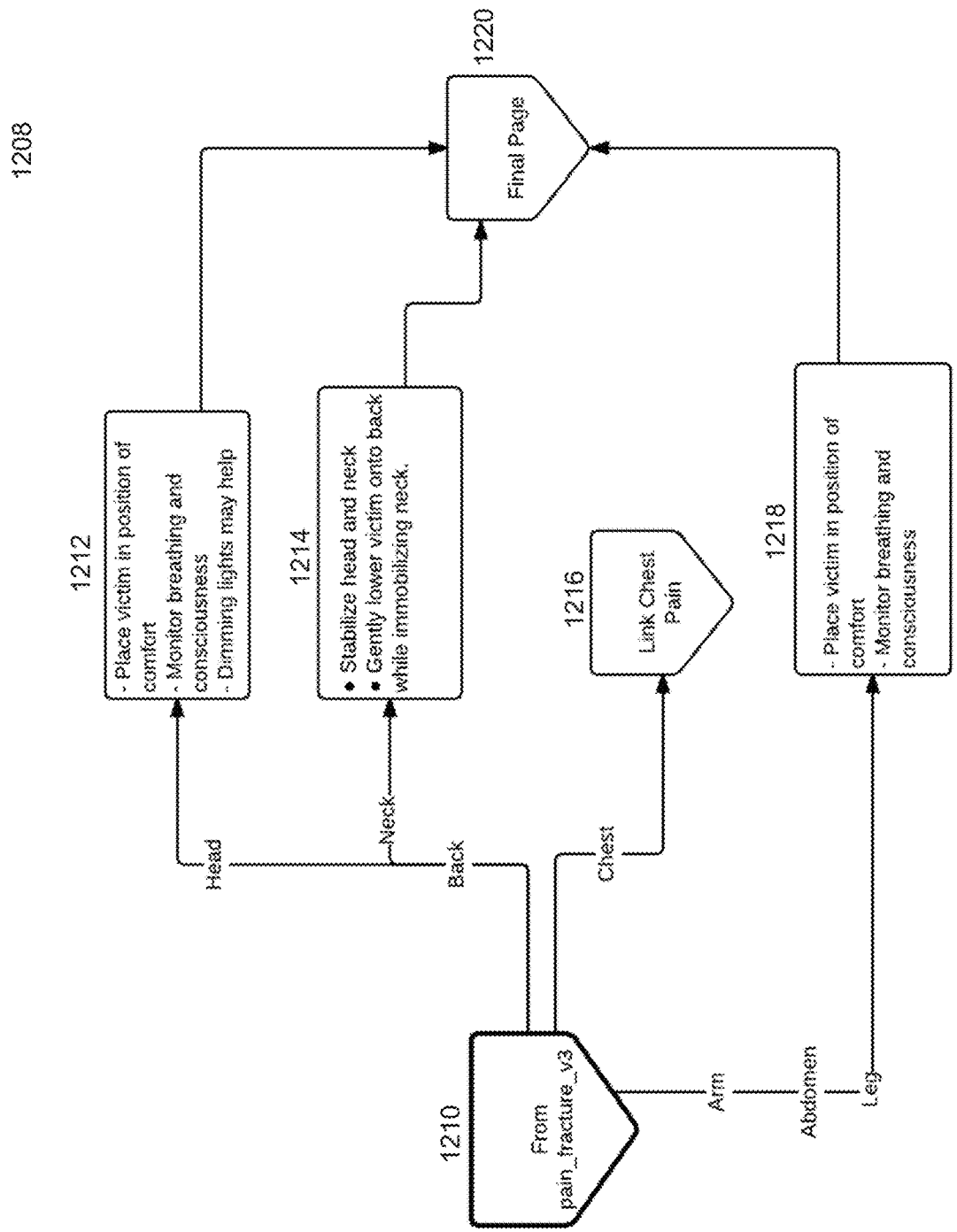
FIG. 27 is a flowchart illustrating an example query flow for general pain, forming part of the triage protocol of FIGS. 2-5.

FIG. 27 illustrates the query flow for general pain 1208, and is accessed when the user selects "Pain" in box 242 of FIG. 5 and/or box 1160 of FIG. 25. The query flow is linked through link box 1210, and may include a GUI screen that displays an interactive diagram of the human body and directs the user to touch the location of the generic pain on the human body diagram. Although not shown in the instant FIG., the body selector would be like those shown and described in similar instances herein elsewhere. For example, if the user selects the head area on the interactive diagram, the computer directs the query flow to box 1212, which represents a GUI screen that instructs the user to place the victim in position of comfort, monitor breathing and consciousness, and dim lights. The flow then proceeds to link box 1220, which links to the Final Protocol of FIG. 59. If the user selects neck or back, the computer directs the query flow to box 1214, which represents a GUI screen instructing the user to stabilize head and neck of victim, and to gently lower victim onto back while immobilizing the neck. The flow then proceeds to link box 1220, which links to the Final Protocol of FIG. 59. If the user selects the chest area on the interactive diagram of the human body, the computer directs the query flow to link box 1216, which links the flow to box 1076 of the Chest Pain query flow 1074, described above with reference to FIG. 24. If the user selects arm, abdomen, or leg (including ankle/foot), the computer directs the query flow to box 1218, which instructs the user to place the victim in a position of comfort, and to monitor breathing and consciousness. The flow then proceeds to link box 1220, which links to the Final Protocol of FIG. 59.

Figure 28:
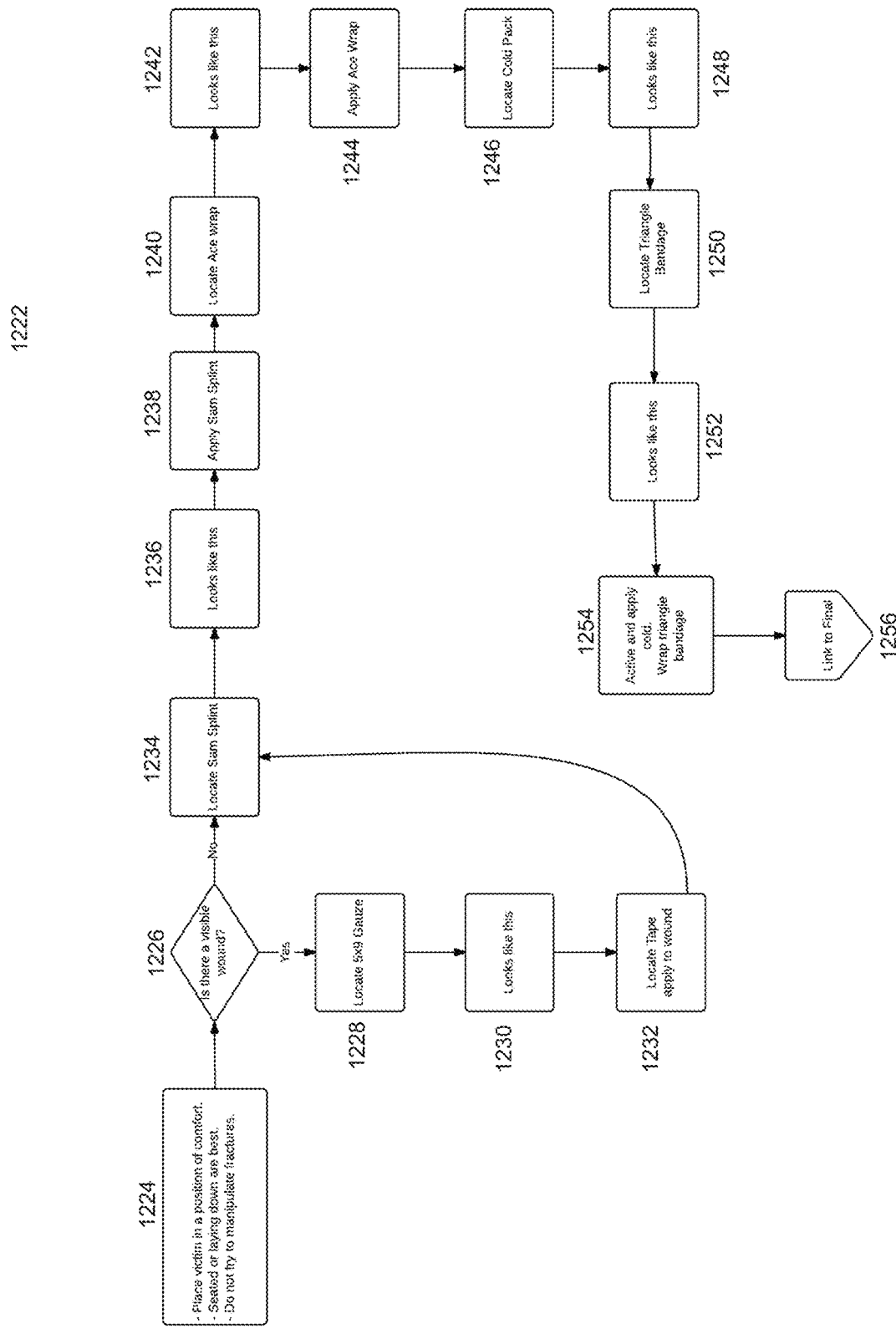
FIG. 28 is a flowchart illustrating an example query flow for a fractured arm, forming part of the triage protocol of FIGS. 2-5.

FIG. 28 illustrates the query flow for a fractured arm 1222, which is accessed from link box 1192 of FIG. 26. By way of example, the query flow begins at box 1224, which represents a GUI screen that instructs the user to place the victim in a position of comfort, seated or laying down are best, and do not try to manipulate fractures. The next box is a query box 1226, which represents a GUI screen that asks the user if there is a visible wound. If the user indicates a "Yes" answer, the computer advances the flow to box 1232, which is an instructional box representing a GUI screen that instructs the user to locate the 5×9 gauze within the accompanying medical tool kit 12. By way of example, the represented GUI screen may also display a layout image of the tool kit and highlight with specificity the location of the 5×9 gauze. The next box 1230 represents a GUI screen that displays a zoomed in image of the 5×9 gauze so the user knows what to look for. The next box in the query flow is an instruction box 1232 that represents a GUI screen that provides specific instruction on how to apply the 5×9 gauze to a wound including locating tape on the medical tool kit 12, for example with text instructions, visual aid (e.g. pictures and/or video) and/or audio instructions.

Once the user indicates that the 5×9 gauze has been successfully taped to the wound, or alternatively if the user indicates a "No" answer to the question of box 1226 (e.g. no visible wound), the query flow advances to box 1234, which is an instructional box representing a GUI screen that instructs the user to locate the SAM splint within the accompanying medical tool kit 12. By way of example, the represented GUI screen may also display a layout image of the tool kit and highlight with specificity the location of the SAM splint. The next box 1236 represents a GUI screen that displays a zoomed in image of the SAM splint so the user knows what to look for. The next box in the query flow is an instruction box 1238 that represents a GUI screen that provides specific instruction on how to apply the SAM splint to a victim, for example with text instructions, visual aid (e.g. pictures and/or video) and/or audio instructions.

Next, the query flow advances to box 1240, which is an instructional box representing a GUI screen that instructs the user to locate the Ace wrap within the accompanying medical tool kit 12. By way of example, the represented GUI screen may also display a layout image of the tool kit and highlight with specificity the location of the Ace wrap. The next box 1242 represents a GUI screen that displays a zoomed in image of the Ace wrap so the user knows what to look for. The next box in the query flow is an instruction box 1244 that represents a GUI screen that provides specific instruction on how to apply the Ace wrap in wrapping the SAM splint, for example with text instructions, visual aid (e.g. pictures and/or video) and/or audio instructions.

Next, the query flow advances to box 1246, which is an instructional box representing a GUI screen that instructs the user to locate the cold pack within the accompanying medical tool kit 12. By way of example, the represented GUI screen may also display a layout image of the tool kit and highlight with specificity the location of the cold pack. The next box 1248 represents a GUI screen that displays a zoomed in image of the cold pack so the user knows what to look for. The next box 1250 represents a GUI screen that instructs the user to locate the triangle bandage within the accompanying medical tool kit 12. By way of example, the represented GUI screen may also display a layout image of the tool kit and highlight with specificity the location of the triangle bandage. The next box 1252 represents a GUI screen that displays a zoomed in image of the triangle bandage so the user knows what to look for. The next box in the query flow is an instruction box 1254 that represents a GUI screen that provides specific instruction on how to activate and apply the cold pack to the wrapped the SAM splint, and then wrapping the triangle bandage about it all, for example with text instructions, visual aid (e.g. pictures and/or video) and/or audio instructions. Once the user indicates that the triangle bandage is wrapped, the query flow advances to link box 1256, which links to the Final Protocol of FIG. 59.

Figure 29:
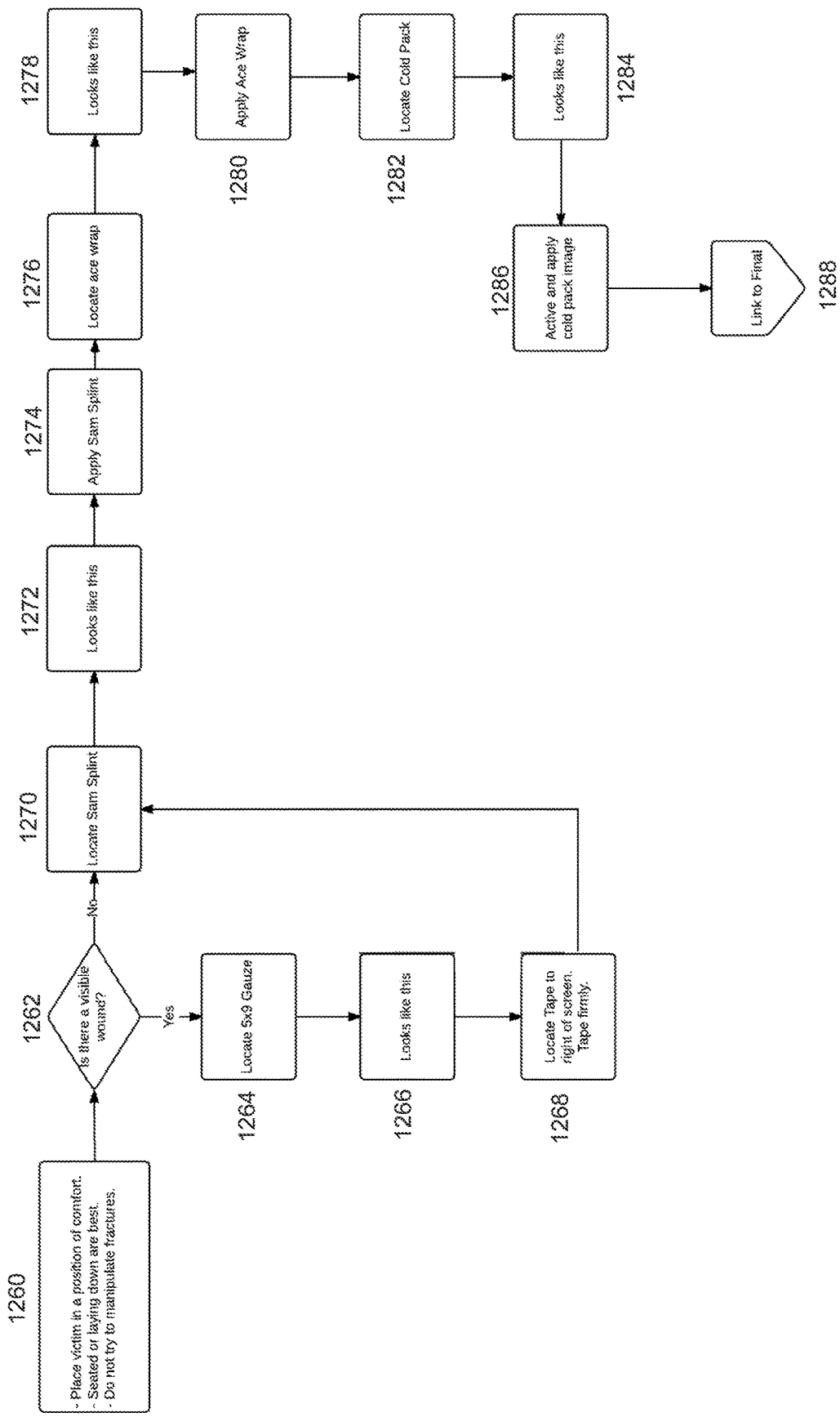
FIG. 29 is a flowchart illustrating an example query flow for a fractured ankle/foot, forming part of the triage protocol of FIGS. 2-5.

FIG. 29 illustrates the query flow for a fractured ankle/foot, which is accessed from link box 1194 of FIG. 26. By way of example, the query flow begins at box 1260, which represents a GUI screen that instructs the user to place the victim in a position of comfort, seated or laying down are best, and do not try to manipulate fractures. The next box is a query box 1262, which represents a GUI screen that asks the user if there is a visible wound. If the user indicates a "Yes" answer, the computer advances the flow to box 1264, which is an instructional box representing a GUI screen that instructs the user to locate the 5×9 gauze within the accompanying medical tool kit 12. By way of example, the represented GUI screen may also display a layout image of the tool kit and highlight with specificity the location of the 5×9 gauze. The next box 1266 represents a GUI screen that displays a zoomed in image of the 5×9 gauze so the user knows what to look for. The next box in the query flow is an instruction box 1268 that represents a GUI screen that provides specific instruction on how to apply the 5×9 gauze to a wound including locating tape on the medical tool kit 12, for example with text instructions, visual aid (e.g. pictures and/or video) and/or audio instructions.

Once the user indicates that the 5×9 gauze has been successfully taped to the wound, or alternatively if the user indicates a "No" answer to the question of box 1262 (e.g. no visible wound), the query flow advances to box 1270, which is an instructional box representing a GUI screen that instructs the user to locate the SAM splint within the accompanying medical tool kit 12. By way of example, the represented GUI screen may also display a layout image of the tool kit and highlight with specificity the location of the SAM splint. The next box 1272 represents a GUI screen that displays a zoomed in image of the SAM splint so the user knows what to look for. The next box in the query flow is an instruction box 1274 that represents a GUI screen that provides specific instruction on how to apply the SAM splint to a victim, for example with text instructions, visual aid (e.g. pictures and/or video) and/or audio instructions.

Next, the query flow advances to box 1276, which is an instructional box representing a GUI screen that instructs the user to locate the Ace wrap within the accompanying medical tool kit 12. By way of example, the represented GUI screen may also display a layout image of the tool kit and highlight with specificity the location of the Ace wrap. The next box 1278 represents a GUI screen that displays a zoomed in image of the Ace wrap so the user knows what to look for. The next box in the query flow is an instruction box 1280 that represents a GUI screen that provides specific instruction on how to apply the Ace wrap in wrapping the SAM splint, for example with text instructions, visual aid (e.g. pictures and/or video) and/or audio instructions.

Next, the query flow advances to box 1282, which is an instructional box representing a GUI screen that instructs the user to locate the cold pack within the accompanying medical tool kit 12. By way of example, the represented GUI screen may also display a layout image of the tool kit and highlight with specificity the location of the cold pack. The next box 1284 represents a GUI screen that displays a zoomed in image of the cold pack so the user knows what to look for. The next box 1286 represents a GUI screen that provides specific instruction on how to activate and apply the cold pack to the wrapped the SAM splint, for example with text instructions, visual aid (e.g. pictures and/or video) and/or audio instructions. Once the user indicates that the triangle bandage is wrapped, the query flow advances to link box 1288, which links to the Final Protocol of FIG. 59.

Figure 30:
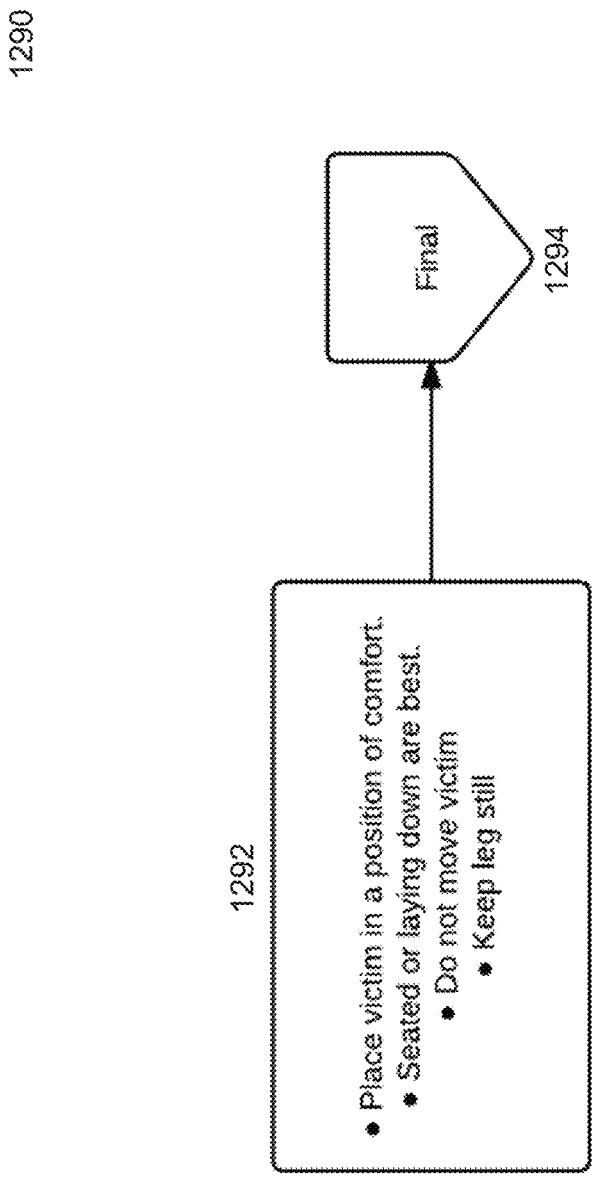
FIG. 30 is a flowchart illustrating an example query flow for a fractured upper leg, forming part of the triage protocol of FIGS. 2-5.

FIG. 30 illustrates the query flow for a fractured upper leg 1290, which is accessed from link box 1196 of FIG. 26. By way of example, box 1292 is an instructional box that represents a GUI screen that instructs a victim to place the victim in a position of comfort, seated or laying down are best, do not move the victim, and keep the leg still. The query flow 1290 then advances to link box 1294, which links to the Final Protocol of FIG. 59.

Figure 31:
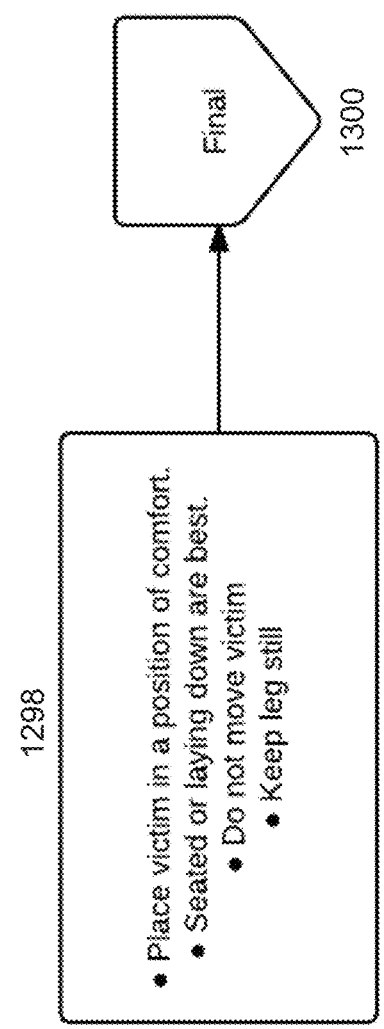
FIG. 31 is a flowchart illustrating an example query flow for a fractured lower leg, forming part of the triage protocol of FIGS. 2-5.

FIG. 31 illustrates the query flow for a fractured lower leg 1296, which is accessed from link box 1198 of FIG. 26. By way of example, box 1298 is an instructional box that represents a GUI screen that instructs a victim to place the victim in a position of comfort, seated or laying down are best, do not move the victim, and keep the leg still. The query flow 1296 then advances to link box 1300, which links to the Final Protocol of FIG. 59.

Figure 32:
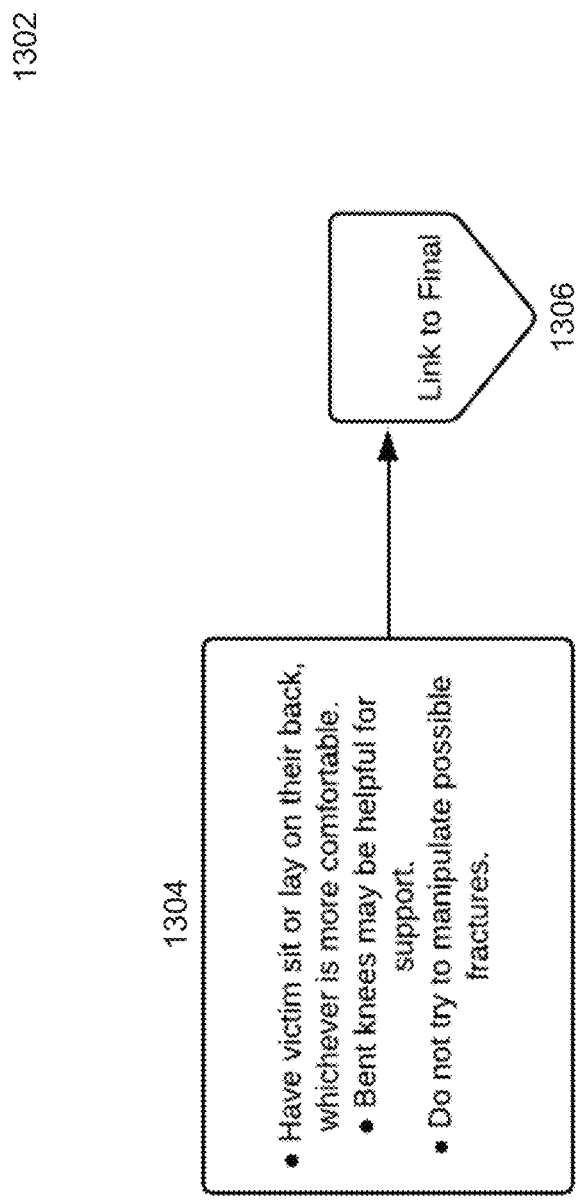
FIG. 32 is a flowchart illustrating an example query flow for a fractured hip, forming part of the triage protocol of FIGS. 2-5.

FIG. 32 illustrates the query flow for a fractured hip 1302, which is accessed from link box 1182 of FIG. 26. By way of example, box 1304 is an instructional box that represents a GUI screen that instructs a victim to have the victim sit or lay on their back, whichever is more comfortable, bent knees may be helpful for support, and do not try to manipulate possible fractures. The query flow 1202 then advances to link box 1306, which links to the Final Protocol of FIG. 59.

Figure 33:
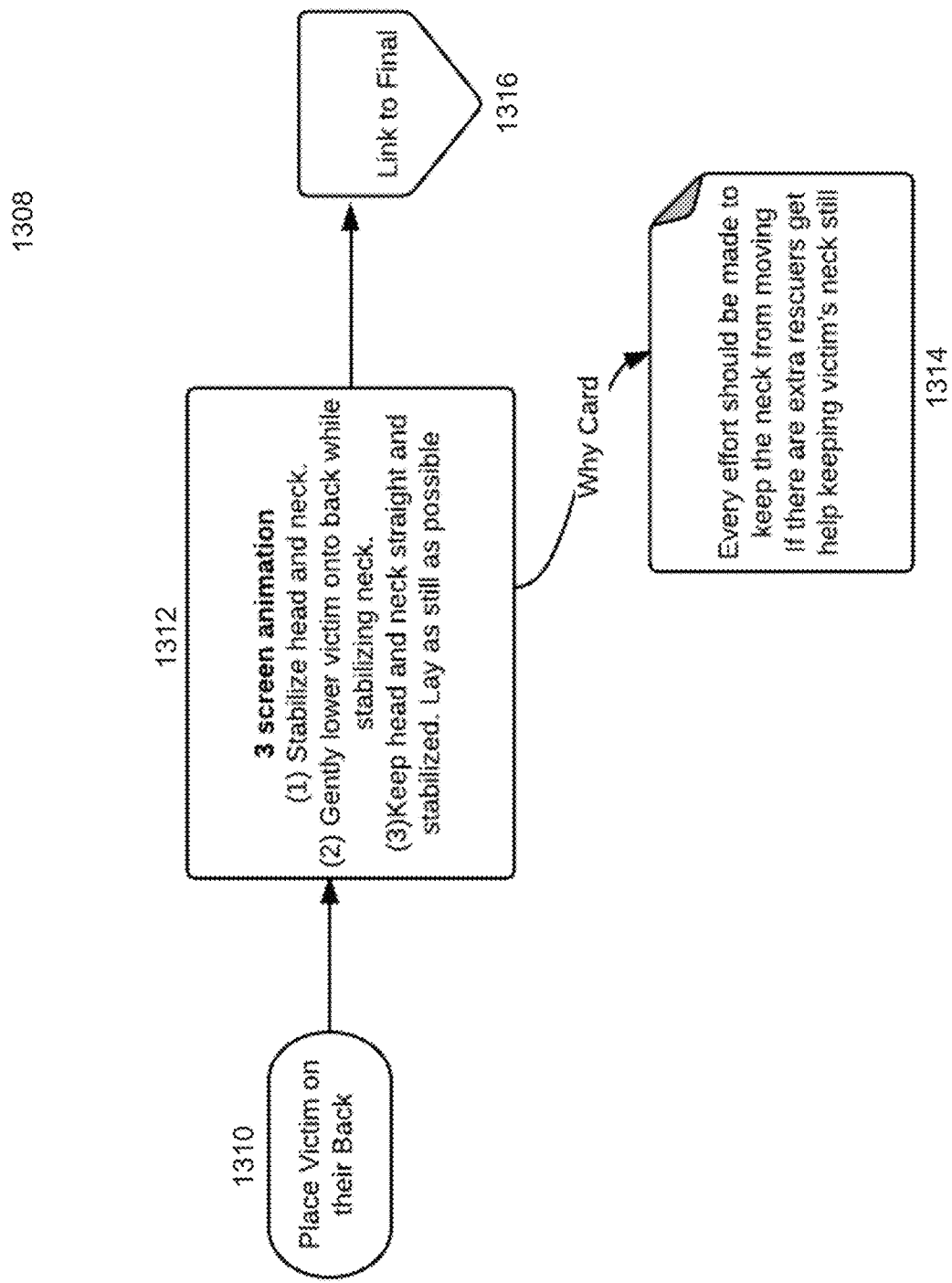
FIG. 33 is a flowchart illustrating an example query flow for a fractured neck/back, forming part of the triage protocol of FIGS. 2-5.

FIG. 33 illustrates the query flow for a fractured neck/back, which is accessed from link box 1200 of FIG. 26. By way of example, box 1310 is an instruction box representing a GUI screen instructing the user to place the victim on their back. The next box 1312 is an instruction box representing a GUI screen including three screen animations: (1) a video animation about how to stabilize the head and neck of the victim, (2) a video animation that shows how to gently lower victim onto their back while stabilizing the neck, and (3) a video animation about how to keep the head and neck straight and stabilized, laying still as possible. A "Why?" icon may be present on the represented GUI that, if activated by the user (e.g. by touch or voice) prompts the computer to display a popup information box 1314 that explains to the user that every effort should be made to keep the neck from moving, and if there are extra rescuers, get help keeping the victim's neck still. From this point the query flow proceeds to link box 1316, which links to the Final Protocol of FIG. 59.

Figure 34:
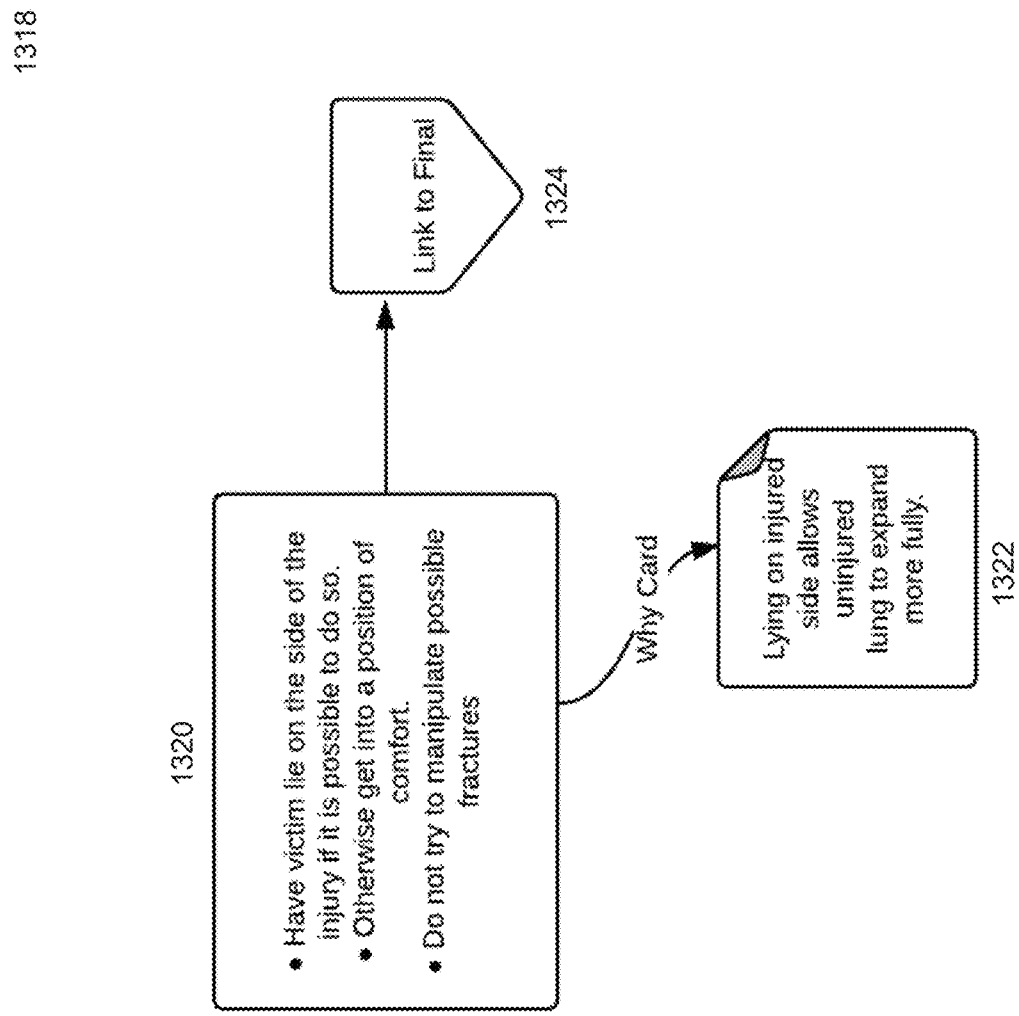
FIG. 34 is a flowchart illustrating an example query flow for fractured ribs, forming part of the triage protocol of FIGS. 2-5.

FIG. 34 illustrates the query flow for fractured ribs 1318, which is accessed from link box 1202 of FIG. 26. By way of example, the instruction box 1320 represents a GUI screen instructing the user to have the victim lie on the side of the injury if possible to do so, otherwise get into a position of comfort, and do not try to manipulate possible fractures. A "Why?" icon may be present on the represented GUI that, if activated by the user (e.g. by touch or voice) prompts the computer to display a popup information box 1322 that explains to the user that laying a victim on his/her injured side allows the uninjured lung to expand more fully. From this point the query flow proceeds to link box 1324, which links to the Final Protocol of FIG. 59.

Figure 35:
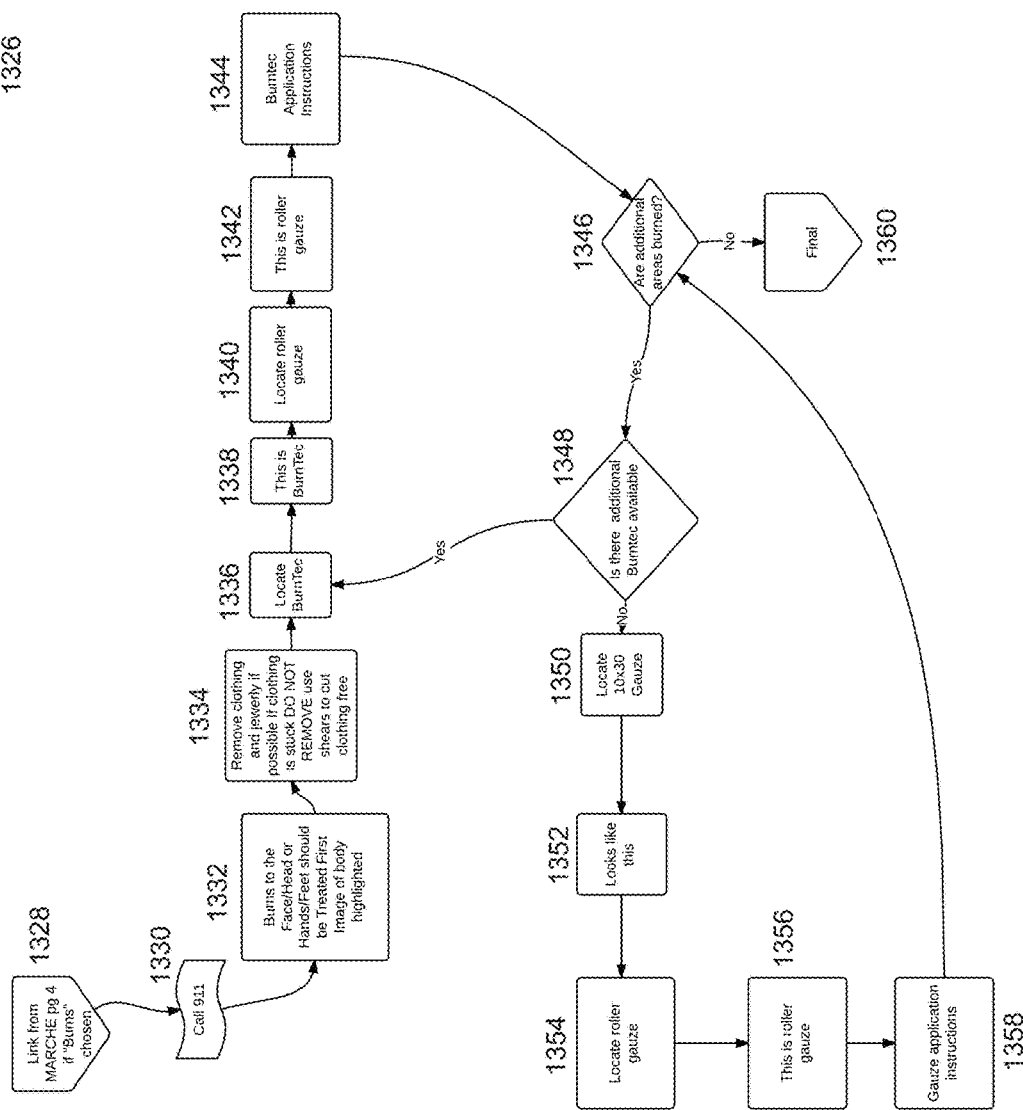
FIG. 35 is a flowchart illustrating an example query flow for burns, forming part of the triage protocol of FIGS. 2-5.

FIG. 35 illustrates the query flow for burns 1326, which is accessed via query box 238 of FIG. 5 (e.g. in response to the user touching or using voice commands on query box 238 to inform the computer that the victim has experienced a burn) and begins at link box 1328. Upon entry into the burn query flow 1326, the user is reminded to call 9-1-1 via alert box 1330 to summons emergency personnel, if that hasn't already been done by the user or a by-stander. The burn query flow then proceeds to instructional box 1332 with a GUI display that informs the user that burns to the face/head or hands/feet should be treated first and presents a display of an interactive diagram of the human body and directs the user to touch the location of the burn on the human body diagram. From there, the burn query flow continues to instructional box 1334 with a GUI display that instructs the user to remove the clothing and jewelry of the victim, if possible, and to refrain from using the shears (e.g. if included in the medical tool kit 12 of FIG. 1) to cut the clothing free if the clothing is stuck to the victim. The user is then instructed (via instructional box 1336) with a GUI with instructions to locate the BurnTec® burn dressing (e.g. from the medical tool kit 12 of FIG. 1). The user is also presented (at instructional box 1338) with an instructional video or image of the BurnTec burn dressing, in order to help the user quickly identify or otherwise recognize it to thus facilitate the location instruction of box 1336. The burn query flow then proceeds to instructional box 1340, which presents a GUI display instructing the user to locate the roller gauze. The user is also presented (at instructional box 1342) with an instructional video or image of the roller gauze in order to help the user quickly identify or otherwise recognize it to thus facilitate the location instruction of box 1340. The user is then presented with an instructional box 1344 with a GUI displaying or otherwise calling up instructions for applying the BurnTec burn dressing to the victim. With these instructions available, the BurnTec burn dressing may be applied by the user to the victim.

The burn query flow then presents a query box 1346 with a GUI display which presents a question to the user as to whether additional areas on the victim are burned. If the user indicates that the answer is "Yes" to that question (at query box 1346), the query flow proceeds to query box 1348, which presents a GUI display with a question to the user as to whether there is additional quantities of BurnTec burn dressing available. If the user indicates that the answer to query box 1348 is "Yes", the query flow returns to instructional box 1336 where the user will be instructed to locate the BurnTec burn dressing for use on the "additional area burned" on the victim as described above. If the user indicates the answer is "No" at query box 1348, the user will then be presented (at instructional box 1350) with a GUI display with instructions to locate gauze (e.g. 10"×30" gauze from the medical tool kit 12 of FIG. 1). The user is also presented (at instructional box 1352) with an instructional video or image of the gauze (e.g. 10"×30" gauze) in order to help the user quickly identify or otherwise recognize it to thus facilitate the location instruction of box 1350. The burn query flow then proceeds to instructional box 1354 with a GUI display instructing the user to locate the roller gauze. The user is also presented (at instructional box 1356) with an instructional video or image of the roller gauze in order to help the user quickly identify or otherwise recognize it to thus facilitate the location instruction of box 1354. The user is then presented with an instructional box 1358 with a GUI displaying or otherwise calling up instructions for applying the roller gauze to the victim. With these instructions available, the roller gauze may be applied by the user to the victim. The burn query flow then proceeds back to query box 1346 to determine whether there are additional areas burned on the victim. If the user indicates the answer is "Yes" in response to query box 1346, the query flow proceeds to query box 1348 and onward. If the user indicates the answer is "No" in response to query box 1346, then query flow proceeds to link box 1360, which then proceeds to the Final Protocol described below in FIG. 59.

Figure 36:
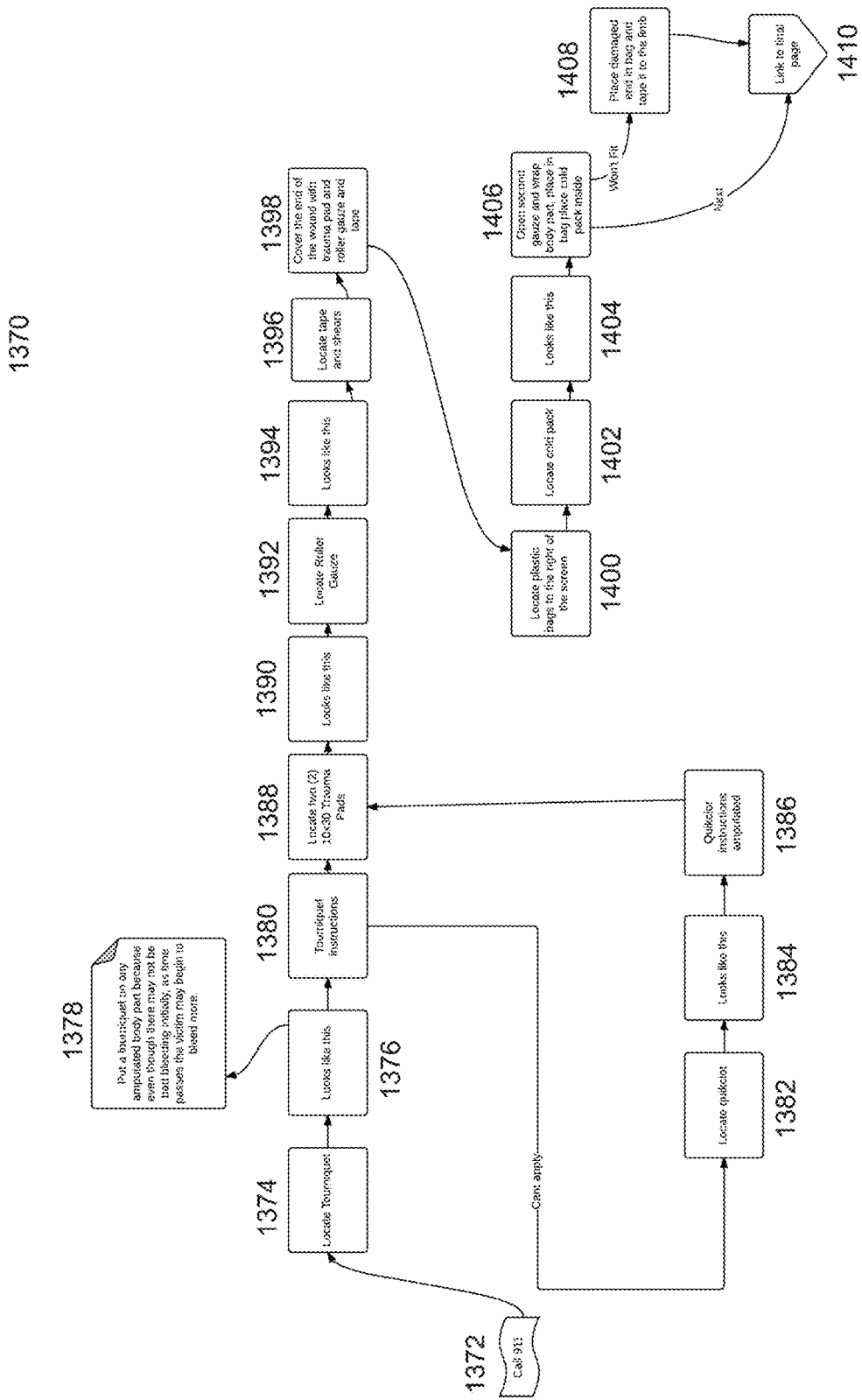
FIG. 36 is a flowchart illustrating an example query flow for severed limbs, forming part of the triage protocol of FIGS. 2-5.

FIG. 36 illustrates the query flow 1370 for severed limbs, which is accessed via query box 238 of FIG. 5 (e.g. in response to the user touching or using voice commands on query box 238 to inform the computer that the victim has a severed limb or amputation). Upon entry into the severed limb query flow 1370, the user is reminded to call 9-1-1 via alert box 1372 to summons emergency personnel, if that hasn't already been done by the user or a by-stander. The user is then instructed (via instructional box 1374) with a GUI display with instructions to locate the tourniquet (e.g. from the medical tool kit 12 of FIG. 1). The user is also presented (at instructional box 1376) with an instructional video or image of the tourniquet in order to help the user quickly identify or otherwise recognize it to thus facilitate the location instruction of box 1374. An additional instructional box 1378 may be provided as a GUI display with reasons for placing a tourniquet around an amputated or severed body part, for example, because even though there may not be bad bleeding initially, as time passes the victim may begin to bleed more and thus require a tourniquet. The user is then presented with an instructional box 1380 with a GUI displaying or otherwise calling up instructions for applying the tourniquet to the victim. With these instructions available, the tourniquet may be applied by the user to the victim.

If the user is unable to apply the tourniquet to the victim, the severed limb query flow proceeds to instructional box 1382 with a GUI display informing the user to locate wound dressing (e.g. QuickClot™ hemostatic wound dressing) for application to the victim. The user is also presented (at instructional box 1384) with an instructional video or image of the QuickClot wound dressing in order to help the user quickly identify or otherwise recognize it to thus facilitate the location instruction of box 1382. The user is then presented with an instructional box 1386 with a GUI displaying or otherwise calling up instructions for applying the QuickClot wound dressing to an amputated limb of the victim. With these instructions available, the wound dressing may be applied by the user to the victim.

If the application of the tourniquet at instructional box 1380 is successful or the application of the QuickClot wound dressing at instructional box 1386 is successful, then the severed limb query flow proceeds to the instructional box 1388, which includes a GUI display instructing the user to locate two (2) trauma pads (e.g. 10"×30" trauma pads. The user is also presented (at instructional box 1390) with an instructional video or image of the trauma pads to help the user quickly identify or otherwise recognize it and thus facilitate the location instruction of box 1388. The severed limb query flow then proceeds to instructional box 1392, which presents a GUI display instructing the user to locate roller gauze (e.g. from medical tool kit 12 of FIG. 1). The user is also presented (at instructional box 1394) with an instructional video or image of the roller gauze to help the user quickly identify or otherwise recognize it and thus facilitate the location instruction of box 1392. The severed limb query flow then proceeds to instructional box 1396, which presents a GUI display instructing the user to locate tape and shears (e.g. from medical tool kit 12 of FIG. 1). The user is then presented with an instructional box 1398 with a GUI display instructing the user to cover the end of the wound with the trauma pad (of instructional box 1388), the roller gauze (of instructional box 1392) and the tape (of instructional box 1396). The severed limb query flow then proceeds to instructional box 1400 which presents a GUI display instructing the user to locate plastic bags (e.g. to the right of the screen of the instructional device 14 of FIG. 1. The severed limb query flow then proceeds to instructional box 1402, which presents a GUI display instructing the user to locate a cold pack (e.g. from medical tool kit 12 of FIG. 1). The user is also presented (at instructional box 1404) with an instructional video or image of the cold pack to help the user quickly identify or otherwise recognize it and thus facilitate the location instruction of box 1402. The severed limb query flow then proceeds to instructional box 1406, which presents a GUI display instructing the user to open the second gauze, wrap the severed limb in the second gauze, and place the severed body part within the bag with a cold pack inside. If the severed limb won't fit in the plastic bag (per instructional box 1406), then the severed limb query flow proceeds to an instructional box 1408 with a GUI display with instructions for the user to place the damaged end of the severed limb in the plastic bag and tape the plastic bag to the limb. If the severed limb will fit in the plastic bag (per instructional box 1406), then the severed limb query flow proceeds to the link box 1410 that directs the user to the Final Protocol of FIG. 59.

Figure 37:
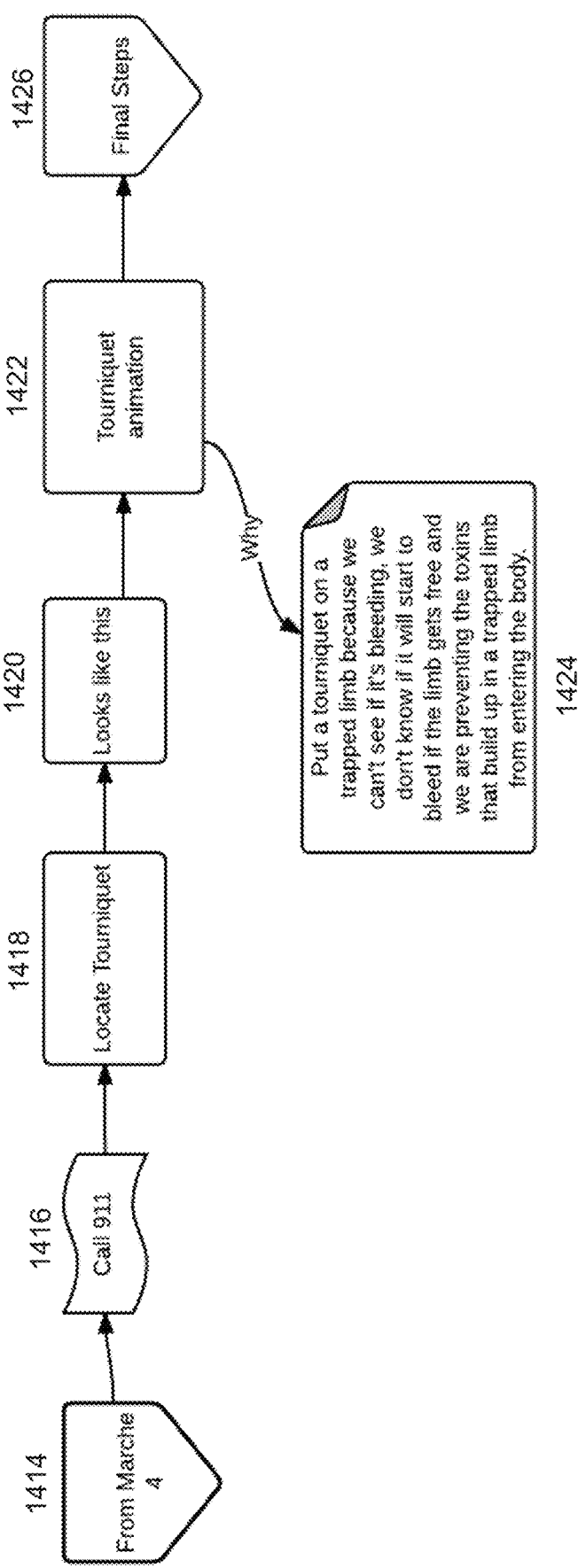
FIG. 37 is a flowchart illustrating an example query flow for a trapped limb, forming part of the triage protocol of FIGS. 2-5.

FIG. 37 illustrates the query flow 1412 for a trapped limb, which is accessed via query box 238 of FIG. 5 (e.g. in response to the user touching or using voice commands on query box 238 to inform the computer that the victim has a trapped limb) and begins at link box 1414. Upon entry into the trapped limb query flow 1414, the user is reminded to call 9-1-1 via alert box 1416 to summons emergency personnel, if that hasn't already been done by the user or a by-stander. The user is then instructed (via instructional box 1418) with a GUI display with instructions to locate the tourniquet (e.g. from the medical tool kit 12 of FIG. 1). The user is also presented (at instructional box 1420) with an instructional video or image of the tourniquet in order to help the user quickly identify or otherwise recognize it to thus facilitate the location instruction of box 1418. The user may be optionally presented with an animation or video at instructional box 1422 with instructional video or audio demonstrating to the user how to apply the tourniquet, or for example the reasons for putting a tourniquet on a trapped limb regarding the tourniquet (as set forth, by way of example only, in instructional box 1424). Once the tourniquet has been applied to the victim by the user, the trapped limb query flow proceeds to the Final Protocol of FIG. 59 as shown in link box 1426.

Figure 38:
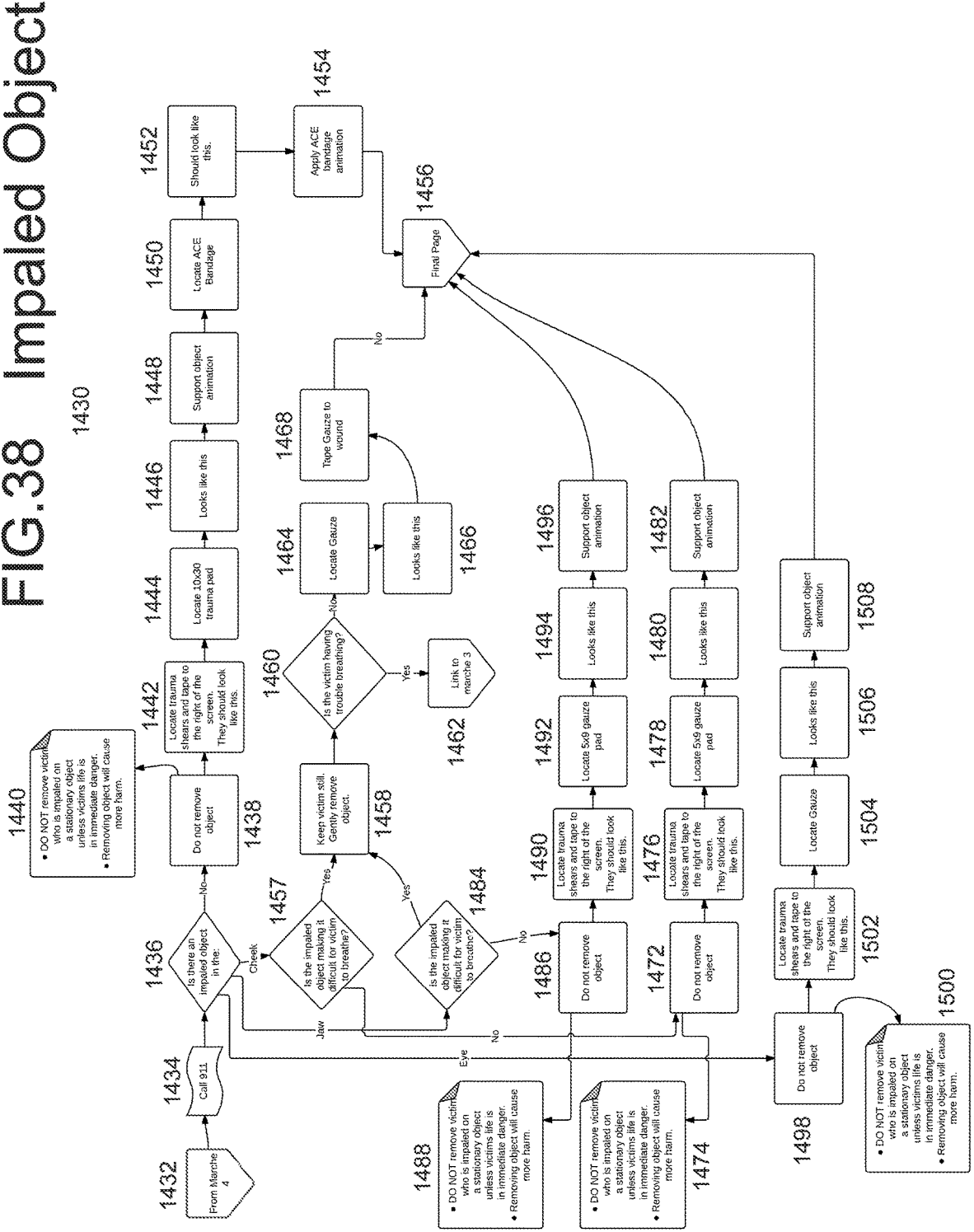
FIG. 38 is a flowchart illustrating an example query flow for an impaled object, forming part of the triage protocol of FIGS. 2-5.

FIG. 38 illustrates the query flow 1430 for an impaled object, which is accessed via query box 238 of FIG. 5 (e.g. in response to the user touching or using voice commands on query box 238 to inform the computer that the victim has an impaled object) and begins at link box 1432. Upon entry into the impaled object query flow 1430, the user is reminded to call 9-1-1 via alert box 1434 to summons emergency personnel, if that hasn't already been done by the user or a by-stander. The impaled object query flow proceeds to query box 1436 which has a GUI display inquiring of the user as to whether there is an object impaled in the cheek, jaw or eye of the victim.

If the answer is "No" to query box 1436, then the impaled object query flow proceeds to instructional box 1438 with a GUI display instructing the user not to remove the object, with an optional explanatory box 1440 with a GUI display that explains not to remove the victim if impaled on a stationary object, unless their life is in immediate danger, because removing the object will cause more harm. The impaled object query flow proceeds to instructional box 1442 with a GUI display with instructions for the user to locate trauma sheers and tape (e.g. to the right of the screen of the instructional device 14 of FIG. 1), along with images or videos of what they look like to help facilitate their location by the user. The user is then instruction (via instructional box 1444) to locate the desired trauma pads (e.g. 10"×30"). The user is also presented (at instructional box 1446) with an instructional video or image of the trauma pads in order to help the user quickly identify or otherwise recognize it to thus facilitate the location instruction of box 1444. At instructional box 1448, an instructional video or animation is presented to the user for the purpose of educating the user on the proper technique for supporting the object impaled in the victim. The user is then presented (at instructional box 1450) with a GUI display instructing the user to locate an ACE bandage. The user is also presented (at instructional box 1452) with an instructional video or image of the ACE bandage in order to help the user quickly identify or otherwise recognize it to thus facilitate the location instruction of box 1450. The impaled object query flow then presents (at instructional box 1454) a video or animation illustrating how to apply the ACE bandage to or around the impaled object. With the ACE bandage wrapped around the impaled object, the user may then proceed to the Final Protocol of FIG. 59 via link box 1456.

If the user selects "Cheek" at query box 1436, then the impaled object query flow proceeds to another query box 1457 with a GUI display inquiring of the user as to whether the impaled object is making it difficult for the victim to breath. If the answer is "Yes" to query box 1457, then an instructional box 1458 is presented to the user with a GUI display with instructions to keep the victim still and gently remove the object. A query box 1460 is then presented to the user with a GUI display asking the user if the victim is having trouble breathing. If the answer is "Yes' to query box 1460, then the computer will redirect the user to the breathing protocol on Marche 3 of FIG. 4 via link box 1462. If the answer is "No" to query box 1460, then an instructional box 1464 is presented to the user with a GUI display instructing the user to locate gauze. The user is also presented (at instructional box 1466) with an instructional video or image of the gauze in order to help the user quickly identify or otherwise recognize it to thus facilitate the location instruction of box 1464. The impaled object query flow then proceeds to an instructional box 1468 with a GUI display that instructs the user to tape gauze to the wound caused by the impaled object. Once the gauze has been applied to the wound, the user may then proceed to the Final Protocol of FIG. 59 via link box 1456.

If the answer is "No" to query box 1457 (in the Impaled Cheek protocol), then the user is presented with an instructional box 1472 with a GUI display with instructions for the user to not remove the object, with an optional explanatory box 1474 with a GUI display that explains not to remove the victim if impaled on a stationary object, unless their life is in immediate danger, because removing the object will cause more harm. The impaled object query flow then proceeds to an instructional box 1476 with a GUI display with instructions to the user to locate trauma shears and tape (e.g. to the right of the screen of the instructional device 14 of FIG. 1), along with images or videos of what they look like to help facilitate their location by the user. The user is then instruction (via instructional box 1478) to locate the desired gauze pads (e.g. 5"×9" gauze pads). The user is also presented (at instructional box 1480) with an instructional video or image of the gauze pads in order to help the user quickly identify or otherwise recognize it to thus facilitate the location instruction of box 1478. At instructional box 1482, an instructional video or animation is presented to the user for the purpose of educating the user on the proper technique for supporting the object impaled in the victim. Once the gauze has been applied to the wound, the user may then proceed to the Final Protocol of FIG. 59 via link box 1456.

If the user selects "Jaw" at query box 1436, then the impaled object query flow proceeds to another query box 1484 with a GUI display inquiring if the impaled object is making it difficult for the victim to breathe. If the answer is "Yes" to query box 1484, then the impaled object query flow returns to instructional box 1458 and proceeds therefrom as described above. If the answer is "No" to query box 1484, then the user is presented with an instructional box 1486 with a GUI display with instructions for the user to not remove the object, with an optional explanatory box 1488 with a GUI display that explains not to remove the victim if impaled on a stationary object, unless their life is in immediate danger, because removing the object will cause more harm. The impaled object query flow then proceeds to an instructional box 1490 with a GUI display with instructions to the user to locate trauma shears and tape (e.g. to the right of the screen of the instructional device 14 of FIG. 1), along with images or videos of what they look like to help facilitate their location by the user. The user is then instructed (via instructional box 1492) to locate the desired gauze pads (e.g. 5"×9" gauze pads). The user is also presented (at instructional box 1494) with an instructional video or image of the gauze pads in order to help the user quickly identify or otherwise recognize it to thus facilitate the location instruction of box 1492. At instructional box 1496, an instructional video or animation is presented to the user for the purpose of educating the user on the proper technique for supporting the object impaled in the victim. Once the gauze has been applied to the wound, the user may then proceed to the Final Protocol of FIG. 59 via link box 1456.

If the user selects "Eye" at query box 1436, then the impaled object query flow proceeds to an instructional box 1498 with a GUI display with instructions for the user to not remove the object, with an optional explanatory box 1500 with a GUI display that explains not to remove the victim if impaled on a stationary object, unless their life is in immediate danger, because removing the object will cause more harm. The impaled object query flow then proceeds to an instructional box 1502 with a GUI display with instructions to the user to locate trauma shears and tape (e.g. to the right of the screen of the instructional device 14 of FIG. 1), along with images or videos of what they look like to help facilitate their location by the user. The user is then instructed (via instructional box 1504) to locate the desired gauze pads (e.g. 5"×9" gauze pads). The user is also presented (at instructional box 1506) with an instructional video or image of the gauze pads in order to help the user quickly identify or otherwise recognize it to thus facilitate the location instruction of box 1504. At instructional box 1508, an instructional video or animation is presented to the user for the purpose of educating the user on the proper technique for supporting the object impaled in the victim. Once the gauze has been applied to the wound, the user may then proceed to the Final Protocol of FIG. 59 via link box 1456.

Figure 39:
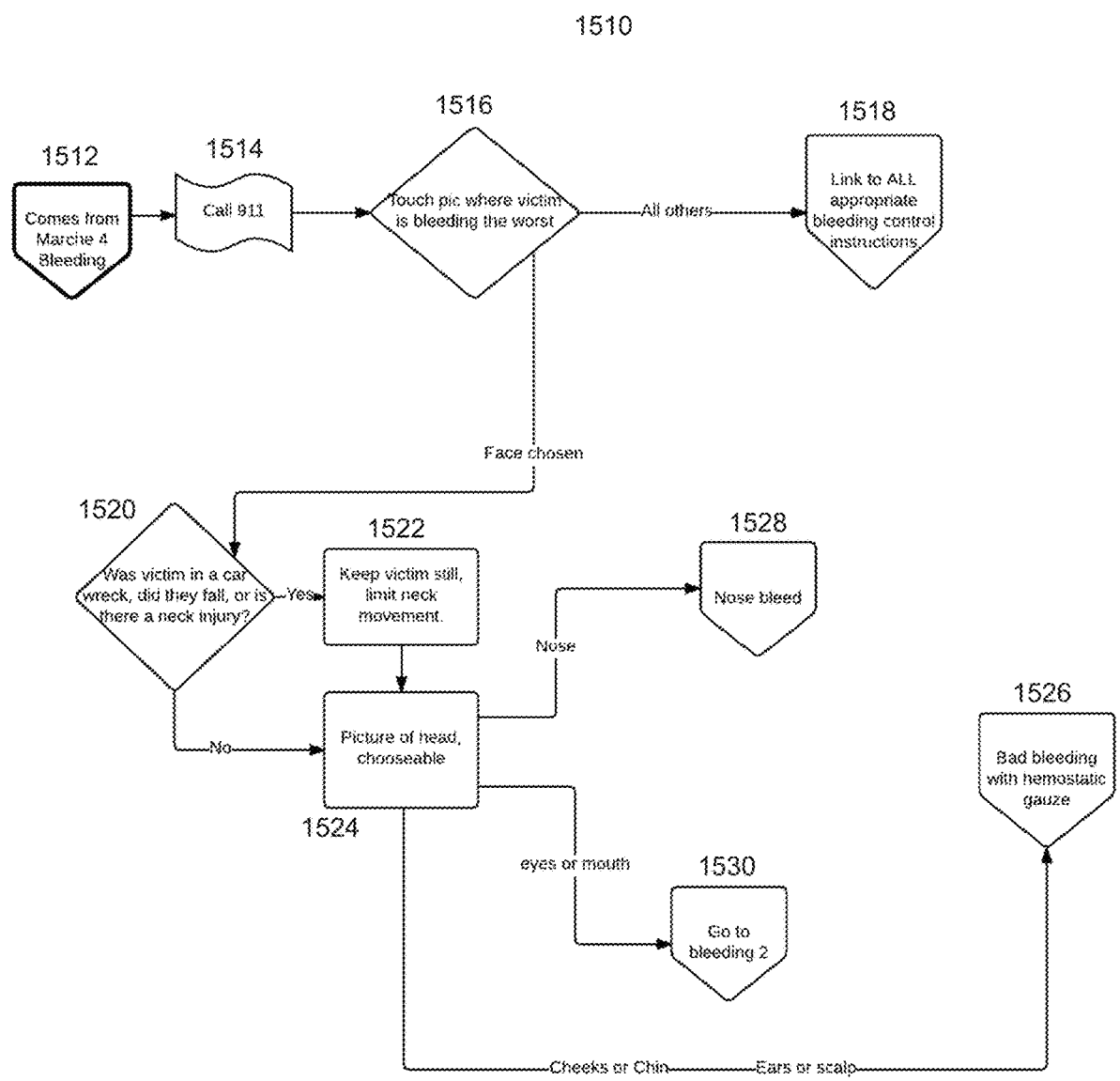
FIG. 39 is a flowchart illustrating an example query flow for non-severe bleeding, forming part of the triage protocol of FIGS. 2-5.

FIG. 39 illustrates the query flow for non-severe bleeding 1510, which is accessed via query box 238 of FIG. 5 (e.g. in response to the user touching or using voice commands on query box 238 to inform the computer that the victim is bleeding) and begins at link box 1512. Upon entry into the burn query flow 1510, the user is reminded to call 9-1-1 via alert box 1514 to summons emergency personnel, if that hasn't already been done by the user or a by-stander. The bleeding query flow then proceeds to query box 1516 with a GUI display presents a display of an interactive diagram of the human body and directs the user to touch the location of the bleeding on the human body diagram. If any body part other than the face is chosen, the burn query flow continues to link box 1518 to link to the Bleeding query flow for that specific body part (e.g., Bleeding Arm flow of FIG. 40, Bleeding Leg flow of FIG. 41, Bleeding Chest flow of FIG. 42, Bleeding Stomach flow of FIG. 43, Bleeding Junctional Arm flow of FIG. 44, Bleeding Junctional Pelvis flow of FIG. 45). If the face is chosen, the computer advances the query flow to query box 1520, which represents a GUI screen asking the user if the victim was in a car wreck, fell from height, or suffered a neck injury. If the user indicates a "Yes" response, the query flow advances to box 1522, which represents a GUI screen instructing the user to keep the victim still and limit neck movement. From this point, or alternatively if the user indicates a "No" response to the question in box 1520, the query flow advances to box 1524, which represents a GUI screen that displays an interactive graphic representation of a human face/head and directs the user to touch the location of the bleeding on the human facial diagram. This will cause the computer to link to the appropriate query flow corresponding to the facial part that the user indicated. For example, the query flows for bad bleeding scalp, neck, ears, chin, and cheek may be accessed through link box 1526. The query flow for bad bleeding nose may be accessed via link box 1528. The query flows for bad bleeding eyes or mouth may be accessed via link box 1530.

Figure 40:
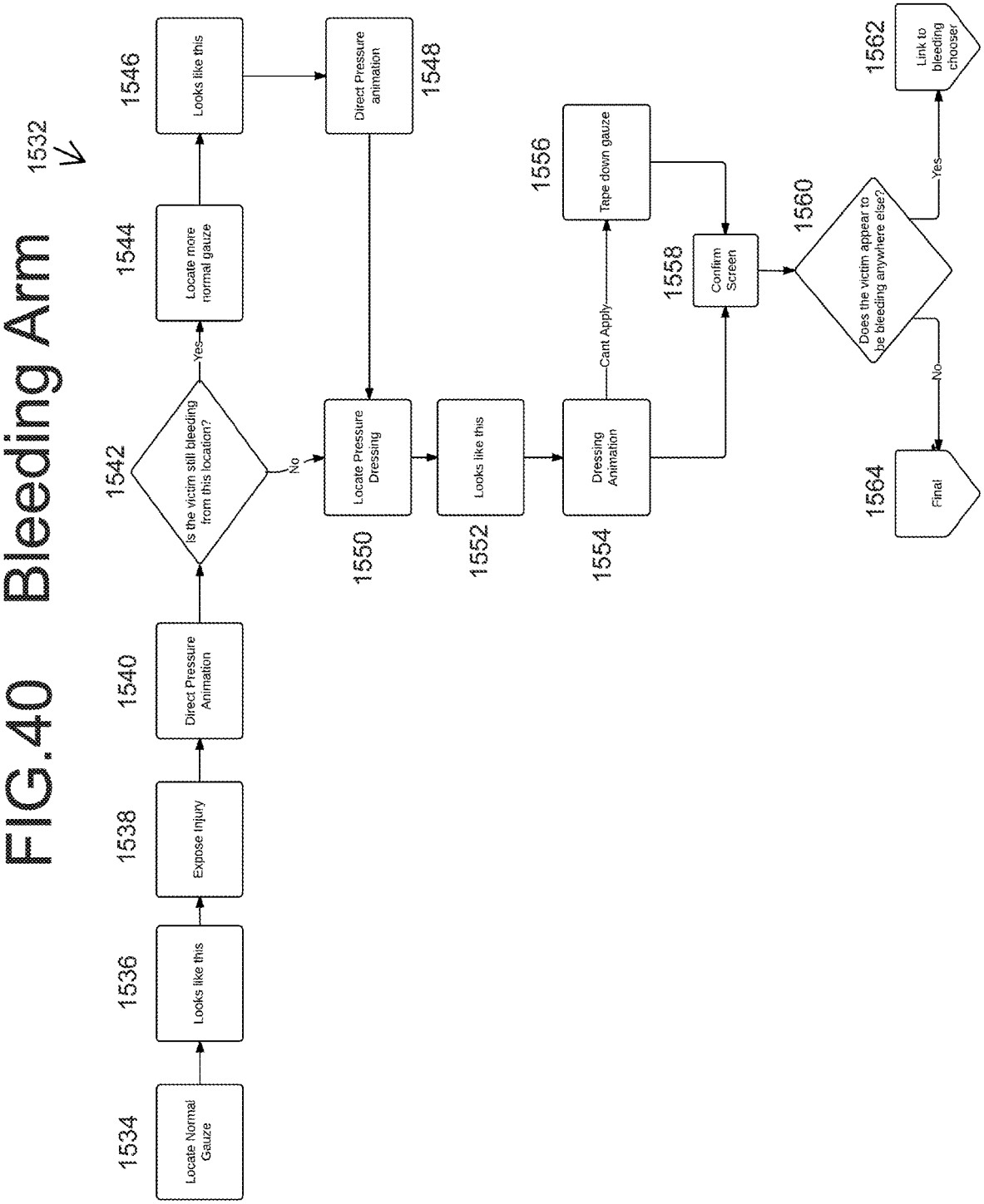
FIG. 40 is a flowchart illustrating an example query flow for a non-severely bleeding arm, forming part of the triage protocol of FIGS. 2-5.

FIG. 40 illustrates the query flow for a non-severely bleeding arm, which is accessed via link box 1518 of FIG. 39 (e.g. in response to the user touching or using voice commands on query box 1516 to inform the computer that the victim has a bleeding arm) and begins at instruction box 1534, which represents a GUI screen instructing the user to locate normal gauze within the accompanying medical tool kit 12. By way of example, the represented GUI screen may also display a layout image of the tool kit and highlight with specificity the location of the normal gauze. The next box 1536 represents a GUI screen that displays a zoomed in image of normal gauze so the user knows what to look for. The next box 1538 is an instruction box directing the user (and optionally demonstrating via animation) to expose the injury for treatment. The next box 1540 represents a GUI screen that provides specific instruction on how to apply direct pressure to a victim's wound using normal gauze, for example with text instructions, visual aid (e.g. pictures and/or video) and/or audio instructions. The next box is query box 1542, which represents a GUI screen asking the user if the victim is still bleeding in this location.

If the user indicates a "Yes" answer (e.g. the victim is still bleeding in this location), the query flow advances to box 1544, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1546 represents a GUI screen that displays a zoomed in image of normal gauze to remind the user what to look for. The next box in the query flow 1548 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1542 (e.g. bleeding has stopped in this location), the query flow proceeds to box 1550, which represents a GUI screen prompting the user to locate the pressure dressing within the accompanying medical tool kit 12. By way of example, the represented GUI screen may also display a layout image of the tool kit and highlight with specificity the location of the pressure dressing. The next box 1552 represents a GUI screen that displays a zoomed in image of pressure dressing so the user knows what to look for. The next box in the query flow is an instruction box 1554 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 1556, which represents a GUI screen that instructs the user to tape the normal gauze to the wound. Once the normal gauze has been taped to the wound, or alternatively if the user was able to apply the pressure dressing to the wound (e.g. box 1554), the next box in the query flow is query box 1558, which represents a GUI screen asking the user to confirm that the victim is no longer bleeding in this location.

After the user positively indicates that the pressure dressing and/or taped gauze are in place, the query flow 1532 proceeds to box 1560, which represents a GUI screen that asks the user if the victim appears to be bleeding anywhere else. If the user indicates a "Yes" answer (e.g. the victim is bleeding elsewhere), then the computer redirects the query flow (via link box 1562) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1564) to the Final Protocol of FIG. 59.

Figure 41:
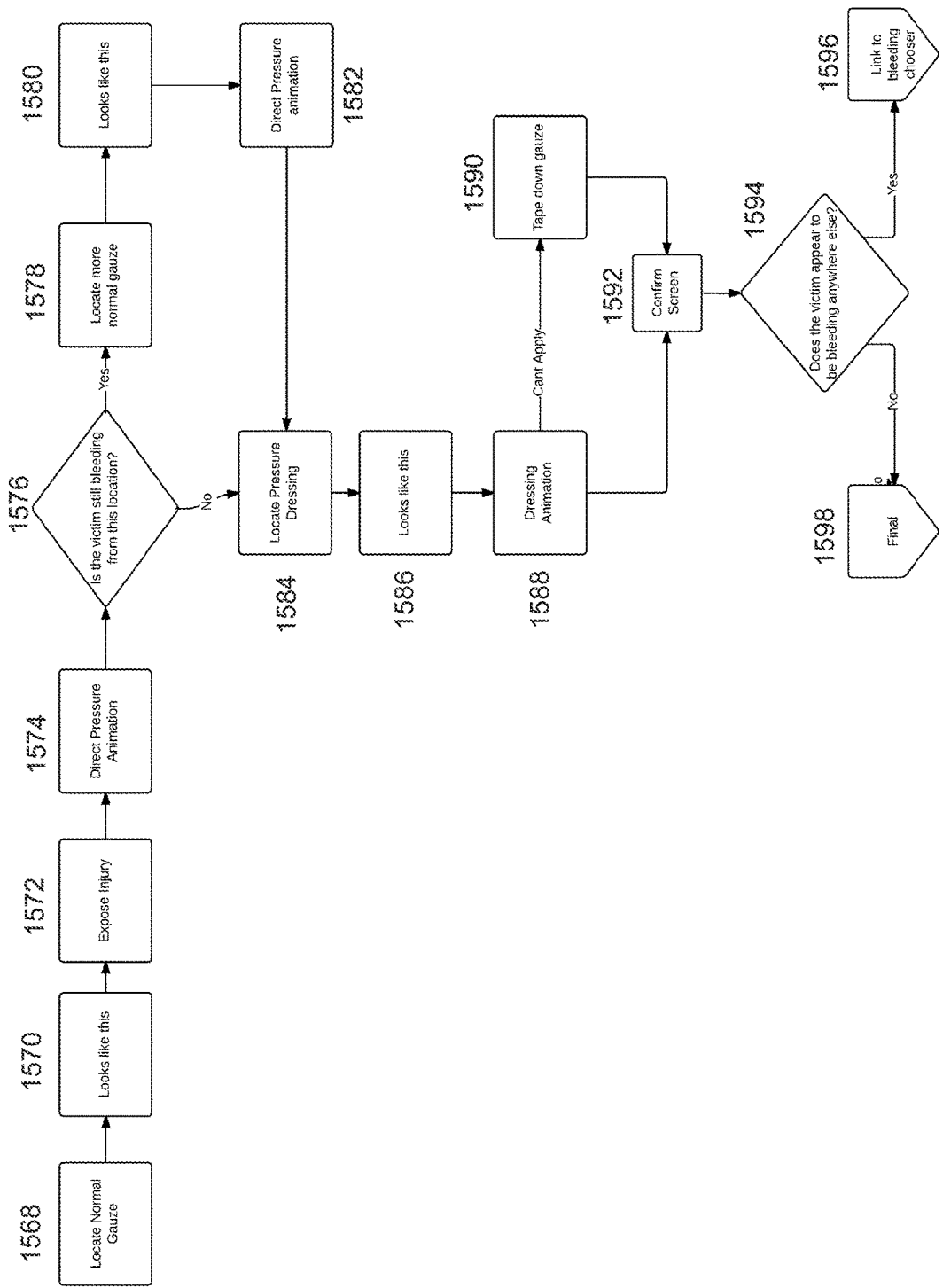
FIG. 41 is a flowchart illustrating an example query flow for a non-severely bleeding leg, forming part of the triage protocol of FIGS. 2-5.

FIG. 41 illustrates the query flow for a non-severely bleeding leg 1566, which is accessed via link box 1518 of FIG. 39 (e.g. in response to the user touching or using voice commands on query box 1516 to inform the computer that the victim has a bleeding leg) and begins at instruction box 1568, which represents a GUI screen instructing the user to locate normal gauze within the accompanying medical tool kit 12. By way of example, the represented GUI screen may also display a layout image of the tool kit and highlight with specificity the location of the normal gauze. The next box 1570 represents a GUI screen that displays a zoomed in image of normal gauze so the user knows what to look for. The next box 1572 is an instruction box directing the user (and optionally demonstrating via animation) to expose the injury for treatment. The next box 1574 represents a GUI screen that provides specific instruction on how to apply direct pressure to a victim's wound using normal gauze, for example with text instructions, visual aid (e.g. pictures and/or video) and/or audio instructions. The next box is query box 1576, which represents a GUI screen asking the user if the victim is still bleeding in this location.

If the user indicates a "Yes" answer (e.g. the victim is still bleeding in this location), the query flow advances to box 1578, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1580 represents a GUI screen that displays a zoomed in image of normal gauze to remind the user what to look for. The next box in the query flow 1582 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1576 (e.g. bleeding has stopped in this location), the query flow proceeds to box 1584, which represents a GUI screen prompting the user to locate the pressure dressing within the accompanying medical tool kit 12. By way of example, the represented GUI screen may also display a layout image of the tool kit and highlight with specificity the location of the pressure dressing. The next box 1586 represents a GUI screen that displays a zoomed in image of pressure dressing so the user knows what to look for. The next box in the query flow is an instruction box 1588 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 1590, which represents a GUI screen that instructs the user to tape the normal gauze to the wound. Once the normal gauze has been taped to the wound, or alternatively if the user was able to apply the pressure dressing to the wound (e.g. box 1588), the next box in the query flow is query box 1592, which represents a GUI screen asking the user to confirm that the victim is no longer bleeding in this location.

After the user positively indicates that the pressure dressing and/or taped gauze are in place, the query flow 1566 proceeds to box 1594, which represents a GUI screen that asks the user if the victim appears to be bleeding anywhere else. If the user indicates a "Yes" answer (e.g. the victim is bleeding elsewhere), then the computer redirects the query flow (via link box 1596) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1598) to the Final Protocol of FIG. 59.

Figure 42:
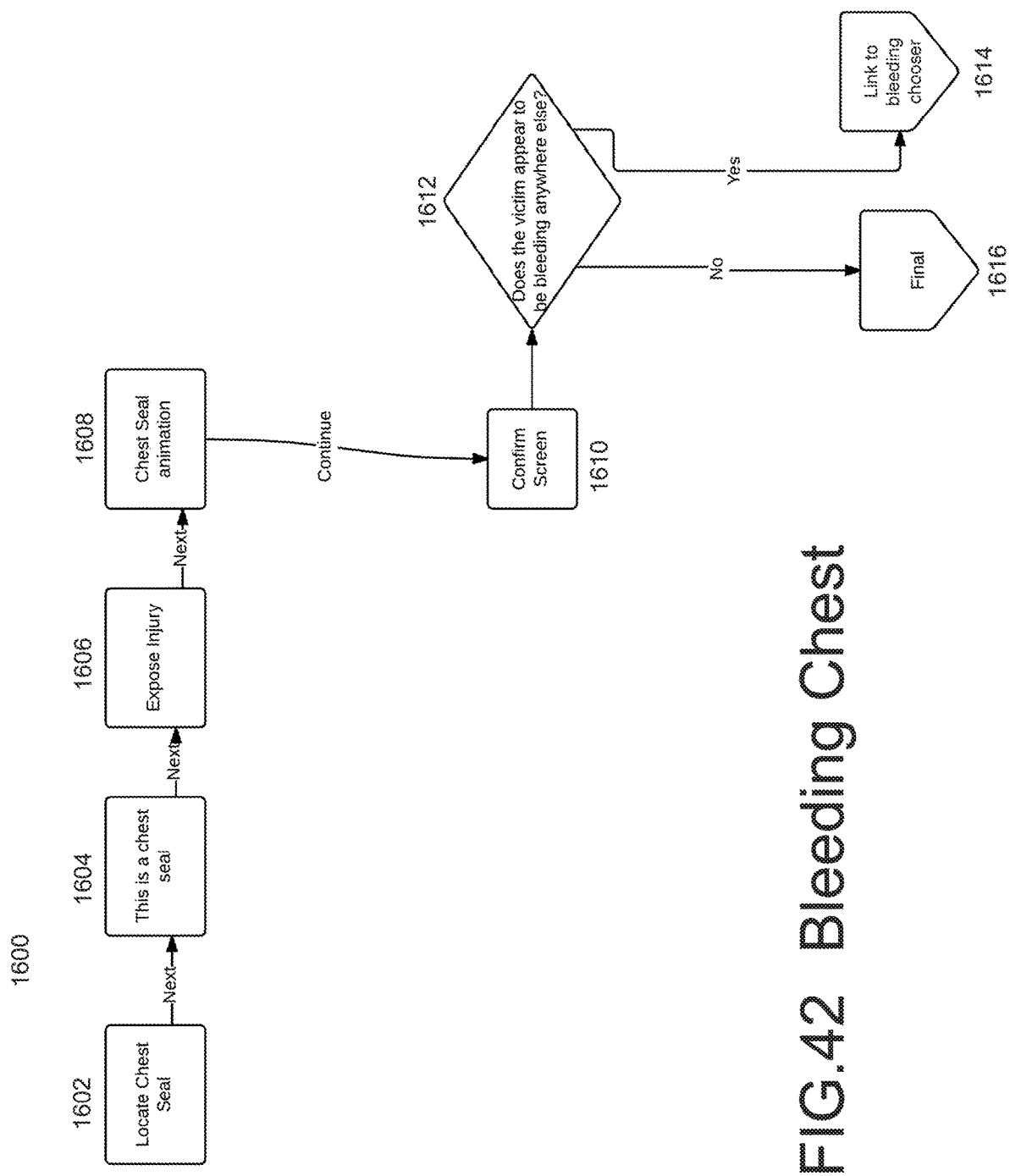
FIG. 42 is a flowchart illustrating an example query flow for a non-severely bleeding chest, forming part of the triage protocol of FIGS. 2-5.

FIG. 42 illustrates the query flow for a non-severely bleeding chest 1600, which is accessed via link box 1518 of FIG. 39 (e.g. in response to the user touching or using voice commands on query box 1516 to inform the computer that the victim has a bleeding chest) and begins at instruction box 1602, which represents a GUI screen instructing the user to locate a chest seal within the accompanying medical tool kit 12. By way of example, the represented GUI screen may also display a layout image of the tool kit and highlight with specificity the location of the chest seal. The next box 1604 represents a GUI screen that displays a zoomed in image of a chest seal so the user knows what to look for. The query flow proceeds to information box 1606, which represents a GUI screen presented by the computer instructing the user to expose the victim's injury. Upon receiving input from the user to proceed (e.g. by tapping an icon or through voice command), the computer advances the flow to box 1608, which represents a GUI screen showing the user how to apply the chest seal to the victim (e.g. through animated video). At this point the user may place the chest seal on the victim as instructed by box 1608. The next box 1610 in the flow represents a GUI screen presented to the user to confirm that the chest seal is in place. After the user positively indicates that the chest seal is in place, the query flow then proceeds to box 1612, which represents a GUI screen that asks the user if the victim appears to be bleeding anywhere else. If the user indicates a "Yes" answer (e.g. the victim is bleeding elsewhere), then the computer redirects the query flow (via link box 1614) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1616) to the Final Protocol of FIG. 59.

Once the user indicates to the app that the chest seal has been applied to the victim, the computer starts a recheck timer to remind/require the user to complete the chest seal reset protocol at a regular specified interval. In the instant example the chest seal recheck interval is set at every five minutes (5:00), however the app may be programmed to include a different medically reasonable time interval (not determined or adjusted by the user in the field). At the expiration of the specified time interval, regardless of the GUI screen the user may be currently viewing, the computer directs the query flow automatically to the Chest Seal Recheck flow of FIG. 62.

Figure 43:
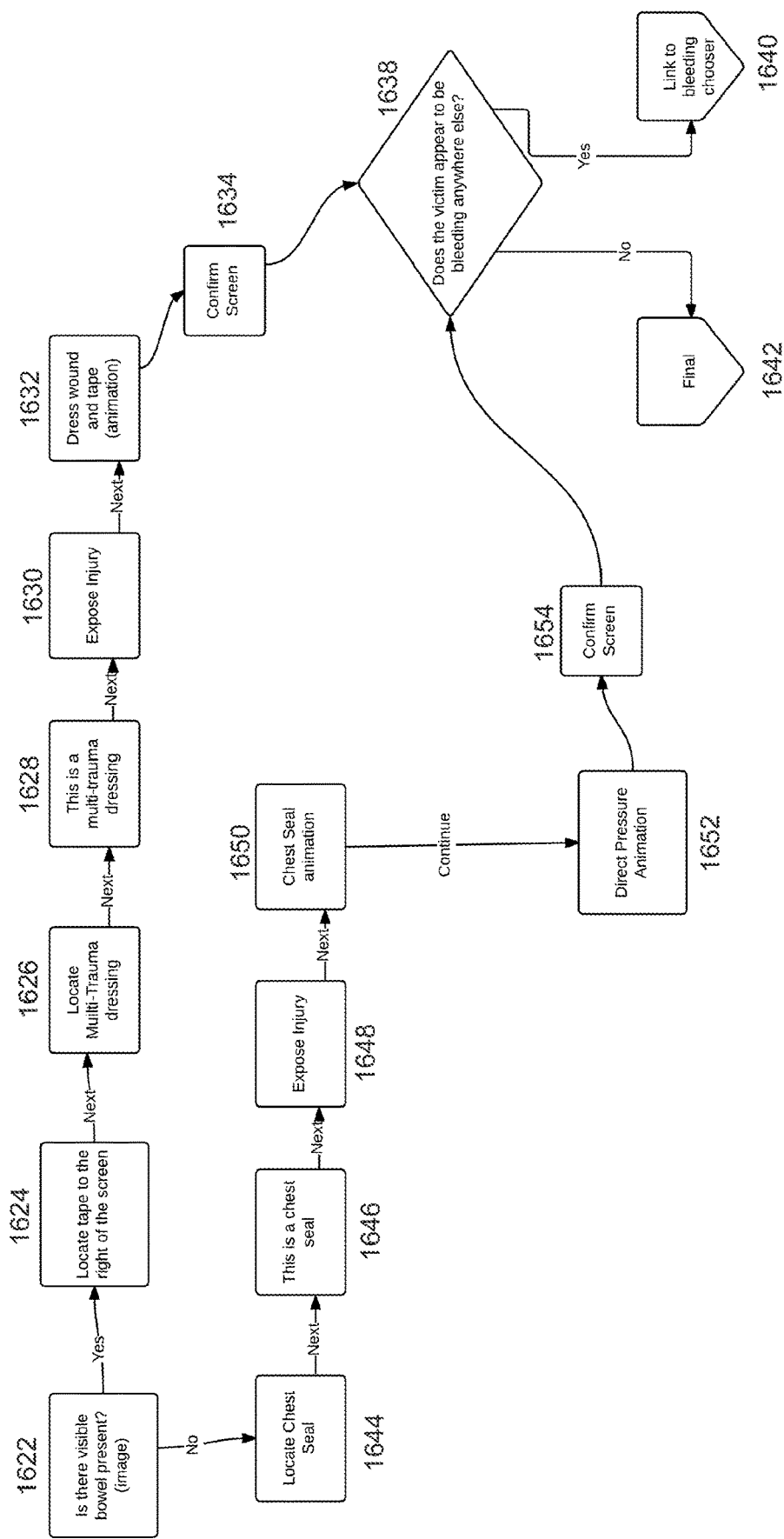
FIG. 43 is a flowchart illustrating an example query flow for a non-severely bleeding stomach, forming part of the triage protocol of FIGS. 2-5.

FIG. 43 illustrates the query flow for a non-severely bleeding stomach 1618, which is accessed via link box 1518 of FIG. 39 (e.g. in response to the user touching or using voice commands on query box 1516 to inform the computer that the victim has a bleeding stomach) and begins at instruction box 1622, which represents a GUI screen that asks the user if there is visible bowel present, and may include a visual image of what this might look like. If the user indicates a "Yes" answer to the computer (e.g. there is visible bowel present), the query flow proceeds to box 1624, which represents a GUI screen that instructs the user to locate tape in the medical tool kit 12, which by way of example may be located to the right of the display screen. The next box 1626 of the query flow 1618 is an instructional box representing a GUI screen that instructs the user to locate a multi-trauma dressing within the accompanying medical tool kit 12. By way of example, the represented GUI screen may also display a layout image of the tool kit and highlight with specificity the location of the multi-trauma dressing. The next box 1628 represents a GUI screen that displays a zoomed in image of a multi-trauma dressing so the user knows what to look for. The query flow proceeds to information box 1630, which represents a GUI screen presented by the computer instructing the user to expose the victim's injury. Upon receiving input from the user to proceed (e.g. by tapping an icon or through voice command), the computer advances the flow to box 1632, which represents a GUI screen showing the user how to apply the multi-trauma dressing and tape to the victim (e.g. through animated video). The next box 1634 in the flow 1618 represents a GUI screen presented to the user to confirm that the multi-trauma dressing and tape are in place. The query flow 1618 then proceeds to box 1638, which represents a GUI screen that asks the user if the victim appears to be bleeding anywhere else. If the user indicates a "Yes" answer (e.g. the victim is bleeding elsewhere), then the computer redirects the query flow (via link box 1640) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1642) to the Final Protocol of FIG. 59.

If the user indicates a "No" answer to the question of box 1622 (e.g. there is no visible bowel present), the query flow 1618 proceeds to box 1644, which represents a GUI screen that instructs the user to locate a chest seal within the accompanying medical tool kit 12. By way of example, the represented GUI screen may also display a layout image of the tool kit and highlight with specificity the location of the chest seal. The next box 1646 represents a GUI screen that displays a zoomed in image of a chest seal so the user knows what to look for. The query flow proceeds to information box 1648, which represents a GUI screen presented by the computer instructing the user to expose the victim's injury. Upon receiving input from the user to proceed (e.g. by tapping an icon or through voice command), the computer advances the flow to box 1650, which represents a GUI screen showing the user how to apply the chest seal to the victim (e.g. through animated video). In a case of a bleeding stomach, a chest seal alone may not be sufficient to stop the bleeding. Thus the next box 1652 of the flow represents a GUI screen showing the user how to also apply direct pressure to the wound (e.g. through animated video). The next box 1654 in the flow represents a GUI screen presented to the user to confirm that the chest seal is in place. The computer then advances query flow to box 1638, which proceeds as discussed above.

Figure 44:
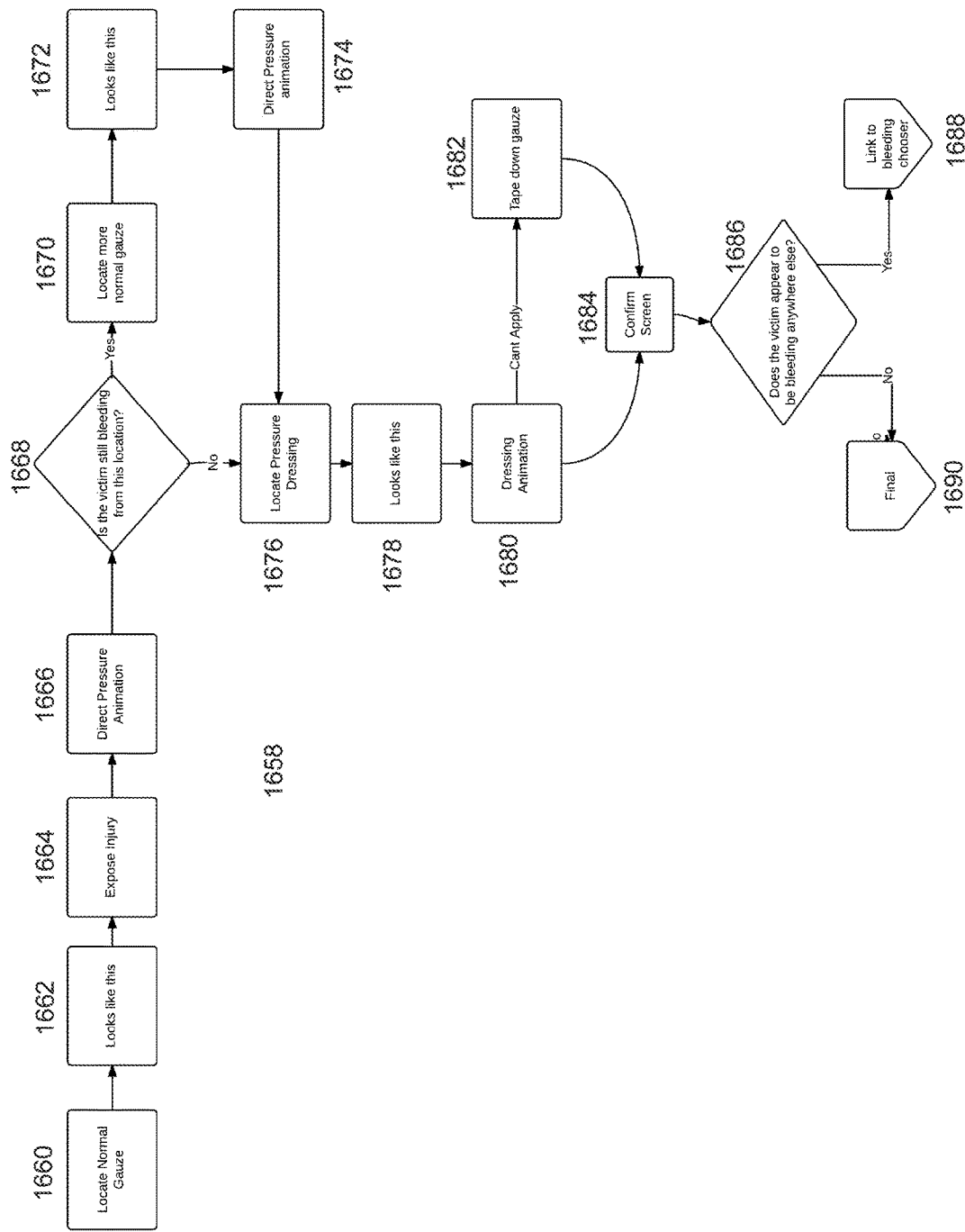
FIG. 44 is a flowchart illustrating an example query flow for a non-severely bleeding junctional arm, forming part of the triage protocol of FIGS. 2-5.

FIG. 44 illustrates the query flow for a non-severely bleeding junctional arm 1658, which is accessed via link box 1518 of FIG. 39 (e.g. in response to the user touching or using voice commands on query box 1516 to inform the computer that the victim has a bleeding shoulder) and begins at instruction box 1660, which represents a GUI screen instructing the user to locate normal gauze within the accompanying medical tool kit 12. By way of example, the represented GUI screen may also display a layout image of the tool kit and highlight with specificity the location of the normal gauze. The next box 1662 represents a GUI screen that displays a zoomed in image of normal gauze so the user knows what to look for. The next box 1664 is an instruction box directing the user (and optionally demonstrating via animation) to expose the injury for treatment. The next box 1666 represents a GUI screen that provides specific instruction on how to apply direct pressure to a victim's wound using normal gauze, for example with text instructions, visual aid (e.g. pictures and/or video) and/or audio instructions. The next box is query box 1668, which represents a GUI screen asking the user if the victim is still bleeding in this location.

If the user indicates a "Yes" answer (e.g. the victim is still bleeding in this location), the query flow advances to box 1670, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1672 represents a GUI screen that displays a zoomed in image of normal gauze to remind the user what to look for. The next box in the query flow 1674 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1668 (e.g. bleeding has stopped in this location), the query flow proceeds to box 1676, which represents a GUI screen prompting the user to locate the pressure dressing within the accompanying medical tool kit 12. By way of example, the represented GUI screen may also display a layout image of the tool kit and highlight with specificity the location of the pressure dressing. The next box 1678 represents a GUI screen that displays a zoomed in image of pressure dressing so the user knows what to look for. The next box in the query flow is an instruction box 1680 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 1682, which represents a GUI screen that instructs the user to tape the normal gauze to the wound. Once the normal gauze has been taped to the wound, or alternatively if the user was able to apply the pressure dressing to the wound (e.g. box 1680), the next box in the query flow is query box 1684, which represents a GUI screen asking the user to confirm that the victim is no longer bleeding in this location.

After the user positively indicates that the pressure dressing and/or taped gauze are in place, the query flow 1658 proceeds to box 1686, which represents a GUI screen that asks the user if the victim appears to be bleeding anywhere else. If the user indicates a "Yes" answer (e.g. the victim is bleeding elsewhere), then the computer redirects the query flow (via link box 1688) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1690) to the Final Protocol of FIG. 59.

Figure 45:
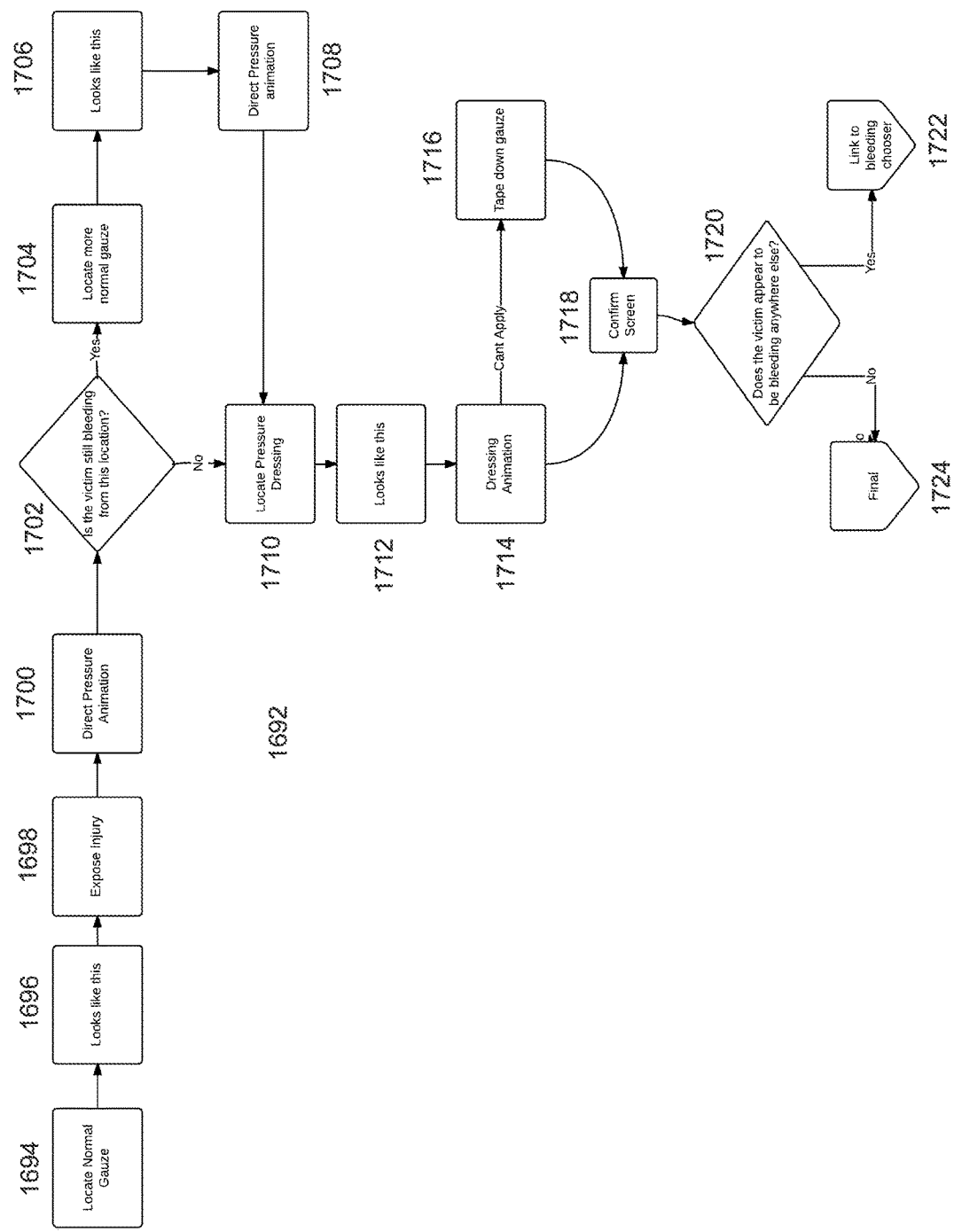
FIG. 45 is a flowchart illustrating an example query flow for a non-severely bleeding junctional pelvis, forming part of the triage protocol of FIGS. 2-5.

FIG. 45 illustrates the query flow for a non-severely bleeding junctional pelvis 1692, which is accessed via link box 1518 of FIG. 39 (e.g. in response to the user touching or using voice commands on query box 1516 to inform the computer that the victim has a bleeding pelvis) and begins at instruction box 1694, which represents a GUI screen instructing the user to locate normal gauze within the accompanying medical tool kit 12. By way of example, the represented GUI screen may also display a layout image of the tool kit and highlight with specificity the location of the normal gauze. The next box 1696 represents a GUI screen that displays a zoomed in image of normal gauze so the user knows what to look for. The next box 1698 is an instruction box directing the user (and optionally demonstrating via animation) to expose the injury for treatment. The next box 1700 represents a GUI screen that provides specific instruction on how to apply direct pressure to a victim's wound using normal gauze, for example with text instructions, visual aid (e.g. pictures and/or video) and/or audio instructions. The next box is query box 1702, which represents a GUI screen asking the user if the victim is still bleeding in this location.

If the user indicates a "Yes" answer (e.g. the victim is still bleeding in this location), the query flow advances to box 1704, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1706 represents a GUI screen that displays a zoomed in image of normal gauze to remind the user what to look for. The next box 1708 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1702 (e.g. bleeding has stopped in this location), the query flow proceeds to box 1710, which represents a GUI screen prompting the user to locate the pressure dressing within the accompanying medical tool kit 12. By way of example, the represented GUI screen may also display a layout image of the tool kit and highlight with specificity the location of the pressure dressing. The next box 1712 represents a GUI screen that displays a zoomed in image of pressure dressing so the user knows what to look for. The next box in the query flow is an instruction box 1714 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 1716, which represents a GUI screen that instructs the user to tape the normal gauze to the wound. Once the normal gauze has been taped to the wound, or alternatively if the user was able to apply the pressure dressing to the wound (e.g. box 1714), the next box in the query flow is query box 1718, which represents a GUI screen asking the user to confirm that the victim is no longer bleeding in this location.

After the user positively indicates that the pressure dressing and/or taped gauze are in place, the query flow 1692 proceeds to box 1720, which represents a GUI screen that asks the user if the victim appears to be bleeding anywhere else. If the user indicates a "Yes" answer (e.g. the victim is bleeding elsewhere), then the computer redirects the query flow (via link box 1722) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1724) to the Final Protocol of FIG. 59.

Figure 46:
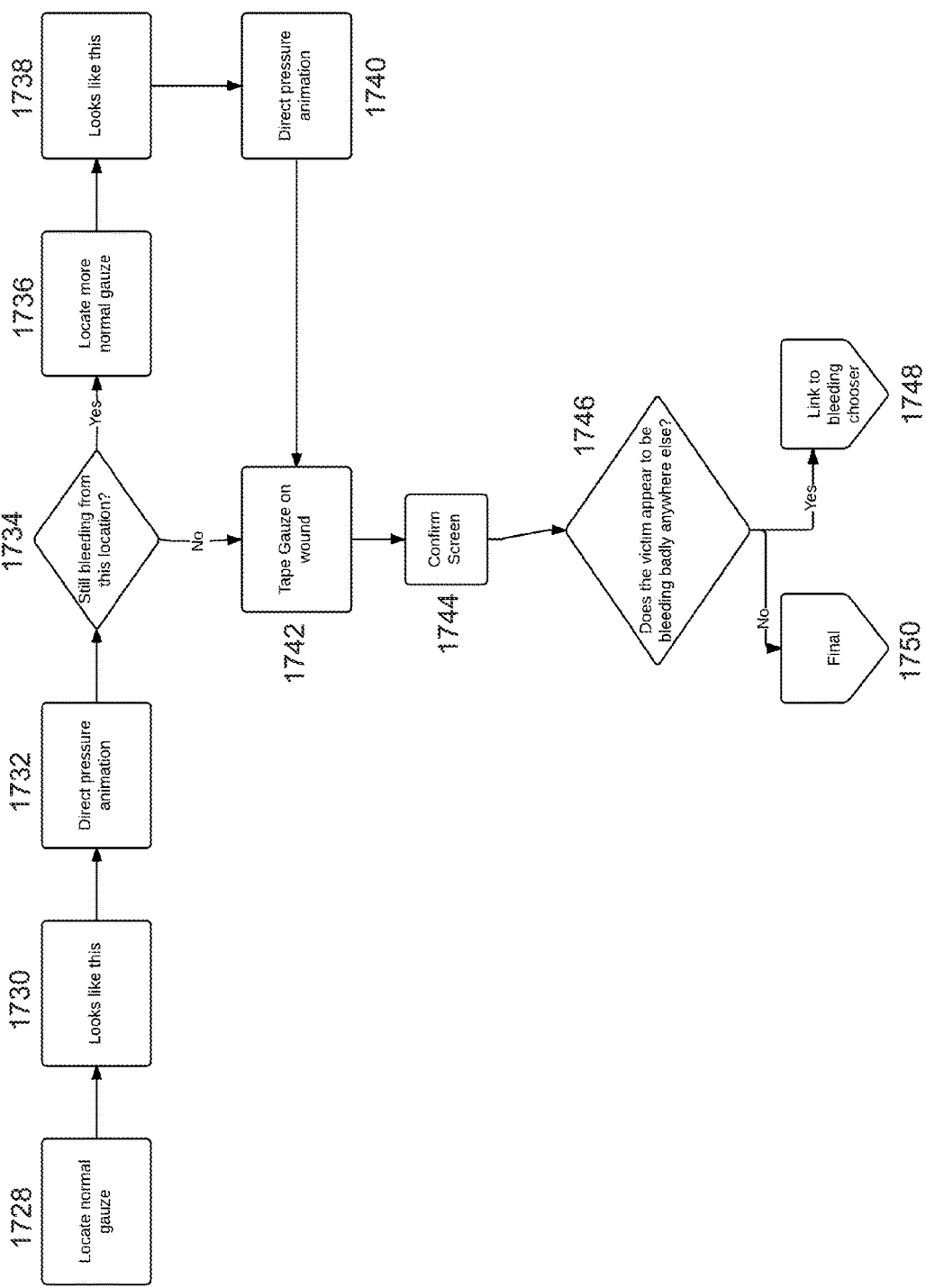
FIG. 46 is a flowchart illustrating an example query flow for a non-severely bleeding chin, forming part of the triage protocol of FIGS. 2-5.

FIG. 46 illustrates the query flow for a non-severely bleeding chin 1726, which is accessed via link box 1526 of FIG. 39 (e.g. in response to the user touching or using voice commands on query box 1524 to inform the computer that the victim has a bleeding chin) and begins at instruction box 1728, which represents a GUI screen instructing the user to locate normal gauze within the accompanying medical tool kit 12. By way of example, the represented GUI screen may also display a layout image of the tool kit and highlight with specificity the location of the normal gauze. The next box 1730 represents a GUI screen that displays a zoomed in image of normal gauze so the user knows what to look for. The next box 1732 represents a GUI screen that provides specific instruction on how to apply direct pressure to a victim's wound using normal gauze, for example with text instructions, visual aid (e.g. pictures and/or video) and/or audio instructions. The next box is query box 1734, which represents a GUI screen asking the user if the victim is still bleeding in this location.

If the user indicates a "Yes" answer (e.g. the victim is still bleeding in this location), the query flow advances to box 1736, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1738 represents a GUI screen that displays a zoomed in image of normal gauze to remind the user what to look for. The next box in the query flow 1740 represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1734 (e.g. bleeding has stopped in this location), the query flow proceeds to box 1742, which represents a GUI screen that instructs the user to tape the normal gauze to the wound. Once the normal gauze has been taped to the wound, the next box in the query flow is query box 1744, which represents a GUI screen asking the user to confirm that the victim is no longer bleeding in this location.

After the user positively indicates that the taped gauze is in place, the query flow 1728 proceeds to box 1746, which represents a GUI screen that asks the user if the victim appears to be bleeding anywhere else. If the user indicates a "Yes" answer (e.g. the victim is bleeding elsewhere), then the computer redirects the query flow (via link box 1748) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1750) to the Final Protocol of FIG. 59.

Figure 47:
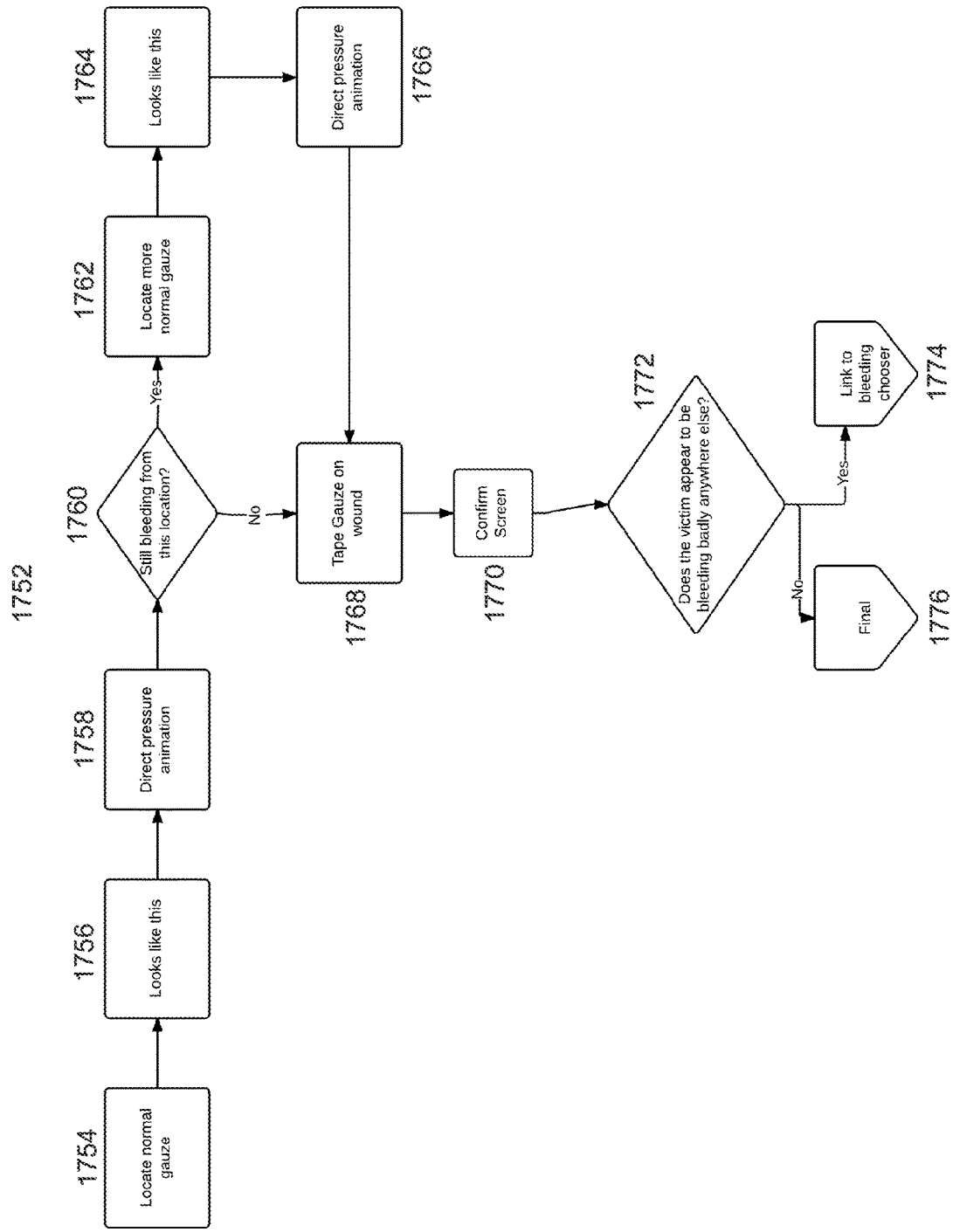
FIG. 47 is a flowchart illustrating an example query flow for a non-severely bleeding eye(s), forming part of the triage protocol of FIGS. 2-5.

FIG. 47 illustrates the query flow for a non-severely bleeding eye(s) 1752, which is accessed via link box 1530 of FIG. 39 (e.g. in response to the user touching or using voice commands on query box 1524 to inform the computer that the victim has a bleeding eye) and begins at instruction box 1754, which represents a GUI screen instructing the user to locate normal gauze within the accompanying medical tool kit 12. By way of example, the represented GUI screen may also display a layout image of the tool kit and highlight with specificity the location of the normal gauze. The next box 1756 represents a GUI screen that displays a zoomed in image of normal gauze so the user knows what to look for. The next box 1758 represents a GUI screen that provides specific instruction on how to apply direct pressure to a victim's wound using normal gauze, for example with text instructions, visual aid (e.g. pictures and/or video) and/or audio instructions. The next box is query box 1760, which represents a GUI screen asking the user if the victim is still bleeding in this location.

If the user indicates a "Yes" answer (e.g. the victim is still bleeding in this location), the query flow advances to box 1762, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1764 represents a GUI screen that displays a zoomed in image of normal gauze to remind the user what to look for. The next box 1766 in the query flow represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1760 (e.g. bleeding has stopped in this location), the query flow proceeds to box 1768, which represents a GUI screen that instructs the user to tape the normal gauze to the wound. Once the normal gauze has been taped to the wound, the next box in the query flow is query box 1770, which represents a GUI screen asking the user to confirm that the victim is no longer bleeding in this location.

After the user positively indicates that the taped gauze is in place, the query flow 1752 proceeds to box 1772, which represents a GUI screen that asks the user if the victim appears to be bleeding anywhere else. If the user indicates a "Yes" answer (e.g. the victim is bleeding elsewhere), then the computer redirects the query flow (via link box 1774) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1776) to the Final Protocol of FIG. 59.

Figure 48:
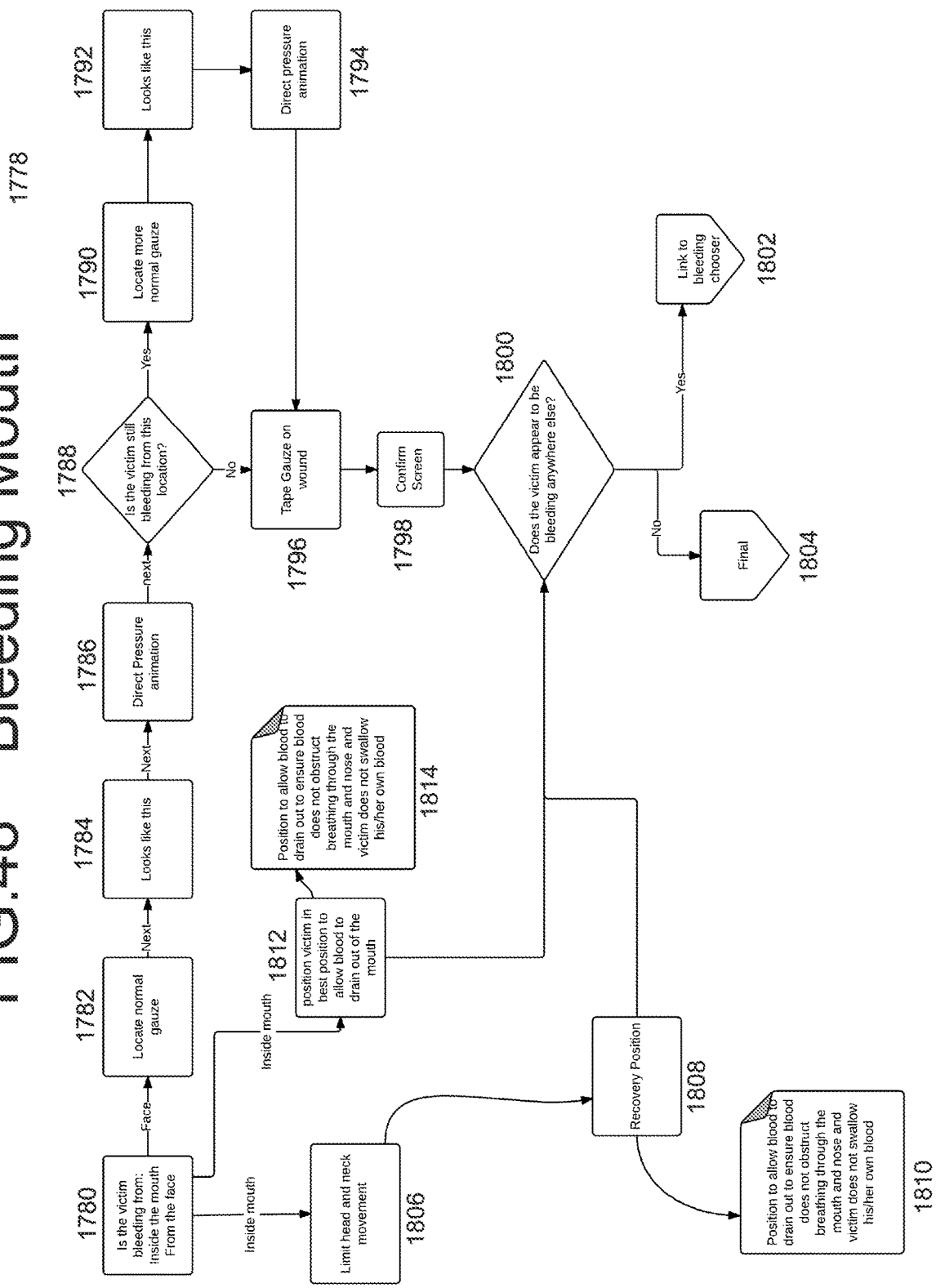
FIG. 48 is a flowchart illustrating an example query flow for a non-severely bleeding mouth, forming part of the triage protocol of FIGS. 2-5.

FIG. 48 illustrates the query flow for a non-severely bleeding mouth 1778, which is accessed via link box 1530 of FIG. 39 (e.g. in response to the user touching or using voice commands on query box 1524 to inform the computer that the victim has a bleeding mouth) and begins at query box 1780, which represents a GUI screen that asks the user if the victim is bleeding from the face or from inside the mouth. If the user indicates an answer of "Face," the computer directs the query flow to instruction box 1782, which represents a GUI screen instructing the user to locate normal gauze within the accompanying medical tool kit 12. By way of example, the represented GUI screen may also display a layout image of the tool kit and highlight with specificity the location of the normal gauze. The next box 1784 represents a GUI screen that displays a zoomed in image of normal gauze so the user knows what to look for. The next box 1786 represents a GUI screen that provides specific instruction on how to apply direct pressure to a victim's wound using normal gauze, for example with text instructions, visual aid (e.g. pictures and/or video) and/or audio instructions. The next box is query box 1788, which represents a GUI screen asking the user if the victim is still bleeding in this location.

If the user indicates a "Yes" answer (e.g. the victim is still bleeding in this location), the query flow advances to box 1790, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1792 represents a GUI screen that displays a zoomed in image of normal gauze to remind the user what to look for. The next box 1794 in the query flow represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1788 (e.g. bleeding has stopped in this location), the query flow proceeds to box 1796, which represents a GUI screen that instructs the user to tape the normal gauze to the wound. Once the normal gauze has been taped to the wound, the next box in the query flow is query box 1798, which represents a GUI screen asking the user to confirm that the victim is no longer bleeding in this location.

After the user positively indicates that the taped gauze is in place, the query flow 1778 proceeds to box 1800, which represents a GUI screen that asks the user if the victim appears to be bleeding anywhere else. If the user indicates a "Yes" answer (e.g. the victim is bleeding elsewhere), then the computer redirects the query flow (via link box 1802) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1804) to the Final Protocol of FIG. 59.

If the user answers "Inside the Mouth" to the question of box 1780 (e.g. victim is bleeding from inside the mouth) and the user answered "Yes" to the question of box 1520 of FIG. 39 (e.g. victim was in car wreck, fell from height, or suffered a neck injury), then the query flow proceeds to instruction box 1806, which represents a GUI screen instructing the user to limit head and neck movement and position the victim in the best position to allow blood to drain out of the mouth. The query flow then proceeds to box 1808, which represents a GUI screen providing instruction on how to place the victim in a proper recovery position. An information box 1810 is available via an interactive icon present on the represented GUI screen if the user needs more information about why the victim needs to be positioned so that the blood drains from his/her mouth (e.g. "Position to allow blood to drain out to ensure blood does not obstruct breathing through the mouth and nose and victim does not swallow blood"). The query flow then proceeds to box 1800 as described above.

If the user answers "Inside the Mouth" to the question of box 1780 (e.g. victim is bleeding from inside the mouth) and the user answered "No" to the question of box 1520 of FIG. 39 (e.g. victim was not in car wreck, did not fell from height, and did not suffer a neck injury), then the query flow proceeds to instruction box 1812, which represents a GUI screen instructing the user to position the victim in the best position to allow blood to drain out of the mouth. An information box 1814 is available via an interactive icon present on the represented GUI screen if the user needs more information about why the victim needs to be positioned so that the blood drains from his/her mouth (e.g. "Position to allow blood to drain out to ensure blood does not obstruct breathing through the mouth and nose and victim does not swallow blood"). The query flow then proceeds to box 1800, and the flow proceeds as described above.

Figure 49:
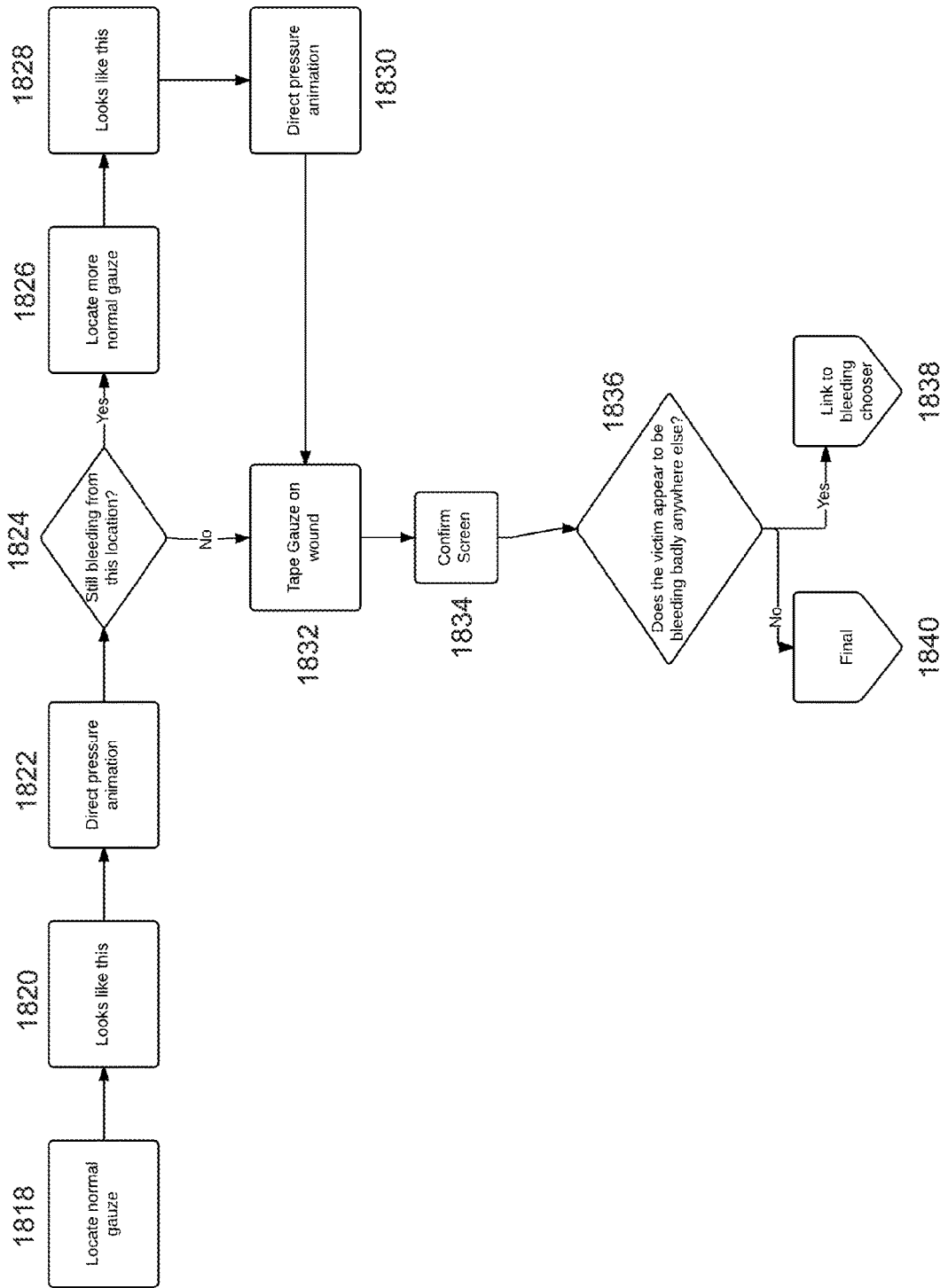
FIG. 49 is a flowchart illustrating an example query flow for a non-severely bleeding cheek(s), forming part of the triage protocol of FIGS. 2-5.

FIG. 49 illustrates the query flow for a non-severely bleeding cheek 1816, which is accessed via link box 1526 of FIG. 39 (e.g. in response to the user touching or using voice commands on query box 1524 to inform the computer that the victim has a bleeding cheek) and begins at instruction box 1818, which represents a GUI screen instructing the user to locate normal gauze within the accompanying medical tool kit 12. By way of example, the represented GUI screen may also display a layout image of the tool kit and highlight with specificity the location of the normal gauze. The next box 1820 represents a GUI screen that displays a zoomed in image of normal gauze so the user knows what to look for. The next box 1822 represents a GUI screen that provides specific instruction on how to apply direct pressure to a victim's wound using normal gauze, for example with text instructions, visual aid (e.g. pictures and/or video) and/or audio instructions. The next box is query box 1824, which represents a GUI screen asking the user if the victim is still bleeding in this location.

If the user indicates a "Yes" answer (e.g. the victim is still bleeding in this location), the query flow advances to box 1826, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1828 represents a GUI screen that displays a zoomed in image of normal gauze to remind the user what to look for. The next box 1830 in the query flow represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1824 (e.g. bleeding has stopped in this location), the query flow proceeds to box 1832, which represents a GUI screen that instructs the user to tape the normal gauze to the wound. Once the normal gauze has been taped to the wound, the next box in the query flow is query box 1834, which represents a GUI screen asking the user to confirm that the victim is no longer bleeding in this location.

After the user positively indicates that the taped gauze is in place, the query flow 1816 proceeds to box 1836, which represents a GUI screen that asks the user if the victim appears to be bleeding anywhere else. If the user indicates a "Yes" answer (e.g. the victim is bleeding elsewhere), then the computer redirects the query flow (via link box 1838) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1840) to the Final Protocol of FIG. 59.

Figure 50:
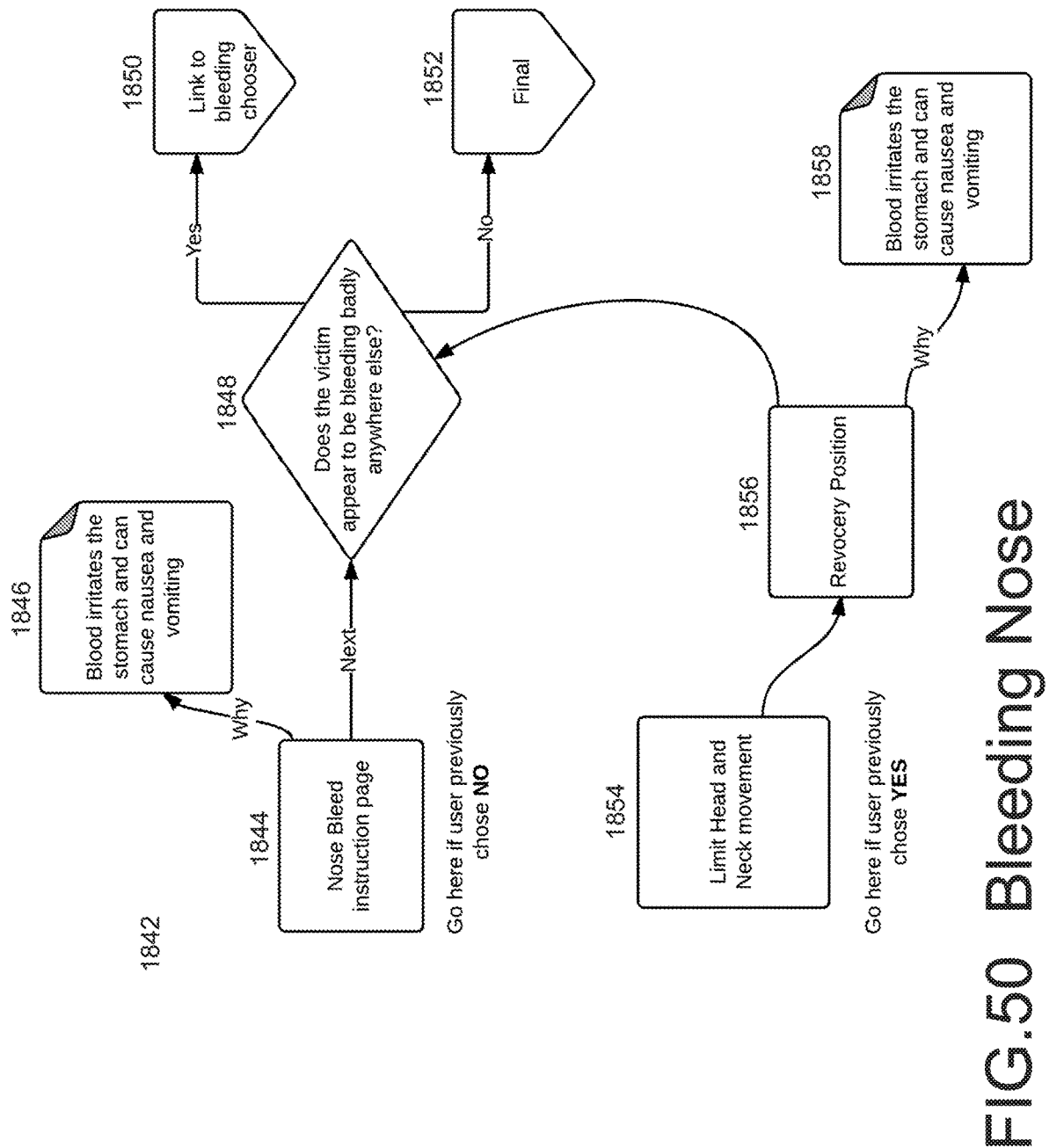
FIG. 50 is a flowchart illustrating an example query flow for a non-severely bleeding nose, forming part of the triage protocol of FIGS. 2-5.

FIG. 50 illustrates the query flow for a non-severely bleeding nose 1842, which is accessed via link box 1528 of FIG. 39 (e.g. in response to the user touching the nose on the graphic representation of a human face/head on the touch screen display). If the user indicated a "No" answer to the question of box 1520 of FIG. 39 (e.g. victim was not in car wreck, did not fall from height, and did not suffer a neck injury), then the query flow 1842 begins with instruction box 1844, which represents a GUI screen providing instruction on how to treat a severely bleeding nose. An information box 1846 is available via an interactive icon present on the represented GUI screen if the user needs more information about why the nosebleed needs to be abated (e.g. "blood irritates the stomach and can cause nausea and vomiting"). After the user positively indicates that the nosebleed has been treated, the query flow 1846 then proceeds to box 1848, which represents a GUI screen that asks the user if the victim appears to be bleeding anywhere else. If the user indicates a "Yes" answer (e.g. the victim is bleeding elsewhere), then the computer redirects the query flow (via link box 1850) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1852) to Final Protocol of FIG. 59.

If the user indicated a "Yes" answer to the question of box 1520 of FIG. 39 (e.g. victim was in car wreck, fell from height, or suffered a neck injury), then the query flow 1842 begins with instruction box 1854, which represents a GUI screen reminding the user to limited head and neck movement. The flow then proceeds to instruction box 1856, which represents a GUI screen providing instruction on how to place the victim in a proper recovery position. An information box 1858 is available via an interactive icon present on the represented GUI screen if the user needs more information about why the nosebleed needs to be abated (e.g. "blood irritates the stomach and can cause nausea and vomiting"). After the user positively indicates that the nosebleed has been treated, the query flow proceeds to query box 1848 and the flow proceeds as described above.

Figure 51:
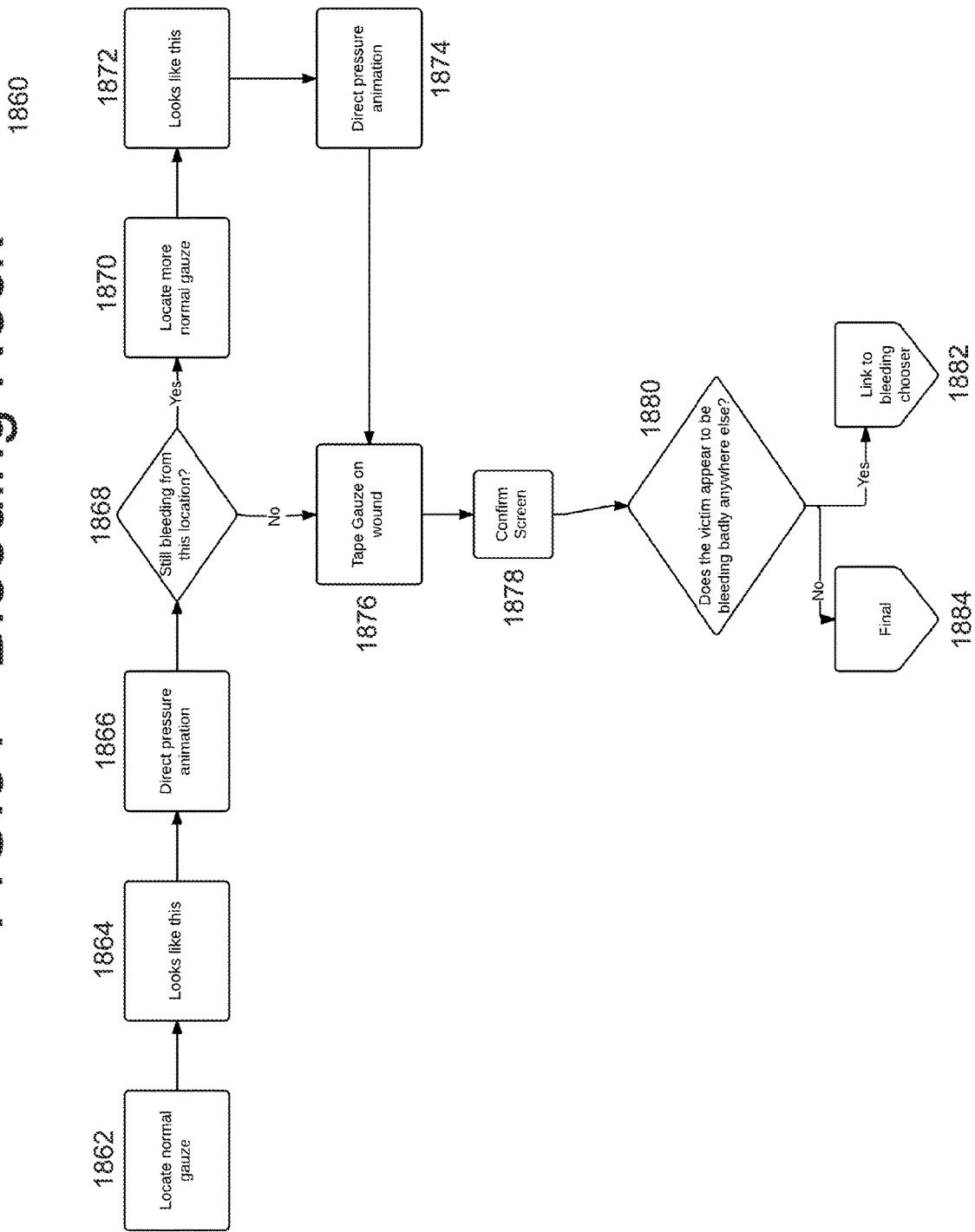
FIG. 51 is a flowchart illustrating an example query flow for a non-severely bleeding neck, forming part of the triage protocol of FIGS. 2-5.

FIG. 51 illustrates the query flow for a non-severely bleeding neck 1860, which is accessed via link box 1526 of FIG. 39 (e.g. in response to the user touching or using voice commands on query box 1524 to inform the computer that the victim has a bleeding neck) and begins at instruction box 1862, which represents a GUI screen instructing the user to locate normal gauze within the accompanying medical tool kit 12. By way of example, the represented GUI screen may also display a layout image of the tool kit and highlight with specificity the location of the normal gauze. The next box 1864 represents a GUI screen that displays a zoomed in image of normal gauze so the user knows what to look for. The next box 1866 represents a GUI screen that provides specific instruction on how to apply direct pressure to a victim's wound using normal gauze, for example with text instructions, visual aid (e.g. pictures and/or video) and/or audio instructions. The next box is query box 1868, which represents a GUI screen asking the user if the victim is still bleeding in this location.

If the user indicates a "Yes" answer (e.g. the victim is still bleeding in this location), the query flow advances to box 1870, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1872 represents a GUI screen that displays a zoomed in image of normal gauze to remind the user what to look for. The next box 1874 in the query flow represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1868 (e.g. bleeding has stopped in this location), the query flow proceeds to box 1876, which represents a GUI screen that instructs the user to tape the normal gauze to the wound. Once the normal gauze has been taped to the wound, the next box in the query flow is instruction box 1878, which represents a GUI screen asking the user to confirm that the victim is no longer bleeding in this location.

After the user positively indicates that the taped gauze is in place, the query flow 1860 proceeds to box 1880, which represents a GUI screen that asks the user if the victim appears to be bleeding anywhere else. If the user indicates a "Yes" answer (e.g. the victim is bleeding elsewhere), then the computer redirects the query flow (via link box 1882) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1884) to the Final Protocol of FIG. 59.

Figure 52:
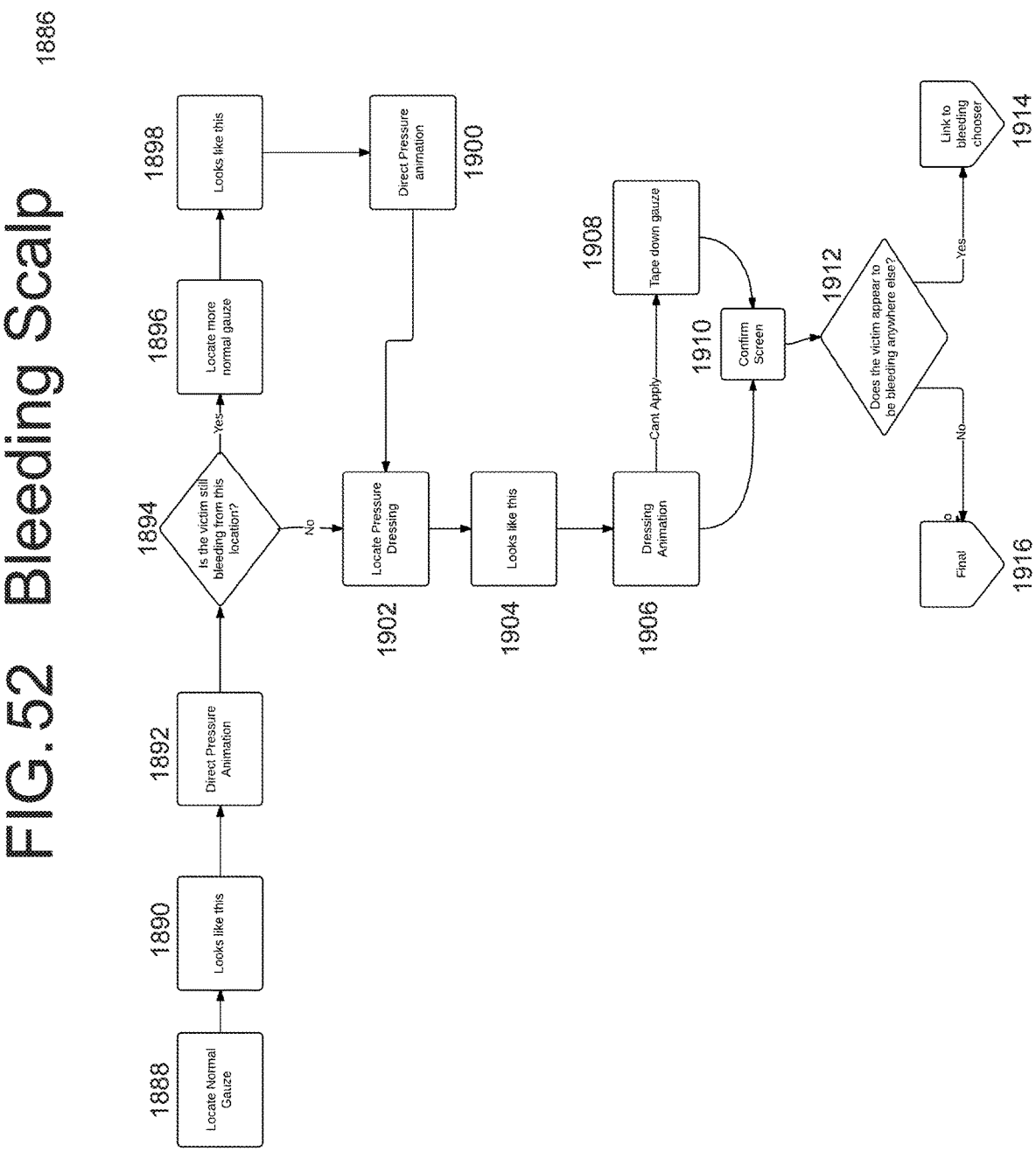
FIG. 52 is a flowchart illustrating an example query flow for a non-severely bleeding scalp, forming part of the triage protocol of FIGS. 2-5.

FIG. 52 illustrates the query flow for a non-severely bleeding scalp 1886, which is accessed via link box 1526 of FIG. 39 (e.g. in response to the user touching or using voice commands on query box 1524 to inform the computer that the victim has a bleeding scalp) and begins at instruction box 1888, which represents a GUI screen instructing the user to locate normal gauze within the accompanying medical tool kit 12. By way of example, the represented GUI screen may also display a layout image of the tool kit and highlight with specificity the location of the normal gauze. The next box 1890 represents a GUI screen that displays a zoomed in image of normal gauze so the user knows what to look for. The next box 1892 represents a GUI screen that provides specific instruction on how to apply direct pressure to a victim's wound using normal gauze, for example with text instructions, visual aid (e.g. pictures and/or video) and/or audio instructions. The next box is query box 1894, which represents a GUI screen asking the user if the victim is still bleeding in this location.

If the user indicates a "Yes" answer (e.g. the victim is still bleeding in this location), the query flow advances to box 1896, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1898 represents a GUI screen that displays a zoomed in image of normal gauze to remind the user what to look for. The next box 1900 in the query flow represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1894 (e.g. bleeding has stopped in this location), the query flow proceeds to box 1902, which represents a GUI screen prompting the user to locate the pressure dressing within the accompanying medical tool kit 12. By way of example, the represented GUI screen may also display a layout image of the tool kit and highlight with specificity the location of the pressure dressing. The next box 1904 represents a GUI screen that displays a zoomed in image of pressure dressing so the user knows what to look for. The next box in the query flow is an instruction box 1906 that represents a GUI screen that provides specific instruction on how to apply the pressure dressing, for example with text instructions, visual aid (e.g. pictures and/or video) and/or audio instructions. If the user is unable to apply the pressure dressing properly, he/she alerts the computer by activating (e.g. physically or vocally) an "I can't apply dressing" button, which prompts the computer to direct the query flow to box 1908, which represents a GUI screen that instructs the user to tape the normal gauze to the wound. Once the normal gauze has been taped to the wound, or alternatively if the user was able to apply the pressure dressing to the wound (e.g. box 1906), the next box in the query flow is query box 1910, which represents a GUI screen asking the user to confirm that the victim is no longer bleeding in this location.

After the user positively indicates that the pressure dressing and/or taped gauze are in place, the query flow 1886 then proceeds to box 1912, which represents a GUI screen that asks the user if the victim appears to be bleeding anywhere else. If the user indicates a "Yes" answer (e.g. the victim is bleeding elsewhere), then the computer redirects the query flow (via link box 1914) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1916) to the Final Protocol of FIG. 59.

Figure 53:
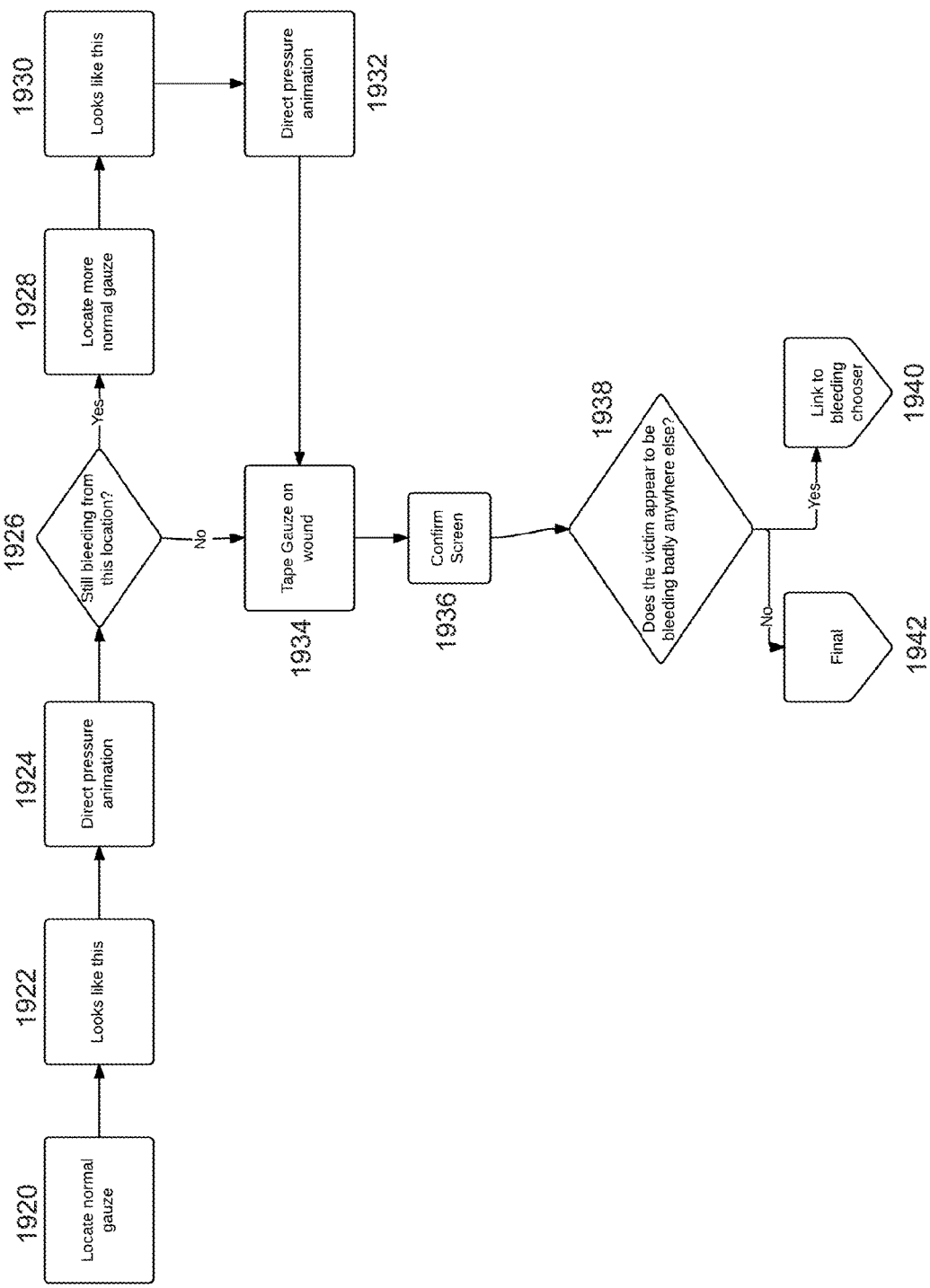
FIG. 53 is a flowchart illustrating an example query flow for a non-severely bleeding ear(s), forming part of the triage protocol of FIGS. 2-5.

FIG. 53 illustrates the query flow for a non-severely bleeding ear(s) 1918, which is accessed via link box 1526 of FIG. 39 (e.g. in response to the user touching or using voice commands on query box 1524 to inform the computer that the victim has a bleeding ear) and begins at instruction box 1920, which represents a GUI screen instructing the user to locate normal gauze within the accompanying medical tool kit 12. By way of example, the represented GUI screen may also display a layout image of the tool kit and highlight with specificity the location of the normal gauze. The next box 1922 represents a GUI screen that displays a zoomed in image of normal gauze so the user knows what to look for. The next box 1924 represents a GUI screen that provides specific instruction on how to apply direct pressure to a victim's wound using normal gauze, for example with text instructions, visual aid (e.g. pictures and/or video) and/or audio instructions. The next box is query box 1926, which represents a GUI screen asking the user if the victim is still bleeding in this location.

If the user indicates a "Yes" answer (e.g. the victim is still bleeding in this location), the query flow advances to box 1928, which represents a GUI screen instructing the user to locate more normal gauze within the accompanying medical tool kit 12. By way of example, the represented GUI screen may also display a layout image of the tool kit and highlight the location of the normal gauze to remind the user where it is located. The next box 1930 represents a GUI screen that displays a zoomed in image of normal gauze to remind the user what to look for. The next box 1932 in the query flow represents a GUI screen that provides specific instruction on how to apply direct pressure to a victim's wound using normal gauze, for example with text instructions, visual aid (e.g. pictures and/or video) and/or audio instructions. When the user indicates that this step has been completed, or alternatively if the user indicates a "No" answer to the question of box 1926 (e.g. bleeding has stopped in this location), the query flow proceeds to box 1934, which represents a GUI screen that instructs the user to tape the normal gauze to the wound. Once the normal gauze has been taped to the wound, the next box in the query flow is query box 1936, which represents a GUI screen asking the user to confirm that the victim is no longer bleeding in this location.

After the user positively indicates that the taped gauze is in place, the query flow 1918 proceeds to box 1938, which represents a GUI screen that asks the user if the victim appears to be bleeding anywhere else. If the user indicates a "Yes" answer (e.g. the victim is bleeding elsewhere), then the computer redirects the query flow (via link box 1940) to box 1516 of FIG. 39 (e.g. graphic representation of a human body on the touch screen display that the user touches to indicate the area where the victim is bleeding the most), and the flow proceeds from there. If the user indicates a "No" answer (e.g. the victim is not bleeding elsewhere), then the computer redirects the query flow (via link box 1942) to the Final Protocol of FIG. 59.

Figure 54:
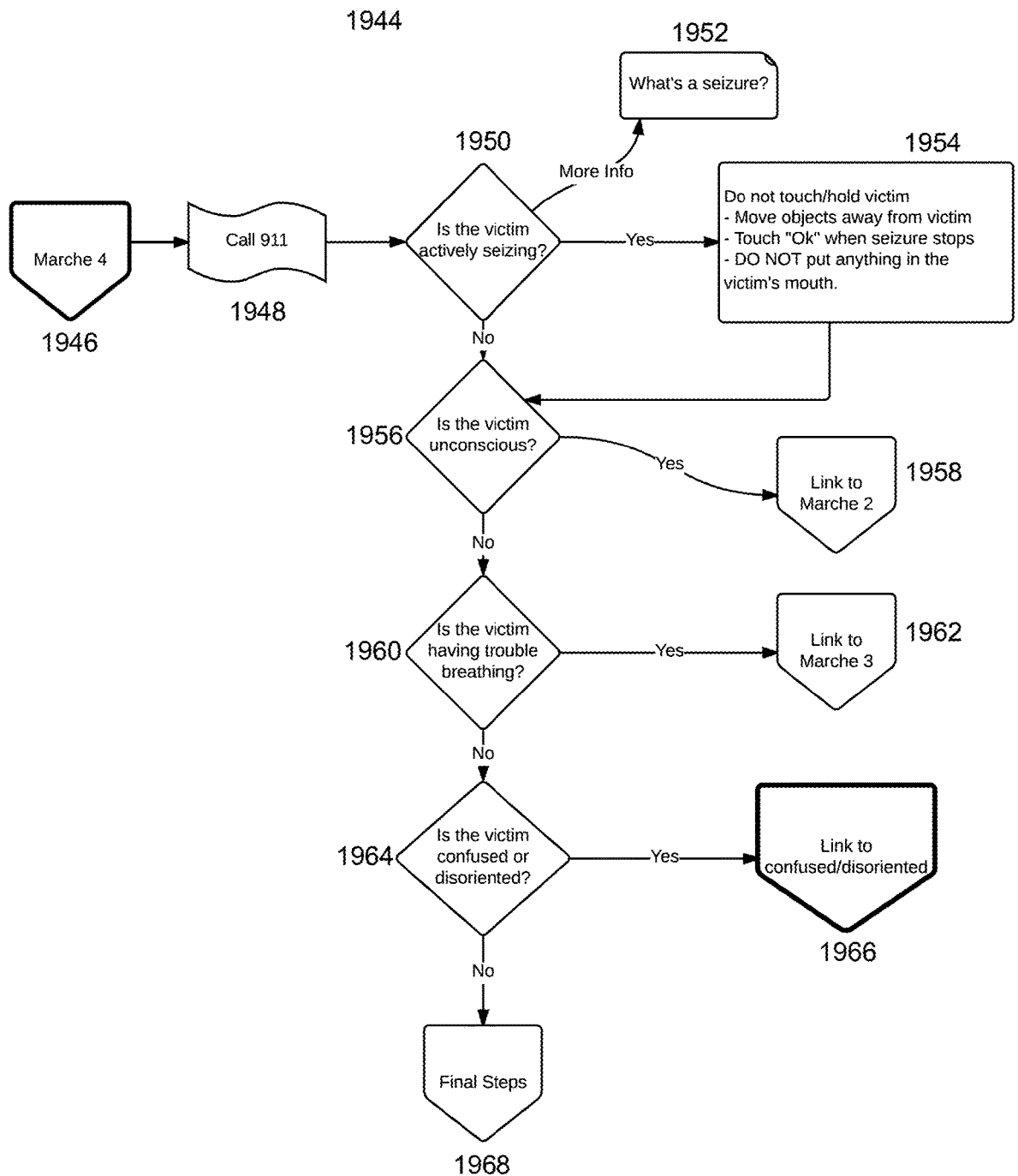
FIG. 54 is a flowchart illustrating an example query flow for a seizure, forming part of the triage protocol of FIGS. 2-5.

FIG. 54 illustrates the query flow 1944 for a seizure, which is accessed via query box 242 of FIG. 5 (e.g. in response to the user touching or using voice commands on query box 242 to inform the computer that the victim is experiencing a seizure) and begins at link box 1946. Upon entry into the seizure query flow 1944, the user is reminded to call 9-1-1 via alert box 1948 to summons emergency personnel, if that hasn't already been done by the user or a by-stander. The user is then presented with a query box 1950 with a GUI display asking whether the victim is actively seizing, along with an optional informational box 1952 with information (e.g. video, images, text, etc. . . . ) to help educate the user to recognize seizures. If the answer is "Yes" to query box 1950, then the user is instructed (via instructional box 1954) with a GUI display with any of a variety of instructions, such as (but not limited to) refrain from touching and/or holding the victim, move objects away from the victim, touch "OK" on the screen when the seizure stops, and refrain from putting anything in the victim's mouth. If the answer is "No" to query box 1950, or after the user has been instructed via instructional box 1954, the seizure query flow proceeds to query box 1956 with a GUI display that asks the user if the victim is unconscious. If the answer is "Yes" to this query box 1956, then the computer directs the user to the Unconscious Protocol of Marche 2 in FIG. 3 via link box 1958. If the answer is "No" to the query box 1956, then the user is directed to another query box 1960 with a GUI display that asks if the victim is having trouble breathing. If the answer is "Yes" to this query box 1960, then the computer directs the user to the Trouble Breathing Protocol of Marche 3 of FIG. 4 via link box 1962. If the answer is "No" to query box 1960, then the user is directed to another query box 1964 with a GUI display that asks if the victim is confused/disoriented. If the answer is "Yes" to this query box 1964, then the computer directs the user to the "Confused/Disoriented" Protocol (via link box 1966) to be described below in FIG. 56. If the answer is "No" to the query box 1964, then the seizure query flow proceeds to the Final Protocol of FIG. 59 as shown in link box 1968.

Figure 55:
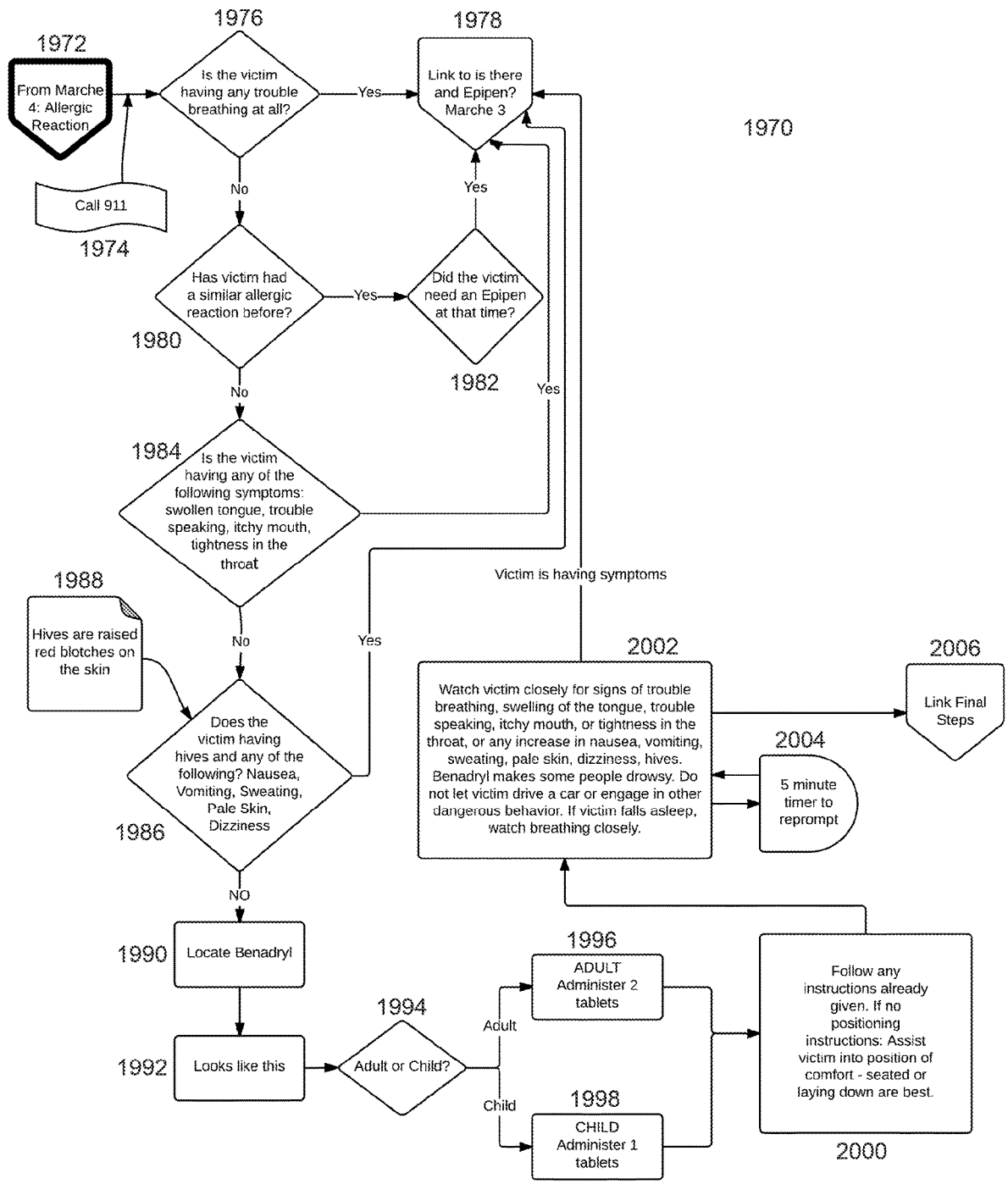
FIG. 55 is a flowchart illustrating an example query flow for an allergic reaction, forming part of the triage protocol of FIGS. 2-5.

FIG. 55 illustrates the query flow 1970 for an allergic reaction, which is accessed via query box 242 of FIG. 5 (e.g. in response to the user touching or using voice commands on query box 242 to inform the computer that the victim is experiencing an allergic reaction) and begins at link box 1972. Upon entry into the allergic reaction query flow 1970, the user is reminded to call 9-1-1 via alert box 1974 to summons emergency personnel, if that hasn't already been done by the user or a by-stander. The user is then presented with a query box 1976 with a GUI display asking whether the victim is having any difficulty breathing. If the answer is "Yes" to query box 1976, then the computer directs the user to the Epinephrine Autoinjector Protocol of Marche 3 of FIG. 4 via link box 1978. If the answer is "No" to query box 1976, the allergic reaction query flow proceeds to query box 1980 with a GUI display that asks the user if the victim has had a similar allergic reaction before. If the answer is "Yes" to this query box 1980, then the user is presented with a query box 1982 with a GUI display that asks the user if the victim needed an Epinephrine Autoinjector at the time of the similar allergic reaction (from query box 1980). If the answer is "Yes" to this query box, the computer directs the user to the Epinephrine Autoinjector Protocol of Marche 3 in FIG. 4 via link box 1978. If the answer is "No" to the query box 1980, then the user is directed to another query box 1984 with a GUI display that asks if the victim is having certain symptoms (e.g. swollen tongue, trouble speaking, itchy mouth, tightness in the throat, etc. . . . ). If the answer is "Yes" to this query box, the computer directs the user to the Epinephrine Autoinjector Protocol of Marche 3 in FIG. 4 via link box 1978. If the answer is "No" to the query box 1984, then the user is directed to another query box 1986 with a GUI display that asks if the victim has hives and any other symptoms (e.g. nausea, vomiting, sweating, pale skin, dizziness, etc. . . . ), with an optional informational box 1988 with information (e.g. video, images, text, etc. . . . ) to help educate the user to recognize hives. If the answer is "Yes" to this query box, the computer directs the user to the Epinephrine Autoinjector Protocol of Marche 3 in FIG. 4 via link box 1978.

If the answer is "No" to query box 1986, the allergic reaction query flow proceeds to an instructional box 1990 with a GUI display instructing the user to locate Benadryl. The user is also presented (at instructional box 1992) with an instructional video or image of the Benadryl in order to help the user quickly identify or otherwise recognize it to thus facilitate the location instruction of box 1990. The user is then presented with a query box 1994 with a GUI display that asks whether the victim is an adult or a child. If the user selects "Adult" at query box 1994, the user is presented with an instructional box 1996 with a GUI display instructing the user to administer two (2) tablets of Benadryl to the victim. If the user selects "Child" at query box 1994, the user is presented with an instructional box 1998 with a GUI display instructing the user to administer one (1) tablet of Benadryl to the victim. The allergic reaction query flow then proceeds to an instructional box 2000 with a GUI display that instructs the user to follow any instructions previously provided, as well as to assist the victim into a position of comfort (seated or laying down) in the absence of any other positioning instructions. The user is then presented with another instructional box 2002 with a GUI display that instructs the user to watch the victim closely for signs of trouble breathing, swelling of the tongue, trouble speaking, itchy mouth, tightness in the throat, or any increase in nausea, vomiting, sweating, pale skin, dizziness, hives. It also may contain warnings or information about Benadryl, such as (but not limited to) Benadryl may cause drowsiness in the victim, the user should not allow the victim to drive automobiles or engage in any other dangerous behavior after the victim has been administered Benadryl, and that the user should closely monitor the victim's breathing if they fall asleep. If the user indicates that the victim is having any such symptoms, the computer directs the user to the Epinephrine Autoinjector Protocol of Marche 3 in FIG. 4 via link box 1978. If the user indicates that the victim isn't experiencing any such symptoms upon initial assessment by the user, a timer 2004 will start (e.g. 5 min) to re-prompt the user to continue their assessment of the victim for the various symptoms set forth in instructional box 2002. If the victim is still not experiencing the various symptoms set forth in instructional box 2002 after the timer 2004 elapses, then the allergic reaction query flow proceeds to the Final Protocol of FIG. 59 as shown in link box 2006.

Figure 56:
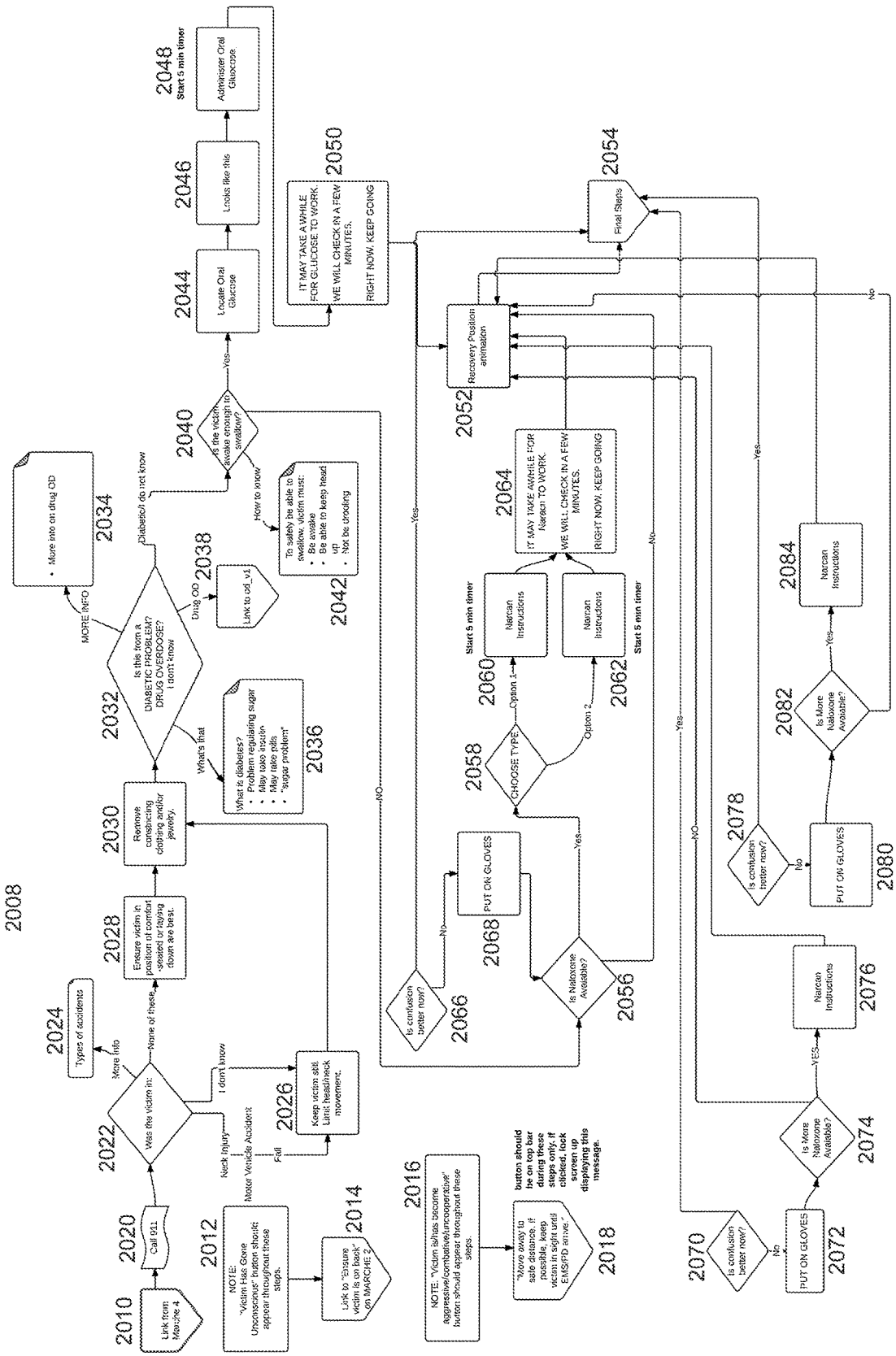
FIG. 56 is a flowchart illustrating an example query flow for confusion/disorientation, forming part of the triage protocol of FIGS. 2-5.

FIG. 56 illustrates the query flow for Confusion/Disorientation 2008, which is accessed via query box 242 of FIG. 5 (e.g. in response to the user touching or using voice commands on query box 242 to inform the computer that the victim is experiencing an allergic reaction) and begins at link box 2010. As an initial matter, the Confusion/Disorientation query flow 2008 includes a first floating instructional box 2012 that notes that a "Victim Has Gone Unconscious" button/icon appears in each GUI screen represented by the various boxes described herein. If at any time the victim goes unconscious, the user indicates this by tapping the "Victim Has Gone Unconscious" button/icon, and the computer will link the query flow (via link box 2014) to box 88 of FIG. 3 (e.g. "Ensure victim is on back") and the flow will continue from there. Additionally, the Confusion/Disorientation query flow 2008 includes a second floating instructional box 2016 that notes that a "Victim Has Become Aggressive/Combative/Uncooperative" button/icon appears in each GUI screen represented by the various boxes described herein. If at any time the victim becomes aggressive, combative, or uncooperative, the user indicates this by tapping the icon of box 2016 and the computer displays (via link box 2018) a message reading for example "Move away to a safe distance. If possible, keep victim in sight until EMS/PD arrive." The screen locks displaying this message and the user should then close and secure the medical tool kit 12, move away to a safe distance, and wait for the emergency responder to arrive.

Upon entry into the confusion/disorientation query flow 2008, the user is reminded to call 9-1-1 via alert box 2020 to summons emergency personnel, if that hasn't already been done by the user or a bystander. The user is then presented with a query box 2022 with a GUI display asking whether the victim was in a car crash, suffered a fall from height, or suffered a neck injury. An information box 2024 is accessible if the user needs more information about what would constitute the different types of accidents. If the user indicates an affirmative answer to any of the three types of accidents, or if the user selects "I don't know" as the answer, the query flow proceeds to box 2026, which is an instructional box representing a GUI screen that instructs the user to keep the victim still and limit head/neck movement. If the user answered "None of these" to the question of box 2022, the query flow advances to instruction box 2028, which represents a GUI screen instructing the user to ensure the victim is in a position of comfort—seated or laying down is best. From either box 2026 or box 2028, the query flow continues to box 2030, which represents a GUI screen instructing the user to remove constricting clothing and/or jewelry.

The next box in the query flow 2008 is a query box 2032 representing a GUI screen that asks the user if the victim is suffering from a diabetic problem or drug overdose. An information box 2034 is available to provide more information to the user about (for example) what constitutes and how to recognize a drug overdose. Another information box 2036 is available to provide more information to the user about (for example) what diabetes is, including but not limited to problem regulating sugar, may take insulin, may take pills, "sugar problem", etc. If the user indicates an answer of "Drug Overdose" to the question of box 2032, then the computer directs the query flow (via link box 2038) to the naloxone/Overdose Flow of FIG. 57. If the user indicates an answer of "Diabetic" or "I don't know" to the question of box 2032, the computer advances the query flow to box 2040, which represents a GUI screen asking if the victim is awake enough to swallow. Information box 2042 is available if the user needs guidance on how to know. By way of example, the information box 2042 may indicate that to safely be able to swallow, the victim must be awake, be able to keep head up, and not be drooling.

If the user indicates a "Yes" answer to the question of box 2040 (e.g. victim is awake enough to swallow), then the user is directed (via instruction box 2044) to locate the oral glucose (if present) in the medical took kit 12. By way of example, the represented GUI screen may also display a layout image of the tool kit and highlight the location of the oral glucose to remind the user where it is located. The next box 2046 represents a GUI screen that displays a zoomed in image of oral glucose to remind the user what to look for. The next box 2048 in the query flow represents a GUI screen that provides specific instruction on how to administer oral glucose, for example with text instructions, visual aid (e.g. pictures and/or video) and/or audio instructions. The user then administers the oral glucose, and the computer starts a five minute (5:00) timer and displays a message (via instruction box 2050) for example that it might take a while for the glucose to work, we'll check in a few minutes, but for now keep going. The query flow then proceeds to box 2052, which provides instruction on proper recovery position while the user waits for the timer to expire, professional rescuer to arrive, or for the victim to become less confused/disoriented. If the victim does become less confused/disoriented before the expiration of the five-minute timer, the flow may advance to the Final Protocol via the link box 2054.

If the user indicates a "No" answer to the question of box 2040 (e.g. the victim is not awake enough to swallow), the computer directs the query flow to box 2056, which represents a GUI screen that asks the user if naloxone (e.g. Narcan) is available. If the user indicates an answer of "No," then the query flow proceeds to box 2052 to help the user position the victim in proper recovery positioning. Once the victim is properly positioned for recover, the flow may advance to the Final Patient Protocol of FIG. 59 via link box 2054.

If the user indicates a "Yes" answer to the question of box 2056 (e.g. naloxone is available), the flow advances to box 2058, which represents a GUI screen prompting the user to choose the type of naloxone between two options (e.g. nasal spray and injection). If the user chooses option 1 (e.g. nasal spray), the query flow advances to box 2060, which represents a GUI screen providing instructions for administering the naloxone spray. If the user chooses option 2 (e.g. injection), the query flow advances to box 2062, which represents a GUI screen providing instructions for administering the naloxone injection. From either box 2060 or box 2062, the user then administers the naloxone, and the computer starts a five minute (5:00) timer and displays a message (via instruction box 2064) for example that it might take a while for the naloxone to work, we'll check in a few minutes, but for now keep going. The query flow then proceeds to box 2052, which provides instruction on proper recovery position while the user waits for the timer to expire, professional rescuer to arrive, or for the victim to wake up. If the victim wakes up prior to the expiration of the 5:00 timer, become less confused/disoriented.

At the expiration of the first five-minute timer, wherever else the user may be in the MOBILIZE app the computer will alert the user that it is time to check on the naloxone recipient by linking to query box 2066 (for example) which represents a GUI screen that asks whether the confusion is better now. If the user answers "Yes" then the computer directs the query flow to the Final Patient Protocol of FIG. 59 via link box 2054. If the user indicates a "No" answer to the question of box 2060, the computer directs the query flow to box 2068, which represents a GUI screen instructing the use to put on gloves (optionally with accompanying animation). The flow is then redirected to box 2056 (e.g. is there naloxone available) and proceeds from there.

If naloxone was administered to the victim a second time and a second five-minute timer was set and subsequently expired, wherever else the user may be in the MOBILIZE app the computer will alert the user that it is time to check on the naloxone recipient by linking to query box 2070 (for example) which represents a GUI screen that asks whether the confusion is better now. If the user answers "Yes" then the computer directs the query flow to the Final Patient Protocol of FIG. 59 via link box 2054. If the user indicates a "No" answer to the question of box 2070, the computer directs the query flow to box 2072, which represents a GUI screen instructing the use to put on gloves (optionally with accompanying animation). The flow then continues to box 2074, which represents a GUI screen asking if more naloxone is available. If the user indicates a "No" answer, then the query flow then proceeds to box 2052, which provides instruction on proper recovery position while the user waits for the professional rescuer to arrive or for the victim to wake up. If the user indicates a "Yes" answer to the question of box 2074 (e.g. more naloxone is available), the query flow is directed to box 2076, which again provides the dosing instructions (as previously discussed). Once the user administers another dose of naloxone, the computer sets another five-minute timer, and the query flow advances to box 2052 (recovery position).

If naloxone was administered to the victim a third time and a third five-minute timer was set and subsequently expired, wherever else the user may be in the MOBILIZE app the computer will alert the user that it is time to check on the naloxone recipient by linking to query box 2078 (for example) which represents a GUI screen that asks whether the confusion is better now. If the user answers "Yes" then the computer directs the query flow to the Final Patient Protocol of FIG. 59 via link box 2054. If the user indicates a "No" answer to the question of box 2078, the computer directs the query flow to box 2080, which represents a GUI screen instructing the use to put on gloves (optionally with accompanying animation). The flow then continues to box 2082, which represents a GUI screen asking if more naloxone is available. If the user indicates a "No" answer, then the query flow then proceeds to box 2052, which provides instruction on proper recovery position while the user waits for the professional rescuer to arrive or for the victim to wake up. If the user indicates a "Yes" answer to the question of box 2082 (e.g. more naloxone is available), the query flow is directed to box 2084, which again provides the dosing instructions (as previously discussed). Once the user administers another dose of naloxone, the computer sets another five-minute timer, and the query flow advances to box 2052 (recovery position). This process can loop until the naloxone supply runs out.

Figure 57:
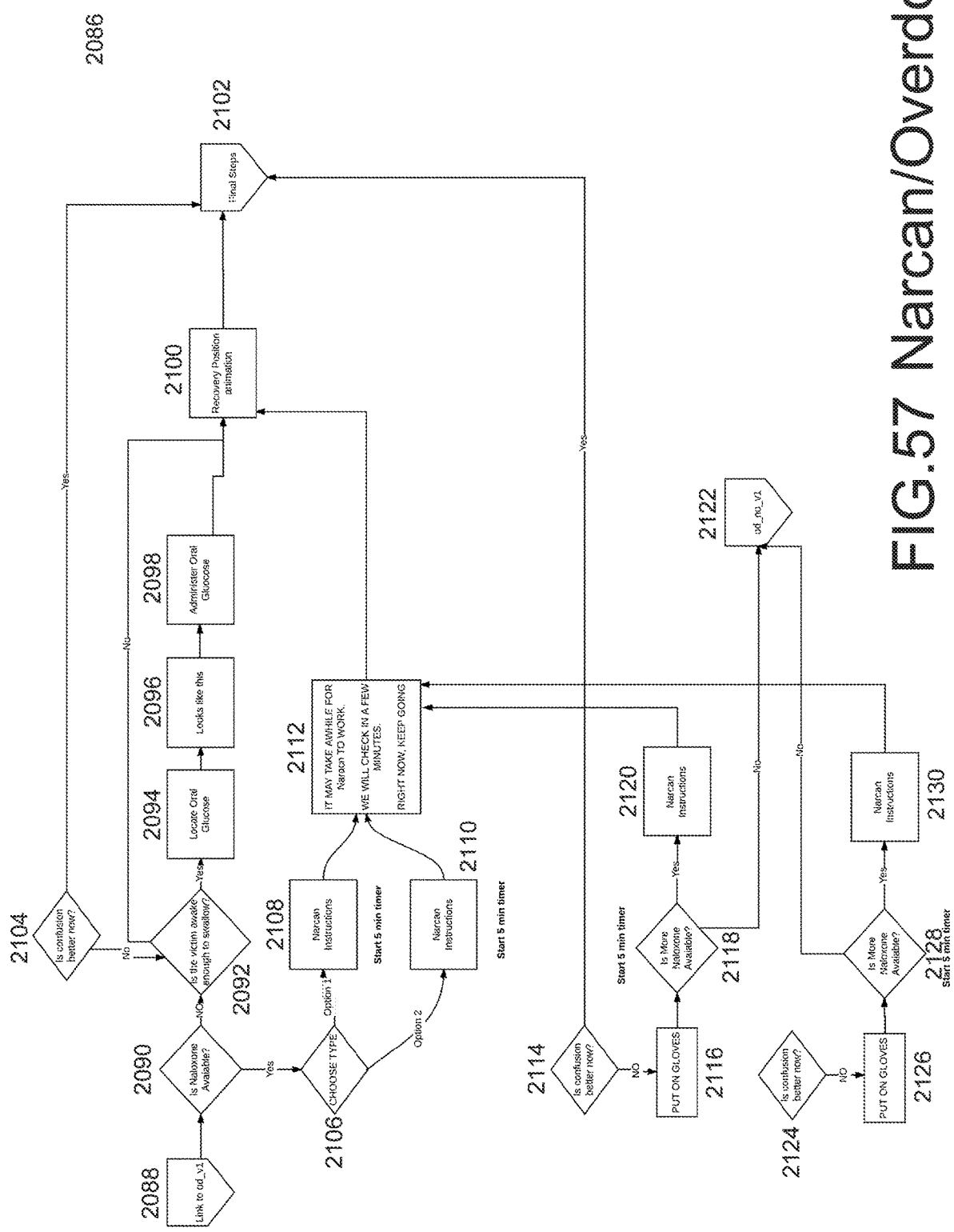
FIG. 57 is a flowchart illustrating an example query flow for Narcan/overdose, forming part of the triage protocol of FIGS. 2-5.

FIG. 57 illustrates the query flow for naloxone/Overdose 2086, which is accessible via link box 2038 of FIG. 56, and begins at link box 2088. Upon entering the query flow 2086, the user is asked (via query box 2090) if naloxone is available. If the user indicates a "No" answer to the question of box 2090 (e.g. naloxone is not available), the computer advances the query flow to box 2092, which represents a GUI screen that asks the user if the victim is awake enough to swallow. If the user indicates a "Yes" answer to the question of box 2092 (e.g. victim is awake enough to swallow), then the user is directed (via instruction box 2094) to locate the oral glucose (if present) in the medical took kit 12 (or elsewhere). By way of example, the represented GUI screen may also display a layout image of the tool kit and highlight the location of the oral glucose to remind the user where it is located. The next box 2096 represents a GUI screen that displays a zoomed in image of oral glucose to remind the user what to look for. The next box 2098 in the query flow represents a GUI screen that provides specific instruction on how to administer oral glucose, for example with text instructions, visual aid (e.g. pictures and/or video) and/or audio instructions. The user then administers the oral glucose, and the computer starts a five minute (5:00) timer and may displays a message for example that it might take a while for the glucose to work, we'll check in a few minutes, but for now keep going. The query flow then proceeds to box 2100, which provides instruction on proper recovery position while the user waits for the timer to expire, professional rescuer to arrive, or for the victim to become less confused/disoriented. If the victim does become less confused/disoriented before the expiration of the five-minute timer, the flow may advance to the Final Protocol via the link box 2102.

If the user indicates a "No" answer to the question of box 2090 (e.g. the victim is not awake enough to swallow), the computer directs the query flow to box 2100 to help the user position the victim in proper recovery positioning. Once the victim is properly positioned for recovery, the flow may advance to the Final Patient Protocol of FIG. 59 via link box 2054.

At the expiry of the five-minute timer for oral glucose, wherever else the user may be in the MOBILIZE app the computer will alert the user that it is time to check on the glucose recipient by linking to query box 2104 (for example) which represents a GUI screen that asks whether the confusion is better now. If the user answers "Yes" then the computer directs the query flow to the Final Patient Protocol of FIG. 59 via link box 2102. If the user indicates a "No" answer to the question of box 2104, the computer directs the query flow to box 2092 and the flow proceeds from there. This loop may occur as long as there is glucose to give or the victim recovers.

If the user indicates a "Yes" answer to the question of box 2090 (e.g. naloxone is available), the flow advances to box 2106, which represents a GUI screen prompting the user to choose the type of naloxone between two options (e.g. nasal spray and injection). If the user chooses option 1 (e.g. nasal spray), the query flow advances to box 2108, which represents a GUI screen providing instructions for administering the naloxone spray. If the user chooses option 2 (e.g. injection), the query flow advances to box 2110, which represents a GUI screen providing instructions for administering the naloxone injection. From either box 2108 or box 2110, the user then administers the naloxone, and the computer starts a five minute (5:00) timer and displays a message (via instruction box 2112) for example that it might take a while for the naloxone to work, we'll check in a few minutes, but for now keep going. The query flow then proceeds to box 2100, which provides instruction on proper recovery position while the user waits for the timer to expire, professional rescuer to arrive, or for the victim to wake up. If the victim wakes up prior to the expiration of the 5:00 timer, or becomes less confused/disoriented, the flow may proceed to the Patient Final Protocol of FIG. 59 via link box 2102.

At the expiration of the first five-minute timer, wherever else the user may be in the MOBILIZE app the computer will alert the user that it is time to check on the naloxone recipient by linking to query box 2114 (for example) which represents a GUI screen that asks whether the victim is better now. If the user answers "Yes" then the computer directs the query flow to the Final Patient Protocol of FIG. 59 via link box 2102. If the user indicates a "No" answer to the question of box 2114, the computer directs the query flow to box 2116, which represents a GUI screen instructing the use to put on gloves (optionally with accompanying animation). The flow is then directed to box 2118, which represents a GUI screen asking if there is more naloxone available. If the answer is "Yes", the computer advances the query flow to box 2120, which represents a GUI screen providing usage instruction for the naloxone (e.g. same as above). The user may administer the naloxone, the computer starts another five-minute timer, and the flow returns to box 2112 and proceeds from there. If the user answers "No" to the question of box 2118 (e.g. No more naloxone available) the flow proceeds to link box 2122, which links back to wherever the user was in the MOBILIZE app when the timer first expired. The victim should be positioned in recovery position to wait for arrival of professional rescuers.

If naloxone was administered to the victim a second time and a second five-minute timer was set and subsequently expired, wherever else the user may be in the MOBILIZE app the computer will alert the user that it is time to check on the naloxone recipient by linking to query box 2124 (for example) which represents a GUI screen that asks whether the confusion is better now. If the user answers "Yes" then the computer directs the query flow to the Final Patient Protocol of FIG. 59 via link box 2102. If the user indicates a "No" answer to the question of box 2124, the computer directs the query flow to box 2126, which represents a GUI screen instructing the use to put on gloves (optionally with accompanying animation). The flow then continues to box 2128, which represents a GUI screen asking if more naloxone is available. If the answer is "Yes", the computer advances the query flow to box 2130, which represents a GUI screen providing usage instruction for the naloxone (e.g. same as above). The user may administer the naloxone, the computer starts another five-minute timer, and the flow returns to box 2112 and proceeds from there. If the user answers "No" to the question of box 2128 (e.g. No more naloxone available) the flow proceeds to link box 2122, which links back to wherever the user was in the MOBILIZE app when the timer first expired. The victim should be positioned in recovery position to wait for arrival of professional rescuers.

Figure 58:
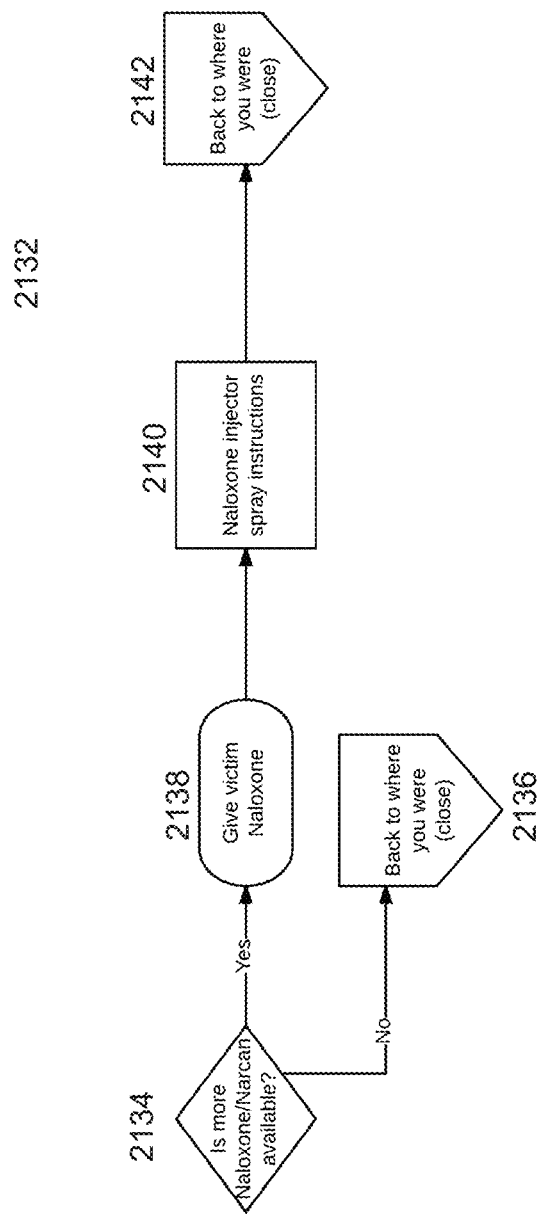
FIG. 58 is a flowchart illustrating an example query flow for Narcan/overdose—second dose, forming part of the triage protocol of FIGS. 2-5.

FIG. 58 illustrates the query flow for naloxone/Overdose Second Dose 2132, which may be linked to by the computer wherever the user is in the MOBILIZE app when the five-minute timer expires. By way of example, the computer links the user to query box 2134, which represents a GUI screen asking the user if there is more naloxone available. If the user answers "No" to the question of box 2134 (e.g. No more naloxone available) the flow proceeds to link box 2136, which links back to wherever the user was in the MOBILIZE app when the timer first expired. The victim should be positioned in recovery position to wait for arrival of professional rescuers. If the user answers "Yes" to the question of box 2134, the computer advances the query flow to box 2138, which instructs the user to give the victim more naloxone. Instruction box 2140 represents a GUI screen providing usage instruction for the naloxone (e.g. same as above). The user may administer the naloxone, the computer starts another five-minute timer, and the flow advances to link box 2142, which returns the user to wherever they were in the MOBILIZE app before the expiration of the five-minute timer.

FIG. 59 illustrates the query flow for the final patient protocol 2144, for example when the user has finished treating the victim and is waiting for professional emergency medical help to arrive. The user is brought to the final protocol flow 2144 via link box 2146. The first query box 2148 represents a GUI screen that asks the user if there is anything else wrong with the current victim. If the user indicates a "Yes" answer, the computer directs the query flow (via link box 2150) to the Injured/Hurt query flow of FIG. 25. If the user indicates a "No" answer, the query flow advances to the next box 2152, which represents a GUI screen asking the user to look for other possible victims (See, e.g. FIG. 110). If the user indicates a "Yes" answer, the computer initiates a new victim persona for data collection for the summary page, and directs the query flow (via link box 2154) to the Injured/Hurt query flow of FIG. 25.

If user answers "No" to the question of box 2152, the query flow is directed to box 2156, which instructs the user to locate an emergency blanket. The flow continues to instructional box 2158, which represents a GUI screen instructing the user that (by way of example and including but not limited to) victims need to stay warm, victims with bad bleeding get priority for blankets, and do not put blankets on over-heated victims. The next step in the query flow is box 2160, which instructs the user to take off their gloves. By way of example, the GUI screen may also demonstrate the proper way to take off gloves without the user exposing their bare hands to contaminants (See, e.g., FIG. 79). Box 2162 represents a GUI screen that advises the user to use hand wipes to wash hands, and wash with warm water and soap as soon as possible. The next box in the flow is instruction box 2164, which instructs the user to fill out the form located to the left of the screen in the medical tool kit 12 to the best of their ability. The next box in the flow is an instruction box 2166 that instructs the user to wait for professional help to arrive if there is nothing else to do.

If the user gets to the end of the flow (e.g. box 2166) and subsequently discovers another person to treat, the user can tap the "I found another victim" icon button present on the GUI screen associated with box 2166. Tapping (or issuing vocal command) on the "I found another victim" icon causes the computer to initiate a new victim persona for data collection for the summary page, and direct the query flow (via link box 2168) to Part 1 of the MARCHE protocol of FIG. 2, since this is a victim that the user wasn't previously aware of.

If something else happens to a victim after the victim has been treated (e.g. the victim has a new problem), the user may press an "Uh Oh" button (box 2170). The query flow then proceeds to box 2172, which represents a GUI screen instructing the user to put on gloves. The computer then directs the query flow (via link box 2174) to the Uh-Oh query flow of FIG. 60, where it will proceed as discussed above to treat the victim's new problem.

Once the user is just waiting for the professional rescuer to arrive because he/she at least thinks they've done all they can, the MOBILIZE app still prompts them to recheck the victim every 5 minutes to make sure nothing is wrong with the applied triage treatment. For example, box 2176 represents a GUI screen that pops up every five minutes to remind the user to check on the victim. If the user does not find any problems, the query flow returns to box 2166. If the user does find a problem, then the flow proceeds to box 2178, which represents a GUI screen instructing the user to put on gloves. Then the user is linked (via link box 2180) to the Injured/Hurt protocol of FIG. 25.

Once the professional rescuer has arrived, the query flow instructs the user (via box 2182) to print a summary page, and give it to the rescuer.

Figure 60:
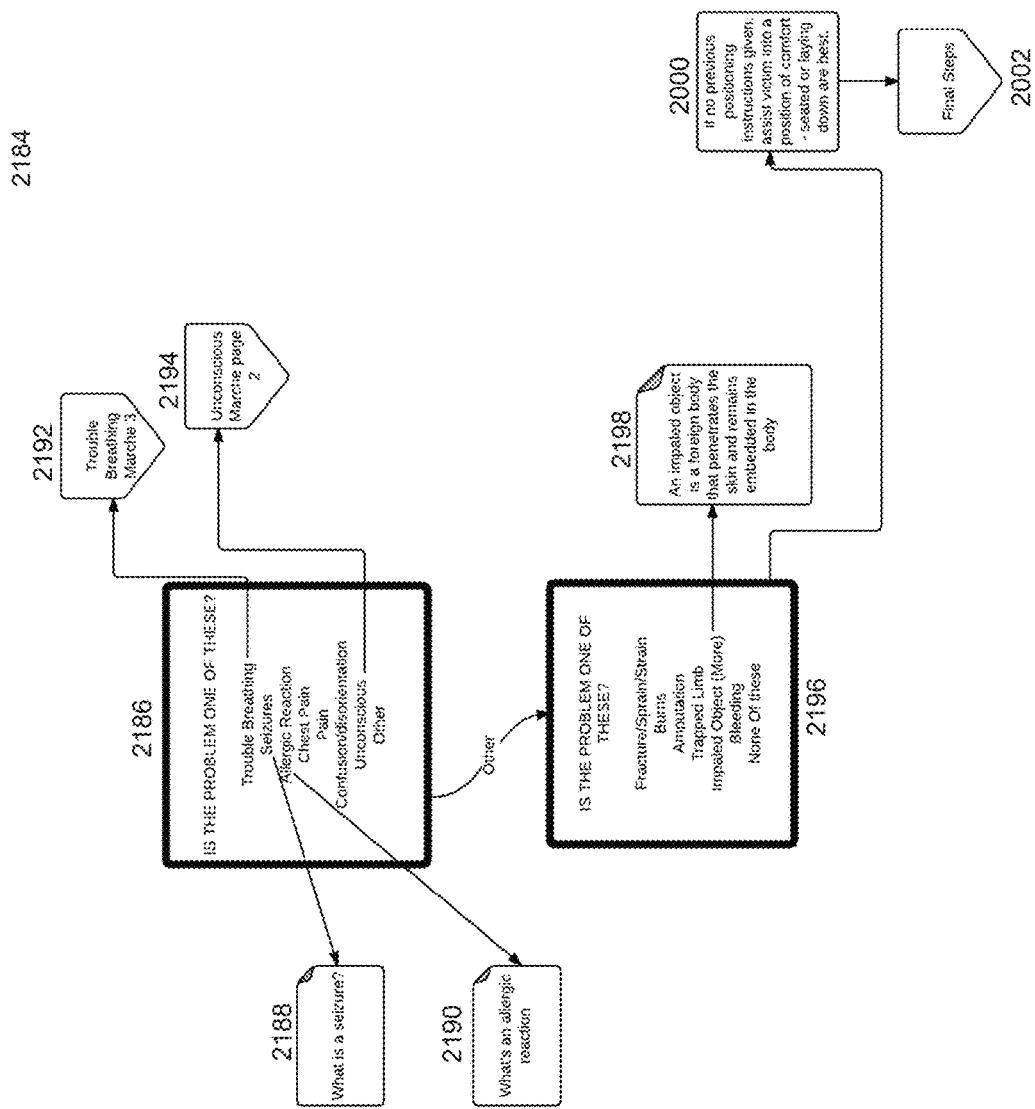
FIG. 60 is a flowchart illustrating an example flow for injury/illness that become apparent after the victim has already been treated for something else, forming part of the triage protocol of FIGS. 2-5.

FIG. 60 illustrates the query flow 2184 for injury/illness that become apparent after the victim has already been treated for something else (Uh-Oh), which is accessed from link box 2174 of the Final Patient Protocol query flow 2144 of FIG. 59. By way of example, the link box 2174 links the query flow to box 2186, which represents a GUI screen that asks the user if the problem is one of: Trouble Breathing, Seizures, Allergic Reaction, Chest Pain, General Pain, Confusion/Disorientation, Unconscious, or Other. For the "Seizure" choice, the represented GUI screen includes a "More Info" icon that, if activated by the user (e.g. by touch or voice) prompts the computer to display a popup information box 2188 that explains a seizure to the user. For the "Allergic Reaction" choice, the represented GUI screen includes a "More Info" icon that, if activated by the user (e.g. by touch or voice) prompts the computer to display a popup information box 2190 that explains an allergic reaction to the user. By way of example, if the user indicates "Trouble Breathing," the computer will direct the query flow to box 140 of the part 3 of the MARCHE protocol (via link box 2192), described above with reference to FIG. 4. If the user indicates "Seizures," the computer will direct the query flow to the Seizures query flow, described above with reference to FIG. 54. If the user indicates "Allergic Reaction," the computer will direct the query flow to the Allergic Reaction query flow, described above with reference to FIG. 55. If the user indicates "Chest Pain," the computer will direct the query flow to the Chest Pain query flow, described above with reference to FIG. 24. If the user indicates "General Pain," the computer will direct the query flow to the General Pain query flow, described above with reference to FIG. 27. If the user indicates "Confusion/Disorientation," the computer will direct the query flow to the Confusion/Disorientation query flow, described above with reference to FIG. 56. If the user indicates "Unconscious," the computer will direct the query flow to box 70 of Part 2 of the MARCHE protocol (via link box 2194), described above with reference to FIG. 3.

If the user indicates "Other" in response to the question displayed by the GUI represented by box 2186, the computer advances the query flow to box 2196, which represents a GUI screen that asks the user if the problem is one of: Fracture/Sprain/Strain, Burns, Amputation, Trapped Limb, Impaled Object, Bleeding, or None of These. For the "Impaled Object" choice, the represented GUI screen includes a "More Info" icon that, if activated by the user (e.g. by touch or voice) prompts the computer to display a popup information box 2198 that explains to the user that an impaled object is a foreign body that penetrates the skin and remains embedded in the body. By way of example, if the user indicates "Fracture/Sprain/Strain," the computer will direct the query flow to the Pain/Fracture (Body Chooser) flow, described above with reference to FIG. 26. If the user indicates "Burns," the computer will direct the query flow to the Burns query flow, described above with reference to FIG. 35. If the user indicates "Amputation," the computer will direct the query flow to the Amputation query flow, described above with reference to FIG. 36. If the user indicates "Trapped Limb," the computer will direct the query flow to the Trapped Limb query flow, described above with reference to FIG. 37. If the user indicates "Impaled Object," the computer will direct the query flow to the Impaled Object query flow, described above with reference to FIG. 38. If the user indicates "Bleeding (mild)," the computer will direct the query flow to the Bleeding (Body Chooser) flow, described above with reference to FIG. 39. If the user indicates "None of These", the computer will advance the query flow to instruction box 2200, which instructs the user to if needed "assist the victim into a position of comfort—seated or laying down are best." From this point the query flow proceeds to link box 2202, which links to the Final Protocol of FIG. 59.

Figure 61:
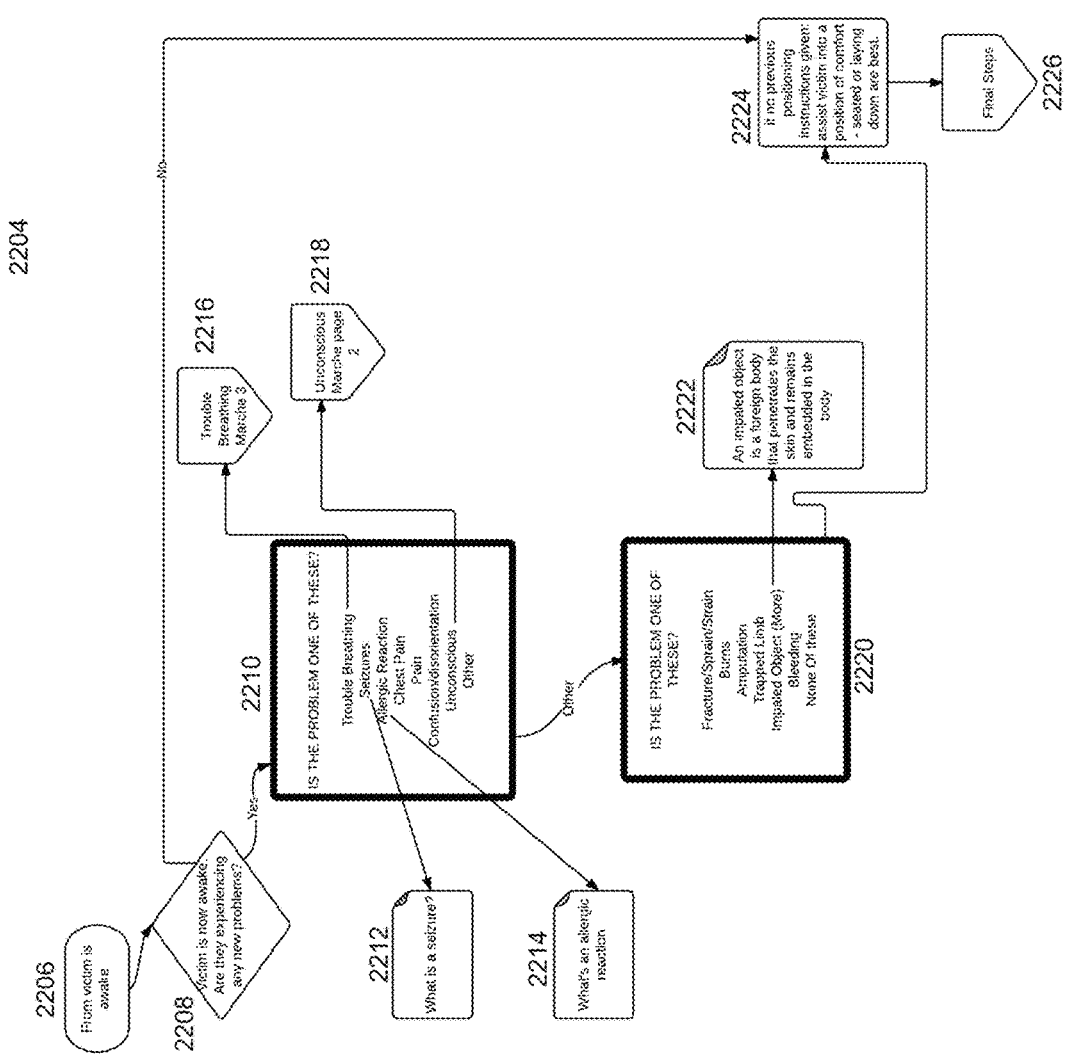
FIG. 61 is a flowchart illustrating an example flow for a victim that awakened from being unconscious, forming part of the triage protocol of FIGS. 2-5.

FIG. 61 illustrates the query flow 2204 for a victim that woke up from being unconscious, which is accessed by the user pressing a "Victim is Awake" button on the GUI at any time. By way of example, the query flow 2204 begins with a link box 2206 from the icon tap, and the flow advances to query box 2208, which asks the user if the victim is experiencing any new problems. If the answer is "Yes", the query flow proceeds to box 2210, which represents a GUI screen that asks the user if the problem is one of: Trouble Breathing, Seizures, Allergic Reaction, Chest Pain, General Pain, Confusion/Disorientation, Unconscious, or Other. For the "Seizure" choice, the represented GUI screen includes a "More Info" icon that, if activated by the user (e.g. by touch or voice) prompts the computer to display a popup information box 2212 that explains a seizure to the user. For the "Allergic Reaction" choice, the represented GUI screen includes a "More Info" icon that, if activated by the user (e.g. by touch or voice) prompts the computer to display a popup information box 2214 that explains an allergic reaction to the user. By way of example, if the user indicates "Trouble Breathing," the computer will direct the query flow to box 140 of the part 3 of the MARCHE protocol (via link box 2216), described above with reference to FIG. 4. If the user indicates "Seizures," the computer will direct the query flow to the Seizures query flow, described above with reference to FIG. 54. If the user indicates "Allergic Reaction," the computer will direct the query flow to the Allergic Reaction query flow, described above with reference to FIG. 55. If the user indicates "Chest Pain," the computer will direct the query flow to the Chest Pain query flow, described above with reference to FIG. 24. If the user indicates "General Pain," the computer will direct the query flow to the General Pain query flow, described above with reference to FIG. 27. If the user indicates "Confusion/Disorientation," the computer will direct the query flow to the Confusion/Disorientation query flow, described above with reference to FIG. 56. If the user indicates "Unconscious," the computer will direct the query flow to box 70 of Part 2 of the MARCHE protocol (via link box 2218), described above with reference to FIG. 3.

If the user indicates "Other" in response to the question displayed by the GUI represented by box 2210, the computer advances the query flow to box 2220, which represents a GUI screen that asks the user if the problem is one of: Fracture/Sprain/Strain, Burns, Amputation, Trapped Limb, Impaled Object, Bleeding, or None of These. For the "Impaled Object" choice, the represented GUI screen includes a "More Info" icon that, if activated by the user (e.g. by touch or voice) prompts the computer to display a popup information box 2222 that explains to the user that an impaled object is a foreign body that penetrates the skin and remains embedded in the body. By way of example, if the user indicates "Fracture/Sprain/Strain," the computer will direct the query flow to the Pain/Fracture (Body Chooser) flow, described above with reference to FIG. 26. If the user indicates "Burns," the computer will direct the query flow to the Burns query flow, described above with reference to FIG. 35. If the user indicates "Amputation," the computer will direct the query flow to the Amputation query flow, described above with reference to FIG. 36. If the user indicates "Trapped Limb," the computer will direct the query flow to the Trapped Limb query flow, described above with reference to FIG. 37. If the user indicates "Impaled Object," the computer will direct the query flow to the Impaled Object query flow, described above with reference to FIG. 38. If the user indicates "Bleeding (mild)," the computer will direct the query flow to the Bleeding (Body Chooser) flow, described above with reference to FIG. 39. If the user indicates "None of These", the computer will advance the query flow to instruction box 2224, which instructs the user to if needed "assist the victim into a position of comfort—seated or laying down are best." From this point the query flow proceeds to link box 2226, which links to the Final Protocol of FIG. 59.

If the user indicates an answer of "No" to the question of box 2208 (e.g. victim is experiencing no new problems, the query flow advances to box 2224 and proceeds as described above.

Figure 62:
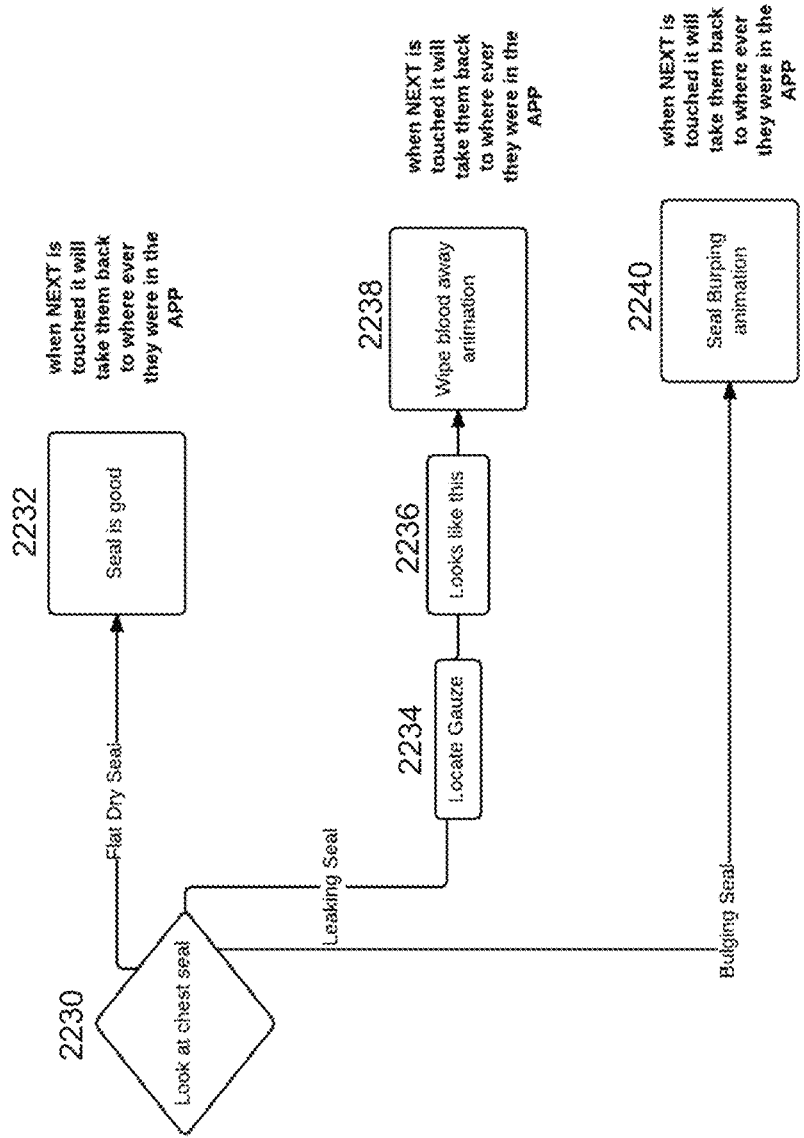
FIG. 62 is a flowchart illustrating an example query flow for chest seal recheck, forming part of the triage protocol of FIGS. 2-5.

FIG. 62 illustrates the query flow for chest seal recheck 2228. One feature of the interactive instructional application disclosed herein is that it includes a built in timer that is automatically activated when certain treatment protocols are needed. For example, if the query flow directs the user to the chest seal treatment protocol (which the user then administers to the victim), the timer is automatically activated. After a certain amount of time, the user is given an audio and visual indication that the timer has run out and it's time to recheck the chest seal.

Figure 117:
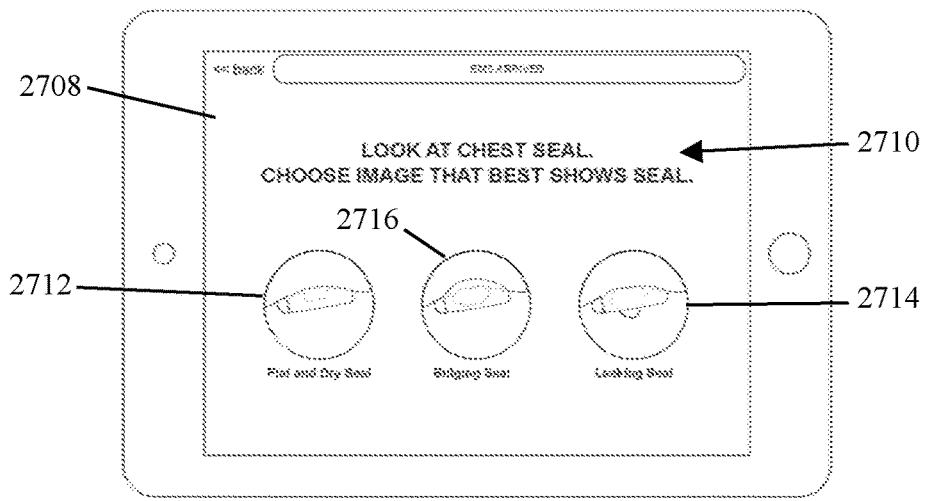

By way of example, when the timer expires, the user is brought to the chest seal recheck flow 2228 from wherever they are in the MOBILIZE app to box 2230, which instructs the user to look at the chest seal and choose the image that best shows the seal: flat dry seal, leaking seal, or bulging seal (See, e.g. FIG. 117). If the user selects "flat dry seal," the computer directs the flow to box 2232, which represents a GUI screen that indicates the seal is good. Then the computer will take the user back to wherever they were in the MOBILIZE app before being brought to the chest seal recheck page. If the user selects "leaking seal", then the query flow proceeds to box 2234, which represents a GUI screen instructing the user to locate normal gauze within the accompanying medical tool kit 12. By way of example, the represented GUI screen may also display a layout image of the tool kit and highlight the location of the normal gauze to remind the user where it is located. The next box 2236 represents a GUI screen that displays a zoomed in image of normal gauze to remind the user what to look for. The next box 2238 in the query flow represents a GUI screen that provides specific instruction on how to wipe away the blood from a leaking chest seal using normal gauze, for example with text instructions, visual aid (e.g. pictures and/or video) and/or audio instructions. When a "continue" icon is tapped, the computer will take the user back to wherever they were in the MOBILIZE app before being brought to the chest seal recheck page. If the user selects "seal burping", then the query flow advances to box 2240, which represents a GUI screen that provides specific instruction on how to alleviate a "burping" chest seal, for example with text instructions, visual aid (e.g. pictures and/or video) and/or audio instructions. When a "continue" icon is tapped, the computer will take the user back to wherever they were in the MOBILIZE app before being brought to the chest seal recheck page.

FIG. 63 illustrates the query flow for a chest pain recheck 2242, which is initiated automatically after the expiration of a five-minute timer that was started due to a victim reporting chest palpitations that would not dissipate. By way of example, the chest pain recheck flow 2242 begins with query box 2244, which represents a GUI screen that asks the user if the victim is still having heart palpitations. If the user indicates an answer of "No", then the computer directs the flow to box 2246, which in turn links the flow back to wherever it was in the app when the chest pain recheck timer expired. If the user indicates a "Yes" answer to the question of box 2244 (e.g., the victim is still experiencing heart palpitations), then the computer advances the flow to box 2248, which represents a GUI screen instructing the user to ask the victim to attempt a forceful cough. After the victim attempts a forceful cough, the computer advances the query flow to box 2250, which represents a GUI screen that asks the user if the palpitations have stopped. If the user indicates a "Yes" answer, then the computer advances the query flow to link box 2252 and links the flow back to wherever it was in the app when the chest pain recheck timer expired. If the user indicates an answer of "No" to the question of box 2250 (e.g. palpitations did not stop), then the query is redirected to box 2248, and the victim is asked to repeat the attempt at a forceful cough. If the user indicates an answer of "No" for a second time to the question of box 2250 (e.g. palpitations did not stop), then the query is redirected to box 2248, and the victim is again asked to repeat the attempt at a forceful cough. If the user indicates an answer of "No" to the question of box 2250 (e.g. palpitations did not stop) for a third time, the computer restarts the five-minute (5:00) timer and directs the query flow to wherever the user was in the app the when the previous chest pain recheck timer expired.

Figure 64:
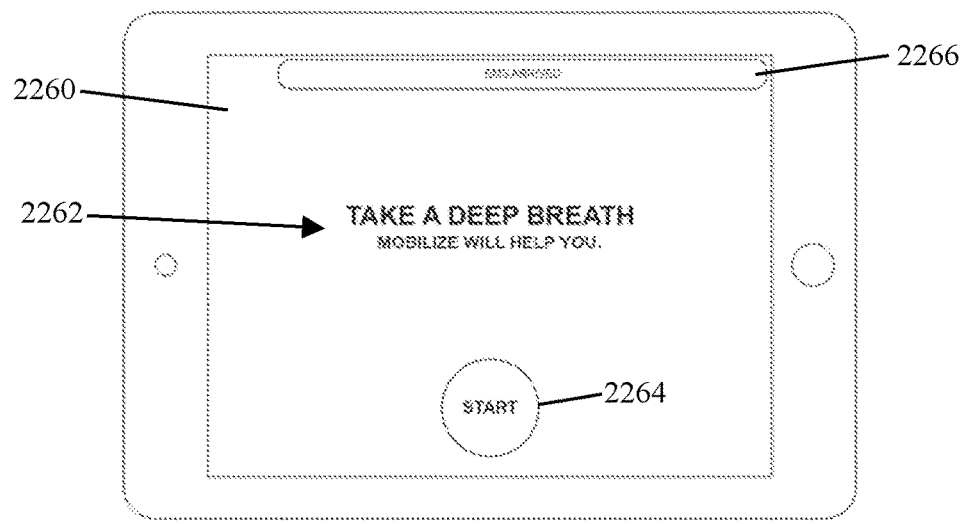
FIGS. 64-119 are representative screen shots depicting one example of a potential user experience.
Figure 119:
Figure 120:
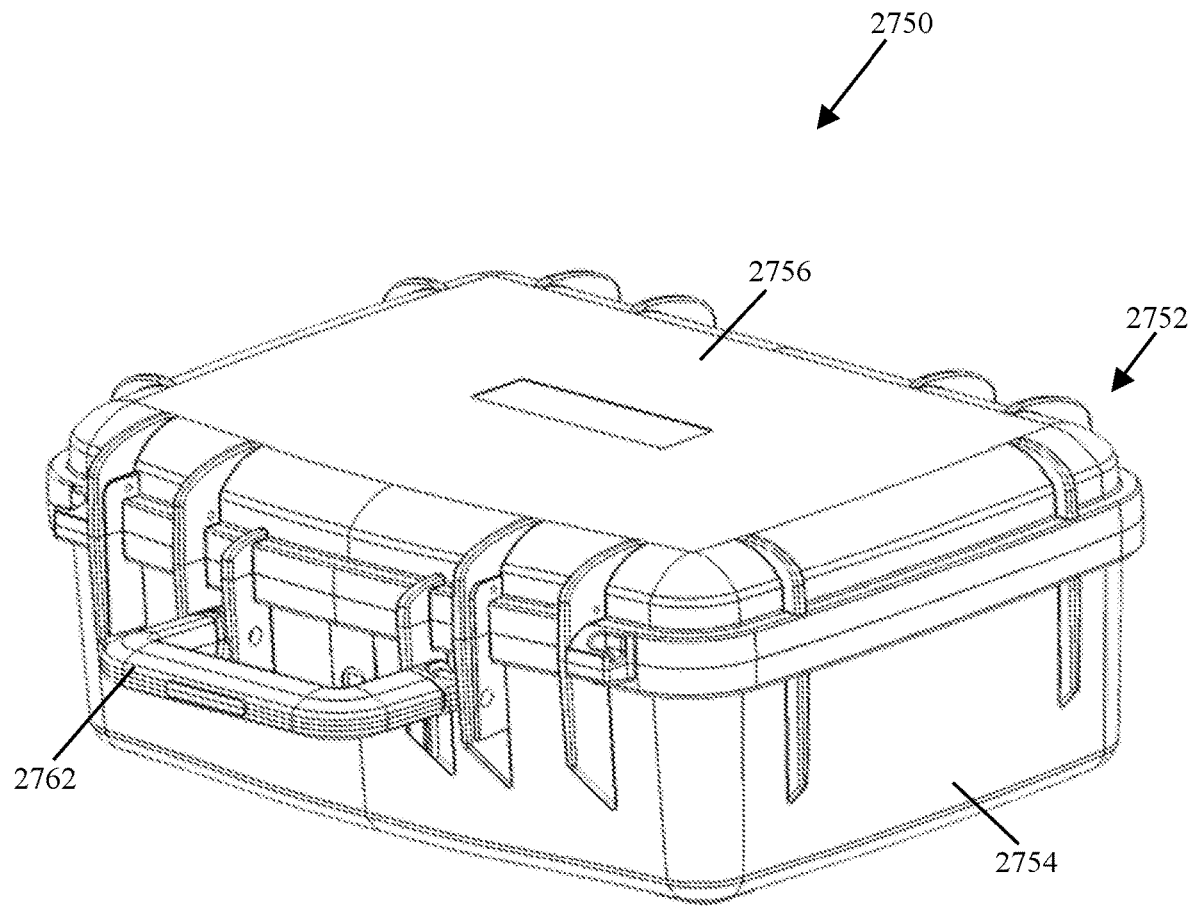
FIGS. 120-121 are perspective views of an example of a portable medical tool kit according to the disclosure shown in the closed and open configurations, respectively.

FIGS. 64-119 illustrate various examples of graphic user interface (GUI) screens that the interactive instructional device 14 may present on a display device to a user using the MOBILIZE app 15 before, during, and after administering an emergency triage protocol. The set of screen shots are shown by way of example only and are not to be construed as a complete set of all screen shots to be viewed during this example experience, but rather is a sampling of at least some of the potential screen shots a user may be lead to during a query flow. FIG. 64 is a graphic representation of the start screen 2260, which corresponds to box 30 of Part 1 of the MARCHE protocol of FIG. 2, and includes a calming message 2262 for the user and a touch-activated (and/or voice-activated) start button 2264, which when touched by the user initiates the MARCHE triage protocol discussed above. Although described herein as touch-activated, many if not all of the choice options/user inputs may also be voice-activated in addition to touch-activated. This ensures that the query flow may continue uninterrupted even if the user's hands are otherwise occupied. Every GUI screen in the app has an "EMS has arrived" button 2266 positioned at the top of the screen, which when tapped by the user alerts the computer that the professional rescuer has arrived. This causes the computer to remind the user to wash their hands, write down contact information, and have the emergency responder review the summary screen.

Figure 65:
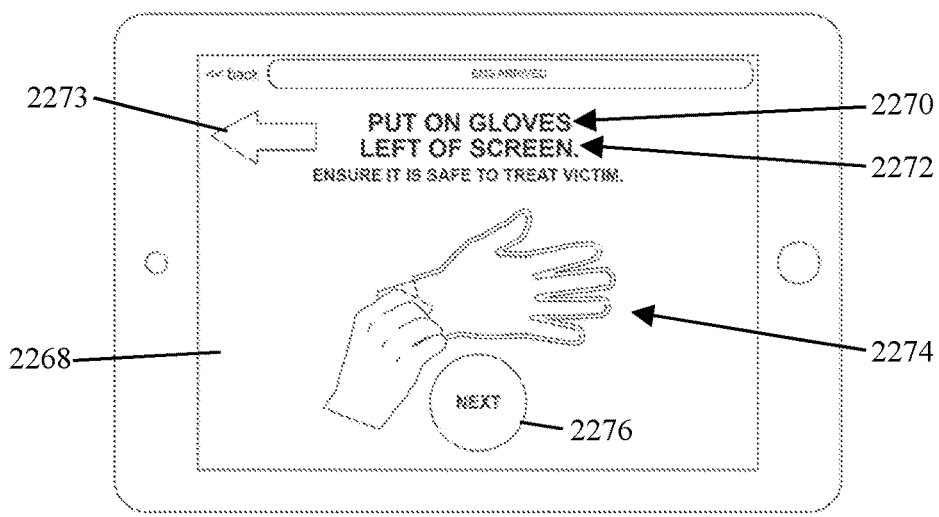

Referring to FIG. 65, starting the triage process in the instant example causes a command screen to appear. The command screen 2268 of the instant example is one example of how the interactive instructional device 14 and medical tool kit 12 interact to create a smooth, efficient, and straight-forward triage process. Specifically, the user is given a command 2270 to use one of the medical supplies provided within the medical tool kit 12. In this case, the user is directed to "put on gloves", in order to minimize cross-contamination between the user and the victim (e.g. box 32 of FIG. 2). One important feature of the triage system 10 however is that the medical supplies 20 are provided in the medical tool kit 12 in a specific identifiable location. Thus, further instruction 2272 as to the specific location of that item within the tool kit 12 is provided to the user. In this instance, "located left of screen" may be sufficient to direct the user to the location of the gloves within the medical tool kit 12. If not, there is a large, flashing arrow 2273 pointing right at the gloves. And since most people know what gloves look like, it is not necessary at this point to provide more instruction. However, because some potential users may be experiencing some degree of shock during the triage process (especially depending on the severity of the emergency situation), the interactive instructional device includes a graphic representation 2274 of a glove being put on hands. Once this task is completed, the user activates the "next" button 2276 (touch or voice) to alert the computer that he/she is ready to continue the query flow.

Figure 66:
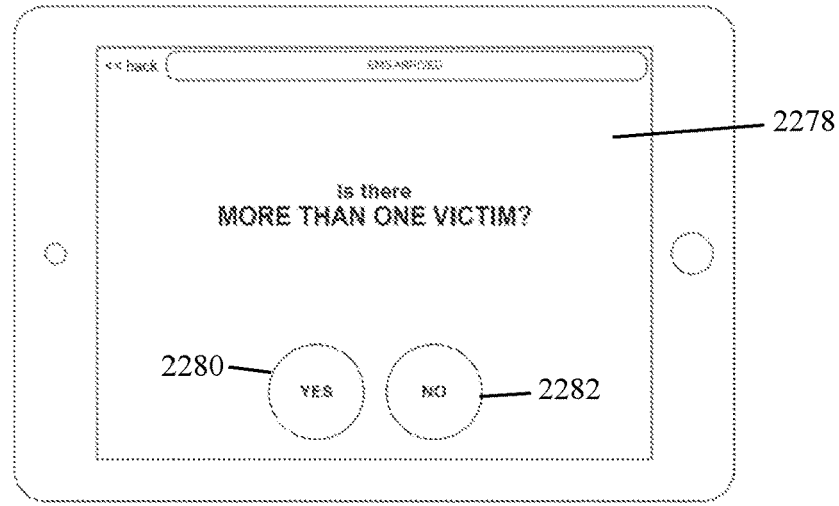

The MOBILIZE app 15 includes numerous screens that ask the user to input certain information that the app stores for later use. For example, FIG. 66 illustrates a GUI screen 2278 presented early on in the query flow (e.g. box 34 of FIG. 2) that asks the user if there is more than one victim present. The screen includes a "Yes" button 2280 and a "No" button" 2282 that the user may select to inform the computer whether there are multiple victims. How many victims there are is not important at this point, and in face asking the user to determine that number might overwhelm them and send them into a panic. By tapping on the "Yes" button 2280, the user alerts the computer to the presence of multiple victims, which enables the computer later on to remind the user to check for other victims after treating the first victim. Pressing the "No" button informs the computer that the user is aware of only one victim. This does not preclude the user from treating multiple victims if more are to be found, as there are several prompts along the way where the app asks the user to determine whether there are other people around in need of assistance.

Figure 67:
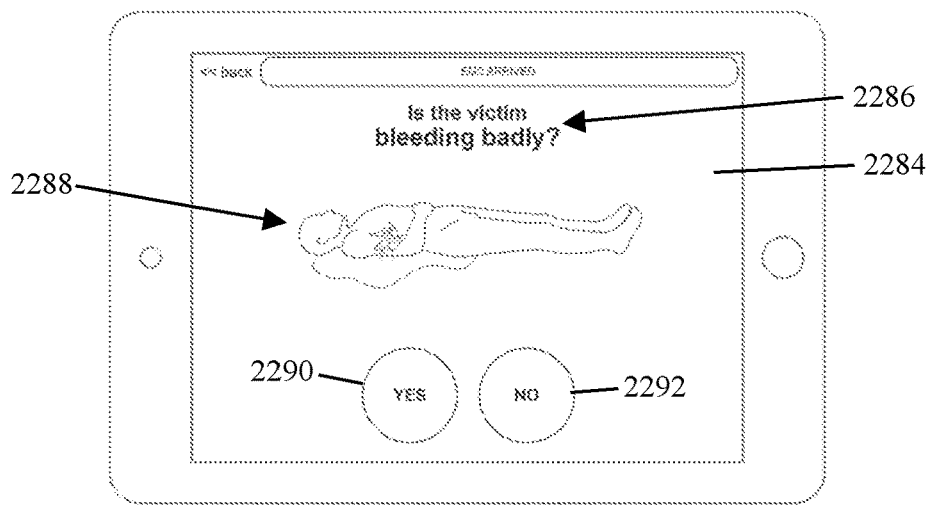

FIG. 67 illustrates the next screen 2284 shown by way of example in the instant query flow, in which the user is asked whether the victim is bleeding badly. This represents a graphic representation of query box 36 of part 1 of the MARCHE protocol discussed above (See. FIG. 2). This screen is representative of the various "Assess Screens" in the app—the GUI screens that the app shows the user when it asks the user to assess the situation. It includes an assessment query 2286 (e.g. "Is the victim bleeding badly?") that informs the app of the situation at hand to enable the app to guide the user through the triage process. These questions are presented to the user in descending order of severity of life threat (starting with bleeding). The screen further includes an illustration 2288 rather than a real image so as to not overwhelm the user (e.g. cartoon blood not as horrifying as real blood). The screen also includes large response buttons to make it easy for the user to activate them. For example, the screen 2284 includes a "Yes" button 2290 and a "No" button 2292. The direction of the query flow is dependent on the answer that the user provides. If the "Yes" button 2290 is activated, the computer is alerted that the victim immediately in front of the user is bleeding badly and is therefore at the biggest risk, and treatment is immediately started. If the user were to press the "No" button 2292, then the computer would have displayed a GUI screen asking the user if anyone else nearby is bleeding badly (e.g. FIG. 77).

Figure 68:
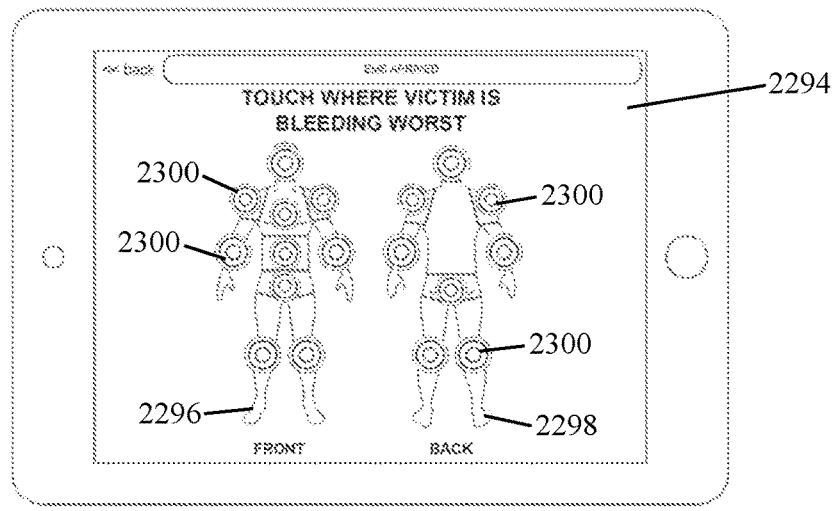

FIG. 68 illustrates an example of a body part target screen 2294 that the MOBILIZE app 15 presents to users to easily inform the app which of the victim's body parts or areas have been injured, hurt, broken, severed, etc. In the instant example, the body part target screen 2294 corresponds to box 38 of FIG. 2, and the computer displayed it in response to the user selecting the "Yes" button 2290 as previously discussed. By way of example only, the body part target screen 2294 shows a graphic representation of a human body front 2296 and human body back 2298 with numerous activation points 2300 distributed thereupon to enable the user to immediately inform the computer where the victim's bleeding is the worst, e.g. by tapping on the activation point located on the affected body part, or optionally by saying the name of the body part. Selection of a specific activation point 2300 causes the query flow to link to the specific treatment protocol for bad bleeding at that body part.

Figure 69:
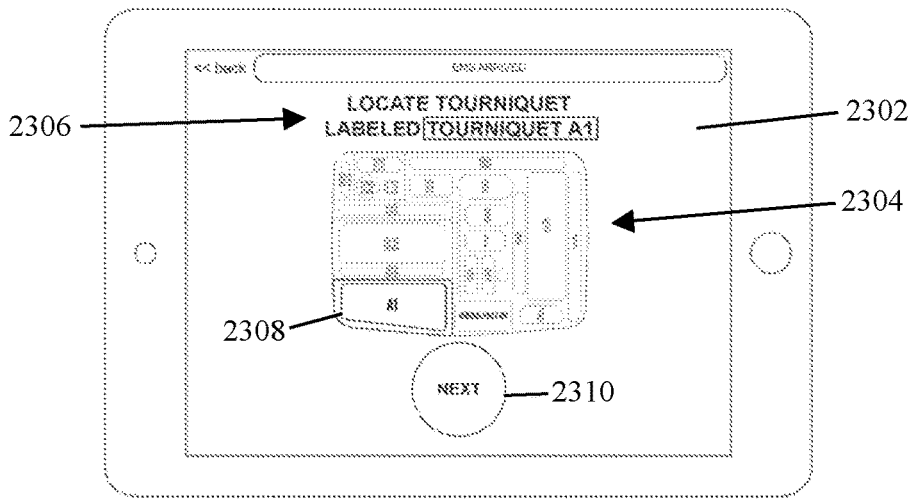

FIGS. 69-73 illustrate several of the important features of the portable triage kit 10 that enable any user under possible duress to successfully treat emergency victims in the field until professional emergency responders can arrive on the scene. In the instant case the user has indicated the location of the bleeding in the previous screen (FIG. 68), and the MOBILIZE app 15 has determined that the proper course of treatment is to apply a tourniquet. As shown in FIG. 69, the application may display a "Locate screen" 2302, which comprises a graphic representation 2304 of the medical tool kit 12, clear instruction on which tool to find 2306 (e.g. "Locate tourniquet") and a highlight 2308 of the exact location of the tourniquet. The products in the tool kit 12 are labeled and color-coded. The product location (e.g. A1 in the instant example) on the display will highlight with the color it is labeled and flash on the display. Thus, even if the user does not know or in their current mental state cannot recall what a tourniquet looks like, they can quickly locate it and remove it from the tool kit.

Figure 70:
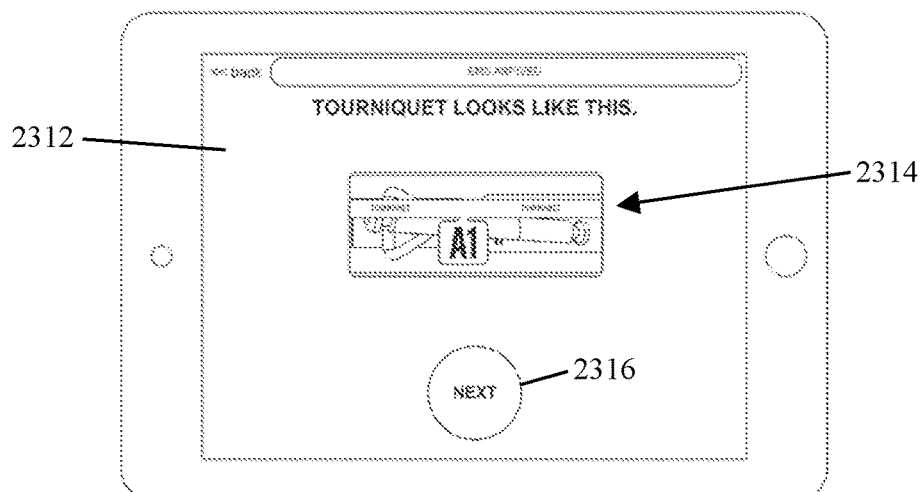

Upon activating the "Next" button 2310, the application presents the user with a "Looks Like" screen 2312, illustrated by way of example in FIG. 70. In general, the "Looks Like" screen 2312 shows the user what the asked-for equipment or item looks like by displaying a picture 2314 of the device and directs the user to confirm they have located the asked-for item (in this case the tourniquet) by pressing on the "Next" button 2316.

Figure 71:
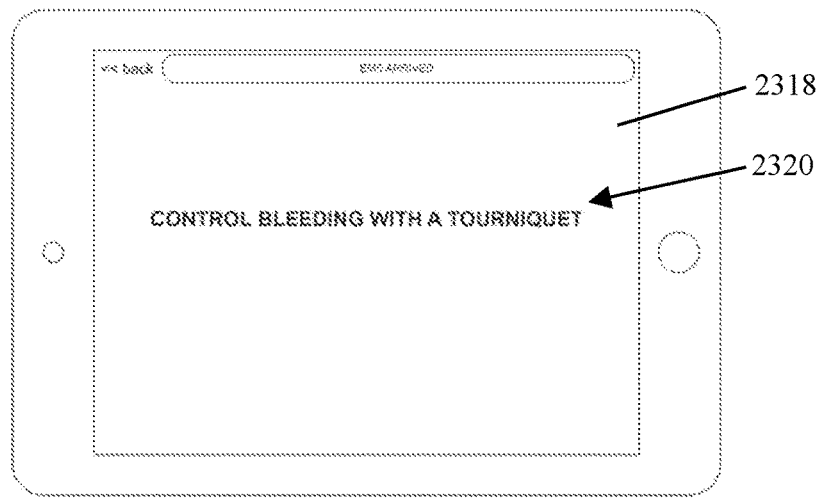

FIG. 71 is an example of a "Black Screen" 2318. Black Screens 2318 are displayed by the computer for a short amount of time (e.g. two or three seconds) before instruction screens. The black screens 2318 have nothing but a message 2320 that gives the user a clear understanding of what they are about to do/perform before the instructions are presented. In the instant example of FIG. 71, the black screen 2318 includes the message 2320 "CONTROL BLEEDING WITH A TOURNIQUET."

Figure 72:
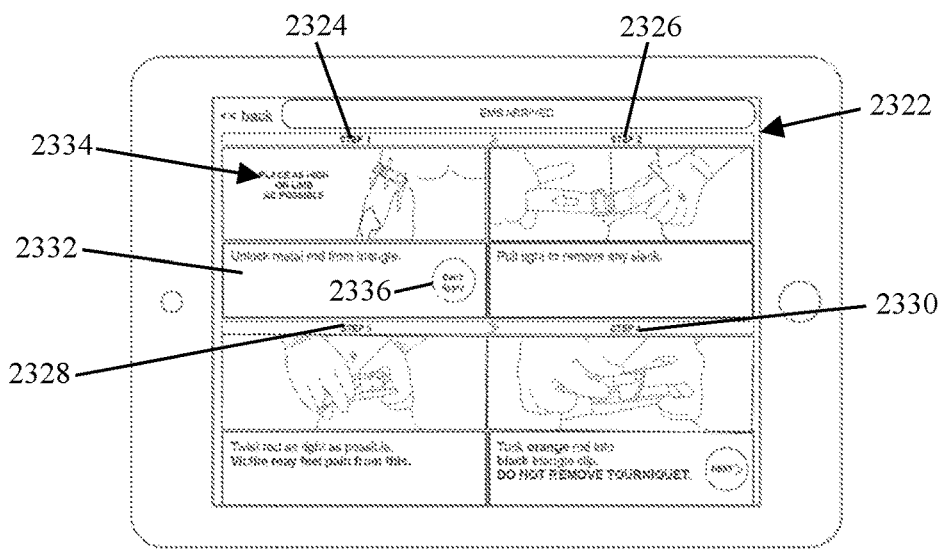

FIG. 72 is an example of an instruction GUI screen 2322 that displays a step-by-step visual (and audio) instruction on how to properly use the equipment, do certain maneuvers, deliver medicine, assist someone, etc. Instruction screens 2322 may include any number of steps. In the instant example, the instruction screen 2322 presented for applying a tourniquet includes four steps clearly labeled with "Step 1" 2324, "Step 2" 2326, "Step 3" 2328, and "Step 4" 2330. Instruction steps may include written instructions 2332, visual demonstration 2334, and/or audio instruction. Visual demonstration 2334 may be in the form of illustration or GIF animation. Interactive radio buttons such as the "Can't Apply" button 2336 appear on instruction screens to troubleshoot the current instruction, take the user to the next logical step, offer additional information, etc.

Figure 73:
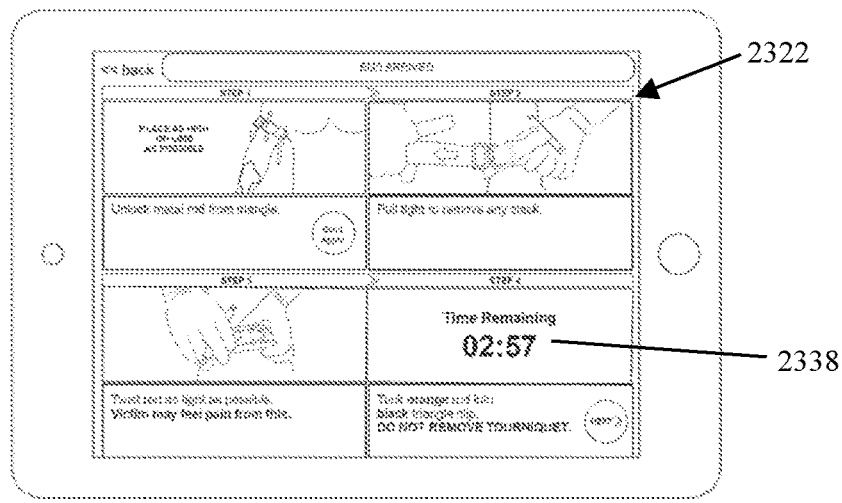

FIG. 73 is an example of an instruction GUI screen 2322 with a timer 2338. Timers 2338 are useful for instructions that include recommended timing for different treatments. For example, "Direct pressure should be held for three minutes . . . ."

Figure 74:
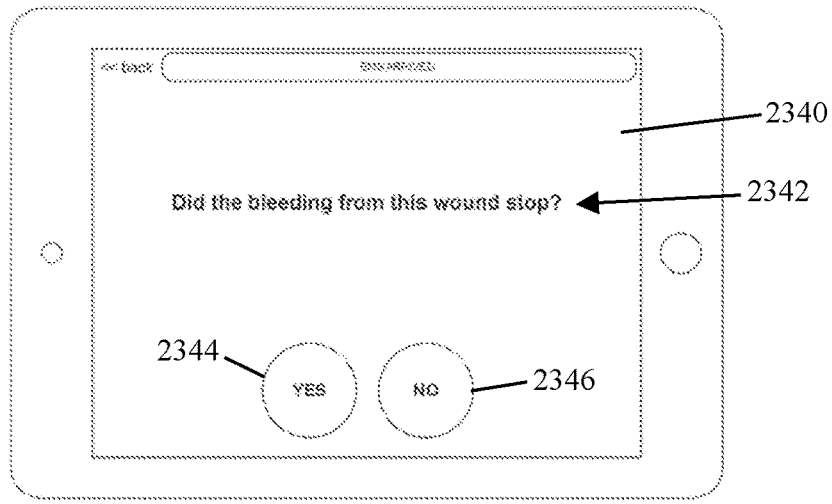

FIG. 74 is an example of a Reassessment GUI screen 2340 according to an aspect of the disclosure. Reassessment screens are presented to the user after the user performs certain tasks, instructions, or product use to make sure that whatever they just did was successful. By way of example, reassessment screens include a question 2342 and at least two response buttons, namely, a "Yes" button 2344 and a "No" button 2346. In the instant example, the reassessment screen presented in FIG. 74 includes the question 2342 "Did the bleeding from this wound stop?" If the user presses the "Yes" button 2344, the query flow would advance to the next step. If the user taps on the "No" button 2346, the computer will direct the user along a path on how to fix something or how to perform the task correctly and ensure the problem is corrected.

Figure 75:
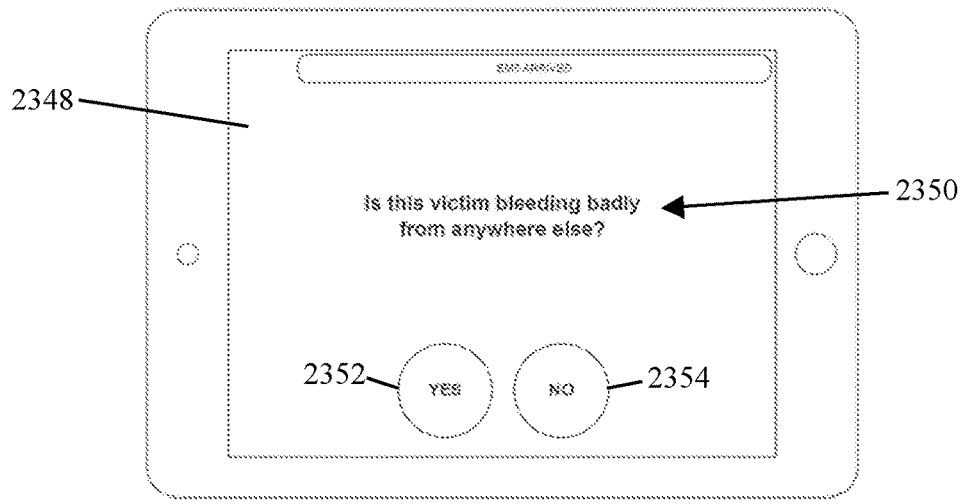

FIG. 75 is an example of a "Confirm no more bleeding" GUI screen 2348 according to one embodiment of the disclosure. The screen 2348 includes a question 2350 (e.g. "Is this victim bleeding badly from anywhere else?") and at least two answer buttons namely, a "Yes" response button 2352 and a "No" response button 2354. If the user taps "Yes" then the app directs them back to the body part target screen 2294 of FIG. 68 so the user can find some more bleeding to fix. If the user tapped "No" then the app will push forward through the queries to other problems with this victim unless another victim nearby has a more life-threatening problem.

Figure 76:
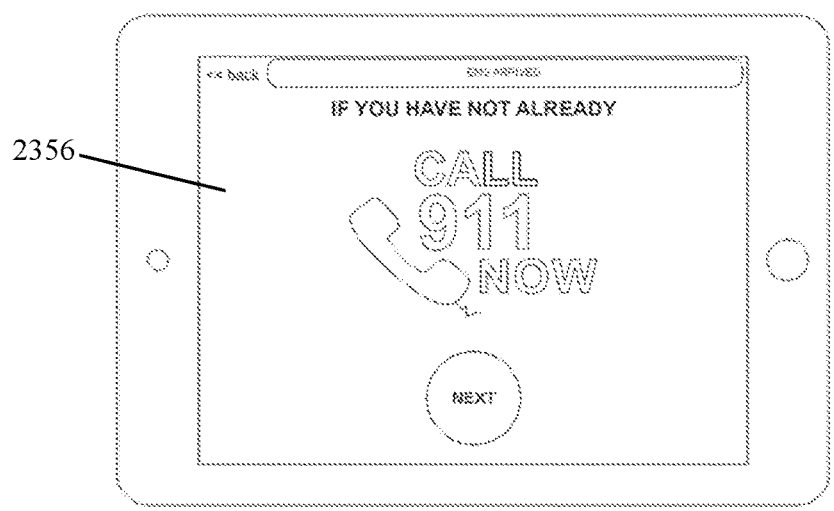

FIG. 76 is an example of a "Call 9-1-1" GUI screen 2356 according to one embodiment. Many of the query flows described above with reference to FIGS. 2-63 at some point include a Call 9-1-1 screen 2356 somewhere therein even though most people would instinctively call 9-1-1 first upon coming to the scene a trauma incident. The reason for the reminder screen is that in some situations (e.g. bad bleeding anything), it may be essential for the first person on the scene to NOT call 9-1-1 immediately but instead, undertake a potentially lifesaving measure in stopping the bleeding. Thus, in some of the flows, the Call 9-1-1 screen is not displayed until the end of the flow.

Figure 77:
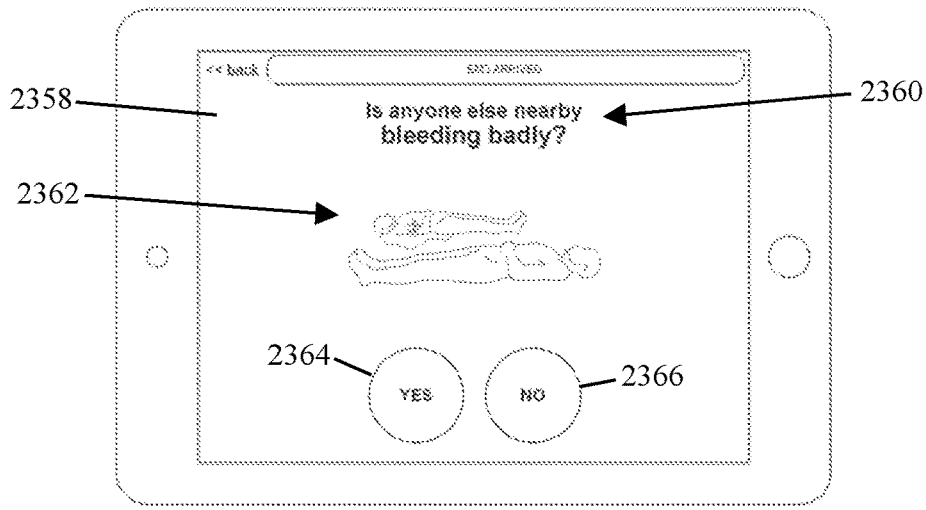

FIG. 77 is an example of an "Anyone else bleeding badly" GUI screen 2358 according to one embodiment. By way of example, the "Anyone else bleeding badly" screen 2358 includes question text 2360, illustration 2362, "Yes" button 2364, and "No" button 2366. Once the user addresses any bleeding of the first victim, it is essential that they take care of any other bleeders in the vicinity. If the user taps the "Yes" button 2364, the app will direct the user to assist that next person. If the user taps the "No" button 2366, the app will direct the user to continue through the query flow for the first victim.

Figure 78:
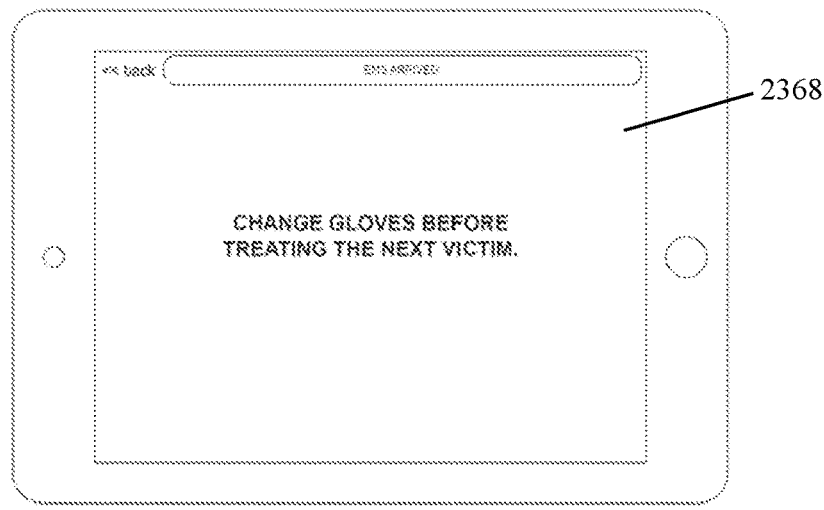
Figure 79:
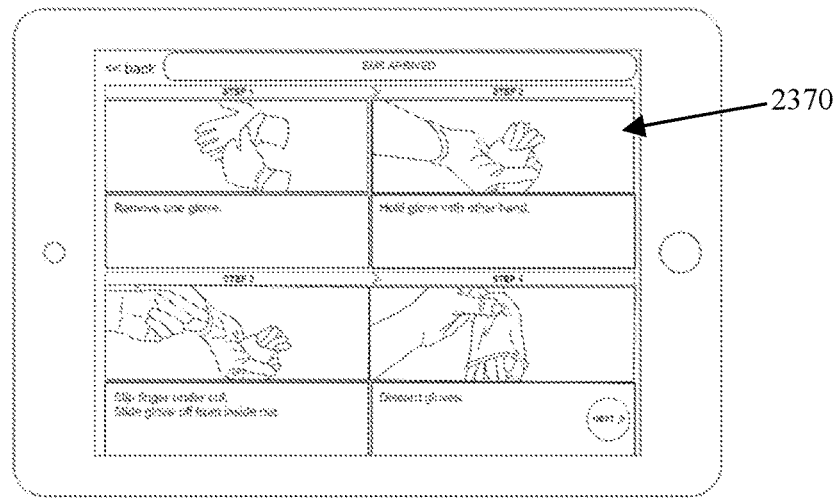
Figure 80:
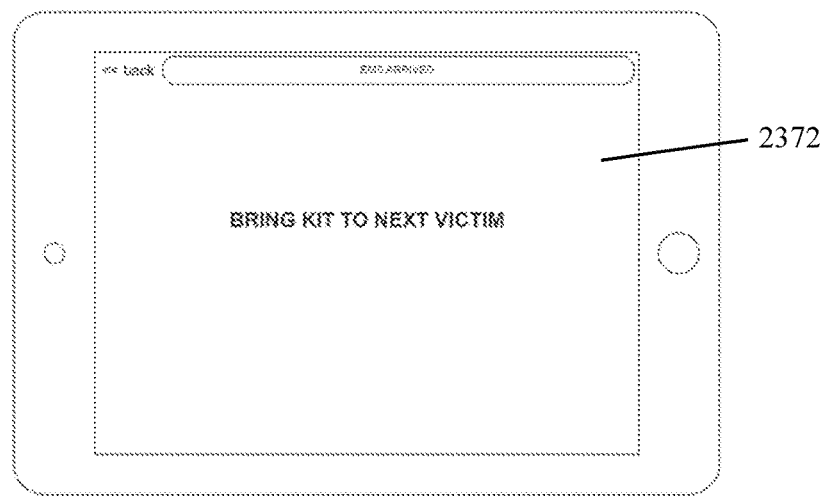

FIGS. 78-81 is an example of a "Change Gloves" GUI sequence (corresponding, for example, to query boxes 58, 60, 62, and 64 of FIG. 2) according to one embodiment of the disclosure. In the case of changing gloves before treating another victim, it is necessary to prevent cross-contamination between victims, especially since multiple bleeding victims all have open wounds. As previously mentioned, black screens appear for two or three seconds before instructions scenes. They are meant to grab the user's attention so they understand the significance of what they are about to do. Thus, FIG. 78 is a "Change Gloves" black screen 2368 to grab the users attention. FIG. 79 is another example of an instruction screen 2370 that gives specific visual (and optionally audio) instruction on how to remove gloves without exposing oneself to contaminants. FIG. 80 is another example of a black screen, for example a "Bring Kit to Next Victim" screen 2372, that alerts the user to go to the next victim.

Figure 81:
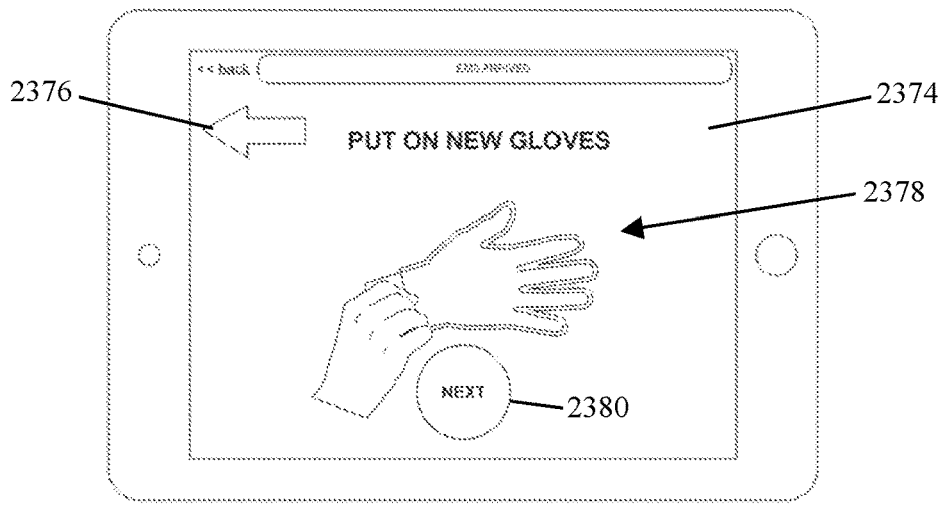

FIG. 81 illustrates an example of a "Put on New Gloves" GUI screen 2374, which completes the changing gloves sequence by having the user put on new gloves. As previously mentioned, one important feature of the triage system 10 is that the medical supplies 20 are provided in the medical tool kit 12 in a specific identifiable location. By way of example the "Put on New Gloves" GUI screen 2374 includes a large, flashing arrow 2376 pointing right at the gloves, a graphic representation 2378 of a glove being put on hands, and a "next" button 2380 that the user activates (via touch or voice) to alert the computer that he/she is ready to continue the query flow.

Figure 82:
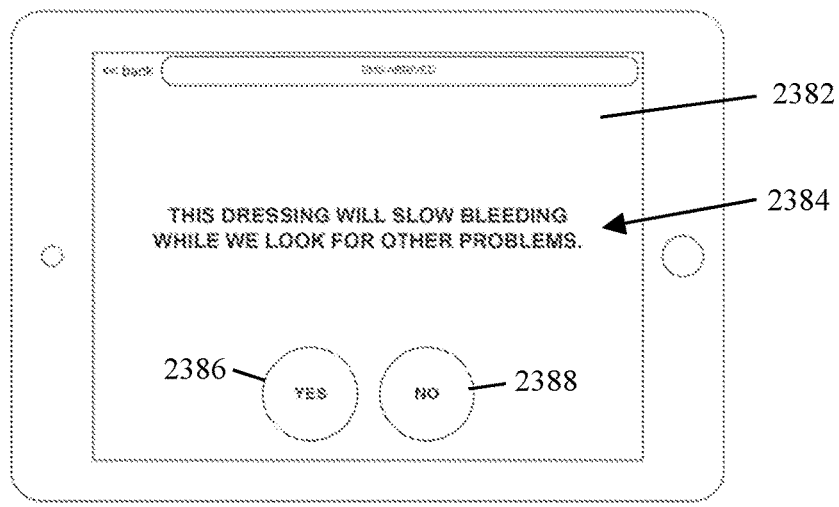

FIG. 82 is an example of a Reassurance screen 2382, which in general lets the user know that what they have done already will help but they need to push forward to figure out if anything else is wrong with this victim, and if there are any other victims. By way of example, the instant reassurance screen 2382 includes a message 2384 (e.g. "This dressing will slow bleeding while we look for other problems," a "Yes" button 2386, a "No" button 2388.

Figure 83:
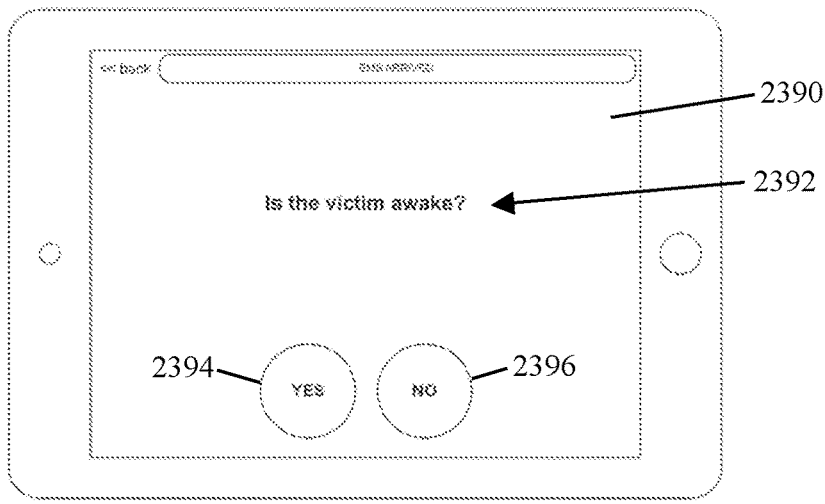

FIG. 83 is an example of a "Victim awake" screen 2390, which appears after the user has either fixed all bleeding issues or there were no bleeding issues (e.g. box 70 of FIG. 3), and includes a question 2392 (e.g. "Is the victim awake?"), a "Yes" button 2394, and a "No" button 2396. If the user taps the "No" button 2396, the computer will direct the flow to the Unconscious victim protocol. If the user taps the "Yes" button 2394, triage will continue with the "Trouble Breathing" screen 2398 shown in FIG. 84 (and corresponding to box 140 of FIG. 4).

Figure 84:
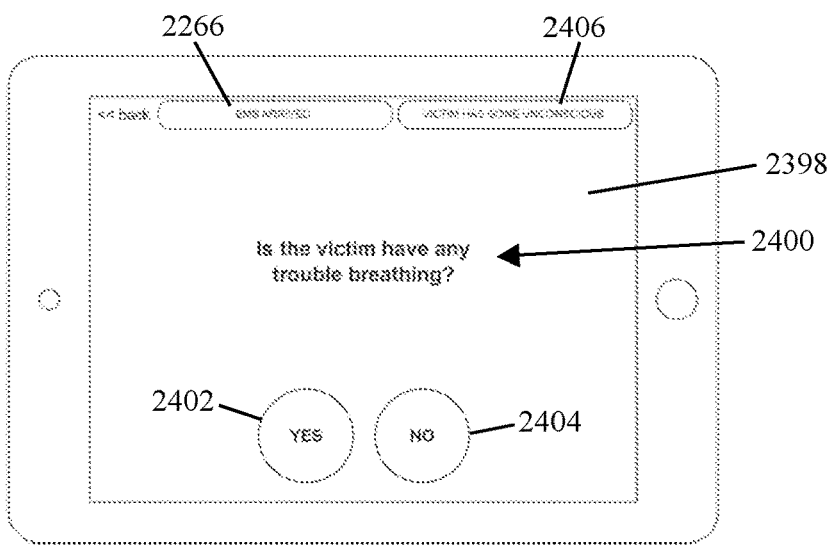

FIG. 84 is an example of a "Trouble Breathing" screen 2398, in which the app ascertains whether the victim is having trouble breathing. By way of example, the Trouble Breathing screen 2398 includes a question 2400 (e.g. "Is the victim having any trouble breathing?"), a "Yes" button 2402, and a "No" button 2404. Notably, because of it's place in the query flow, this screen 2398 and every screen after it will include a "Victim has gone unconscious" button 2406 at the top of the screen next to the "EMS has arrived" button 2266. The "Victim has gone unconscious" button 2406 is significant because no matter what else is happening, if the victim fall into unconsciousness then something is wrong. Tapping the "Victim has gone unconscious" button 2406 will cause the computer to direct the user to the Unconscious Victim protocol (e.g. starting with box 76 of FIG. 3).

Figure 85:
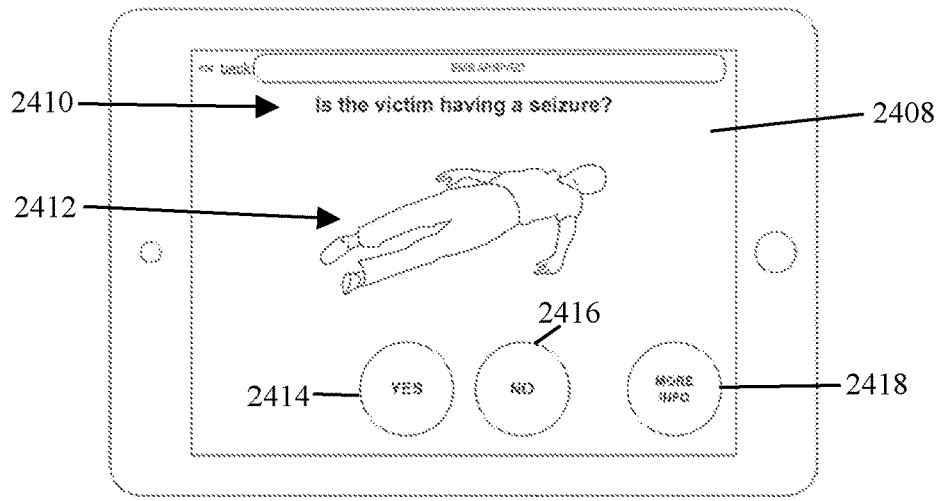
Figure 86:
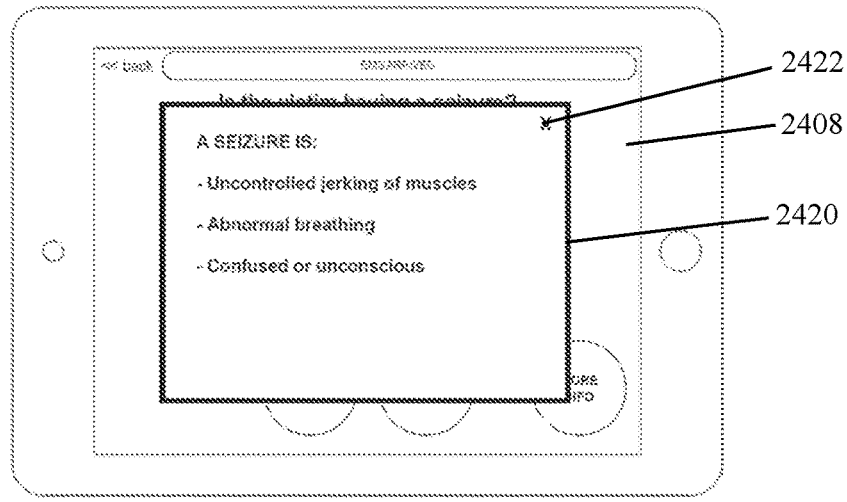

FIG. 85 is an example of a "Seizure" screen 2408 according to one embodiment, and is also an example of an "Image Plus" screen found throughout the app. The "Image Plus" screens ask questions 2410 (e.g. "Is the victim having a seizure?") and include an associated image 2412 to help the user better understand the question and/or the situation unfolding in front of them. Also, in addition to the "Yes" button 2414 (which for example directs the computer to proceed with the seizure protocol) and "No" button (which for example directs the computer to proceed with the exploratory path), the screen includes a "Why/More Info" button 2418. The "Why/More Info" button 2418 helps the user get a better understanding of what they are experiencing. When the user taps on the "Why/More Info" button 2418 a popup information box 2420 appears on the screen, as shown in FIG. 86. The popup information box 2420 will include information about the specific issue, treatment, instructions, etc that will help the user clarify what they are seeing, doing, etc. The popup information box 2420 includes an "X" icon 2422 that, when pressed by the user, closes the popup information box 2420.

Figure 87:
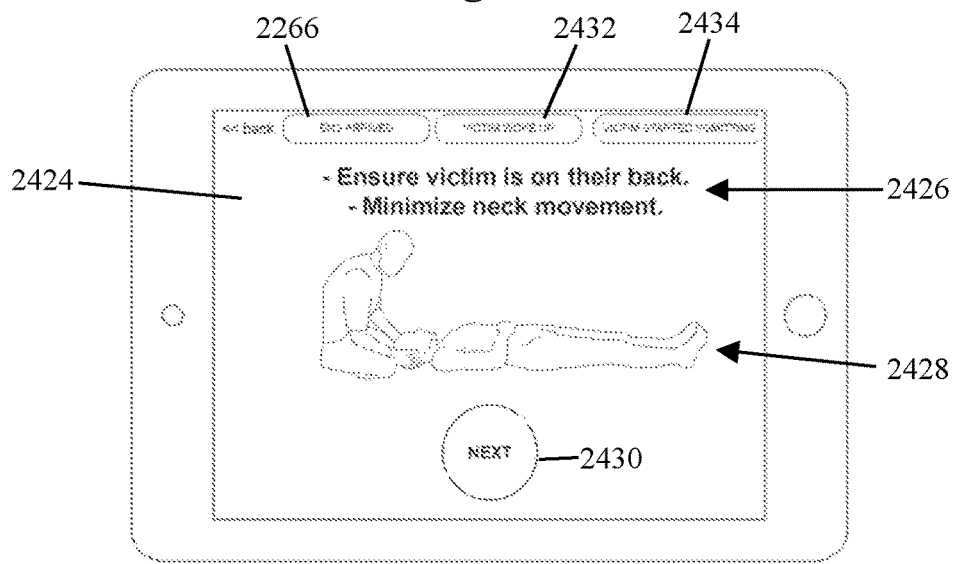

FIG. 87 is an example of a "Neck Injury Positioning screen" 2424 according to one embodiment, and is a broader example of "positioning instruction" screens that appear throughout the app. Positioning instruction screens include text instructions 2426, a demonstrative image 2428, and a "Next" button 2430 that the user presses to inform the app that the victim is positioned as instructed. Also relevant about this screen is that the various buttons on top of the screen may change in response to where the user is in the query flow. As mentioned, some top buttons such as the "EMS has arrived" button 2266 will remain from start to finish ("finish" being defined as the moment a professional responder arrives), while others appear after certain points in the flow. For example, in the Unconscious Victim protocol flow, the screens will include a "Victim woke up" button 2432 and a "Victim started vomiting" button 2434. If the user taps the "Victim woke up" button 2432 the app redirects the flow to a place that steps the user how to treat the victim now that they are awake (See, e.g. FIG. 61). If the user taps the "Victim started vomiting" button 2434, the app redirects to a place in the flow that instructs how to deal with the vomiting but unconscious victim and then returns to the place in the flow that the user was at before the victim started vomiting.

FIG. 88 is an example of a "possible neck injury" screen 2436 according to one embodiment, for example corresponding with (among others) box 82 of FIG. 3. The "possible neck injury screen" 2436 includes text question 2438 (e.g. "Is the problem because of") and then several option buttons for the user to choose, including by way of example "Vehicle accident" button 2440, "Fall" button 2442, "Neck Injury" button 2444, and "None of these" button 2446. The app will remember the user's response because in this case it will affect positioning instructions for this victim throughout the app. In other words, the app will remember the answer from this screen and follow a certain path based on this answer. In the instant case, a vehicle accident, fall, and obvious neck injury are all scenarios in which special care should be taken to keep the victim's neck stable.

FIG. 89 is another example of an instruction screen, for example a pre-CPR "Look, Listen & Feel" screen 2448 that instructs the user how to listen for/determine that the victim is breathing. If the victim is not breathing normally the next screen (not shown) would prompt them through the drug overdose and CPR protocols.

FIG. 90 is an example of an Examine screen, for example "Examine Chest" screen 2450. The examine screens have a question 2452 and an image 2454 which highlights the body part the user should be examining (in this instance, the chest). Also includes a "Yes" button 2456 and "No" button 2458 for navigation within the app.

Figure 91:
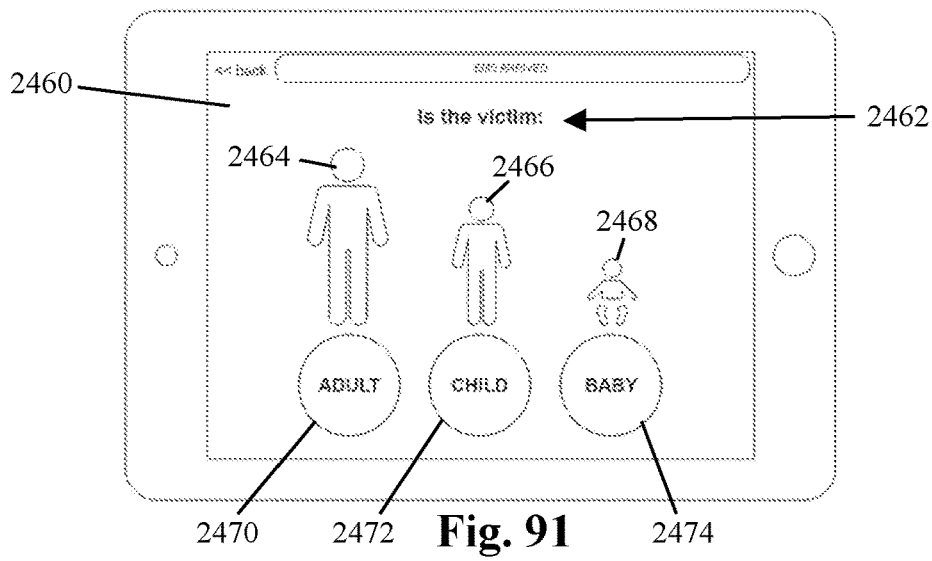

FIG. 91 is an example of a "Victim chooser" screen 2460 according to one embodiment. The "Victim chooser" screen 2460 gives the user the ability to choose the relative age of the victim, which is important for age sensitive treatments (e.g. CPR, medicine dosage, etc). By way of example, the "Victim chooser" screen 2460 includes a question 2462, an adult image 2464, child image, 2466, infant image 2468, adult button 2470, child button 2472, and infant button 2474. Like the "possible neck injury" screen 2436 of FIG. 88, the selection the user makes in this screen will affect the screens that are presented to the user later on in the app flow.

Figure 92:
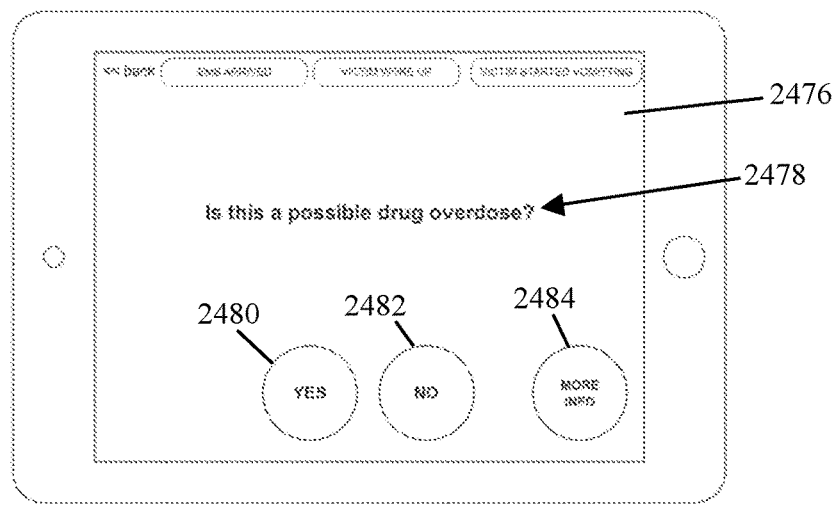

FIG. 92 is an example of a "possible drug overdose" screen 2476. In addition to the text question 2478, "Yes" button 2480, and "No" button 2482, there is a "More info" button 2484 that the user can press to get more information about how to spot a possible drug overdose before answering the question.

Figure 93:
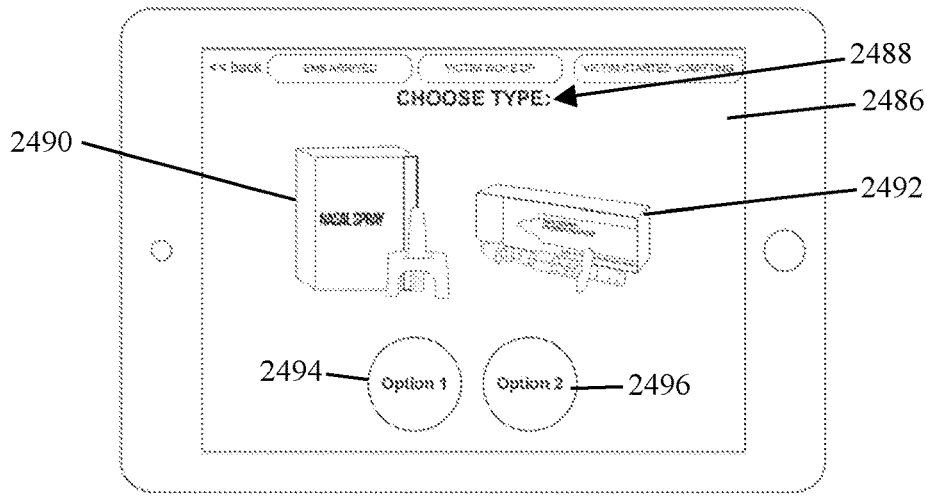

FIG. 93 is an example of a Product Chooser screen, for example a "Naloxone Chooser" screen 2486 that gives the user the ability to choose the type of medication that is available. The product chooser screen includes a text instruction 2488 (e.g. "Choose type"), a first image 2490 of the first type of product, a second image 2492 of the second type of product, an "Option 1" button 2494 under the first image 2490, and an "Option 2" button 2496 under the second image 2492. The user chooses the product by pressing the option button under the image of that product, for example in this case the "Option 1" button 2494 for spray and the "Option 2" button 2496 for injection. The app will present different usage instructions based on the option chosen.

Figure 94:
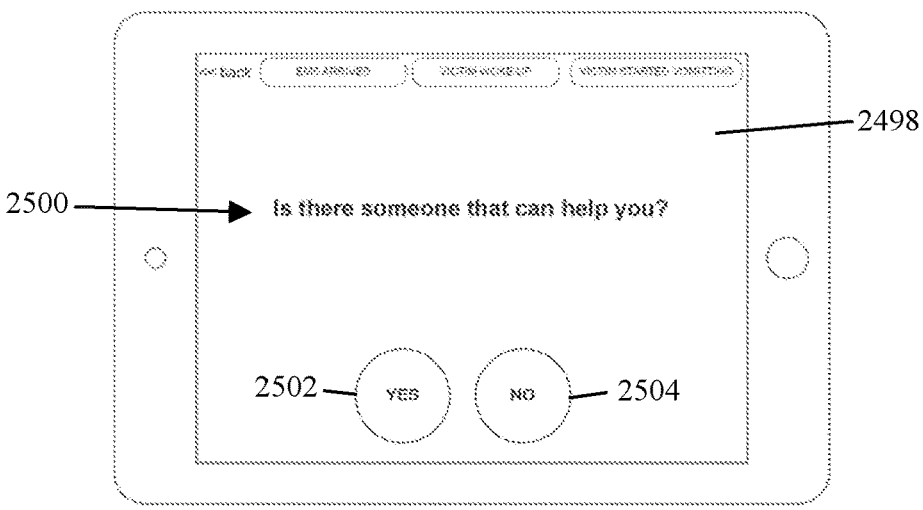

FIG. 94 is an example of a "help available" screen 2498 according to one embodiment. By way of example the "help available" screen 2498 includes a question (e.g. "is there someone that can help you?") 2500, a "Yes" button 2502, and a "No" button 2504. If the user has help (and presses the "Yes" button 2502), then the app will prompt the helper to do certain things in certain tasks (e.g. CPR) to assist the user. If the does not have help (and presses the "No" button), then the app will direct the user to flows enabling the user to manage the problem without help.

Figure 95:
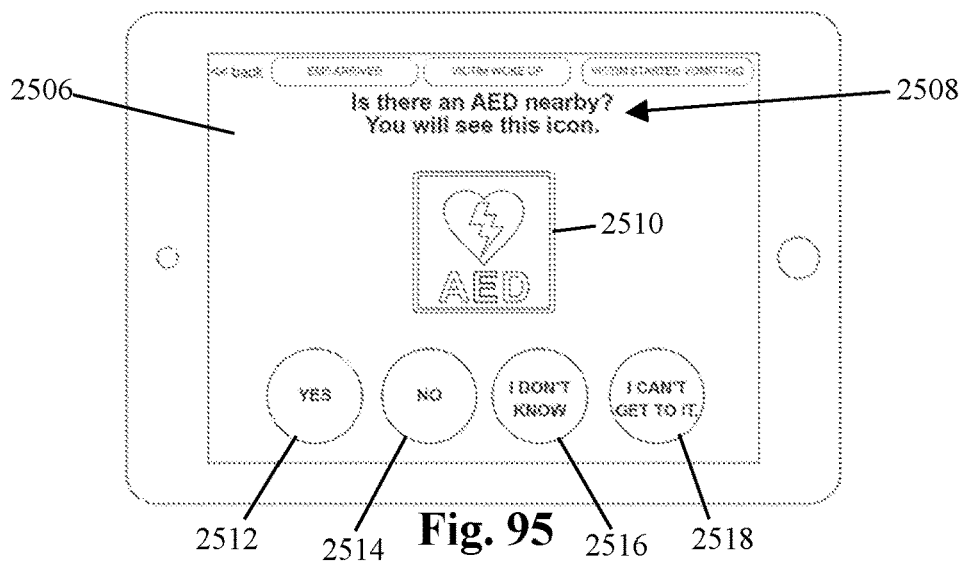

FIG. 95 is an example of "Is there an AED" screen 2506. By way of example, the "Is there an AED" screen 2506 includes a text question/message 2508, logo image 2510, "Yes" button 2512, "No" button 2514, "I don't know" button 2516, and "I can't get to it" button 2518. This screen asks the user, or someone helping the user, if there is an AED nearby. The screen 2506 shows the AED logo image 2510 to give the user/helper a visual clue as to what they are looking for. If there is an AED available (and the user presses the "Yes" button 2512), then the app will instruct the user on how to get the AED, for example have a helper get it if help is available, get it themselves if CPR-trained help is available, or get it themselves if the user does not have help and the AED is not too far away.

Figure 96:
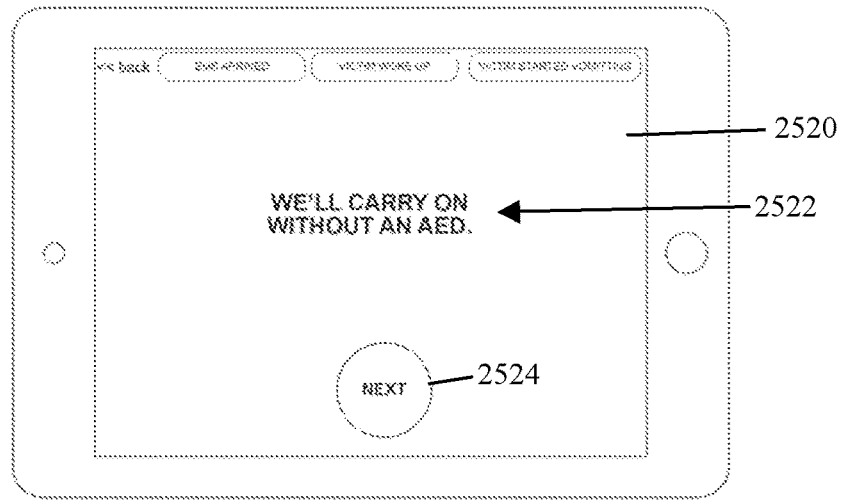

FIG. 96 is an example of a "No AED" screen 2520 and is also another example of a reassurance screen. By way of example, the "No AED" screen 2520 includes a message 2522 (e.g. "We'll carry on without an AED") and a "Next" button 2524. In this instance, the app is telling the user to carry on without an AED because there isn't one available or the user is unsure whether there is one available, and it is important to start CPR as soon as possible.

Figure 97:
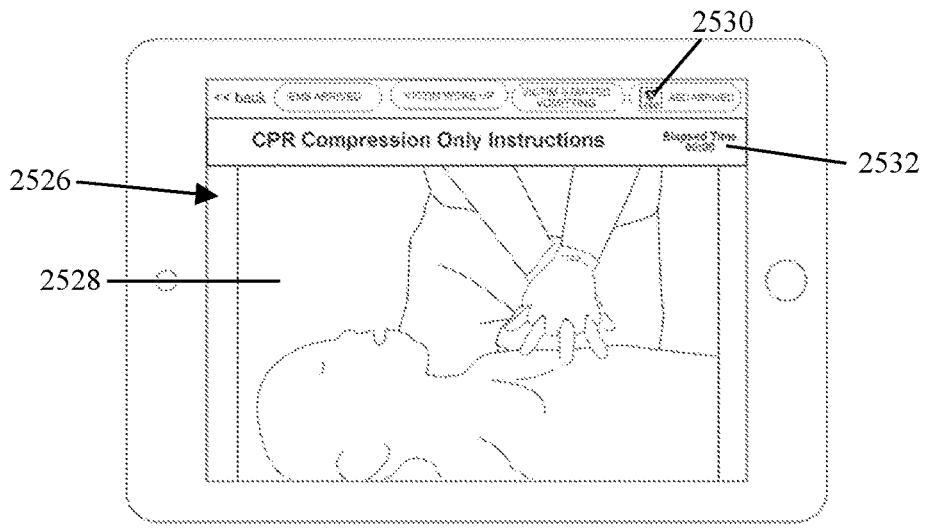

FIG. 97 is an example of a "CPR compression" instruction screen 2526 according to one embodiment (e.g. corresponding to box 908 of FIG. 21). By way of example, the CPR compression screen 2526 may contain a looping CPR animation video 2528, including audio using a metronome beep to keep the user on track (in rhythm) while giving compressions. The animation proceeds at the pace of the metronome beep so the user may strive to match what they see on the screen. There may be an elapsed time timer 2530 on the screen that starts when the user begins CPR so that the user (and professional responder, when arrived) can know how long CPR has been performed on the victim. An "AED has arrived" button 2532 is also present to enable the user to alert the computer that an AED has arrived. The audio is mutable if the user so desires.

Figure 98:
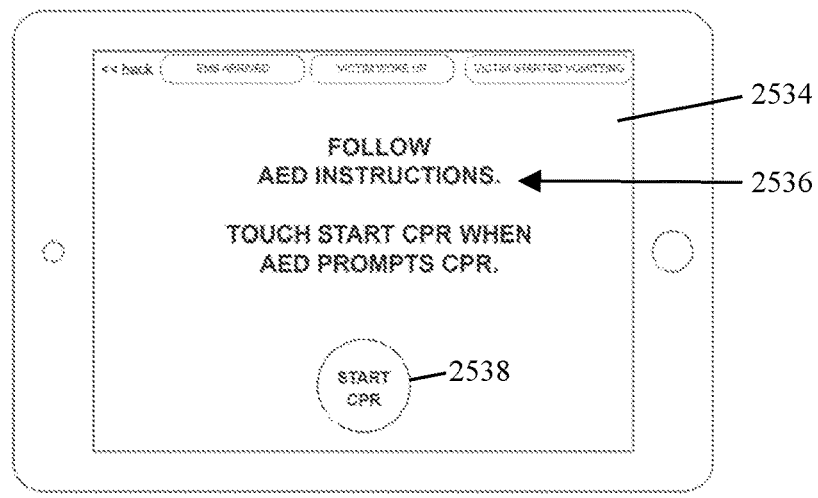

FIG. 98 is an example of an "AED has arrived" screen 2534, which is presented when the user taps on the "AED has arrived" button 2532 of FIG. 97 (for example). Now that an AED is available, the MOBILIZE app will prompt the user to follow the AED instructions (text message 2536) once it is turned on. The instant screen 2534 includes a "Start CPR" button 2538 that the user taps when the AED instructs them to start CPR.

Figure 99:
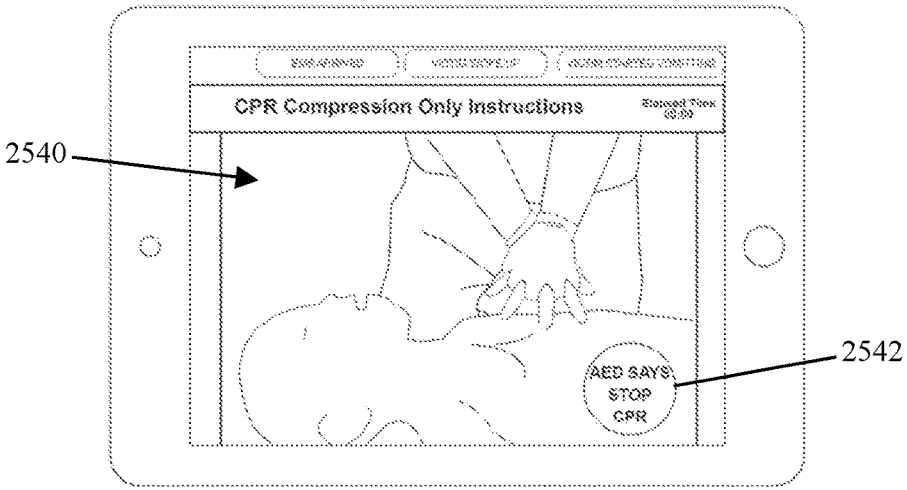
Figure 100:
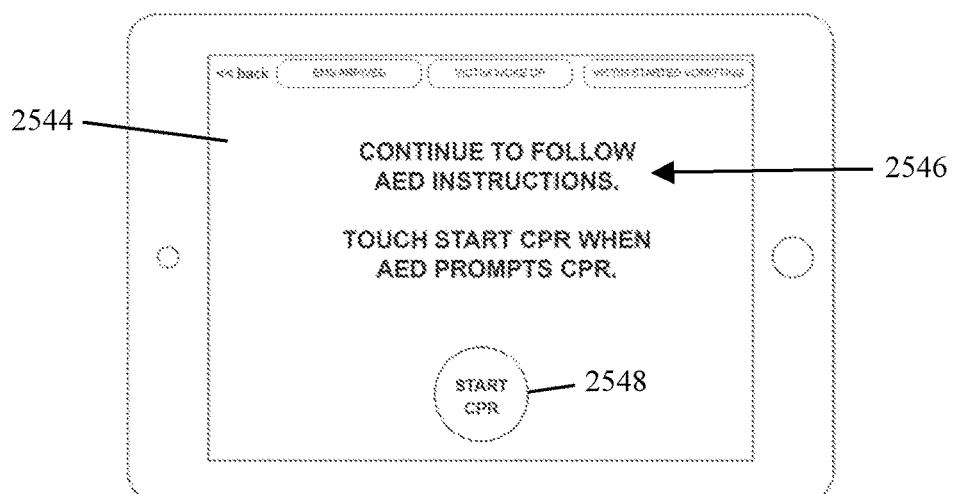

FIG. 99 is an example of a "CPR compression with AED Integration" screen 2540 according to one embodiment. By way of example, the "CPR compression with AED Integration" screen 2540 is like the "CPR compression" instruction screen 2526 of FIG. 97 except that it also includes "AED says Stop CPR" button 2542. When the user presses the "AED says Stop CPR" button 2542, the app presents the "Continue AED Instructions" screen 2544, shown by way of example in FIG. 100. By way of example, the "Continue AED Instructions" screen 2544 includes a text message 2546 and a "Start CPR" button 2548, which the user will press once the AED tells them to continue CPR. The interaction between the MOBILIZE app and the AED will continue until the victim wakes up, EMS arrives, or the AED instructs the user to stop.

Figure 101:
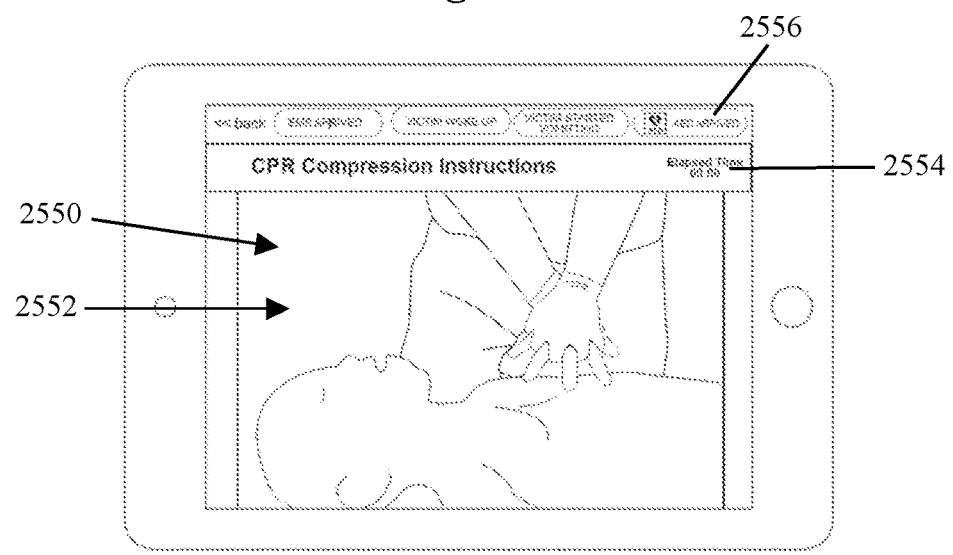
Figure 102:
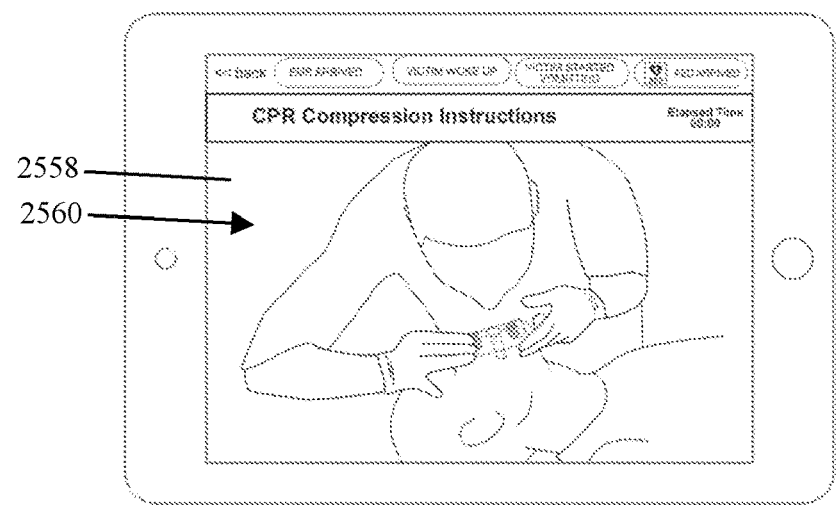

FIG. 101 is an example of a "Child CPR Compression" instruction screen 2550 according to one embodiment. By way of example, the Child CPR compression screen 2550 may contain a CPR animation video 2552, including audio using a metronome beep to keep the user on track (in rhythm) while giving compressions. The animation proceeds at the pace of the metronome beep so the user may strive to match what they see on the screen. There may be an elapsed time timer 2554 on the screen that starts when the user begins CPR so that the user (and professional responder, when arrived) can know how long CPR has been performed on the victim. An "AED has arrived" button 2556 is also present to enable the user to alert the computer that an AED has arrived. The audio is mutable if the user so desires. The animation 2552 proceeds for a set number of compressions (e.g. 30), and then the screen will automatically change to the "Child CPR Breathing" instruction screen 2558 shown by way of example in FIG. 102. By way of example, the "Child CPR Breathing" instruction screen 2558 prompts the user to give two breaths to the victim. The "Child CPR Breathing" instruction screen 2558 includes an animation video 2560, which shows the head of the user/helper (on screen) going down to the mouth of the victim, breaths going into the victim, and the victim's chest rising. The user/helper's head will rise back up and then down again to give another breath. The audio component instructs the user to perform the shown maneuvers and also reminds the user that the victim's chest should rise and fall when giving breaths (e.g. "successful breaths"). The "Child CPR Compression" instruction screen 2550 and "Child CPR Breathing" instruction screen 2558 will continue to alternate until EMS arrives, the victim wakes up, or an AED arrives (in which case the app will prompt the user to follow the AED instructions).

Figure 103:
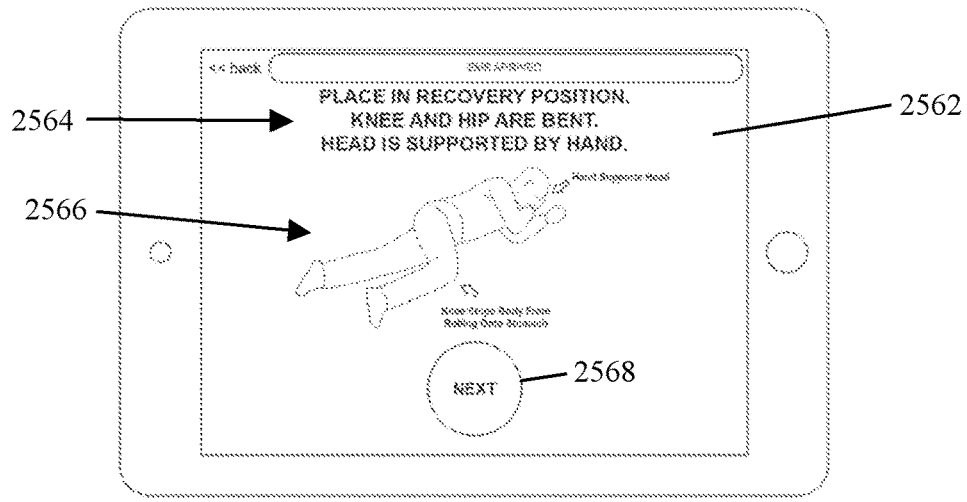

FIG. 103 is another example of a procedural/medical instructional screen, in this case for example a "Recovery Position" screen 2562. By way of example, the "Recovery Position" screen 2562 includes a text instruction 2564, a demonstrative image 2566, and a "Next" button 2568 that the user may press when the victim is positioned as shown by the image 2566.

Figure 104:
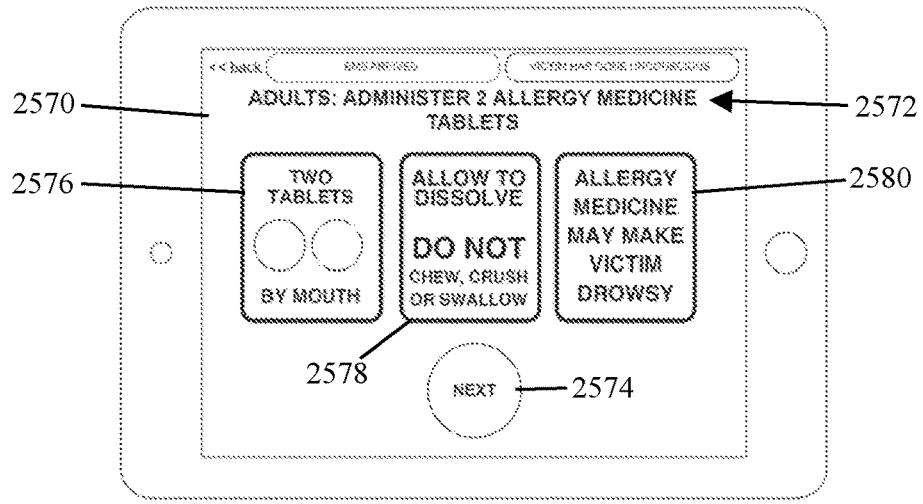

FIG. 104 in an example of an Administer Medicine screen according to one embodiment of the disclosure, for example an "administer allergy medicine" screen 2570. By way of example, the "administer allergy medicine" screen 2570 includes text instructions 2572, a "Next" button 2574, and a series of instruction panels specific to the medication, for example a first panel 2576 instructing on the amount of medicine, a second panel 2578 instructing on how to administer the medication, and a third panel 2580 instructing on warnings/possible side effects of the medication.

Figure 105:
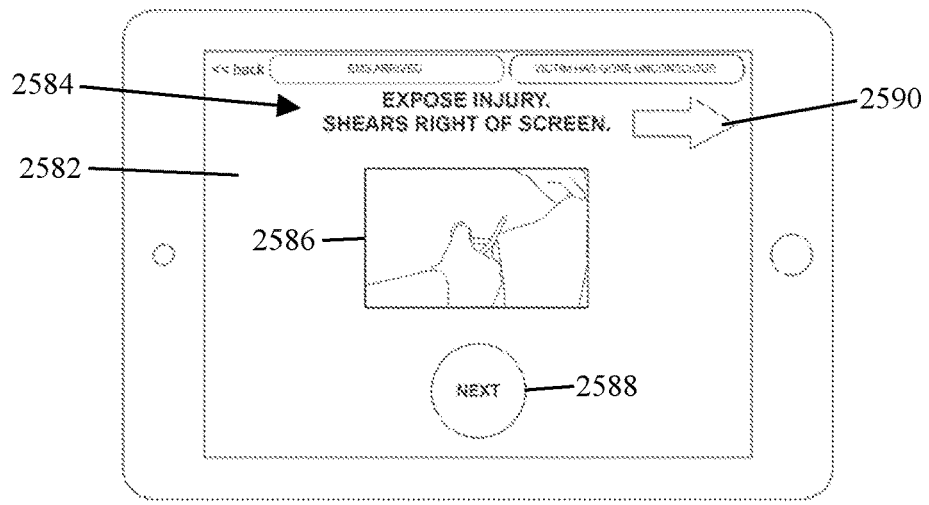

FIG. 105 is an example of an "Expose Injury" screen 2582, which includes (by way of example) a text instruction 2584, demonstrative image 2586, "Next" button 2588, and a blinking arrow 2590 pointing to the location in the medical tool kit 12 in which they will find the required instrument (in this case, shears). The demonstrative image 2586 illustrates how to accomplish what the user is instructed to do.

Figure 106:
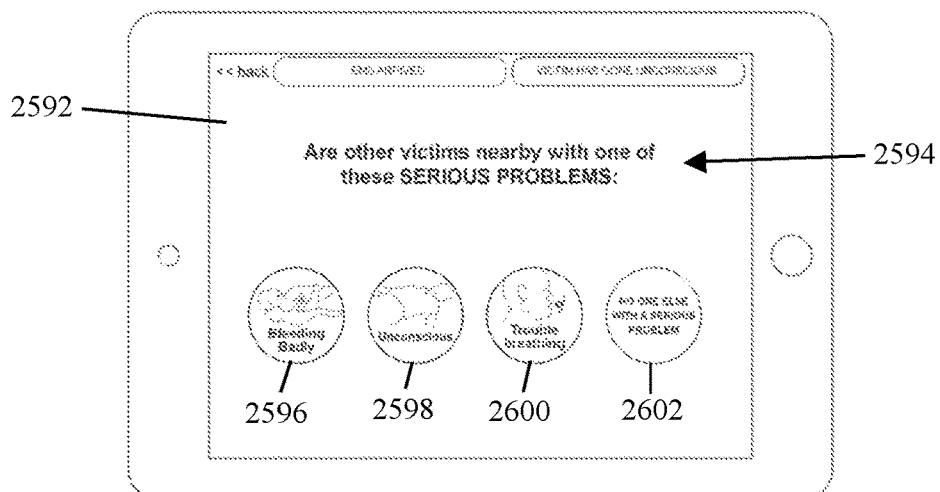

FIG. 106 is an example of an "Other Victims with Serious Problems" screen 2592 according to one embodiment. By way of example, the "Other Victims with Serious Problems" screen 2592 includes a text message 2594 and option buttons representing the three major life threats, for example a "Bleeding Badly" button 2596, an "Unconscious" button 2598, a "Trouble Breathing" button 2600, and a "No One Else Has a Serious Problem" button 2602. As previously mentioned, before moving on in treating less severe problems with a single victim, the user should find victims nearby with immediate life threats. If the user selects one of the life threat buttons, then the computer will direct to the appropriate query flow and present the user with the appropriate GUI screens to manage that life threat. For example, the "Bleeding Badly" button 2596 prompts the computer to shift to the Bad Bleeding protocol (e.g. box 38 of FIG. 2), the "Unconscious" button 2598 prompts the computer to shift to the Unconscious Victim protocol (e.g. box 70 of FIG. 3), and the "Trouble Breathing" button 2600 prompts the computer to shift to the Trouble Breathing protocol (e.g. box 140 of FIG. 4). Pressing the "No One Else Has a Serious Problem" button 2602 prompts the computer to continue the triage protocol for the current victim.

Figure 107:
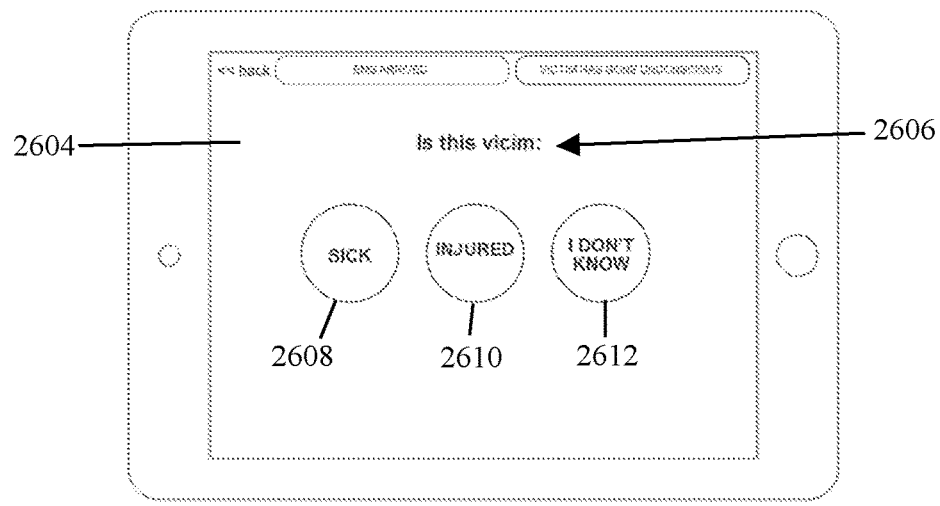

FIG. 107 is another example of an Assess screen, this time for less serious problems. By way of example, the assess screen 2604 of the current example includes a text message/question 2606 (e.g. "Is the victim:") and a number of option buttons (three, in this case). In this example, the option buttons are "Sick" 2608, "Injured" 2610, and "I don't know" 2612. This screen 2604 may be presented after all the major life threats have been treated or ruled out. If the user indicates the victim is sick (e.g. by pressing "Sick" button 2608 or giving a vocal command) then the app will present a screen with medical emergencies for sick people (See, e.g. box 242 of FIG. 5 and screen 2614 of FIG. 108). If the user indicates the victim is injured (e.g. by pressing "Injured" button 2610 or giving a vocal command) then the app will present a screen with medical emergencies for injured people (See, e.g. box 238 of FIG. 5 and screen 2638 of FIG. 109). If the user selects "I don't know" 2612, the app will prompt the user through both options to find out what is wrong.

Figure 108:
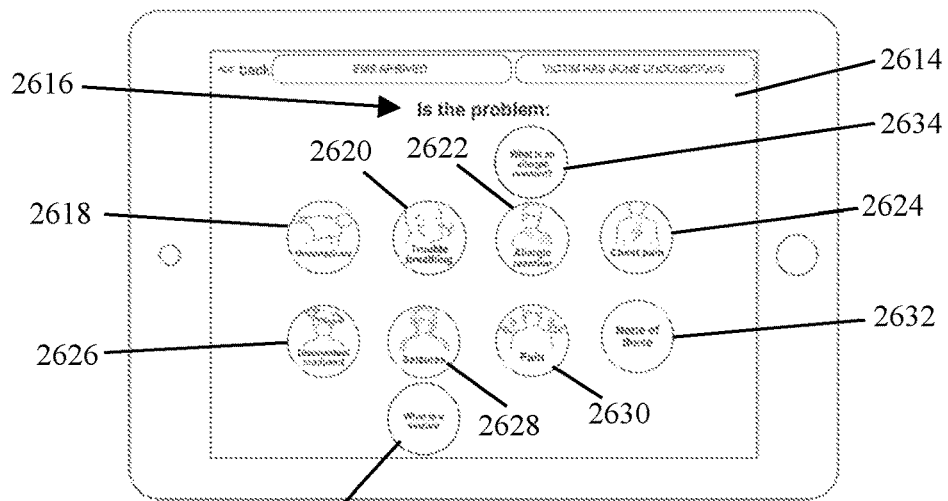

FIG. 108 is an example of a "Medical Emergencies—Sick" screen 2614 according to one embodiment. By way of example, the "Medical Emergencies—Sick" screen 2614 includes a text message/question 2616 (e.g. "Is the problem:") an "Unconscious" button 2618, "Trouble Breathing" button 2620, "Allergic Reaction" button 2622, "Chest Pain" button 2624, "Disoriented/Confused" button 2626, "Seizures" button 2628, "Pain" button 2630, and "None of These" button 2632. The screen also includes a "Why/More Info" button 2634 for the "Allergic Reaction" choice and a "Why/More Info" button 2636 for the "Seizure" choice. By way of example, if the user presses the "Unconscious" button 2618, the computer will direct the query flow to Part 2 of the MARCHE protocol (e.g. FIG. 3). If the user presses the "Trouble Breathing" button 2620, the computer will direct the query flow to box 140 of part 3 of the MARCHE protocol (e.g. FIG. 4). If the user presses the "Allergic Reaction" button 2622, the computer will direct the query flow to the Allergic Reaction protocol (e.g. FIG. 55). If the user presses the "Chest Pain" button 2624, the computer will direct the query flow to the Chest Pain protocol (e.g. FIG. 24). If the user presses the "Disoriented/Confused" button 2626, the computer will direct the query flow to the Confusion/Disorientation protocol (e.g. FIG. 56). If the user presses the "Seizures" button 2628, the computer will direct the query flow to the Seizures protocol (e.g. FIG. 54). If the user presses the "Pain" button 2630, the computer will direct the query flow to the General Pain protocol (e.g. FIG. 27). If the user presses the "None of These" button 2632, the computer will present the next screen with more options. Pressing the "Why/More Info" button 2634 for the "Allergic Reaction" choice prompts the computer to display a popup information box that explains allergic reaction to the user. Pressing the "Why/More Info" button 2636 for the "Seizure" choice prompts the computer to display a popup information box that explains a seizure to the user.

Figure 109:
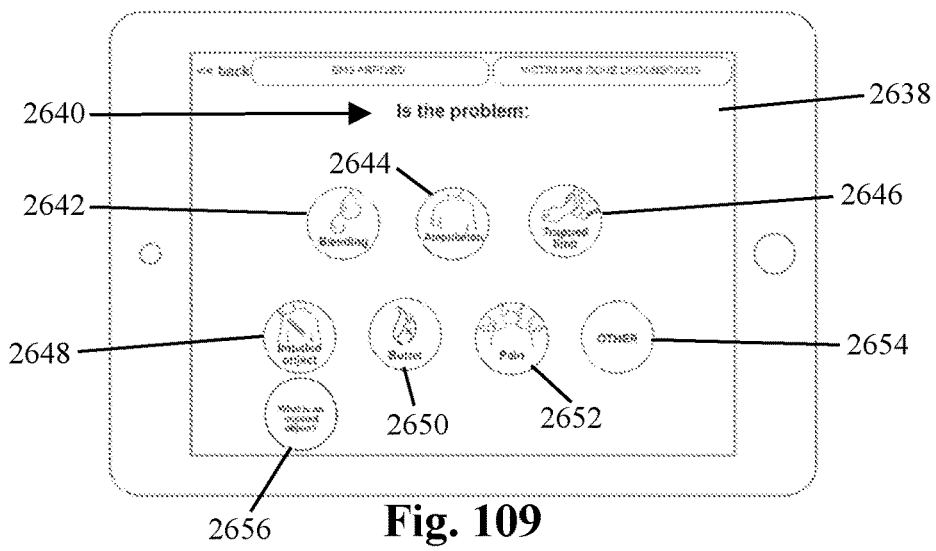

FIG. 109 is an example of a "Medical Emergencies—Injured" screen 2638 according to one embodiment. By way of example, the "Medical Emergencies—Sick" screen 2638 includes a text message/question 2640 (e.g. "Is the problem:") a "Bleeding" button 2642, "Amputation" button 2644, "Trapped Limbs" button 2646, "Impaled Object" button 2648, "Burns" button 2650, "Pain" button 2652, and "Other" button 2654. The screen also includes a "Why/More Info" button 2656 for the "Impaled Object" choice. By way of example, if the user presses the "Bleeding" button 2642, the computer will direct the query flow to the Bleeding (Body Chooser) flow (e.g. FIG. 39). If the user presses the "Amputation" button 2644, the computer will direct the query flow to the Amputation query flow (e.g. FIG. 36). If the user presses the "Trapped Limb" button 2646, the computer will direct the query flow to the Trapped Limb query flow (e.g. FIG. 37). If the user presses the "Impaled Object" button 2648, the computer will direct the query flow to the Impaled Object query flow (e.g. FIG. 38). If the user presses the "Burns" button 2650, the computer will direct the query flow to the Burns query flow (FIG. 35). If the user presses the "Pain" button 2652, the computer will direct the query flow to the General Pain protocol (e.g. FIG. 27). If the user presses the "Why/More Info" button 2656 for the "Impaled Object" choice, the computer displays a popup information box that explains to the user that an impaled object is a foreign body that penetrates the skin and remains embedded in the body.

Figure 110:
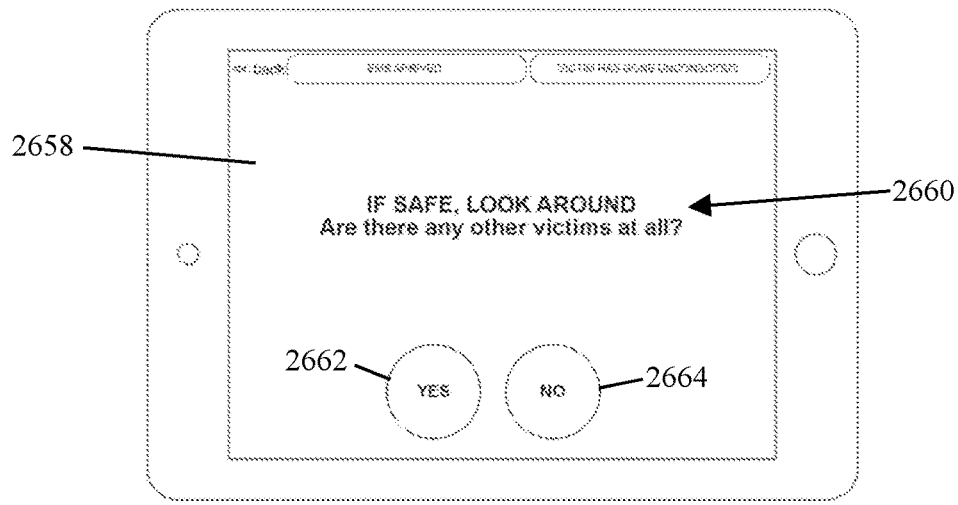

FIG. 110 is an example of a "Find all victims" GUI screen 2658 according to one embodiment. By way of example, the "Find all victims" GUI screen 2658 includes a text message/question 2660 (e.g. "If safe, look around. Are there any other victims at all?"), a "Yes" button 2662, and a "No" button 2664. This is another example of a reminder screen in which the app reminds the user to make sure there are no other victims before finishing up.

Figure 111:
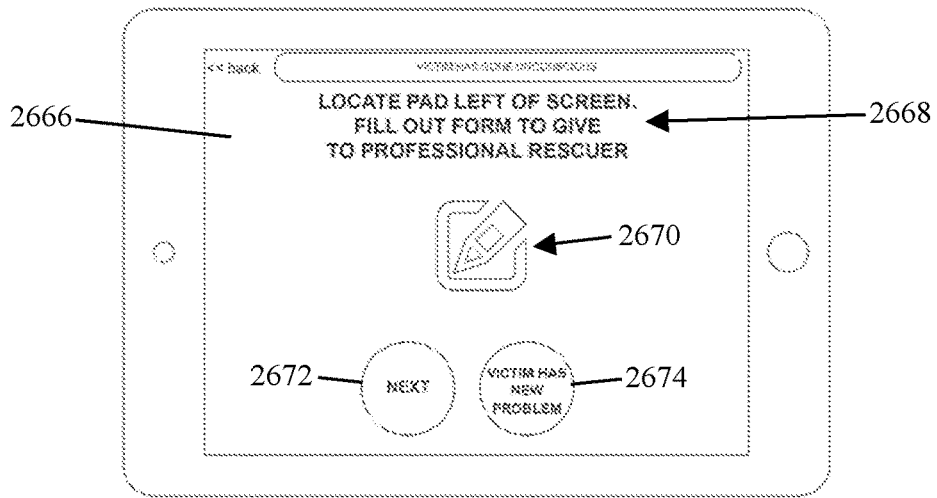

FIG. 111 is an example of a "Fill out" screen 2666 that is part of the Final Protocol (e.g. FIG. 59). This screen has a text message 2668 that prompts the user to locate the pad and fill out a form to give to the EMS/professional rescuer upon arrival. Image 2670 indicates to the user to put pen to paper. There is also a "Next" button 2672 that the user presses when finished and a "Victim Has a New Problem" button 2674 that appears on all the screens in the Final protocol in case the user notices something else is wrong with the victim. Pressing the "Victim Has a New Problem" button 2674 button prompts the user to put on new gloves and then presents the medial emergency screens (e.g. FIGS. 108, 109).

Figure 112:
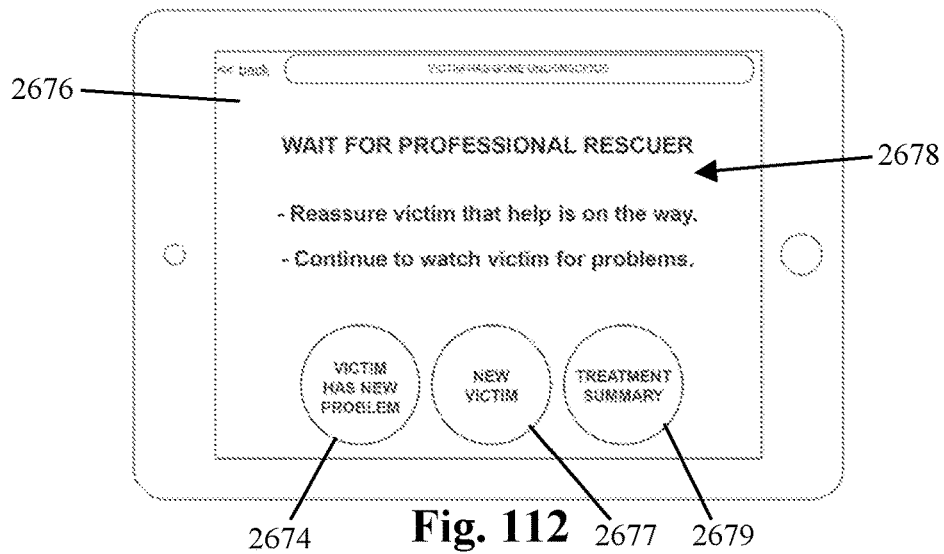

FIG. 112 is an example of a "Wait for Professional Rescuer" screen 2676. By way of example, the "Wait for Professional Rescuer" screen 2676 includes text message/instruction 2678 (e.g. "Reassure victim that help is on the way" and "Continue to watch victim for problems"), a "Victim has New Problem" button 2674 (described above), "New Victim" button 2677, and "Treatment Summary" button 2679. If the user discovers a new victim, they should press "New Victim" button 2677, which alerts the app to the presence of a new victim and directs the user to Part 1 of the MARCHE triage protocol (e.g. FIG. 2). If the user presses the "Treatment Summary" button 2679, the computer will display a treatment summary for viewing by the EMS/professional rescuer once arrived.

Upon arrival, the professional emergency responder is able to access a summary of the actions that the user undertook. This is because the interactive instructional device 14 includes a processor that is capable of recording and storing the step-by-step data, as well as generating a summary page for quick review, for example the Treatment Summary screen 2680 shown in FIG. 113. By way of example, the treatment summary screen 2680 includes the date of treatment 2682, time stamps for each action 2684, and the action 2686 undertaken by the user. This data, as well as the summary page may be transmitted to the emergency responder or to an offsite location for storage and/or review via an appropriate data transmission method, including but not limited to wired Internet, wireless Internet, direct connection to separate device, and the like.

Figure 114:
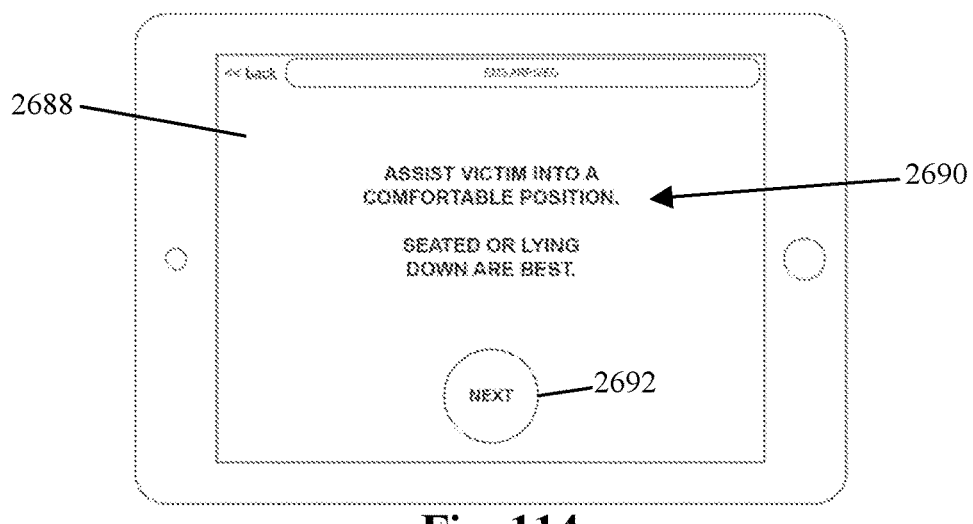

FIG. 114 is an example of a positioning screen 2688 without an image. By way of example, the positioning screen 2688 includes text 2690 as well as a "Next" button 2692. This type of positioning screen may be used when there is no objectively correct position (e.g. victim's comfort is subjective). The app takes into account whether the victim has a neck injury before presenting this screen.

Figure 115:
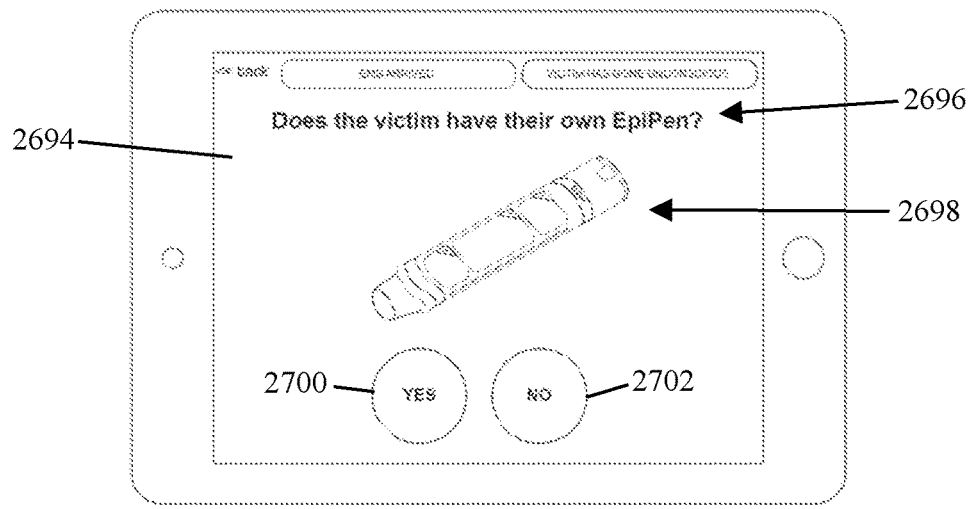

FIG. 115 is an example of a "Victim has own medication" screen 2694. This type of screen asks the user if the victim has their own medication/equipment. Examples would include medication/equipment not included in the attached medical tool kit 12, such as (by way of example and not limited to) epinephrine autoinjector (e.g. Epipen), inhaler, naloxone (e.g. Narcan), etc. By way of example, the screen 2694 includes a text question 2696, image 2698, and a "Yes" button 2700 and "No" button 2702.

Figure 116:
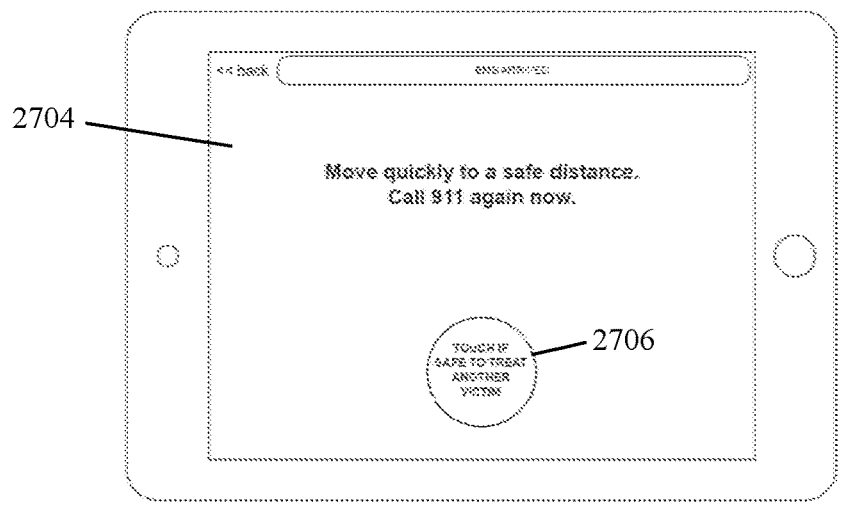

FIG. 116 is an example of a "User in danger" screen 2704 that the computer presents if the user indicates that the victim has gone combative. At this point it is not safe for the user and the app prompts the user to get to a safe distance. The user can continue if they feel safe to go treat another victim, in which case they will press a "Touch if safe to treat another victim" button 2706 to alert the computer to that fact.

FIG. 117 is an example of a Chest Seal Recheck screen 2708 according to one embodiment. As previously mentioned, one feature of the interactive instructional application disclosed herein is that it includes a built in timer that is automatically activated when certain treatment protocols are needed. For example, if the query flow directs the user to the chest seal treatment protocol (which the user then administers to the victim), the timer is automatically activated. After a certain amount of time, the user is given an audio and visual indication that the timer has run out and it's time to recheck the chest seal. By way of example, when the timer expires, the user is presented with the chest seal recheck screen 2708 automatically and regardless of what else they were doing in the MOBILIZE app. The chest seal recheck screen 2708 includes instruction text 2710 (e.g. "Look at the chest seal and choose the image that best shows the seal:"), a "Flat Dry Seal" button 2712, "Leaking Seal" button 2714, "Bulging Seal" button 2716. If the user presses the "Flat Dry Seal" button 2712, the computer presents a GUI screen that indicates the seal is good, and take the user back to wherever they were in the MOBILIZE app before being brought to the chest seal recheck page. If the user presses the "Leaking Seal" button 2714, then the computer presents a series of GUI screens that instructing the user to clean the seal with normal gauze. If the user presses the "Bulging Seal" button 2716, the computer presents a GUI screen that provides specific instruction on how to alleviate a bulging chest seal, for example with text instructions, visual aid (e.g. pictures and/or video) and/or audio instructions (see e.g. FIG. 62).

Figure 118:
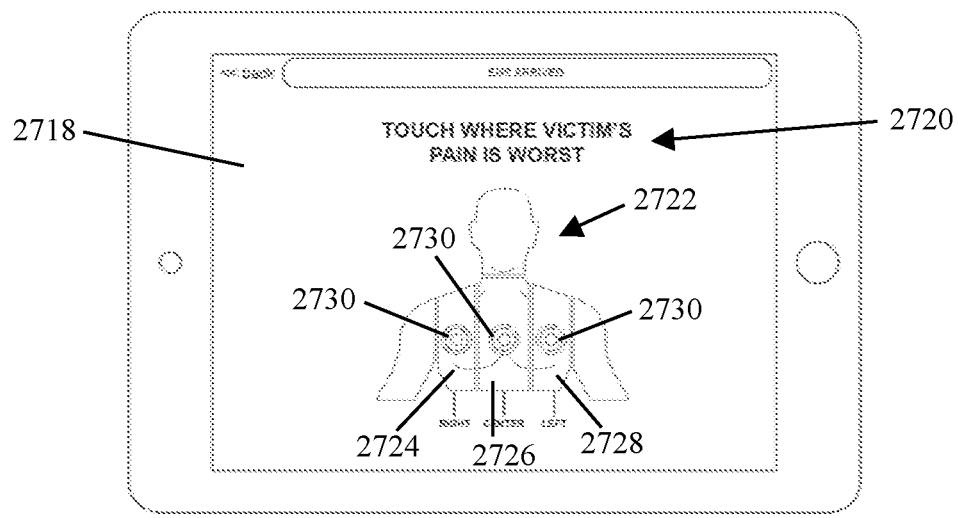

FIG. 118 is an example of a "Target body remember" screen 2718. These screens are used to inform the app where a victim had pain, broken bone, soreness, or other discomfort or emergency. The app stores this information for later use (e.g. helps determine what screens are presented downstream) as well as includes it in the treatment summary. By way of example only, the "Target body remember" screen 2718 of FIG. 118 includes a text instruction 2720 (e.g. "Touch where victim's pain is worst") and an interactive image 2722 (e.g. the human torso) divided into three sections (e.g. Right 2724, Center 2726, and Left 2728), with each section having an activation button 2730. By pressing the activation button 2730 associated with the location of the victim's injury (or pain, discomfort, etc.), the user in inputting this information into the app for later use.

FIG. 119 is an example summary of the various buttons that appear at the top of the screen while using the MOBILIZE app. The "EMS arrived" button 2266, "Victim has gone unconscious" button 2406, "Victim woke up" button 2432, "Victim started vomiting" button 2434, and "AED arrived" button 2532 have all been discussed previously. The "Victim has gone combative" button 2732 appears during the Confusion/Disorientation flows (e.g. FIG. 56) and when the user presses it, the computer displays the "User in Danger" screen 2704 of FIG. 116. The Start Over button 2734 appears at the top of the Summary screen 2680 (e.g. FIG. 113), and pressing it resets the app (e.g. erases timers, data, victims, etc) and takes the user back to the beginning.

Any of a variety of cases may be used to house the instructional device 14 described above, beyond or incorporating features of the portable medical triage kit described above with reference to FIG. 1. These includes, but are not necessarily limited to, the medical tool kits described in commonly owned U.S. Pat. No. 8,911,677, issued Dec. 16, 2014 (incorporated by reference) and commonly owned and co-pending U.S. patent application Ser. No. 14/539,376, filed Nov. 12, 2014 (incorporated by reference). By way of example only, FIGS. 120-129 illustrate one such alternate embodiment forming part of the present disclosure, including a medical triage kit 2750 including a case 2752 (with a base 2754 and lid 2756), an interactive instructional device 2758 housed within the lid 2756, and a supply carrier 2760 housed in the base 2754.

The interactive instructional device 2758 may be a customized touch screen tablet computer, for example a tablet computer similar to an Apple iPad, Microsoft Surface, Samsung Galaxy, and the like. The interactive instructional device 2758 may include but is not limited to a two-way communication assembly with a microphone and speaker, GPS locator, battery, touch screen LCD, programmable memory, a central processing unit (CPU), and wireless connectivity. The interactive instructional device 2758 further includes the interactive instructional application 15 described above (also referred to herein as "app" and "MOBILIZE app") and graphic user interface (GUI) configured to visually, audibly, and interactively guide a user through a triage process regardless of the number of victims present and severity of injuries, to enable preservation of the victim(s) until professional medical help arrives on the scene.

The case 2752 includes a handle 2762 to facilitate the carrying and handling of the case 2752 by a user. In the case of an emergency requiring the administration of emergency assistance or first aid, the user will preferably place the case 2752 such that the base 2754 will rest on a flat surface. The lid 2756 may thereafter be opened to avail the contents of the medical triage kit 2750. The base 2754 is preferably is more heavily weighted than the lid 2756 such that the case 2752 is stable on the flat surface and will not tip over when the lid 2756 is opened for use.

Figure 121:
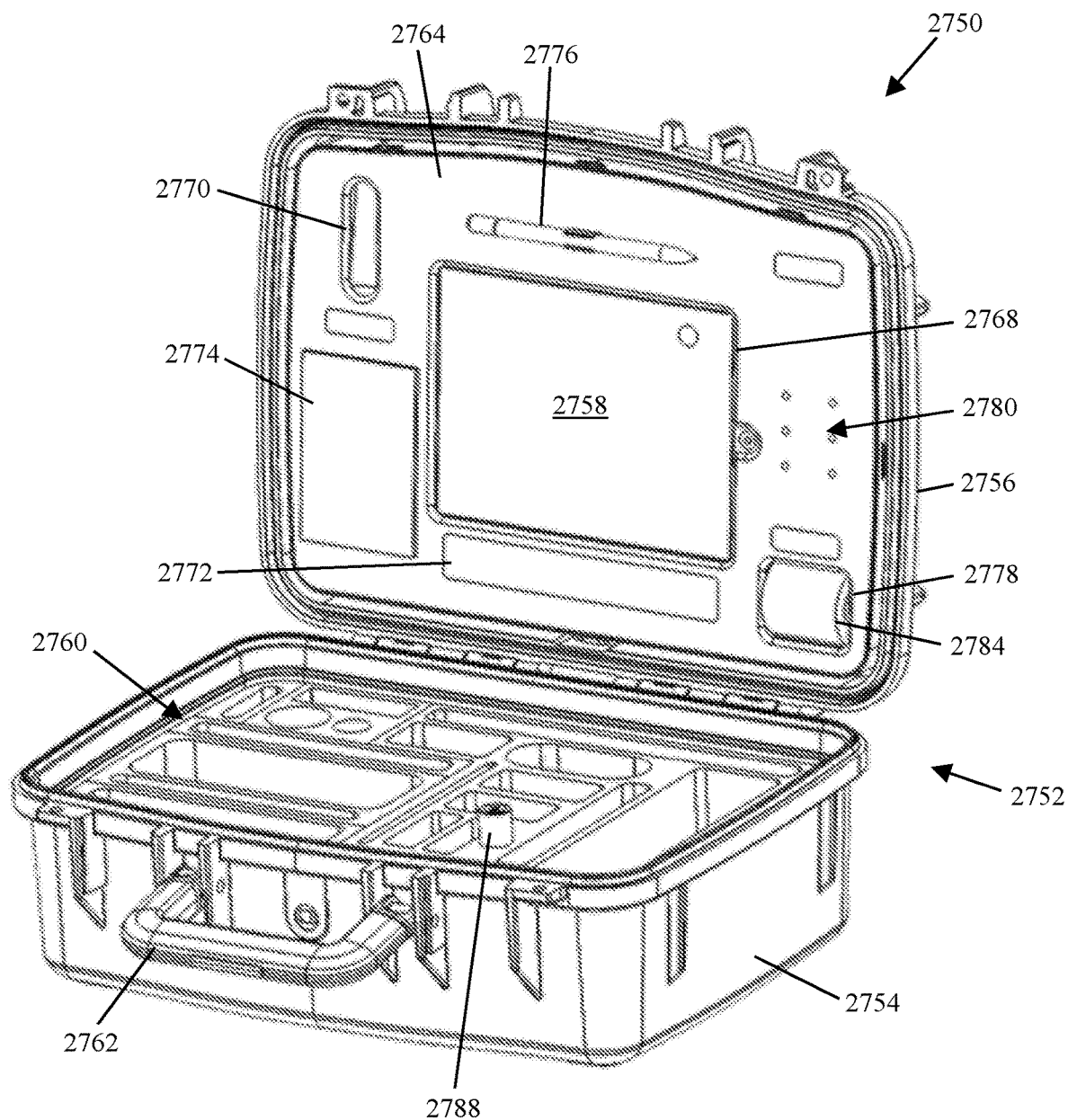
Figure 122:
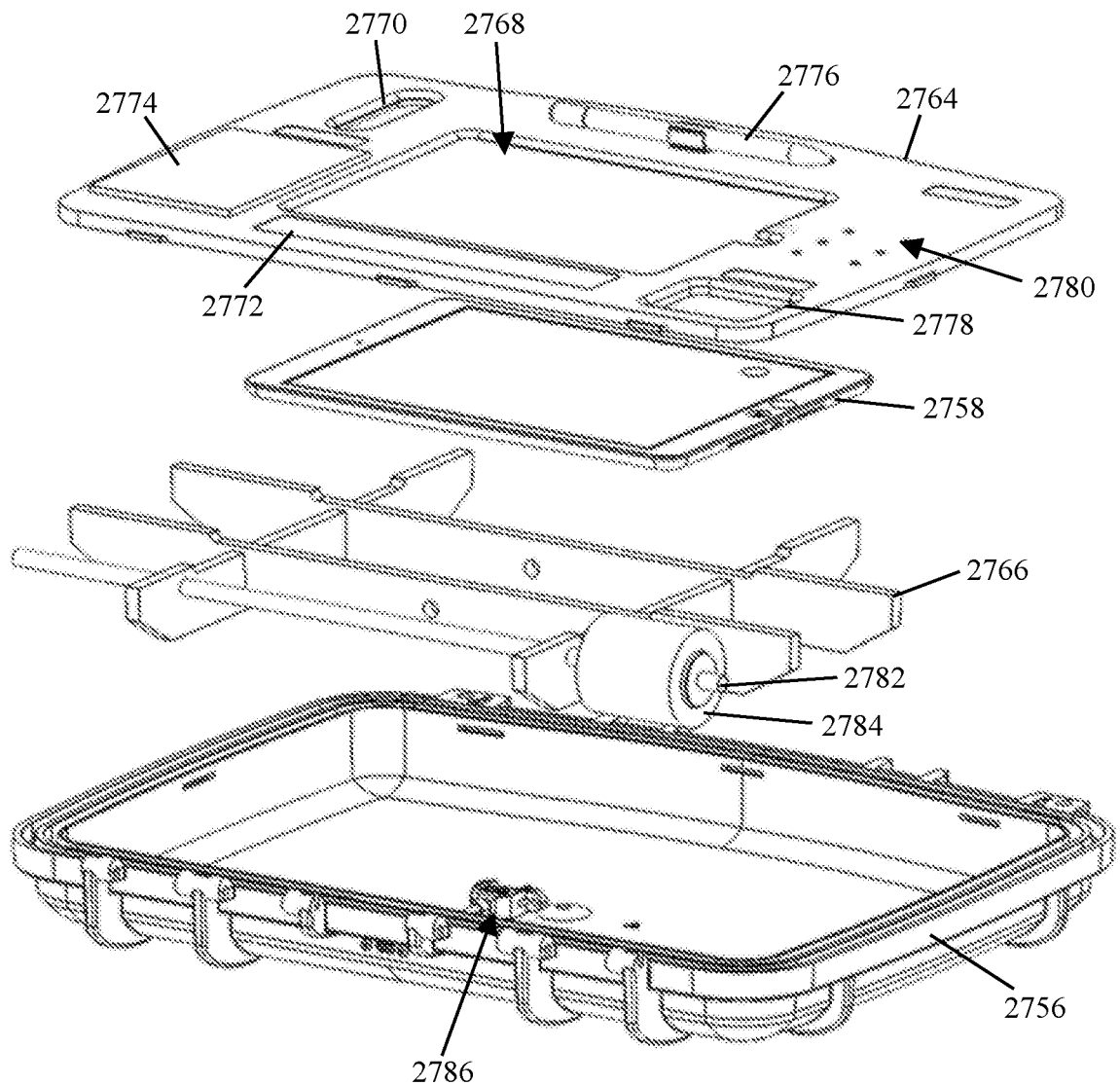
FIG. 122 is a perspective exploded view of a lid component of a case forming part of the portable medical tool kit of FIGS. 120-121, including an interactive instructional device and mounting elements according to one aspect of the present disclosure.

As best viewed in FIGS. 121-122, the lid 2756 includes a variety of components to securely house the interactive instructional device 2758. These include, but are not necessarily limited to, a bezel 2764 for housing the instructional device 2758 and various medical supplies (to be described below), a lattice structure 2766 disposed within a recess in the lid 2756 that forms a protective cradle for the instructional device 2758, and a cushion element disposed in between the instructional device 2758 and the lattice structure 2766 to provide added protection and shock absorption for the instructional device 2758 during use or transportation of the case 2752. The cushion element may be provided such that it adheres directly to the bottom of the instructional device 2758 (and is not coupled to the bezel 2764) or may be coupled to the bezel 2764 and assist in maintaining the instructional device 2758 in coupled relation with the bezel 2764.

The bezel 2764 may be composed of any number of suitable materials but preferably of light-weight construction to ensure the lid 2756 is lighter than the base 2754 when the case 2752 is in use (see above). The bezel 2764 includes a host of apertures and features, including a display aperture 2768, glove-dispensing aperture 2770, Epipen recess 2772, Care Record forms 2774, a combined pen and stylus 2776, a tape dispensing aperture 2778, and aperture array 2780 for holding a shear or scissors (not shown).

The lattice structure 2766 includes a spindle 2782 for carrying a spool of medical tape 2784 that can be dispensed during use through the dispensing aperture 2778 of the bezel 2764. The glove-dispensing aperture 2770 allows a user to remove surgical gloves (not shown) that are housed within a compartment formed by one region of the lattice structure 2776, akin to removing tissue from a tissue box (e.g. Kleenex-brand tissue) so the gloves are compactly stored but yet accessible by pulling an exposed portion of a surgical glove that extends through or is accessible via the glove-dispensing aperture 2770. The Care Record forms 2774 include a variety of blanks so the user can fill them in with the pen 2776 after care has been provided, which may be helpful to provide to the professional first responders upon arrival. An optional charging port 2786 may be provided within the recess of the lid 2756, which establishes electrical connectivity to the instructional device 2758 during storage. The charging port 2786 may be coupled to a battery and/or an electrical outlet.

Figure 123:
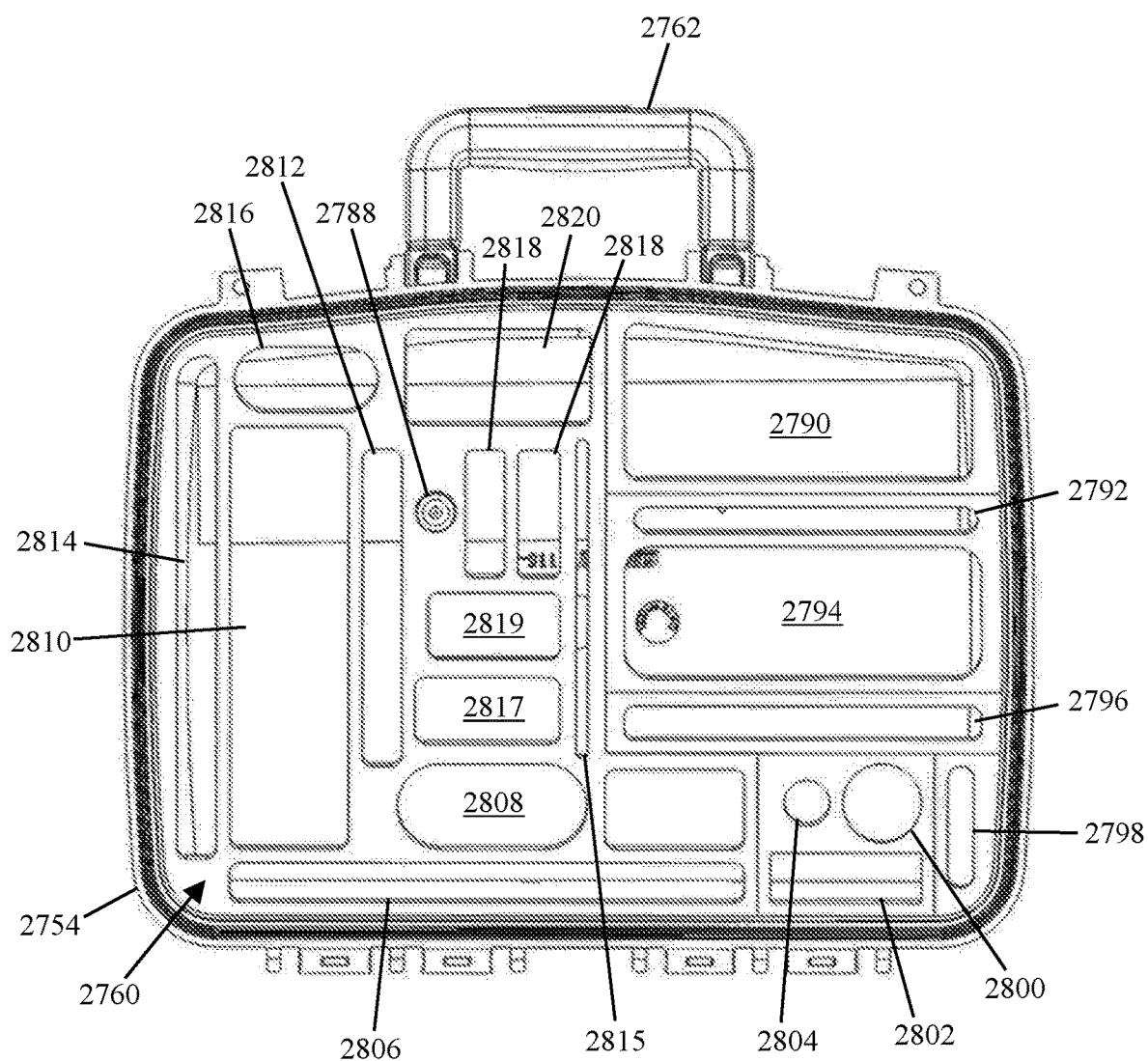
FIG. 123 is a top view of a base component forming part of the portable medical tool kit of FIGS. 120-121 according to an aspect of the present disclosure.

With reference to FIG. 123, the supply carrier 2760 of the base 2754 includes a host of recesses and features. These include, but are not necessarily limited to, a magnetic post 2788 for interacting with a magnetic-enabled sleep mode to power-on and power-off the instructional device 2758, a tourniquet recess 2790 for receiving one or more tourniquets, a hemostatic gauze recess 2792 for receiving hemostatic gauze, a pressure dressing recess 2794 for receiving pressure dressing, a chest seal recess 2796 for receiving a chest seal, a face shield recess 2798 for receiving a CPR face shield, an aspirin recess 2800 for receiving a bottle of aspirin, allergy medication recess 2802 for receiving allergy medication(s), a glucose recess 2804 for receiving a tube of glucose, a burn dressing recess 2806 for receiving burn dressing, a compression dressing recess 2808 for receiving compression dressing (e.g. Ace® bandages), a first standard gauze recess 2810 for receiving a standard gauze of a first length, a second standard gauze recess 2812 for receiving a standard gauze of a second length shorter than the first standard gauze, a splint recess 2814 for receiving a flexible splint (e.g. flexible metal with foam covering), a first aid instructions recess 2815 for receiving a set of first aid instructions, an ice pack recess 2816 for receiving one or more ice packs, a regular gauze recess 2817 for receiving a regular gauze, hand-wipe recesses 2818 for receiving one or more hand-wipes or hand-cleansers, an emergency blanket recess 2819 for receiving an emergency blanket, and an OSHA-Supply recess 2820 for receiving non-emergency medical supplies required by OSHA (e.g. band-aides, etc. . . . ).

Figure 124:
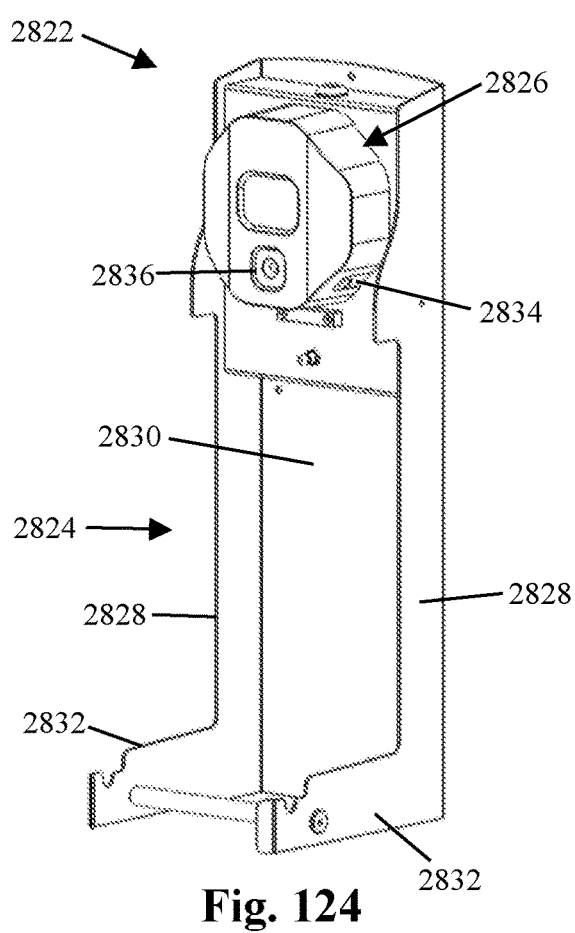
FIGS. 124-126 are perspective, front and side views, respectively, of an alarm-enabled mounting system for holding the portable medical tool kit of FIGS. 120-121 prior to use.
Figure 125:
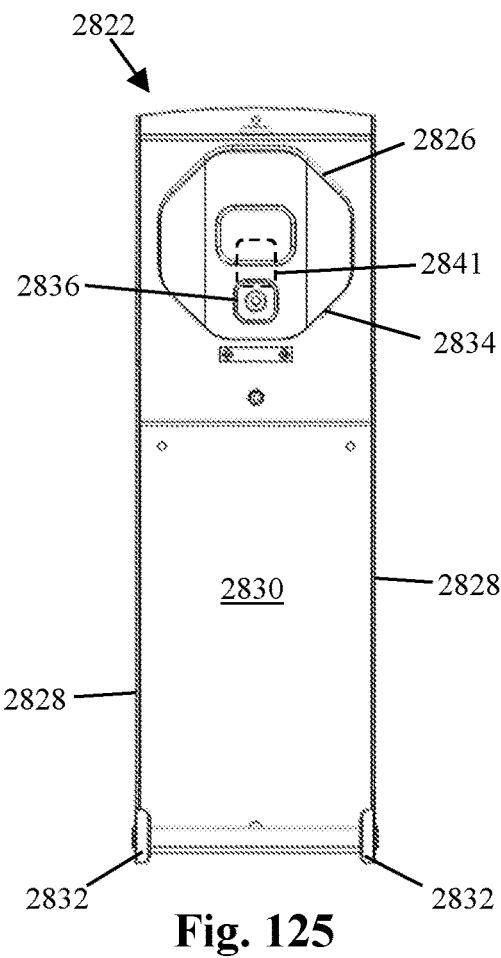
Figure 126:
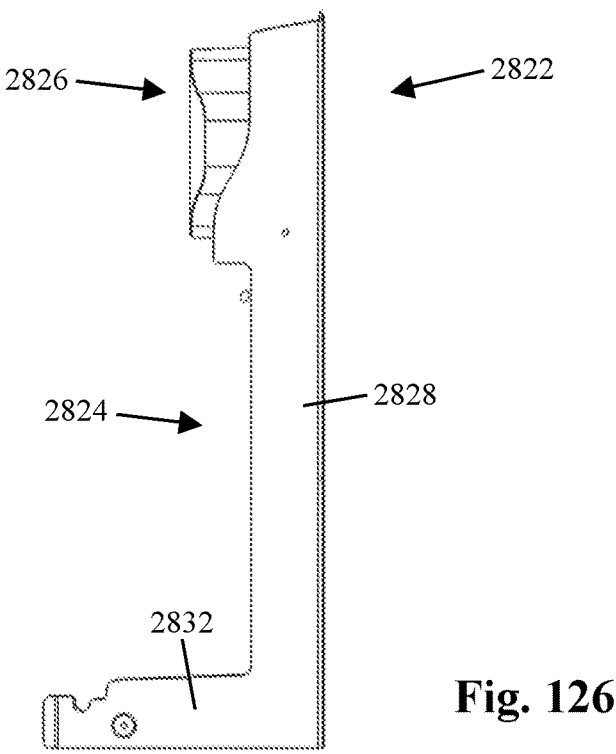

FIGS. 124-126 illustrate a mounting assembly 2822 for use with the medical triage kit 2750 of FIGS. 121-123 according to an aspect of the present disclosure. The mounting assembly 2822 includes a rack assembly 2824 and an alarm assembly 2826. The rack assembly 2824 includes a pair of vertical struts 2828, a base 2830 extending between the vertical struts 2828, and a pair of horizontal arms 2832. The rack assembly 2824 may be made of any suitable material, but preferably of sufficiently robust construction to carry and maintain the mobile triage kit 2750 in a safe and stable condition until use. The vertical struts 2828 and horizontal arms 2832 are configured in a manner that supports the base 2754 of the case 2752 until use (see, e.g. FIG. 128).

Figure 127:
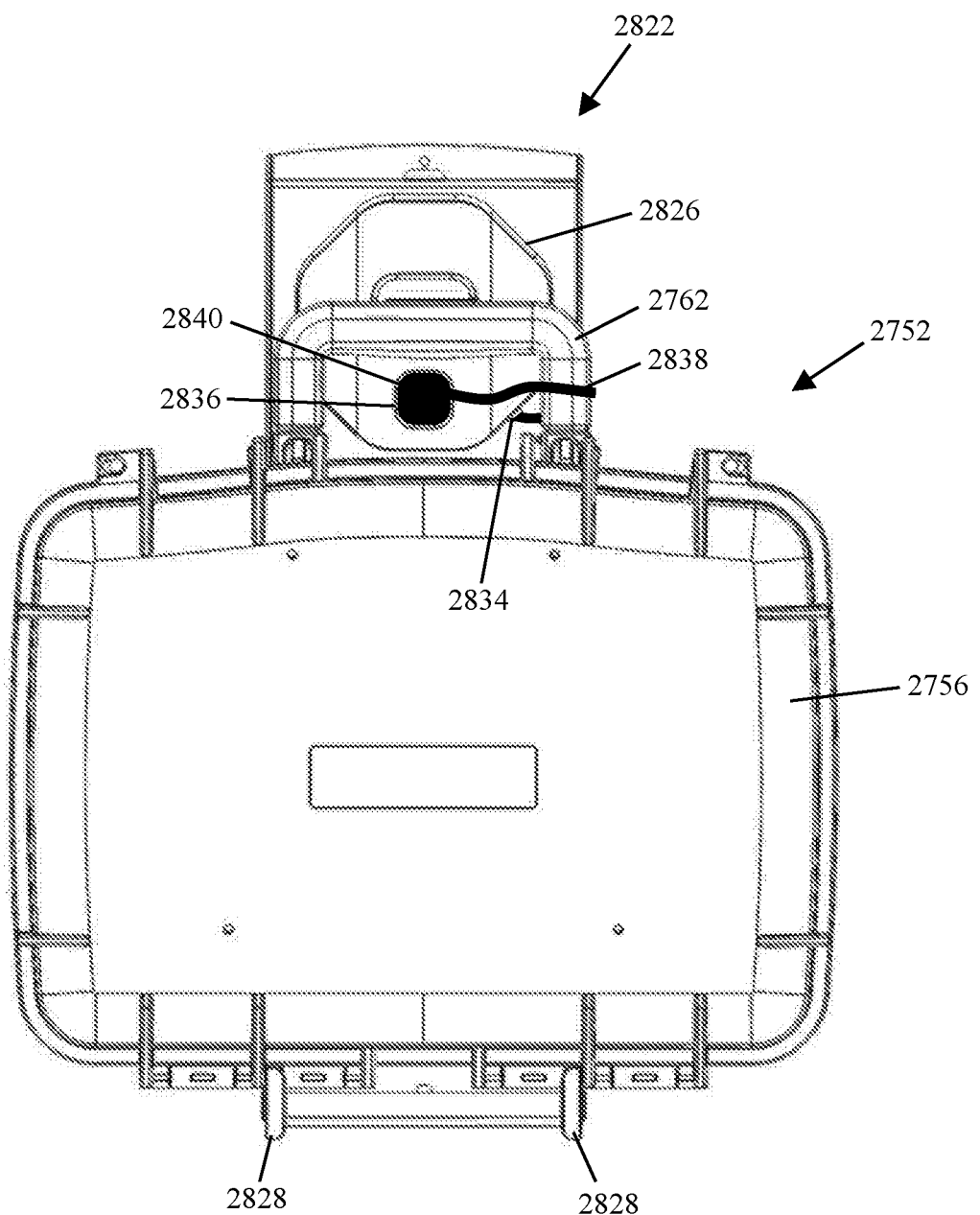
FIGS. 127-129 are front, side and top views, respectively, of the portable medical tool kit of FIGS. 120-121 held on the mounting system of FIGS. 124-126 prior to use.
Figure 128:
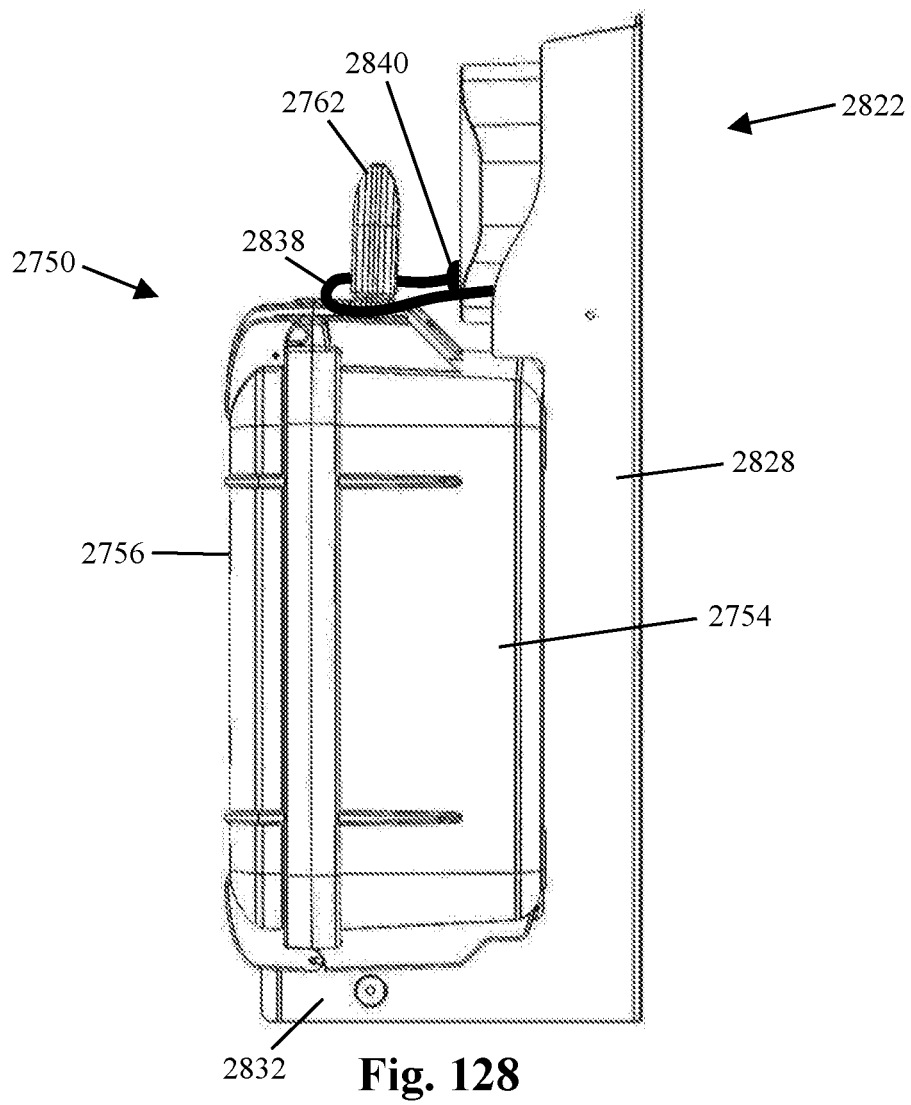
Figure 129:
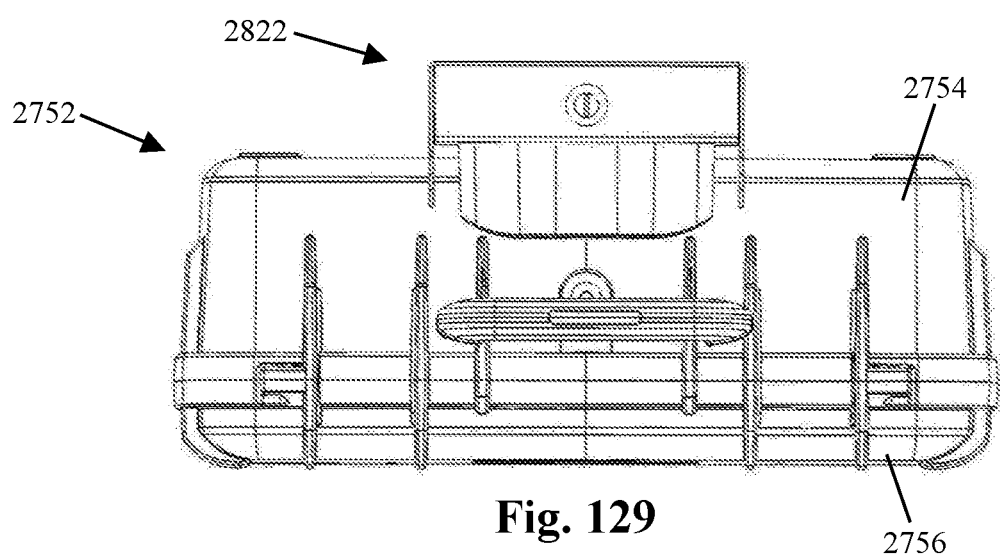

The alarm assembly 2826 includes circuitry and sufficient power (e.g. battery and/or via electrical outlet) to drive an internally disposed alarm to generate an alarm signal when the case 2752 has been removed from the mounting assembly 2822. As shown in FIGS. 127-129, a cable 2838 is used to trigger the alarm functionality of the alarm assembly 2826 when the case 2752 (and specifically the handle 2762) has been removed from the mounting assembly 2822. One end of the cable is coupled to or extends from the alarm assembly 2826. The other end of the cable includes a coupler 2840 capable of being removably coupled within a recess 2836 on the alarm assembly 2826. A slidable element 2841 (phantom in FIG. 125) is disposed within the alarm assembly 2826. When the coupler 2840 is disposed within the recess 2836, the slidable element 2841 is disposed generally above the recess 2836. When the coupler 2840 is removed, the slidable element 2841 falls under the weight of gravity and closes a circuit within the alarm assembly 2826 to generate an alarm signal. During storage (that is, when the case 2752 is mounted within the mounting assembly 2822), the cable 2838 is passed from the port 2834 and through the handle 2762 such that the coupler 2840 is holding the slidable element 2841 in the "open circuit" configuration.

When the coupler 2840 is removed from the recess 2836 (such as when the case 2752 is removed from the mounting assembly 2822 such that the handle 2762 pulls the coupler 2840 out of the recess 2836), an internal circuit within the alarm assembly 2826 will turn on, which triggers an alarm signal. The alarm signal may be an audible and/or visual (e.g. strobe light) alarm that is generated at the alarm assembly 2826 and/or a remotely communicated alarm signal (e.g. via wireless to a guard station, security personnel, school administration, etc.). In either event, the alarm may be useful in alerting others that the case 2752 has been removed from the mounting assembly 2822, such as for theft prevention and/or mobilizing professional first responders. To help ensure that administrative or maintenance personnel are able to inspect the triage kit 2750 after each use, the slidable element 2841 can be moved back into the "open circuit" configuration such that the coupler 2840 may be repositioned in the recess 2836. To do so, the maintenance or administrative personnel may simply use a magnetic positioned vertically above the recess 2836 to overcome the force of gravity and move the slidable element 2841 vertically upwards so it no longer presents a physical barrier to the entry of the coupler 2840 into the recess 2836.

The portable triage kit 10 may have multiple levels of integration with 9-1-1 and/or professional health care providers. As previously mentioned, the triage kit may be configured to automatically alert first responders and provide GPS location when the user performs a task (e.g. upon opening of the kit or upon the user proactively confirming the need for EMT services once the system has been activated). Also, it may allow for 3rd party offsite viewing/interaction to allow for extra real time support from medical professionals.

The portable triage kit 10 may include various features not described herein above but nonetheless enhance the ability of the MOBILIZE rescue kit to save lives. According to one example, the MOBILIZE rescue kit may be modified for remote delivery via unmanned aerial vehicles (e.g. drones). In such an example, the rescue kit is attached to a drone and then the drone is flown remotely to a known location by a pilot on the ground, and may include live camera feed to a base station and/or night vision/infrared camera navigation. Alternatively, the drone may be able to fly automatically in response to a distress signal from a beacon and therefore reach victims that human rescuers can't find.

The rescue kit of the present disclosure may be modified to connect with 9-1-1 through the device, either automatically or user-controlled, via cellular network or VOIP Wifi to 9-1-1 Public Safety Answering Point, and be able to transmit using an open microphone hands free voice channel, transmit GPS location, and transmit diagnostic information via Text-to-voice. Additionally, the MOBILIZE rescue unit may be equipped to transmit a distress signal via US Coast Guard EPIRB radio system, and transmit images from incident scene to 9-1-1 PSAP, telemedicine call center, or receiving hospital.

Another feature of the app is expanded voice integration, including user voice initiation (e.g. Alexa, Siri, etc), text-to-voice questioning of the user, app responding to voice input, and the like.

Another feature of the portable medical kit not included above includes treatment for chemical burns. For example, if the user recognizes burn from chemical, the app may have a query flow that helps the user determine whether the chemical is wet or dry, and then follow appropriate treatment for each (e.g. brush away dry chemical, flush wet chemical with water). The app would then direct further supportive care (gauze, etc).

In addition to a chemical burn protocol, the portable medical triage kit may include a protocol for emergency childbirth. The app may include a query flow that assesses the likelihood of imminent delivery, tracks maternal data, directs user to prepare field for birth, directs user to assist in proper delivery, directs user to assess infant, tracks initial infant data (e.g. APGAR scale), and directs user to provide supportive care to infant, directs user to provide supportive care to mother.

Another query flow that may be part of the medical triage kit relates to envenomation. For example, the query flow starts when a user indicates an envenomated victim (e.g. snakebite). The app directs the user to take proper personal precautions and then to proper care, including rapid immobilization of affected limb. The app may dispel envenomation myths (e.g. tourniquet is not, in fact, helpful), and assist the user in identifying suspect venom.

Another query flow that may be part of the medical triage kit relates to Hazardous Materials. For example, a User/Administrator inputs Hazardous Materials at designated work location. The User/Rescuer starts the MOBILIZE app and indicates hazardous materials exposure OR unknown problem. The app prompts the user to investigate signs and symptoms including (but not limited to): skin temperature (warm/dry/cool), skin color (red/pink/pale/blue), skin moisture (wet/moist/normal/dry), turgor (normal/tented), pupils (constricted/reactive/dilated/fixed), salivation (absent/present/excessive/frothy/bloody), nasal discharge (absent/present/frothy/bloody), lacrimation (absent/present/excessive), eye sensation (normal/grit), GI disturbance (none/nauseated/vomiting/flatulent/diarrhea/other), incontinence (absent/present), reported tastes (floral/mustard/chlorine/other), reported odors (almond/floral/mustard/spice/chlorine/other), ambulation (ambulatory/with assistance/non-ambulatory), level of consciousness (alert/to voice/to pain/unresponsive), breathing (normal/rapid/slow/irregular), musculature (normal/flaccid/constricted/tetanic/seizing), or other. The app then draws inference on most likely exposed substance from User/Administrator inputted list, and also suggests possible non-inputted hazardous materials. The app then suggests initial first aid treatment and directs responders to most likely hazardous materials treatment protocol.

Another feature that may be part of the medical triage kit relates to user inputted medical baselines, for use in rescue where the app tracks rescuers for post-exertion changes, for example confined space, hazardous materials, dive rescue, and fire fighters. Could also be used for sports-related concussion evaluation. Generally, the user inputs baseline medical data and answers to cognitive questions. The app stores the data. User indicates post event evaluation required. The app queries same data points as baseline and then displays before/after results. As a result, the rescuer may trigger further evaluation, while sports teams may require immediate removal from a game until cleared by MD.

Another feature that may be part of the medical triage kit relates to using a stethoscope and/or tuning fork (or other sound emitting device) for fracture determination.

Other features include supply tracking (app recognizes inventory depletion, directs user to next most appropriate treatment modality if low on supplies, and then summarizes supplies used and offers one-click reordering), enhanced triage (app tracks victims and assigns each a severity code based on START—Simple Triage And Rapid Transport system, and then directs responders to most severely injured victims), oxygen (app directs users to apply oxygen), diagnostic screens (non-invasive diagnostic testing, e.g. liver flap test for hepatic encephalopathy, cold water Nystagmus test for stroke, etc)

Another feature that may be part of the medical triage kit relates to veterinary first aid, and specific canine first aid. The app may direct user to take precautions, examine the canine for bleeding (reminding the user that canines can exsanguinate from a tail bleed) assess for other life-threatening problems, and asks if Solu-Medrdol is available (and directs user how to administer).

Another feature that may be part of the medical triage kit relates to advanced provider prompts, for certified medical providers who infrequently use advanced medical emergency skills. The app verifies medical provider skills in advance, and then provides instruction for (including but not limited to) suturing, thoracotomy, cut-down, tracheotomy, fasciotomy, intubation, intravenous therapy, intravenous drug dosing.

Additional hardware features may include: a waterproof or dustproof case, external scene light from kit, backlit gear compartment (with color-coded light in medical tool compartments), power (e.g. battery capable of supporting defibrillation, battery capable of years-long sleep, solar charging, 12-volt charging, external rechargeable battery packs, etc), lockable prescription medication/equipment compartment that is unlockable by medical provider on the scene or remotely (e.g. needle decompression kit for independent duty paramedic on oil rig, remote unlocking by medical provider following teleconference), and an accelerometer (with pressure sensor for measuring efficacy of user's CPR compressions and real-time feedback from app).

Various modifications may be made to the medical tool kit itself as well. For example, a mobile kit may be provided with contents and functionality identical to the main kit medical triage kit 2750 disclosed above, but comes in a soft-sided backpack-style carrying case. The carrying case may have shoulder straps and a waist strap to allow for comfortable carrying of the tool kit over any terrain. The app may run on an attached manufacturer-provided tablet computer or alternatively may run on a user-provided tablet computer.

Another variation of the medical tool kit is a split-side tool kit with two equally sized compartments that does not include a supplied tablet computer, but rather is supply-only. The app thus runs on a user-supplied tablet or smart phone. The split-side tool kit may have different supplies inside depending on where the kits are being used. In home use, for example, one side may have emergency medical supplies (including "one of each" from comprehensive kit) and a plastic breakable "lock," while the other side has common household minor first aid supplies, including adhesive bandages (band-aid style), ibuprofen, and ice packs. The app gives direction on the emergency medical supplies. In professional responder use, for example, one side may have emergency medical supplies (including "one of each" from comprehensive kit) and a plastic breakable "lock," while the other side has automated external defibrillator and supplies. The app provides instruction for both, if necessary. In school use, for example, one side may have emergency medical supplies (including "one of each" from comprehensive kit) and a plastic breakable "lock," while the other side has common items used by athletic trainers and coaches, such as compression bandages (e.g. Ace-style wrap), ice packs, and athletic tape.

Another variation of the medical tool kit is a compact kit, which for example may be an individual first aid kit. By way of example, the compact kit may include (but is not limited to) gloves, tourniquet, hemostatic gauze (e.g. QuikClot), pressure dressing, chest seal, CPR face shield, shears, and an emergency blanket. The app runs on the user's own smart phone, and directs the user to appropriate lifesaving medical equipment. When the app runs on a user-supplied phone, it recognizes the limited equipment and thus may run a scaled-back version of the app. The compact kit may include a MOLLE-style attachment system, in that it can be mounted on a Mil Spec pack, and can be worn on a standard or police duty-sized belt.

Another variation of the medical tool kit is a multiple-casualty bleeding control kit, which, by way of example, may be several compact kits contained in a portable bag. The bag can standalone or be housed in an alarmed box. Each compact kit has a First Care Provider instruction card. One benefit of a multiple-casualty bleeding control kit is that a workplace, for example, can have multiple copies of the same kit at different locations, and also ensure that all employees have the MOBILIZE app on their phones. Thus, anyone may be capable of assisting in a medical emergency.

Additional diagnostic tools that may be included in the medical tool kit include (but are not limited to: Heart Rate monitor, Automated Blood Pressure Cuff, Galvanic Skin Sensor, Temperature reader, Microphone for stethoscopic auscultation of lungs, belly, fractures, bruits, etc. (App "listens" to sounds and determines "most likely" sound), Electro Cardiogram (App interprets cardiogram), Pulse Oximeter, Glucometer, Instant blood lab results (e.g. iSTAT style), and triage "tags" including biometric sensors: Sense heart rate, respiratory rate; User inputs ambulation; User inputs mental status; Sensor turns on correct START color light; Sensor sends signal to base receiver in kit; Allows User to direct resources to most seriously injured.

Figure 130:
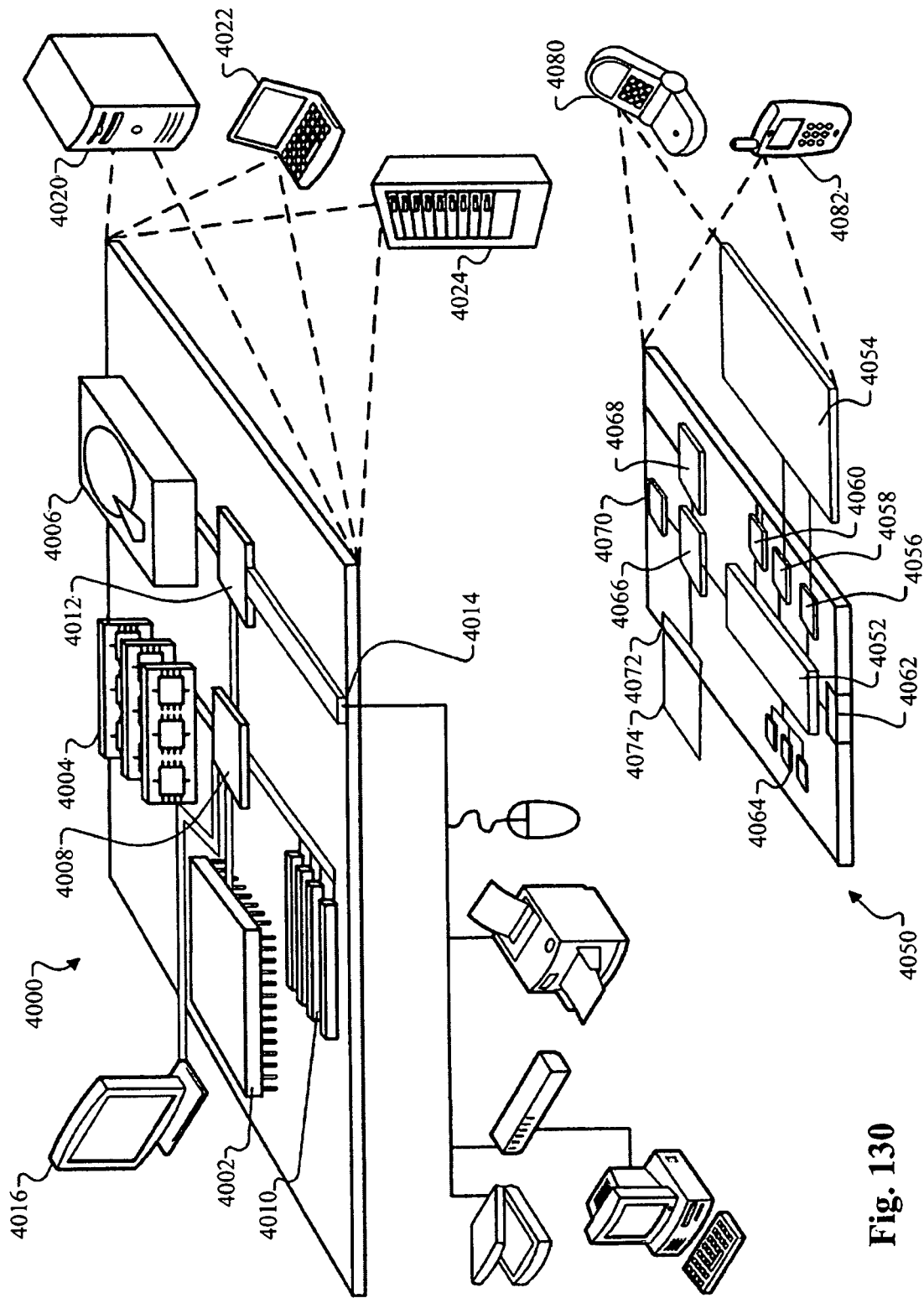
FIG. 130 is a block diagram of computer systems forming part of the portable medical tool kit of FIG. 1.

FIG. 130 is a block diagram of computing devices 4000, 4050 that may be used to implement the systems and methods described in this document, as either a client or as a server or plurality of servers. Computing device 4000 is intended to represent various forms of digital computers, such as laptops, desktops, workstations, personal digital assistants, servers, blade servers, mainframes, and other appropriate computers. Computing device 4050 is intended to represent various forms of mobile devices, such as personal digital assistants, cellular telephones, smartphones, and other similar computing devices. In this example, computing device 4050 may represent electronic device 17, while computing device 4000 may represent computing systems that serve as the "cloud" referenced in this disclosure. The components shown here, their connections and relationships, and their functions, are meant to be examples only, and are not meant to limit implementations described and/or claimed in this document.

Computing device 4000 includes a processor 4002, memory 4004, a storage device 4006, a high-speed interface 4008 connecting to memory 4004 and high-speed expansion ports 4010, and a low speed interface 4012 connecting to low speed bus 4014 and storage device 4006. Each of the components 4002, 4004, 4006, 4008, 4010, and 4012, are interconnected using various busses, and may be mounted on a common motherboard or in other manners as appropriate. The processor 4002 can process instructions for execution within the computing device 4000, including instructions stored in the memory 4004 or on the storage device 4006 to display graphical information for a GUI on an external input/output device, such as display 4016 coupled to high-speed interface 4008. In other implementations, multiple processors and/or multiple buses may be used, as appropriate, along with multiple memories and types of memory. Also, multiple computing devices 4000 may be connected, with each device providing portions of the necessary operations (e.g., as a server bank, a group of blade servers, or a multi-processor system).

The memory 4004 stores information within the computing device 4000. In one implementation, the memory 4004 is a volatile memory unit or units. In another implementation, the memory 4004 is a non-volatile memory unit or units. The memory 4004 may also be another form of computer-readable medium, such as a magnetic or optical disk.

The storage device 4006 is capable of providing mass storage for the computing device 4000. In one implementation, the storage device 4006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 4004, the storage device 4006, or memory on processor 4002.

The high-speed controller 4008 manages bandwidth-intensive operations for the computing device 4000, while the low speed controller 4012 manages lower bandwidth-intensive operations. Such allocation of functions is by way of example only. In one implementation, the high-speed controller 4008 is coupled to memory 4004, display 4016 (e.g., through a graphics processor or accelerator), and to high-speed expansion ports 4010, which may accept various expansion cards (not shown). In the implementation, low-speed controller 4012 is coupled to storage device 4006 and low-speed expansion port 4014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 4000 may be implemented in a number of different forms, as shown in the figure. For example, it may be implemented as a standard server 4020, or multiple times in a group of such servers. It may also be implemented as part of a rack server system 4024. In addition, it may be implemented in a personal computer such as a laptop computer 4022. Alternatively, components from computing device 4000 may be combined with other components in a mobile device (not shown), such as device 4050. Each of such devices may contain one or more of computing device 4000, 4050, and an entire system may be made up of multiple computing devices 4000, 4050 communicating with each other.

Computing device 4050 includes a processor 4052, memory 4064, an input/output device such as a display 4054, a communication interface 4066, and a transceiver 4068, among other components. The device 4050 may also be provided with a storage device, such as a microdrive or other device, to provide additional storage. Each of the components 4050, 4052, 4064, 4054, 4066, and 4068, are interconnected using various buses, and several of the components may be mounted on a common motherboard or in other manners as appropriate.

The processor 4052 can execute instructions within the computing device 4050, including instructions stored in the memory 4064. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 4050, such as control of user interfaces, applications run by device 4050, and wireless communication by device 4050.

Processor 4052 may communicate with a user through control interface 4058 and display interface 4056 coupled to a display 4054. The display 4054 may be, for example, a TFT (Thin-Film-Transistor Liquid Crystal Display) display or an OLED (Organic Light Emitting Diode) display, or other appropriate display technology. The display interface 4056 may comprise appropriate circuitry for driving the display 4054 to present graphical and other information to a user. The control interface 4058 may receive commands from a user and convert them for submission to the processor 4052. In addition, an external interface 4062 may be provided in communication with processor 4052, so as to enable near area communication of device 4050 with other devices. External interface 4062 may provide, for example, for wired communication in some implementations, or for wireless communication in other implementations, and multiple interfaces may also be used.

The memory 4064 stores information within the computing device 4050. The memory 4064 can be implemented as one or more of a computer-readable medium or media, a volatile memory unit or units, or a non-volatile memory unit or units. Expansion memory 4074 may also be provided and connected to device 4050 through expansion interface 4072, which may include, for example, a SIMM (Single In Line Memory Module) card interface. Such expansion memory 4074 may provide extra storage space for device 4050, or may also store applications or other information for device 4050. Specifically, expansion memory 4074 may include instructions to carry out or supplement the processes described above, and may include secure information also. Thus, for example, expansion memory 4074 may be provided as a security module for device 4050, and may be programmed with instructions that permit secure use of device 4050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, cause performance of one or more methods, such as those described above. The information carrier is a computer- or machine-readable medium, such as the memory 4064, expansion memory 4074, or memory on processor 4052 that may be received, for example, over transceiver 4068 or external interface 4062.

Device 4050 may communicate wirelessly through communication interface 4066, which may include digital signal processing circuitry where necessary. Communication interface 4066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 4068. In addition, short-range communication may occur, such as using a Bluetooth, WiFi, or other such transceiver (not shown). In addition, GPS (Global Positioning System) receiver module 4070 may provide additional navigation- and location-related wireless data to device 4050, which may be used as appropriate by applications running on device 4050.

Device 4050 may also communicate audibly using audio codec 4060, which may receive spoken information from a user and convert it to usable digital information. Audio codec 4060 may likewise generate audible sound for a user, such as through a speaker, e.g., in a handset of device 4050. Such sound may include sound from voice telephone calls, may include recorded sound (e.g., voice messages, music files, etc.) and may also include sound generated by applications operating on device 4050.

The computing device 4050 may be implemented in a number of different forms, some of which are shown in the figure. For example, it may be implemented as a cellular telephone 4080. It may also be implemented as part of a smartphone 4082, personal digital assistant, or other similar mobile device.

Additionally computing device 4000 or 4050 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube)

or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

While the inventive features described herein have been described in terms of a preferred embodiment for achieving the objectives, it will be appreciated by those skilled in the art that variations may be accomplished in view of these teachings without deviating from the spirit or scope of the invention.

What is claimed is:

1. A portable medical treatment system including:
   a user-carryable medical case adapted to be carried by a user from a storage location to a location of a victim requiring medical assistance, the user-carryable medical case having a plurality of tool-receiving receptacles configured to receive multiple medical tools arranged according to a preselected arrangement;
   a plurality of medical tools arranged within the plurality of tool-receiving receptacles according to the preselected arrangement; and
   a computer that is contained within an interior of the user-carryable medical case, the computer being configured to provide an interactive query flow that guides the user in providing care to the victim, the computer comprising: a touchscreen; one or more processors; and computer-readable media including instructions that, when executed by the one or more processors, are configured to cause the computer to perform operations that include:
   (i) presenting, on the touchscreen, a first prompt for user input to specify whether the victim is suffering from a first type of condition;
   (ii) receiving, through user interaction with the touchscreen, a first user response that specifies whether the victim is suffering from the first type of condition;
   (iii) selecting, responsive to the first user response specifying that the victim is suffering from the first type of condition, a first computer-selected medical tool from among the medical tools located in the user-carryable medical case with which to treat the first type of condition;
   (iv) presenting, on the touchscreen responsive to the computer selecting the first computer-selected medical tool from among the medical tools located in the user-carryable medical case, information that instructs the user to retrieve the first computer-selected medical tool from the user-carryable medical case and that assists the user in locating the first computer-selected medical tool from among medical tools located within the user-carryable medical case;
   (v) presenting, on the touchscreen responsive to the computer selecting the first computer-selected medical tool, information that instructs the user how to apply the first computer-selected medical tool to the victim to treat the first type of condition;
   (vi) presenting, on the touchscreen responsive to the first user indicating that the first computer-selected medical tool cannot be applied according to the information that instructs the user how to apply the first computer-selected medical tool, a second computer-selected medical tool from among the medical tools located in the user-carryable medical case with which to treat the first type of condition:
   (vii) presenting, on the touchscreen responsive to the computer selecting the second computer-selected medical tool from among the medical tools located in the user-carryable medical case, information that instructs the user to retrieve the second computer-selected medical tool from the user-carryable medical case and that assists the user in locating the second computer-selected medical tool from among medical tools located within the user-carryable medical case; and
   (viii) presenting, on the touchscreen responsive to the computer selecting the second computer-selected medical tool information that instructs the user how to apply the second computer-selected medical tool to the victim to treat the first, type of condition.

2. The portable medical treatment system of claim 1, wherein the interactive query flow includes an audio component and a video component.

3. The portable medical treatment system of claim 1, wherein the interactive query flow leads the user to provide care to medical emergency victims of severe life threats before other medical emergencies.

4. The portable medical treatment system of claim 3, wherein the severe life threats that are treated before other medical emergencies include severe bleeding, unconsciousness, and trouble breathing.

5. The portable medical treatment system of claim 1, wherein the interactive query flow includes a built-in timer for automatically alerting the user to perform tasks.

6. The portable medical treatment system of claim 1, wherein the interactive query flow presents a treatment screen based on a user response supplied in a previous treatment screen.

7. The portable medical treatment system of claim 1, wherein the interactive query flow manages treatment of multiple victims at the same time.

8. The portable medical treatment system of claim 1, wherein the computer stores data related to the interactive query flow, including input by the user.

9. The portable medical treatment system of claim 1, wherein the computer is configured to display a summary of treatment.

10. The portable medical treatment system of claim 9, wherein the summary of treatment includes at least one of an action performed by the user, a date, or a time of action performed by the user.

11. The portable medical treatment system of claim 1, wherein the computer is configured to present a prompt for user input to specify whether the victim is suffering from a second type of condition, in distinction to presenting the information that instructs the user to retrieve the first computer-selected medical tool, as a consequence of the first user response specifying that the victim is not suffering from the first type of condition.

12. The portable medical treatment system of claim 11, wherein the computer is configured to present prompts during the interactive query flow with reference to injuries in a descending order of severity, such that the first condition that is a subject of the first prompt represents a more severe type of condition than the second condition that is a subject of another prompt that the computer is configured to present should the first user response specify that the victim is not suffering from the first type of condition.

13. The portable medical treatment system of claim 1, wherein the computer is configured so that the interactive query flow provides instructions for treating a victim condition after differing numbers of prompts, based on content of user responses to the prompts.

14. The portable medical treatment system of claim 1, wherein presenting the first prompt for user input to specify whether the victim is suffering from the first type of condition includes presenting text on the touchscreen that identifies the first type of condition and presenting an image on the touchscreen that visually depicts the first type of condition on a human body.

15. The portable medical treatment system of claim 1, wherein: the medical tools that are located in the user-carryable medical case are coded with different colors; and
presenting the information that instructs the user to retrieve the first computer-selected medical tool from among the medical tools in the user-carryable medical case includes presenting a coding for the first computer-selected medical tool according to the coding of the different colors for the medical tools in the user-carryable medical case, to assist the user in finding the first computer-selected medical tool in the user-carryable medical case.

16. The portable medical treatment system of claim 1, wherein the presentation by the touchscreen of the information that instructs the user how to apply the first computer-selected medical tool to the victim to treat the first type of condition includes (i) text instructions that specify how to apply the first computer-selected medical tool to the victim, and (ii) a visual picture or video that depicts how to apply the first computer-selected medical tool to the victim.

17. The portable medical treatment system of claim 1, wherein:
the first type of condition is a condition of a first portion of the victim;
presenting the first prompt for user input to specify whether the victim is suffering from the first type of condition includes depicting a human body on the touchscreen; and
receiving the first user response that specifies whether the victim is suffering from the first type of condition includes receiving user input that contacts a first portion of the human body that is depicted on the touchscreen, the first portion of the victim corresponding to the first portion of the human body that is depicted on the touchscreen.

18. The portable medical treatment system of claim 1, wherein the operations comprise:
(ix) automatically activating a recheck timer to remind the user to recheck the application of the first computer-selected medical tool to the victim;
(x) continuing the interactive query flow, after presentation of the treatment information that indicates how to apply the first computer-selected medical tool to the victim to treat the first type of condition, by presenting multiple prompts for user input to specify whether the victim is suffering from multiple respective types of injuries; and
(xi) upon expiration of the recheck timer:
automatically changing the touchscreen to present a second prompt for user input to specify a status of the application of the first computer-selected medical tool to the victim, and
receiving, through user interaction with the touchscreen responsive to the presentation of the second prompt, a second user response that indicates a status of the application of the first computer-selected medical tool to the victim,
wherein the computer is configured to present alternative treatment information that instructs the user how to treat the first type of condition, responsive to the second user response indicating that the application of the first computer-selected medical tool to the victim has unsatisfactorily addressed the second type of condition, and
wherein the computer is configured to return to the continuation of the query flow that presents the multiple prompts, in distinction to presenting the alternative treatment information, responsive to the second user response indicating that the application of the first computer-selected medical tool to the victim has satisfactorily addressed the second type of condition.

19. The portable medical treatment system of claim 18, wherein a time interval of the recheck timer is not determined or adjusted by user input during treatment of the victim.

20. The portable medical treatment system of claim 1, wherein the operations comprise:
(ix) presenting, on the touchscreen, a summary of treatment that identifies: multiple actions undertaken by the user in treating the victim according to the interactive query flow, and
multiple respective times of the multiple actions undertaken by the user in treating the victim, a first time of the multiple respective times being different from a second time of the multiple respective times.

21. The portable medical treatment system of claim 20, wherein:
the computer is configured to present, on the touchscreen of the computer during the presentation of the first prompt, an interface element that the computer indicates is to be selected upon arrival of professional medical help; and
the computer is configured to end the interactive query flow and present the summary of treatment responsive to user selection of the interface element.

22. The portable medical treatment system of claim 20, wherein:

the computer is configured to present the summary of treatment responsive to the computer receiving user input that indicates that treatment of the victim is complete, and the computer is configured to, upon expiration of a recheck timer that is automatically activated by the computer upon application of the first computer-selected medical tool to the victim, automatically change from presenting the summary of treatment to presenting a prompt for user input to specify a status of the victim or a status of the application of the first computer-selected medical tool to the victim.

23. The portable medical treatment system of claim 1, wherein the operations comprise:

presenting, on the touchscreen of the computer, a prompt for user input to specify whether a second victim has experienced a condition;

receiving, through user interaction with the touchscreen, a second user response that specifies that a second victim has experienced a second type of condition;

selecting, by the computer, to present the information that instructs the user to retrieve the first computer-selected medical tool from the user-carryable medical case and present the information that instructs the user how to apply the first computer-selected medical tool to the victim to treat the first type of condition, before presenting second victim treatment information that instructs the user how to treat the second type of condition of the second victim, based on the computer identifying that the first type of condition is more severe than the second third type of condition; and presenting, by the touchscreen after the computer has presented the information that instructs the user to retrieve the first computer-selected medical tool from the user-carryable medical case and present the information that instructs the user how to apply the first computer-selected medical tool to the victim to treat the first type of condition, the second victim treatment information that instructs the user how to treat the second type of condition of the second victim, the second victim treatment information including:

information instructing the user to retrieve a third computer-selected medical tool from among the medical tools located in the user-carryable medical case, and information that instructs the user how to apply the third computer-selected medical tool to the second victim to treat the second type of condition.

24. The portable medical treatment system of claim 1, wherein presenting the information that instructs instructing the user to retrieve the first computer-selected medical tool from the user-carryable medical case includes presenting information that indicates a location of the first computer-selected medical tool within the user-carryable medical case.

25. The portable medical treatment system of claim 1, wherein presenting the information instructing the user to retrieve the first computer-selected medical tool from the user-carryable medical case includes presenting a graphical depiction of the first computer-selected medical tool, to assist the user in finding the first computer-selected medical tool in the user-carryable medical case.

26. The portable medical treatment system of claim 1, wherein:

the information instructing the user to retrieve the first computer-selected medical tool from the user-carryable medical case is presented by the touchscreen on a first user interface screen;

the information that instructs the user how to apply the first computer-selected medical tool to the victim to treat the first type of condition is presented by the touchscreen on a second user interface screen; and the computer is configured to replace the first user interface screen with the second user interface screen upon receipt of user input that interacts with the touchscreen to indicate that the user has located the first computer-selected medical tool in the user-carryable medical case.

27. The portable medical treatment system of claim 1, wherein:

the user-carryable medical case includes a base and a lid;

the base is configured to lay on a flat surface at the location of the victim;

the lid is configured to be opened by the user to expose the interior of the user-carryable case while the base is laid on the flat surface; and the touchscreen is retained by the lid of the user-carryable case and exposed to the user upon the user opening the lid of the user-carryable case.

28. The portable medical treatment system of claim 1, wherein the second computer-selected medical tool is a different type of tool than the first computer-selected medical tool.

29. The portable medical treatment system of claim 1, wherein the plurality of medical tools arranged within the plurality of tool-receiving receptacles of the user-carryable medical case includes one or more of a bandage, gauze, medicine, or gloves; and the instructions that, when executed by the one or more processors, are configured to cause the computer to perform operations that include:

(ix) presenting, by the touchscreen responsive to presenting the information that instructs the user how to apply the first computer-selected medical tool to the victim, a second prompt for user input to specify whether application of the first computer-selected medical tool to the victim successfully treated the first type of condition; and (x) receiving, through user interaction with the touchscreen, a second user response that specifies whether application of the first computer-selected medical tool to the victim successfully treated the first type of condition, wherein the computer is configured to:

responsive to the second user response specifying that application of the first computer-selected medical tool to the victim did not successfully treat the first type of condition, present alternative treatment information on the touchscreen that instructs the user how to treat the first type of condition with a second computer-selected medical tool that is stored in the user-carryable medical case, including a presentation of:

information that instructs the user to retrieve the second computer-selected medical tool from among the medical tools located in the user-carryable medical case, and information that instructs the user how to apply the second computer-selected medical tool to the victim to treat the first type of condition, and responsive to the second user response specifying that application of the first computer-selected medical tool to the victim successfully treated the first type of condition, present a third prompt on the touchscreen for user input to specify whether the victim is suffering from a second type of condition, in distinction to presenting the alternative treatment information, the second type of condition being a less-severe type of condition than the first condition, as a result of the interactive query flow being configured to present prompts with reference to multiple different types of injuries in a descending order of severity so that the portable medical treatment system causes the victim to be treated for the first type of condition before being treated for the second type of condition.

30. A portable medical treatment system including:
a user-carryable medical case adapted to be carried by a user from a storage location to a location of a victim requiring medical assistance, the user-carryable medical case having a plurality of tool-receiving receptacles configured to receive multiple medical tools arranged according to a preselected arrangement;
a plurality of medical tools arranged within the plurality of tool-receiving receptacles according to the preselected arrangement; and
a computer that is contained within an interior of the user-carryable medical case, the computer being configured to provide an interactive query flow that guides the user in providing care to the victim, the computer comprising: a touchscreen; one or more processors; and computer-readable media including instructions that, when executed by the one or more processors, are configured to cause the computer to perform operations that include:
(i) presenting, on the touchscreen, a first prompt for user input to specify whether the victim is suffering from a first type of condition;
(ii) receiving, through user interaction with the touchscreen, a first user response that specifies whether the victim is suffering from the first type of condition;
(iii) selecting, responsive to the first user response specifying that the victim is suffering from the first type of condition, a first computer-selected medical tool from among the medical tools located in the user-carryable medical case with which to treat the first type of condition;
(iv) presenting, on the touchscreen responsive to the computer selecting the first computer-selected medical tool from among the medical tools located in the user-carryable medical case, information that instructs the user to retrieve the first computer-selected medical tool from the user-carryable medical case and that assists the user in locating the first computer-selected medical tool from among medical tools located within the user-carryable medical case;
(v) presenting, on the touchscreen responsive to the computer selecting the first computer-selected medical tool, information that instructs the user how to apply the first computer-selected medical tool to the victim to treat the first type of condition; and
(vi) prior to the presenting of the first prompt, receiving the first user response, selecting the first computer-selected medical tool, presenting the information that instructs the user to retrieve the first computer-selected medical tool, and presenting the information that instructs the user how to apply the first computer-selected medical tool:
receiving verification of medical provider skill of the user such that the medical provider skill of the user being as a certified medical provider causes the interactive query flow to include advanced medical prompts and such that the medical provider skill of the user not being as a certified medical provider causes the interactive query flow to exclude advanced medical prompts.

31. The portable medical treatment system of claim 30, wherein the advanced medical prompts can include instruction for at least one of suturing, thoracotomy, cut-down, tracheotomy, fasciotomy, intubation, intravenous therapy, intravenous drug dosing.

32. A portable medical treatment system including:
a user-carryable medical case adapted to be carried by a user from a storage location to a location of a victim requiring medical assistance, the user-carryable medical case having a plurality of tool-receiving receptacles configured to receive multiple medical tools arranged according to a preselected arrangement;
a plurality of medical tools arranged within the plurality of tool-receiving receptacles according to the preselected arrangement; and
a computer that is contained within an interior of the user-carryable medical case, the computer being configured to provide an interactive query flow that guides the user in providing care to the victim, the computer comprising: a touchscreen; one or more processors; and computer-readable media including instructions that, when executed by the one or more processors, are configured to cause the computer to perform operations that include:
(i) presenting, on the touchscreen, a first prompt for user input to specify whether the victim is suffering from a first type of condition;
(ii) receiving, through user interaction with the touchscreen, a first user response that specifies whether the victim is suffering from the first type of condition;
(iii) (a) selecting, responsive to the first user response specifying that the victim is suffering from the first type of condition, a first computer-selected medical tool from among the medical tools located in the user-carryable medical case with which to treat the first type of condition,
(b) presenting, on the touchscreen responsive to the computer selecting the first computer-selected medical tool from among the medical tools located in the user-carryable medical case, information that instructs the user to retrieve the first computer-selected medical tool from the user-carryable medical case and that assists the user in locating the first computer-selected medical tool from among medical tools located within the user-carryable medical case, and
(c) presenting, on the touchscreen responsive to the computer selecting the first computer-selected medical tool, information that instructs the user how to apply the first computer-selected medical tool to the victim to treat the first type of condition; and
(iv) (a) selecting, responsive to the first user response specifying that the victim is not suffering from the first type of condition, a second computer-selected medical tool from among the medical tools located in the user-carryable medical case, and (b) presenting, on the touchscreen responsive to the computer selecting the second computer-selected medical tool from among the medical tools located in the user-carryable medical case, information that instructs the user to retrieve the second computer-selected medical tool from the user-carryable medical case and that assists the user in locating the second computer-selected medical tool from among medical tools located within the user-carryable medical case.

33. The portable medical treatment system of claim 32, wherein the operations include:
   (v) (a) selecting, responsive to the first user response indicating that the first computer-selected medical tool is inadequate to treat the first type of condition, a second computer-selected medical tool from among the medical tools located in the user-carryable medical case,
   (b) presenting, on the touchscreen responsive to the computer selecting the second computer-selected medical tool from among the medical tools located in the user-carryable medical case, information that instructs the user to retrieve the second computer-selected medical tool from the user-carryable medical case and that assists the user in locating the second computer-selected medical tool from among medical tools located within the user-carryable medical case, and
   (c) presenting, on the touchscreen responsive to the computer selecting the second computer-selected medical tool, information that instructs the user how to apply the second computer-selected medical tool to the victim to treat the first type of condition.

\* \* \* \* \*